US008067394B2

(12) United States Patent
Honda et al.

(10) Patent No.: US 8,067,394 B2
(45) Date of Patent: *Nov. 29, 2011

(54) **SYNTHESIS AND BIOLOGICAL ACTIVITIES OF NEW TRICYCLIC-*BIS*-ENONES (TBES)**

(75) Inventors: Tadashi Honda, Hanover, NH (US); Chitra Sundararajan, Hamilton (CA); Gordon W. Gribble, Lebanon, NH (US); Michael B. Sporn, Tunbridge, VT (US); Karen T. Liby, West Lebanon, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/777,120

(22) Filed: May 10, 2010

(65) Prior Publication Data

US 2011/0009363 A1  Jan. 13, 2011

Related U.S. Application Data

(63) Continuation of application No. 11/941,820, filed on Nov. 16, 2007, now Pat. No. 7,714,012.

(60) Provisional application No. 60/866,330, filed on Nov. 17, 2006.

(51) Int. Cl.
| | |
|---|---|
| *A61K 31/695* | (2006.01) |
| *A61K 31/277* | (2006.01) |
| *A61K 31/4164* | (2006.01) |
| *A61K 31/40* | (2006.01) |
| *A61P 35/00* | (2006.01) |
| *A61P 35/02* | (2006.01) |

(52) U.S. Cl. ......... 514/63; 514/400; 514/428; 514/510; 514/564; 514/662

(58) Field of Classification Search ............... 514/63, 514/400, 428, 510, 564, 662
See application file for complete search history.

(56) References Cited

U.S. PATENT DOCUMENTS

| | | | |
|---|---|---|---|
| 4,395,423 A | 7/1983 | Neumann | 424/304 |
| 4,808,614 A | 2/1989 | Hertel | 514/45 |
| 5,013,649 A | 5/1991 | Wang et al. | 435/69.1 |
| 5,064,823 A | 11/1991 | Lee et al. | 514/198 |
| 5,401,838 A | 3/1995 | Chou | 536/281 |
| 5,426,183 A | 6/1995 | Kjell | 536/285.5 |
| 5,464,826 A | 11/1995 | Grindey et al. | 514/50 |
| 5,521,294 A | 5/1996 | Wildfeuer | 536/187 |
| 5,597,124 A | 1/1997 | Kessel et al. | 241/30 |
| 5,603,958 A | 2/1997 | Morein et al. | 424/489 |
| 5,606,048 A | 2/1997 | Chou et al. | 536/271.1 |
| 5,972,703 A | 10/1999 | Long et al. | 435/372 |
| 6,025,395 A | 2/2000 | Breitner et al. | 514/570 |
| 6,303,569 B1 | 10/2001 | Greenwald et al. | 514/2 |
| 6,326,507 B1 | 12/2001 | Gribble et al. | 558/415 |
| 6,485,756 B1 | 11/2002 | Aust et al. | 424/725 |
| 6,974,801 B2 | 12/2005 | Honda et al. | 514/25 |
| 7,176,237 B2 | 2/2007 | Honda et al. | 514/519 |
| 7,265,096 B2 | 9/2007 | Gallop et al. | 514/49 |
| 7,288,568 B2 | 10/2007 | Gribble et al. | 514/519 |
| 7,435,755 B2 | 10/2008 | Konopleva et al. | 514/510 |
| 7,714,012 B2 | 5/2010 | Honda et al. | 514/396 |
| 2002/0042535 A1 | 4/2002 | Gribble et al. | 558/429 |
| 2005/0276836 A1 | 12/2005 | Wilson et al. | 424/434 |
| 2005/0288363 A1 | 12/2005 | Gribble et al. | 558/303 |
| 2007/0155742 A1 | 7/2007 | Honda et al. | 514/519 |
| 2008/0220057 A1 | 9/2008 | Gribble et al. | 514/522 |
| 2008/0233195 A1 | 9/2008 | Sporn et al. | 514/63 |
| 2009/0048205 A1 | 2/2009 | Meyer et al. | 514/49 |
| 2009/0060873 A1 | 3/2009 | Sporn et al. | 424/85.6 |
| 2009/0093447 A1 | 4/2009 | Konopleva et al. | 514/510 |

FOREIGN PATENT DOCUMENTS

| | | |
|---|---|---|
| DE | 10 2005 04161 | 3/2007 |
| EP | 0 272 891 A2 | 6/1988 |
| EP | 0 329 348 B1 | 7/1995 |
| EP | 0 376 518 B1 | 11/1995 |
| EP | 0 576 230 B1 | 4/1996 |
| EP | 0 577 303 B1 | 10/1997 |
| EP | 0 712 860 B1 | 12/2001 |
| WO | WO 91/15498 | 10/1791 |
| WO | WO 98/00173 | 1/1998 |
| WO | WO 98/32762 | 7/1998 |
| WO | WO 99/33483 | 7/1999 |
| WO | WO 99/65478 | 12/1999 |
| WO | WO 00/73253 | 12/2000 |
| WO | WO 01/01135 | 1/2001 |
| WO | WO 02/03996 | 1/2002 |
| WO | WO 02/47611 | 6/2002 |
| WO | WO 03/043631 | 5/2003 |
| WO | WO 03/059339 | 7/2003 |

(Continued)

OTHER PUBLICATIONS

Choi et al., Clin Cancer Res 2009; 15; 5258-5266.*
Phipps et al., caplus an 2009:547977.*
"CDDO in treating patients with metastatic or unresectable solid tumors or lymphoma," http://www.clinicaltrials.gov/ct2/show/NCT00352040?term=CDDO&rank=1, Dec. 14, 2008.
"FDA mulls drug to slow late-stage Alzheimer's," http://www.cnn.com/2003/HEALTH/conditions/09/24/alzheimers.drug.ap/index.html, Retrieved on Sep. 23, 2003.
"Phase IIa trail to determine the effects of bardoxolone methyl on renal function in patients with diabetic nephropathy," http://www.clinicaltrials.gov/ct2/show/NCT00664027?term=rta&rank=10, Dec. 14, 2008.

(Continued)

*Primary Examiner* — Sun Jae Loewe
(74) *Attorney, Agent, or Firm* — Fulbright & Jaworski LLP

(57) ABSTRACT

This invention describes novel tricyclic-bis-enone derivatives (TBEs), such as TBE-31, TBE-34, TBE-45 and water-soluble TBEs. The methods of preparing these compounds are also disclosed. The inventors demonstrate the ability of these new TBEs to inhibit proliferation of human myeloma cells, inhibit the induction of iNOS in cells stimulated with interferon-γ, induce heme oxygenase-1 (HO-1), induce CD11b expression—a leukemia differentiation marker, inhibit proliferation of leukemia cells, induce apoptosis in human lung cancer, and induce apoptosis in other cancerous cells. The TBEs of this invention are expected to be useful agents for the treatment and prevention of many diseases, including cancer, neurological disorders, inflammation, and pathologies involving oxidative stress.

9 Claims, 14 Drawing Sheets

FOREIGN PATENT DOCUMENTS

| WO | WO 2005/042002 | 5/2005 |
|---|---|---|
| WO | WO 2005/046732 | 5/2005 |
| WO | WO 2006/029221 | 3/2006 |
| WO | WO 2007/005879 | 1/2007 |
| WO | WO 2007/069895 | 6/2007 |
| WO | WO 2008/111497 | 9/2008 |
| WO | WO 2008/136838 | 11/2008 |
| WO | WO 2009/023232 | 2/2009 |

OTHER PUBLICATIONS

"RTA 402 in advanced solid tumors or lymphoid malignancies," http://www.clinicaltrials.gov/ct2/show/NCT00508807?term=rta&rank=2&show_desc=Y, Dec. 14, 2008.

"Study to assess the safety, tolerability, and pharmacodynamics of RTA 402 in patients with the hepatic dysfunction," http://www.clinicaltrials.gov/ct2/show/NCT00550849?term=rta&rank=4, Dec. 14, 2008.

Abraham and Kappas, "Heme oxygenase and the cardiovascular-renal system," *Free Radic Biol Med.*, 39(1):1-25, 2005.

Agarwal and Mehta, "Possible involvement of Bcl-2 pathway in resinoid X receptor alpha-induced apoptosis of HL-60 cells," *Biochem Biophys Res Common*, 230(2):251-253, 1997.

Ahmad et al., "Triterpenoid CDDO-Me blocks the NF-κB pathway by direct inhibition of IKKβ on Cys-179", *J. Biol. Chem.*, 281:35764-9, 2006.

Akrivakis et al., "Prolonged infusion of gemcitabine in stage IV breast cancer: a phase I study," *Anti-Cancer Drugs*, 10 (6): 525-531, 1999.

Al-alami et al., "Divergent effect of taxol on proliferation, apoptosis and nitric oxide production in MHH225 CD34 positive and U937 CD34 negative human leukemia cells," *Leukemia Res.*, 22:939-945, 1998.

Alexander et al., "Synthesis and cytotoxic activity of two novel 1-dodecylthio-2-decyloxypropyl-3-phosphatidic acid conjugates with gemcitabine and cytosine arabinoside," *J. Med. Chem.*, 46 (19): 4205-4208, 2003.

Ambs et al., "p53 and vascular endothelial growth factor regulate tumor growth of NOS2-expressing human carcinoma cells," *Nat. Med.*, 4(12):1371-1376, 1998.

Amstutz et al., "Die position 5 im oxotremorin-gerust: eine zentrale stelle fur die steuerung der aktivitat am muscarinischen rezeptor," *Helv. Chim. Acta.*, 70:2232-2244, 1987.

Andreeff et al., "Expression of bcl-2-related genes in normal and AML progenitors: Changes induced by chemotherapy and cationic acid," *Leukemia*, 13:1881-1892, 1999.

Andreeff et al., "PPARgamma nuclear receptor as a novel molecular target in leukemias," *2002 Keystone Symposia*, Abstract No. 501, 2002.

Andreeff, "Acute myeloid leukemia," *In: Cancer Treatment*, Haskell (Ed.), W. B. Saunders, 911-922, 1995.

Araujo et al., "Systemic rather than local heme oxygenase-1 overexpression improves cardiac allograft outcomes in a new transgenic mouse," *J Immunol.*, 171(3):1572-1580, 2003.

Ardestani et al., "Effects of dexamethasone and betamethasone as COX-2 gene expression inhibitors on rigidity in a rat model of Parkinson's disease," *Indian J. Pharmacol.*, 39:235-9, 2007.

Ariga et al., "Role of sphingolipid-mediated cell death in neurodegenerative diseases," *Journal of Lipid Research*, 39:1-16, 1998.

Bach, "Heme oxygenase-1 and transplantation tolerance," *Hum Immunol.* 67(6):430-432, 2006.

Baeuerle, "NF-κB: ten years after," *Cell*, 87:13-20, 1996.

Bagasra et al., "Activation of the inducible form of nitric oxide synthase in the brains of patients with multiple sclerosis," *Proc. Natl. Acad. Sci. USA*, 92:12041-12045, 1995.

Baker et al., "2'-Deoxy-2'-methylenecytidine and 2'-deoxy-2',2'-difluorocytidine 5'-diphosphates: potent mechanism-based inhibitors of ribonucleotide reductase," *J. Med. Chem.*, 34 (6): 1884, 1991.

Baldwin, "The NF-κB and IκB proteins: new discoveries and insights," *Annu. Rev. Immunol.*, 14:649-681, 1996.

Balkwill et al., "Smoldering and polarized inflammation in the initiation and promotion of malignant disease," *Cancer Cell*, 7 (3): 211-217, 2005.

Bargou et al., "Constitutive nuclear factor κB-RelA activation is required for proliferation and survival of Hodgkin's disease tumor cells," *J. Clin. Invest.*, 100:2961-2969, 1997.

Barkett and Gilmore, "Control of apoptosis by Re1/NF-κB transcription factors," *Oncogene*, 18:6910-6924, 1999.

Barnes and Karin, "Nuclear factor-κB—a pivotal transcription factor in chronic inflammation diseases," *N. Engl. J. Med.*, 336:1066-1071, 1997.

Beal, "Mitochondria, free radicals, and neurodegeneration," *Curr. Opin. Neurobiol.*, 6:661-666, 1996.

Beran et al., "Topotecan and cytarabine is an active combination regimen in myelodysplastic syndromes and chronic myelomonocytic leukemia," *J. Clinical Oncology*, 17(9):2819-2830, 1999.

Bliard et al., "Glycosylation of acids under phase transfer conditions. Partial synthesis of saponins," *Tetrahedron Lett.*, 35:6107-6108, 1994.

Bogdan et al., "Contrasting mechanisms for suppression of macrophage cytokine release by transforming growth factor-β and interleukin-10," *J. Biol. Chem.*, 267:23301-23308, 1992.

Bogdon and Ding, "Taxol, a microtubule-stabilizing antineoplastic agent, induces expression of tumor necrosis factor α and interleukin-1 in macrophages," *J. Leukoc. Biol.*, 52(1):119-121, 1992.

Bollag and Holdener, "Retinoids in cancer prevention and therapy," *Annals of Oncology*, 3:513-526, 1992.

Boolbol et al., "Cyclooxygenase-2 overexpression and tumor formation are blocked by sulindac in a murine model of familial adenomatous polyposis," *Cancer Res.*, 56(11):2556-2560, 1996.

Bore et al., "The anti-inflammatory triterpenoid methyl 2-cyano-3, 12-dioxoolean 1,9(11)-dien-28-oate methanol solvate hydrate," *Acta Crystallorg C.*, 58(Pt 3):o199-o200, 2002.

Brookes et al., "The triterpenoid 2-cyano-3,12-dioxooleana-1,9-dien-28-oic acid and its derivatives elicit human lymphoid cell apoptosis through a novel pathway involving the unregulated mitochondrial permeability transition pore," *Cancer Res.*, 67:1793-1802, 2007.

Bruder and Caplan, "First bone formation and the dissection of an osteogenic lineage in the embryonic chick tibia is revealed by monoclonal antibodies against osteoblasts," *Bone*, 10:359-375, 1989.

Bruder and Caplan, "A monoclonal antibody against the surface of osteoblasts recognizes alkaline phosphatase isoenzymes in bone, liver, kidney, and intestine," *Bone*, 11:189-198, 1990.

Bruder et al., "Terminal Osteogenic cell differentiation in culture requires beta-glycerol phosphate," *Trans. Ortho. Res. Soc.*, 16:58, 1991.

Bruland et al., "Expression and characteristics of a novel human osteosarcoma-associated cell surface antigen," *Cancer Res.*, 48:5302-5308, 1988.

Buzoni-Gatel et al., "Intraepithelial lymphocytes traffic to the intestine and enhance resistance to Toxoplasma gondii oral infection," *J. Immunol.*, 162:5846-5852, 1999.

Buzoni-Gatel et al., "Murine ileitis after intracellular parasite infection is controlled by TGF-beta-producing intraepithelial lymphocytes," *Gastroenterolog*, 120:914-924, 2001.

Cai et al., "A new protecting group for alkynes: orthogonally protected dialkynes," *Helv. Chim. Acta.*, 78:732-757, 1995.

Carter et al., "Expression of survivin, a member of the inhibitor of apoptosis (IAP) family of caspase inhibitors is expressed in AML and regulated by cytokines and ATRA," *Blood*, 94(Suppl 1):479a, Abstract # 2142, 1999.

Cassady and Suffness, In *Anticancer Agents Based on Natural Product Models*; Academic Press, NY, 254-269, 1980.

Castaigne et al., "All-trans retinoic acid as a differentiation therapy for acute promyelocytic leukemia," *Blood*, 76(9):1704-1709, 1990.

Cerwenka and Swain, "TGF-β1. immunosuppressant and viability factor for T lymphocytes," *Microbes and Infection*, 1: 1291-1296, 1999.

Chauhan et al., "The bortezomib/proteasome inhibitor PS-341 and triterpenoid CDDO-Im induce synergistic anti-multiple myeloma (MM) activity and overcome bortezomib resistance," *Blood*, 103:3158-3166, 2004.

Chen et al., "Chondrogenesis in chick limb bud mesodermal cells: reciprocal modulation by activin and inhibin," *Exp. Cell. Res.*, 206:119-27, 1993.

Chen et al., "Stimulation of chondrogenesis in limb bud mesoderm cells by recombinant human bone morphogenetic protein 2B (BMP-2B) and modulation by transforming growth factor beta 1 and beta 2," *Exp. Cell. Res.*, 195:509-15, 1991.

Cheng et al., "Differentiation of human bone marrow osteogenic stromal cells in vitro: induction of the osteoblast phenotype by dexamethasone," *Endocrinology*, 134:277-86, 1994.

Chintharlapalli et al., "2-Cyano-3,12-dioxoolean-1,9-dien-28-oic acid and related compounds inhibit growth of colon cancer cells through peroxisome proliferator-activated receptor gamma-dependent and -independent pathways," *Mol. Pharmacol.*, 68:119-128, 2005.

Cho et al., "The transcription factor NRF2 protects against pulmonary fibrosis," *FASEB Journal*, 18:1-29, 2004.

Chou et al., "Sterospecific Synthesis of 2-Deoxy-2,2-difluororibonolactone and its Use in the Preparation of 2'-Deoxy-2', 2'-difluoro-B—D-ribofuranosyl Pyrimidine Nucleosides: The Key Role of Selective Crystallization," *Synthesis*, 565-570, 1992.

Chung and Wasicak, "Synthesis of chiral ∀-acetylenic cyclic amines from ∀-amino acids: applications to differentially constrained oxotremorine analogues as muscarinic agents," *Tetrahedron Lett.*, 31:3957-3960, 1990.

Cianchi et al., "Cyclooxygenase-2 activation mediates the proangiogenic effect of nitric oxide in colorectal cancer," *Clinical Cancer Research*, 10:2694-2704, 2004.

Clinton et al., "Steroidal[3,2-c]pyrazoles. II. Androstanes, 19-norandrostanes and their unsaturated analogs," *J. Am. Chem. Soc.*, 83:1478-1491, 1961.

Corey and Ruden, "Stereoselective methods for the synthesis of terminal *cis* and *trans* enyne units," *Tetrahedron Lett.*, 1495-1499, 1973.

Coyle and Puttfarcken, "Oxidative stress, glutamate, and neurodegenerative disorders," *Science*, 262:689-695, 1993.

Cripe, "Adult Acute Leukemia," *Current Problems in Cancer*, 21 (1): 4-64, 1997.

Cui, "A material science perspective of pharmaceutical solids," *Int. J. Pharmceutics*, 339 (1-2): 3-18, 2007.

Dean et al., "Halogenolysis of methyl glycyrrhetate with lithium iodidedimethylformamide," *J. Chem. Soc.*, 6655-6659, 1965.

Dezube et al., "Interim results of a phase I trial with a novel orally administered synthetic triterpenoid RTA 402 (CDDO-Me) in patients with solid tumors and lymphoid malignancies," *J. Clin. Oncol.*, 2007 ASCO Annual Meeting Proceedings, 25(18S):14101, 2007.

Di Stefano et al., "Inhibition of [3H]thymidine incorporation into DNA of rat regenerating liver by 2',2'-difluorodeoxycytidine coupled to lactosaminated poly-L-lysine," *Biochem. Pharmacol.*, 57 (7): 793-799, 1999.

Ding et al., "Macrophage deactivating factor and transforming growth factors-$\beta_1$ $\beta_2$ and $\beta_3$, inhibit induction of macrophage nitrogen oxide synthesis by IFNγ[1]," *J. Immunol.*, 145:940-944, 1990.

Dinkova-Kostova et al., "Extremely potent triterpenoid inducers of the phase 2 response: correlations of protection against oxidant and inflammatory stress," *Proc. Natl. Acad. Sci. USA*, 102(12):4584-4589, 2005.

Drach et al., "Induction of differentiation in myeloid leukemia cell lines and acute promyelocytic leukemia cells by liposomal all-trans-retinoic acid," *Cancer Research*, 53:2100-2104, 1993.

Dragnev et al., "The retinoids and cancer prevention mechanisms," *The Oncologist*, 5:361-368, 2000.

Drefahl and Huneck, "Nor-olea-12-enol-17-amin und Olea-12-enol-28-amin," *Chem. Ber.*, 91:278-281, 1958.

DuBois et al., "G$_1$ delay in cells overexpressing prostaglandin endoperoxide synthase-2[1]," *Cancer Res.*, 56(4):733-737, 1996.

DuBois et al., "Increased cyclooxygenase-2 levels in carcinogen-induced rat colonic tumors," *Gastroenterology*, 110:1259-1262, 1996.

Dutcher et al., "Pentacyclic triterpene synthesis. 5. Synthesis of optically pure ring AB precursors," *J. Org. Chem.*, 41:2663-2669, 1976.

Ekmekcioglu et al., "Tumor iNOS predicts poor survival for stage III melanoma patients," *Int. J. Cancer*, 119:861-866, 2006.

Ellies et al., "Mammary tumor latency is increased in mice lacking the inducible nitric oxide synthase," *Int. J. Cancer*, 106:1-7, 2003.

Elliot et al., "The triterpenoid CDDO inhibits expression of matrix metalloproteinase-1, matrix metalloproteinase-13 and Bcl-3 in primary human chondrocytes," *Arthritis Res. Ther.*, 5:R285-R291, 2003.

Elsawa et al., "Preferential Inhibition of Malignant Cell Growth by CDDO in Waldenstrom Macroglobulinemia," *Blood*, 108(11):2528, 2006.

Elstner et al., "Ligands for peroxisome proliferator-activated receptorgamma and retinoic acid receptor inhibit growth and induce apoptosis of human breast cancer cells in vitro and in BNX mice," *Proc. Natl. Acad. Sci. USA*, 95:8806-8811, 1998.

Embleton et al., "Antitumour reactions of monoclonal antibody against a human osteogenic-sarcoma cell line," *Br. J. Cancer*, 43:4801-4805, 1981.

Engel et al., "Quantitation of minimal residual disease in acute myelogenous leukemia and myelodysplastic syndromes in complete remission by molecular cytogenetics of progenitor cells," *Leukemia*, 13:568-577, 1999.

Estey et al., "Molecular remissions induced by liposomal-encapsulated all-trans retinoic acid in newly diagnosed acute promyelocytic leukemia," *Blood*, 94:2230-2235, 1999.

Estey et al., "Randomized phase II study of fludarabine + cytosine arabinoside + idarubicin + all-trans retinoic acid + granulocyte-colony stimulating factor in poor prognosis newly diagnosed acute myeloid leukemia and myelodysplastic syndrom," *Blood*, 93(8):2478-2484, 1998.

Favaloro et al., "Design and synthesis of tricyclic compounds with enone functionalities in rings A and C: a novel class of highly active inhibitors of nitric oxide production in mouse macrophages," *J Med. Chem.*, 45:4801-4805, 2002.

Finkbeiner and Stiles, "Chelation as a driving force in organic reactions. IV. Synthesis of a ∀-nitro acids by control of the carboxylation-decarboxylation equilibrum," *J. Am. Chem. Soc.*, 85:616-622, 1963.

Gandhi et al., "Prolonged infusion of gemcitabine: clinical and pharmacodynamic studies during a phase I trial in relapsed acute myelogenous leukemia," *J. Clin. Oncol.*, 20 (3): 665-673, 2002.

Genain and Hauser, "Creation of a model for multiple sclerosis in *Callithrix jacchus* marmosets," *J. Mol. Med.*, 75:187-197, 1997.

Ghosh et al., "NF-κB and Rel proteins: evolutionarily conserved mediators of immune response," *Annu Rev Immunol.*, 16:225-260, 1998.

Godoy et al., "Central and systemic IL-I exacerbates neurodegeneration and motor symptoms in a model of Parkinson's disease," *Brain*, 131:1880-1894, 2008.

Grieco and Speake, "Synthetic Studies on Quassinoids: Total Synthesis and Biological Evaluation of (+)-Des-D-chaparrinone," *J. Org. Chem.*, 63:5929-5936, 1998.

Guo et al., "Selective Protection of 2',2'-Diflurodeoxycytidine (Gemcitabine),"*J. Org. Chem.*, 64: 8319-8322, 1999.

Guo et al., "Targeted delivery of a peripheral benzodiazepine receptor ligand-gemcitabine conjugate to brain tumors in a xenograft model," *Cancer Chemother. Pharmacol.*, 48 (2): 169-176, 2001.

Gura et al., "Systems for identifying new drugs are often faulty," *Science*, 278:1041-1042, 1997.

Guttridge et al., "NF-kappaB controls cell growth and differentiation through transcriptional regulation of cyclin D1," *Mol. Cell. Biol.*, 19:5785-5799, 1999.

Hail et al., "Evidence supporting a role for calcium in apoptosis induction by the synthetic triterpenoid 2-cyano-3,12-dioxooleana-1,9-dien-28-oic acid (CDDO)," *J. Biol. Chem.*, 279:11179-11187, 2004.

Heiner et al., "Localization of GD2-specific monoclonal antibody 3F8 in human osteosarcoma," *Cancer Res.*, 47:5377-5384, 1987.

Hidvegi et al., "A low temperature method of isolating normal human articular chondrocytes," *Osteoarthr. Cartil.*, 14:89-93, 2006.

Hinz et al., "NF-kappaB function in growth control: regulation of cyclin D1 expression and G0/G1-to-S-phase transition," *Mol. Cell Biol.*, 19:2690-2698, 1999.

Hirota et al., "Stereoselective total synthesis of (±)-eperuane-8β,15-diol[1]," *Bull. Chem. Soc. Jpn.*, 61:4023-4028, 1988.

Hirota et al., "Suppression of tumor promoter-induced inflammation of mouse ear by ursolic acid and 4,4-dimethycholestane derivatives" *Agric. Biol. Chem.*, 54:1073-1075, 1990.

Hirota et al., "Total synthesis of (±)-amarolide, a quassinoid bitter principle," *J. Org. Chem.*, 56:1119-1127, 1991.

Honda et al., "A novel dicyanotriterpenoid, 2-cyano-3,12-dioxooleanan-1,9(11)-dien-28-onitrile, active at picomolar concentrations for inhibition of nitric oxide production," *Bioorganic & Medicinal Chemistry Letters*, 12:1027-1030, 2002.

Honda et al., "An efficient synthesis of tricyclic compounds (±)—(4aβ, 8aβ, 10aα)—1,2,3,4,4a,6,7,8,8a,9,1-,10a-Dodecahydro-1,1,4a-Trimethy1-2-0xophenanthrene-8a-Carboxolic acid, its methyl ester, and (±)-(4aβ, 8aβ, 10aα)-3,4,4a,6,7,8,8a,9,10,10a-Decahydro-8a-Hydroxymethyl-1,1,4a-Trimethylphenanthren-2(1H)-one," *Org. Prep. Proced. Int.*, 37 (6):546-550, 2005.

Honda et al., "Design and synthesis of 2-cyano-3,12-dioxooleanan-1,9-dien-28-oic acid, a novel and highly active inhibitor of nitric oxide production in mouse macrophages," *Bioorg Med Chem Lett.*, 8(19):2711-2714, 1998.

Honda et al., "Design, synthesis, and biological evaluation of biotin conjugates of 2-cyano-3,12-dioxooleana-1,9(11)-dien-28-oic acid for the isolation of the protein targets," *J. Med. Chem.*, 47 (20): 4923-4932, 2004.

Honda et al, "Efficient synthesis of (−)—and (+)-tricyclic compounds with enome functionalities in rings A and C. A novel class of orally active anti-inflammatory and cancer chemopreventive agents," *Org Biomol Chem*, 1:4384-4391, 2003.

Honda et al., "New enone derivatives of oleanolic acid and ursolic acid as inhibitors of nitric oxide production in mouse macrophages," *Bioorg. Med. Chem. Lett.*, 7:1623-1628, 1997.

Honda et al., "Novel synthetic oleanane and ursane triterpenoids with various enone functionalities in ring A as inhibitors of nitric oxide production in mouse macrophages," *J. Med. Chem.*, 43:1866-1877, 2000.

Honda et al., "Novel synthetic oleanane triterpenoids: a series of highly active inhibitors of nitric oxide production in mouse macrophages," *Bioorg. Med. Chem. Lett.*, 9(24):3429-3434, 1999.

Honda et al., "Novel tricyclic compounds having acetylene groups at C-8a and cyano enones in rings A and C: highly potent anti-inflammatory and cytoprotective agents," *J. Med. Chem.*, 50:1731-1734, 2007.

Honda et al., "Synthesis of (±)-3,3-ethylenedioxy-14α-hydroxy-5-picrasene-11,16-dione, a 14αH-picrasane derivative," *Chem. Lett.*, 299-302, 1981.

Honda et al., "Synthesis of a novel dicyano abietane analogue: a potential antiinflammatory agent," *J. Org. Chem.*, 71:3314-3316, 2006.

Honda et al., "Synthetic oleanane and ursane triterpenoids with modified rings A and C: A series of highly active inhibitors of nitric oxide production in mouse macrophages," *J. Med. Chem.*, 43:4233-4246, 2000.

Hong et al., "Phase I trial of a novel oral NF-κB/pSTAT3 inhibitor RTA-402 in patients with solid tumors and lymphoid malignancies," *44th Annual Meeting of the American Society of Clinical Oncology*, 2008.

Hosoi et al., "Detection of human osteosarcoma-associated antigen(s) by monoclonal antibodies," *Cancer Res.*, 42:654-661, 1982.

Huang et al., "Inhibition of skin tumorigenesis by Rosemary and its constituents carnosol and ursolic acid," *Cancer Res.*, 54:701-708, 1994.

Huang et al., "Inhibitory effects of dietary curcumin on forestomach, duodenal, and colon carcinogenesis in mice," *Cancer. Res.*, 54:5841-5847, 1994.

Huang et al., "Structure of a WW domain containing fragment of dystrophin in complex with β-dystroglycan," *Nat. Struct. Biol.*, 7:634-638, 2000.

Hyer et al., "Synthetic triterpenoids cooperate with tumor necrosis factor-related apoptosis-inducing ligand to induce apoptosis of breast cancer cells," *Cancer Res.*, 65:4799-4808, 2005.

Iguchi et al., "Lipid peroxidation and disintegration of the cell membrane structure in cultures of rat lung fibroblasts treated with asbestos," *J. Appl. Toxicol.*, 13:269-275, 1993.

Ikeda et al., "Induction of redox imbalance and apoptosis in multiple myeloma cells by the novel triterpenoid 2-cyano-3,12-dioxooolean-1,9-dien-28-oic acid," *Mol. Cancer Ther.*, 3:39-45, 2004.

Ikeda et al., "The novel triterpenoid CDDO and its derivatives induce apoptosis by disruption of intracellular redox balance," *Cancer Res.*, 63:5551-5558, 2003.

Ishikawa et al., "Heme oxygenase-1 inhibits atherogenesis in Watanabe heritable hyperlipidemic rabbits," *Circulation*, 104(15):1831-1836, 2001.

Ito et al., "Involvement of caspase-8 in the induction of osteosarcoma cell apoptosis by the novel triterpenoid CDDO," *47th Annual Meeting, Orthopaedic Research Society*, Feb. 25-28, 2001, San Francisco, California, p. 0863, Poster Session, 2001.

Ito et al., "The novel triterpenoid 2-cyano-3,12-dioxooolean-1,9-dien-28-oic acid induces apoptosis of human myeloid leukemia cells by a caspase-8-dependent mechanism," *Cell Growth Differ.*, 11:261-267, 2000.

Ito et al., "The novel triterpenoid CDDO induces apoptosis and differentiation of human osteosarcoma cells by a caspase-8 dependent mechanism," *Mol. Pharmacol.*, 59:1094-1099, 2001.

Johansen et al., "Pharmacology and preclinical pharmacokinetics of the triterpenoid CDDO methyl ester," *Proc. Amer. Assoc. Cancer Res.*, 44:1728, 2003.

Johnson et al., "A plan for distinguishing between some five- and six-membered ring ketones," *J. Am Chem. Soc.*, 67:1745-1754, 1945.

Johnson et al., "Relationships between drug activity in NCI preclinical in vitro and in vivo models and early clinical trials," *Br. J. Cancer*, 84:1424-1431, 2001.

Joyce et al., "Integration of Rac-dependent regulation of cyclin D1 transcription through a nuclear factor-kappaB-dependent pathway," *J. Biol. Chem.*, 274:25245-25249, 1999.

Kahne and Collum, "Kinetic cyanations of ketone enolates," *Tetrahedron Lett.*, 22:5011-5014, 1981.

Kaltschmidt et al., "Transcription factor NF-kappaB is activated in primary neurons by amyloid beta peptides and in neurons surrounding early plaques from patients with Alzheimer disease," *Proc. Natl. Acad. Sci. USA*, 94:2642-2647, 1997.

Karin, "Nuclear factor-kappaB in cancer development and progression," *Nature*, 441:431-436, 2006.

Kasinski et al., "Inhibition of IkappaB kinase-nuclear factor-kappaB signaling pathway by 3,5-bis(2-flurobenzylidene)piperidin-4-one (EF24), a novel monoketone analog of curcumin," *Mol. Pharmacology*, 74 (3): 654-661, 2008.

Kawamori et al., "Chemopreventive activity of celecoxib, as specific cyclooxygenase-2 inhibitor, against colon carcinogenesis," *Cancer Res.*, 58(3):409-412, 1998.

Kerwin et al., "Quassinoid synthesis. 2. Preparation of a tetracyclic intermediate having the Bruceantin tetrahydrofuran ring," *J. Org. Chem.*, 52:1686-1695, 1987.

Khan et al., "A dichotomous role for nitric oxide during acute Toxoplasma gondii infection in mice," *Proc. Natl. Acad. Sci. USA*, 94:13955-13960, 1997.

Kim et al., "Capasase-3 activation is involved in apoptosis induced by a synthetic triterpenoid in Non-small cell lung cancer (NSCLC) cells," *Proc. Amer. Assoc. Cancer Res.*, 41:770, Abstract #4894, 2000.

Kim et al, "Identification of a novel synthetic triterpenoid, methyl-2-cyano-3,12-dioxooleana-1,9-dien-28-oate, that potently induces caspase-mediated apoptosis in human lung cancer cells," Molecular Cancer Therapeutics, 1:177-184, 2002.

Kircher, "Triterpenes, in organ pipe cactus," *Phytochemistry*, 19:2707-2712, 1980; Database CAPLUS on STN AN:1981:550946.

Klotz et al., "Selective expression of inducible nitric oxide synthase in human prostate carcinoma," *Cancer*, 82:1897-1903, 1998.

Konopleva and Andreeff, "Regulatory pathways in programmed cell death," *Cancer Mol Biol.*, 6:1229-1260, 1999.

Konopleva et al., "Activation of nuclear transcription factor PPARgamma by the novel triterpenoid CDDO as targeted therapy in breast cancer," *2002 Keystone Symposium*, Abstract No. 539, 2002.

Konopleva et al., "Apoptosis: molecules and mechanisms," *Adv Exp Med Biol*, 457:217-236, 1998.

Konopleva et al., "Engraftment potential of AML progenitors into NOD/scid mice is dependent on baseline CXCR4 expression," *Blood*, 94(Suppl 1):166b, Abstract #3916, 1999.

Konopleva et al., "Mechanisms and Activity of PPARgamma-Active Triterpenoids CDDO and CDDO-Me in Leukemias," *Blood*, 106:2460, 2005.

Konopleva et al., "Novel synthetic triterpenoid CDDO-Me: potent antiproliferative, proapoptotic and differentiating agent in AML," *Blood*, 96(11), Part 1: 121A, abstract # 522, 2000.

Konopleva et al., "Novel synthetic triterpenoid, CDDO, and its methyl ester: Potent antiproliferative, proapoptotic and differentiating agents in AML," *Blood*, 94(Suppl 1):479a, Abstract #2140, 1999.

Konopleva et al., "Novel triterpenoid CDD0-Me is a potent inducer of apoptosis and differentiation in acute myelogenous leukemia," *Blood*, 99(1):326-335, 2002.

Konopleva et al., "Peroxisome proliferator-activated receptor gamma and retinoid X receptor ligands are potent inducers of differentiation and apoptosis in leukemias," *Mol. Cancer Ther.*, 3:1249-1262, 2004.

Konopleva et al., "PPARγ nuclear receptor as a novel therapeutic target in AML," *Blood*, 96(11):460a, Abstract #1982, 2000.

Konopleva et al., "PPARgamma Ligand CDDO Induces Apoptosis in Leukemias Via Multiple Apoptosis Pathways," *Abstracts of the 44th Annual Meeting of the American Society of Hematology*, Abstract No. 2209, 2002.

Konopleva et al., "PPARgamma Ligands Are Potent Inducers of Apoptosis in Leukemias and Lymphomas," *American Society of Hematology 43rd Annual Meeting and Exposition*, Abstract No. 501, 2001.

Konopleva et al., "PPARgamma Nuclear Receptor as a Novel Molecular Target in Leukemia Therapy," *Proc. Amer. Assoc. Cancer Res.*, 43:4730, 2002.

Konopleva et al., "PPARgamma Nuclear Receptor as a Novel Therapeutic Target in AML," *Proc. Amer. Assoc. Cancer Res.*, 42:4458, 2001.

Konopleva et al., "Suppression of ERK Activation is Required for Triterpenoid Methyl-CDDO-Induced Apoptosis in AML," *Blood*, 102(11):1404, 2003.

Konopleva et al., "Synthetic triterpenoid 2-cyano-3,12-dioxooleana-1,9-dien-28-oic acid induces growth arrest in HER2-overexpressing breast cancer cells," *Mol. Cancer Ther.*, 5:317-328, 2006.

Konopleva et al., "Synthetic triterpenoid CDDO as a novel therapy for resistant breast cancer," *Proc. Amer. Assoc. Cancer Res.*, 44:2726, 2003.

Konopleva et al., "The novel triterpenoid CDDO-Me suppresses MAPK pathways and promotes p38 activation in acute myeloid leukemia cells," *Leukemia*, 19:1350-1354, 2005.

Konopleva et al., "The synthetic triterpenoid 2-cyano-3,12-dioxooleana-1,9-dien-28-oic acid induces caspase-dependent and -independent apoptosis in acute myelogenous leukemia," *Cancer Res.*, 64:7927-7935, 2004.

Konopleva et al., "Triterpenoid Methyl-CDDO Is a Potent Inducer of Apoptosis in CD34+ AML Progenitor Cells Via Activation of SAPK Pathways and Inhibition of MAPK Cascades," *Blood*, 104:2533, 2004.

Kornblau et al., "Apoptosis regulating proteins as targets of therapy for hematological malignancies," *Exp. Opin. Inv. Drugs*, 8:2027-2057, 1999.

Kornblau et al., "Phase I study of mitoxantrone plus etoposide with multidrug blockage by SDZ PSC-833 in relapsed or refractory acute myelogenous leukemia," *J. Clin. Oncol.*,15(5):1796-1802, 1997.

Kowalski and Reddy, "Ester homologation revisited: a reliable, higher yielding and better understood procedure," *J. Org. Chem.*, 57:7194-7208, 1992.

Kress et al., "Triterpenoids Display Single Agent Activity in a Mouse Model of CLL/SBL," *Blood*, 108(11):2530, 2006.

Kress et al., "Triterpenoids Display Single Agent Anti-tumor Activity in a Transgenic Mouse Model of Chronic Lymphocytic Leukemia and Small B Cell Lymphoma," *PLoS ONE*, 6(e559):1-11, 2007.

Kruger et al., "Up-regulation of heme oxygenase provides vascular protection in an animal model of diabetes through its antioxidant and antiapoptotic effects," *J Pharmacol Exp Ther.*, 319:1144-52, 2006.

Kurbacher et al., "Ascorbic acid (vitamin C) improves the antineoplastic activity of doxorubicin, cisplatin, and paclitaxel in human breast carcinoma cells in vitro," *Cancer Lett.*, 103:183-189, 1996.

Kurinna et al., "The novel triterpenoid CDDO-Me promotes apoptosis in Gleevec-resistant chronic myeloid leukemia cells by caspase-independent mechanisms," *Proc. Amer. Assoc. Cancer Res.*, 46:2240, 2005.

Lala et al., "Role of nitric oxide in tumor progression: lessons from experimental tumors," *Cancer and Metastasis Reviews*, 17 (1): 91-106, 1998.

Langille et al., "Differential effects of physiological concentrations of retinoic acid in vitro on chondrogenesis and myogenesis in chick craniofacial mesenchyme," *Differentiation*, 40:84, 1989.

Lapillonne et al., "Activation of peroxisome proliferator-activated receptor gamma by a novel synthetic triterpenoid 2-cyano-3,12-dioxooleana-1,9-dien-28-oic acid induces growth arrest and apoptosis in breast cancer cells," *Cancer Res.*, 63:5926-5939, 2003.

Lawson et al., "Isolation and preliminary characterization of a monoclonal antibody that interacts preferentially with the liver isoenzyme of human alkaline phosphatase," *Clin. Chem.*, 31:381-385, 1985.

Lee et al., "Functional and quantitative analysis of splenic T cell immune responses following oral toxoplasma gondii infection in mice, "*Experimental Parasitology*, 91:212-221, 1999.

Lemieux, "Acylglycosyl Halides. [55] tetra-O-acetyl-α-D-glucopyranosyl bromide," *Methods Carbohydr. Chem.*, 2:221-222, 1963.

Leonard et al., "Expression of nitric oxide synthase in inflammatory bowel disease is not affected by corticosteroid treatment," *J. Clin. Pathol.*, 51:750-753, 1998.

Li and Nel, "Role of the Nrf2-mediated signaling pathway as a negative regulator of inflammation: implications for the impact of particulate pollutants on asthma," *Antioxidants & Redox Signaling*, 8:88-98, 2006.

Liby et al., "A novel acetylenic tricyclic bis-(cyano enone) potently induces phase 2 cytoprotective pathways and blocks liver carcinogenesis induced by aflatoxin," *Cancer Res.*, 68:6727-6733, 2008.

Liby et al., "The rexinoid LG100268 and the synthetic triterpenoid CDDO-methyl amide are more potent than erlotinib for prevention of mouse lung carcinogenesis," *Mol. Cancer Ther.*, 7:1251-1257, 2008.

Liby et al., "The synthetic triterpenoids, CDDO and CDDO-imidazolide, are potent inducers of heme oxygenase-1 and Nrf2/ARE signaling," *Cancer Res.*, 65:4789-4798, 2005.

Liby et al., "Triterpenoids and rexinoids as multifunctional agents for the prevention and treatment of cancer," *Nature Reviews*, 7:357-69, 2007.

Lieu et al., "Dual cytotoxic mechanisms of submicromolar taxol on human leukemia HL-60 cells," *Biochem. Pharmacology*, 53:1587-1596, 1997.

Ling et al., "The novel triterpenoid C-28 methyl ester of 2-cyano-3, 12-dioxoolen-1, 9-dien-28-oic acid inhibits metastatic murine breast tumor growth through inactivation of STAT3 signaling," *Cancer Res.*, 67:4210-4218, 2007.

Ling et al., "The novel triterpenoid CDDO-Me inhibits metastatic murine breast tumor through inhibition of Stat3 signaling," 2007 AACR Annual Meeting, Abstract No. 301, 2007.

Liotta et al., "A simple method for the efficient sysnthesis of unsaturated ∃-dicarbonyl compunds," *J. Org. Chem.*, 46:2920-2923, 1981.

Liu et al., "Heme oxygenase-1 (HO-1) inhibits postmyocardial infarct remodeling and restores ventricular function," *FASEB J.*, 20(2):207-216, 2006.

Long, "Regulation of human bone marrow-derived osteoprogenitor cells by osteogenic growth factors ," *Clin. Invest.*, 95:881-887, 1995.

Luo et al., "IKK/NF-kappaB signaling: balancing life and death—a new approach to cancer therapy," *J. Clin. Invest.*, 115 (10): 2625-2631, 2005.

MacMicking et al., "Altered responses to bacterial infection and endotoxic shock in mice lacking inducible nitric oxide synthase," *Cell*, 81:641-650, 1995.

Mantovani et al., "Inflammation by remote control," *Nature*, 435:752-753, 2005.

Marnett, "Aspirin and the potential role of prostaglandins in colon cancer," *Cancer Res.*, 52(20):5575-5589, 1992.

Marrogi et al., "Nitric oxide synthase, cyclooxygenase 2, and vascular endothelial growth factor in the angiogenesis of non-small cell lung carcinoma," *Clinical Cancer Research*, 6:4739-4744, 2000.

Maurel et al., "Phase I trial of weekly gemcitabine at 3-h infusion in refractory, heavily pretreated advanced solid tumors," *Anti-Cancer Drugs*, 12 (9): 713-717, 2001.

McGeer and McGeer, "The inflammatory response system of brain: implications for therapy of Alzheimer and other neurodegenerative diseases," *Brain Res. Brain Res. Rev.*, 21:195-218, 1995.

Mehta et al., "Activation of retinoid receptors RAR alpha and RXR alpha induces differentiation and apoptosis, respectively, in HL-60 cells," *Cell, Growth Differ*, 7(2): 179-186, 1996.

Melichar et al., "Growth-inhibitory effect of a novel synthetic triterpenoid, 2-cyano-3,12-dioxooolean-1,9-dien-28-oic acid, on ovarian carcinoma cell lines not dependent on peroxisome proliferator-activated receptor-gamma expression," *Gynecologic Oncology*, 93:149-154, 2004.

Mella et al., "1, 2-dideoxy-3, 4:5, 7-bis-o—(1-methylethylidene)—D-gluco- and—D-galacto-hept-1-ynitols : synthesis and conformational studies, " *Tetrahedron*, 44:1673-1678, 1988.

Merril and Benveniste, "Cytokines in inflammatory brain lesions: helpful and harmful," *Trends Neurosci.*, 19:331-338, 1996.

Minns et al., "A novel triterpenoid induces transforming growth factor beta production by intraepithelial lymphocytes to prevent ileitis," *Gastroenterology*, 127:119-126, 2004.

Mix et al., "A synthetic triterpenoid selectively inhibits the induction of matrix metalloproteinases 1 and 13 by inflammmatory cytokines," *Arthritis Rheum.*, 44:1096-1104, 2001.

Mix et al., "Peroxisome proliferator-activated receptor-gamma-independent repression of collagenase gene expression by 2-cyano-3,12-dioxooleana-1,9-dien-28-oic acid and prostaglandin 15-deoxy-delta(12,14) J2: a role for Smad signaling," *Mol. Pharmacol.*, 65:309-318, 2004.

Moncada et al., "Nitric oxide: physiology, pathophysiology, and pharmacology," *Pharmacol. Rev.*, 43:109-142, 1991.

Morris et al., "Association of a functional inducible nitric oxide synthase promoter variant with complications in type 2 diabetes," *J. Mol. Med.*, 80 (2): 96-104, 2002.

Morse and Choi, "Heme oxygenase-1: from bench to bedside," *Am. J. Respir. Crit. Care Med.*, 172(6):660-670, 2005.

Morse and Choi, "Heme oxygenase-1: the "emerging molecule"has arrived," *Am. J. Respir. Crit. Care Med.*, 27(1):8-16, 2002.

Murphy et al., "Immunomodulatory Effects of the Triterpenoid CDDO after Allogeneic Bone Marrow Transplantation in Mice: Reduction of Acute Graft-Versus-Host Disease Lethality," *Blood*, 106:1316, 2005.

Murray and Zweifel, "Preparation of Phenyl Cyanate and Its Utilization for the Synthesis of $\alpha$, $\beta$-Unsaturated Nitriles," *Synthesis*, 150-151, 1980.*Synthesis*, 150-151, 1980.

Muzart, "Synthesis of unsaturated carbonyl compounds via a chromium-mediated allylic oxidation by 70% tert.butylhydroperoxide," *Tetrahedron Lett.*, 28:4665-4668, 1987.

Na and Surh et al., "Transcriptional regulation via cysteine thiol modification: a novel molecular strategy for chemoprevention and cytoprotection," *Mol. Carcinog.*,45 (6): 368-380, 2006.

Nathan and Xie, "Nitric oxide synthases: roles, tolls, and controls," *Cell*, 78:915-918, 1994.

Nathan et al., "Protection from Alzheimer's-like disease in the mouse by genetic ablation of inducible nitric oxide synthase," *The Journal of Experimental Medicine*, 202:1163-1169, 2005.

Nathan, "Points of control in inflammation," *Nature*, 420:846-852, 2002.

Nicholson et al., "Lethality of endotoxin in mice genetically deficient in the respiratory burst oxidase, inducible nitric oxide synthase, or both, "*Shock*, 11:253-258, 1999.

Nishino et al., "Inhibition of the tumor-promoting action of 12-O tetradecanoylphorbol-13-acetate by some oleanane-type triterpenoid compounds," *Cancer Res.*, 48:5210-5215, 1988.

Office Action, in Canadian Patent App. No. 2,335,505, mailed Jan. 10, 2008.

Office Action, in Canadian Patent App. No. 2,335,505, mailed Nov. 23, 2006.

Office Action, in Canadian Patent App. No. 2,335,505, mailed Sep. 22, 2008.

Office Action, in Canadian Patent App. No. 2,430,454, mailed Jan. 20, 2009.

Office Action, in European Patent App. No. 01 989 130, mailed Jul. 31, 2008.

Office Action, in European Patent App. No. 03 729 681, mailed Nov. 6, 2008.

Office Action, in European Patent App. No. 99 928 731, mailed Aug. 1, 2008.

Office Action, in European Patent App. No. 99 928 731, mailed Dec. 9, 2008.

Office Action, in European Patent App. No. 99 928 731, mailed Dec. 15, 2004.

Office Action, in European Patent App. No. 99 928 731, mailed Feb. 14, 2007.

Office Action, in U.S. Appl. No. 09/335,003, mailed Aug. 28, 2000.
Office Action, in U.S. Appl. No. 09/335,003, mailed Mar. 15, 2001.
Office Action, in U.S. Appl. No. 09/335,003, mailed Nov. 2, 2000.
Office Action, in U.S. Appl. No. 09/927,081, mailed Feb. 22, 2002.
Office Action, in U.S. Appl. No. 09/998,009, mailed Apr. 4, 2007.
Office Action, in U.S. Appl. No. 09/998,009, mailed Jul. 11, 2005.
Office Action, in U.S. Appl. No. 09/998,009, mailed Jul. 14, 2004.
Office Action, in U.S. Appl. No. 09/998,009, mailed Jul. 3, 2006.
Office Action, in U.S. Appl. No. 09/998,009, mailed Mar. 24, 2004.
Office Action, in U.S. Appl. No. 09/998,009, mailed Nov. 30, 2005.
Office Action, in U.S. Appl. No. 09/998,009, mailed Nov. 16, 2007.
Office Action, in U.S. Appl. No. 09/998,009, mailed Oct. 20, 2004.
Office Action, in U.S. Appl. No. 10/345,053, mailed Aug. 25, 2004.
Office Action, in U.S. Appl. No. 10/345,053, mailed Dec. 23, 2004.
Office Action, in U.S. Appl. No. 10/345,053, mailed Dec. 6, 2005.
Office Action, in U.S. Appl. No. 10/345,053, mailed Mar. 1, 2006.
Office Action, in U.S. Appl. No. 10/345,053, mailed May 31, 2005.
Office Action, in U.S. Appl. No. 10/395,372, mailed Apr. 28, 2006.
Office Action, in U.S. Appl. No. 10/395,372, mailed Aug. 4, 2005.
Office Action, in U.S. Appl. No. 10/395,372, mailed Dec. 20, 2006.
Office Action, in U.S. Appl. No. 10/395,372, mailed Feb. 7, 2007.
Office Action, in U.S. Appl. No. 10/395,372, mailed Jan. 28, 2004.
Office Action, in U.S. Appl. No. 10/395,372, mailed Jul. 9, 2004.
Office Action, in U.S. Appl. No. 10/395,372, mailed Jun. 12, 2006.
Office Action, in U.S. Appl. No. 10/395,372, mailed May 23, 2005.
Office Action, in U.S. Appl. No. 10/395,372, mailed Nov. 23, 2005.
Office Action, in U.S. Appl. No. 10/435,925, mailed Sep. 30, 2005.
Office Action, in U.S. Appl. No. 11/121,316, mailed Apr. 16, 2009.
Office Action, in U.S. Appl. No. 11/121,316, mailed Jul. 21, 2008.
Office Action, in U.S. Appl. No. 11/121,316, mailed Mar. 17, 2008.
Office Action, in U.S. Appl. No. 11/672,449, mailed Jun. 13, 2008.
Office Action, in U.S. Appl. No. 11/672,449, mailed Mar. 20, 2009.
Office Action, in U.S. Appl. No. 11/927,418, mailed Mar. 2, 2009.
Office Action, in U.S. Appl. No. 11/941,723, mailed Mar. 9, 2009.
Office Action, in U.S. Appl. No. 11/941,820, mailed Apr. 21, 2009.

Ohshima and Bartsch, "Chronic infections and inflammatory process as cancer risk factors: possible role of nitric oxide in carcinogenesis," *Mutat. Res.*, 305:253-264, 1994.

Omura and Swern, "Oxidation of Alcohols by 'Activated' Dimethyl Sulfoxide. A Preparative, Steric and Mechanistic Study," *Tetrahedron*, 34:1651-1660, 1978.

Ono et al., "A convenient procedure for esterification of carboxylic acids," *Bull. Chem. Soc. Jpn.*, 51:2401-2404, 1978.

Osburn et al., "Genetic of pharmacologic amplification of Nrf2 signaling inhibits acute inflammatory liver injury in mice," *Toxicological Sciences*, 104:218-227, 2008.

Oshima et al., "Suppression of intestinal polyposis in Apc$^{V716}$ knock-out mice by inhibition of cyclooxygenase 2 (COX-2)," *Cell*, 87:803-809, 1996.

Pahl, "Activators and target genes of Rel/NF-κB transcription factors," *Oncogene*, 18:6853-6866, 1999.

Palcy and Goltzman, "Protein kinase signalling pathways involved in the up-regulation of the rat alphal (I) collagen gene by transforming growth factor beta 1 and bone morphogenetic protein 2 in osteoblastic cells," *Biochem. J.*, 343:21-27, 1999.

Patel et al., "Phase II clinical investigation of gemcitabine in advanced soft tissue sarcomas and window evaluation of dose rate on gemcitabine triphosphate accumulation," *J. Clin. Oncol.*, 19 (15): 3483-3489, 2001.

Paul et al., "Design and synthesis of a self-assembled photochemical dyad based on selective imidazole recognition," *Inorg. Chem.*, 41:3699-3704, 2002.

Paul et al., "Effective expression of small interfering RNA in human cells," *Nature Biotechnol.*, 20:505-508, 2002.

PCT International Search Report and Written Opinion, issued in International Application No. PCT/US2007/085010, dated Apr. 16, 2008.

PCT, International Preliminary Examination Report, in Int. App. No. PCT/US1999/13635, mailed Sep. 6, 2000.

PCT, International Preliminary Examination Report, in Int. App. No. PCT/US2001/44541, mailed Jan. 15, 2004.

PCT, International Preliminary Examination Report, in Int. App. No. PCT/US2003/01307, mailed Oct. 20, 2003.

PCT, International Search Report and Written Opinion, in Int. App. No. PCT/US2008/073352, mailed Feb. 13, 2009.

PCT, International Search Report and Written Opinion, in Int. App. No. PCT/US2009/030771, mailed Apr. 9, 2009.

PCT, International Search Report and Written Opinion, in Int. App. No. PCT/US2007/071933, mailed Nov. 26, 2007.

PCT, International Search Report, in Int. App. No. PCT/US1999/13635, mailed Oct. 20, 1999.

PCT, International Search Report, in Int. App. No. PCT/US2001/44541, mailed Jan. 24, 2003.

PCT, International Search Report, in Int. App. No. PCT/US2003/01307, mailed May 12, 2003.

PCT, International Search Report, in Int. App. No. PCT/US2003/14904, mailed Jul. 23, 2004.

PCT, Written Opinion, in Int. App. No. PCT/US1999/13635, mailed May 15, 2000.

PCT, Written Opinion, in Int. App. No. PCT/US2001/44541, mailed Sep. 23, 2003.

Pedersen et al., "The triterpenoid CDDO induces apoptosis in refractory CLL B cells," *Blood*, 100:2965-2972, 2002.

Petition Decision, issued in U.S. Appl. No. 10/345,053, mailed May 22, 2006.

Picard et al, "The triterpene resinols and related acids, part VI," *J. Chem. Soc.*, 1045-108, 1939.

Place et al., "The novel synthetic triterpenoid, CDDO-imidazolide, inhibits inflammatory response and tumor growth in vivo," *Clin. Cancer Res.*, 9:2798-2806, 2003.

Pollard, "Tumour-educated macrophages promote tumour progression and metastasis," *Nature Reviews*, 4:71-78, 2004.

Prescott and White, "Self-promotion? Intimate connections between APC and prostaglandin H synthase-2," *Cell*, 87(5):783-786, 1996.

Rangasamy et al., "Disruption of Nrf2 enhances susceptibility to severe airway inflammation and asthma in mice," *Journal of Experimental Medicine*, 202:47-59, 2005.

Rayet and Gelinas, "Aberrant rel/nfkb genes and activity in human cancer," *Oncogene*, 18:6938-6947, 1999.

Reddy et al., "Evaluation of cyclooxygenase-2 inhibitor for potential chemopreventive properties in colon carcinogenesis," *Cancer Res.*, 56(20):4566-4569, 1996.

Response to Office Action, in Canadian Patent App. No. 2,335,505, dated Jul. 10, 2008.

Response to Office Action, in Canadian Patent App. No. 2,335,505, dated May 11, 2007.

Response to Office Action, in European Patent App. No. 01 989 130, dated Sep. 5, 2008.

Response to Office Action, in European Patent App. No. 99 928 731, dated Oct. 1, 2008.

Response to Office Action, in European Patent App. No. 99 928 731, dated Mar. 9, 2009.

Response to Office Action, in European Patent App. No. 99 928 731, dated Jun. 23, 2005.

Response to Office Action, in European Patent App. No. 99 928 731, dated Aug. 14, 2007.

Response to Office Action, in U.S. Appl. No. 09/335,003, dated Sep. 28, 2000.

Response to Office Action, in U.S. Appl. No. 09/335,003, dated Mar. 2, 2001.

Response to Office Action, in U.S. Appl. No. 09/335,003, dated Apr. 16, 2001.

Response to Office Action, in U.S. Appl. No. 09/927,081, dated Jun. 24, 2002.

Response to Office Action, in U.S. Appl. No. 09/998,009, dated Apr. 21, 2004.

Response to Office Action, in U.S. Appl. No. 09/998,009, dated Sep. 14, 2004.

Response to Office Action, in U.S. Appl. No. 09/998,009, dated Apr. 19, 2005.

Response to Office Action, in U.S. Appl. No. 09/998,009, dated Oct. 11, 2005.

Response to Office Action, in U.S. Appl. No. 09/998,009, dated Mar. 30, 2006.

Response to Office Action, in U.S. Appl. No. 09/998,009, dated Jan. 3, 2007.

Response to Office Action, in U.S. Appl. No. 09/998,009, dated Sep. 4, 2007.

Response to Office Action, in U.S. Appl. No. 09/998,009, dated Feb. 18, 2008.

Response to Office Action, in U.S. Appl. No. 10/345,053, dated Sep. 24, 2004.

Response to Office Action, in U.S. Appl. No. 10/345,053, dated Mar. 23, 2005.

Response to Office Action, in U.S. Appl. No. 10/345,053, dated Sep. 3, 2005.

Response to Office Action, in U.S. Appl. No. 10/345,053, dated Feb. 6, 2006.

Response to Office Action, in U.S. Appl. No. 10/395,372, dated Apr. 28, 2004.

Response to Office Action, in U.S. Appl. No. 10/395,372, dated Nov. 9, 2004.

Response to Office Action, in U.S. Appl. No. 10/395,372, dated Jul. 25, 2005.

Response to Office Action, in U.S. Appl. No. 10/395,372, dated Nov. 23, 2005.

Response to Office Action, in U.S. Appl. No. 10/395,372, dated Apr. 21, 2006.

Response to Office Action, in U.S. Appl. No. 10/395,372, dated Oct. 12, 2006.

Response to Office Action, in U.S. Appl. No. 10/395,372, dated Jan. 12, 2007.

Response to Office Action, in U.S. Appl. No. 10/395,372, dated Feb. 14, 2007.

Response to Office Action, in U.S. Appl. No. 10/435,925, dated Mar. 30, 2005.

Response to Office Action, in U.S. Appl. No. 11/121,316, dated Apr. 4, 2008.

Response to Office Action, in U.S. Appl. No. 11/121,316, dated Dec. 19, 2008.

Response to Office Action, in U.S. Appl. No. 11/672,449, dated Dec. 15, 2008.

Response to Office Action, in U.S. Appl. No. 11/927,418, dated Apr. 2, 2009.

Response to Written Opinion, in Int. App. No. PCT/US1999/13635, dated Jul. 14, 2000.

Response to Office Action, in U.S. Appl. No. 11/941,820, dated Oct. 21, 2009.

Richardson et al., "Synthesis and restriction enzyme analysis of oligodeoxyribonucleotides containing the anti-cancer drug 2',2'-difluoro-2'-deoxycytidine," *Nucleic Acid Res.*, 20 (7): 1763-1769, 1992.

Rizzieri et al., "Phase I evaluation of prolonged-infusion gemcitabine with mitoxantrone for relapsed or refractory acute leukemia," *J. Clin. Oncol.*, 20 (3): 674-679, 2002.

Robbins et al., "Inflammation and Repair," *In*: Basic Pathology 3$^{rd}$ Edition, W.B. Saunders Company, Chapter 2, p. 28, 1981.

Rossi et al., "Anti-inflammatory cyclopentenone prostaglandins are direct inhibitors of IkappaB kinase," *Nature*, 403:103-108, 2000.

Ruvolo et al., "The novel triterpenoid methyl-CDDO inhibits Bc12 phosphorylation and potently kolls U937 cells," *Blood*, 94(10), Suppl. 1, Part 1: 280A, abstract #1251, 1999.

Sacerdoti et al., "Heme oxygenase overexpression attenuates glucose-mediated oxidative stress in quiescent cell phase: linking heme to hyperglycemia complications," *Curr Neurovasc Res.*, 2(2):103-111, 2005.

Salvemini et al., "Endogenous nitric oxide enhances prostaglandin production in a model of renal inflammation," *J. Clin. Invest.*, 93(5):1940-1947, 1994.

Salvemini et al., "Nitric oxide activates cyclooxygenase enzymes," *Proc. Natl. Acad. Sci. USA*, 90(15):7240-7244, 1993.

Samudio et al., "2,cyano-3,12 dioxoolean-1,9 diene-28-imidazolide induces apoptosis in pancreatic cancer via redox-dependent cytoplasmic stress," *Proc. Amer. Assoc. Cancer Res.*, 46:5899, 2005.

Samudio et al., "2-Cyano-3,12-dioxooleana-1,9-dien-28-imidazolide (CDDO-Im) directly targets mitochondrial glutathione to induce apoptosis in pancreatic cancer," *J. Biol. Chem.*, 280:36273-36282, 2005.

Samudio et al., "A novel mechanism of action of methyl-2-cyano-3,12 dioxoolean-1,9 diene-28-oate: direct permeabilization of the inner mitochondrial membrane to inhibit electron transport and induce apoptosis," *Mol. Pharmacol.*, 69:1182-1193, 2006.

Samudio et al., "A novel mechanism of action of methyl-2-cyano-3,12 dioxoolean-1,9 diene-28-oate (CDDO-Me): Direct permeabilization of the inner mitochondrial membrane to inhibit electron transport and induce apoptosis," *Proc. Am. Assoc. Cancer Res.*, 47: 4693, 2006.

Samudio et al., "A Novel Mechanism of Action of Methyl-2-cyano-3,12 dioxoolean-1,9 diene-28-oate (CDDO-Me): Direct Permeabilization of the Inner Mitochondrial Membrane to Inhibit Electron Transport and Induce Apoptosis," *Blood*, 106:4462, 2005.

Samudio et al., "The novel triterpenoid CDDOme potently synergizes with inhibition of bcl-2 function to induce apoptosis in AML via disruption of intracellular redox homeostasis," *Proc. Amer. Assoc. Cancer Res.*, 46:4955, 2005.

Satoh et al., "Activation of the Keap1/Nrf2 pathway for neuroprotection by electrophilic [correction of electrophillic] phase II inducers," *Proc Natl Acad Sci USA*, 103(3):768-773, 2006.

Scholz et al., "Sensitive and specific methods for the determination of CDDO methyl ester in mouse, rat, dog, monkey, and human plasma by LC-tandem mass spectrometry," *Proc. Amer. Assoc. Cancer Res.*, 4:6321, 2003.

Seibert and Masferrer, "Role of inducible cyclooxygenase (COX-2) in inflammation," *Receptor*, 4(1):17-23, 1994.

Sharpless et al., "Electrophilic and nucleophilic organoselenium reagents. New routes to alpha, beta-unsaturated carbonyl compounds," *J. Am. Chem. Soc.*, 95:6137, 1973.

Sheng et al., "A selective cyclooxygenase 2 inhibitor suppresses the growth of H-ras-transformed rat intestinal epithelial cells," *Gastroenterology*, 113(6):1883-18891, 1997.

Sheng et al., "Inhibition of human colon cancer cell growth by selective inhibition of cyclooxygenase-2," *J. Clin. Invest.*, 99(9):2254-2259, 1997.

Shishodia et al., "A synthetic triterpenoid, CDDO-Me, inhibits IkappaBalpha kinase and enhances apoptosis induced by TNF and chemotherapeutic agents through down-regulation of expression of nuclear factor kappaB-regulated gene products in human leukemic cells," *Clin. Cancer Res.*, 12:1828-1838, 2006.

Shull et al., "Identification of a vitamin D-responsive protein on the surface of human osteosarcoma cells," *Proc. Natl. Acad. Sci. USA*, 86:5405-5410, 1989.

Shull et al., "Morphologic and biochemical studies of canine mucopolysaccharidosis I," *Am. J. Pathol.*, 114:487-495, 1984.

Simonian and Coyle, "Oxidative stress in neurodegenerative diseases," *Annu. Rev. Pharmacol. Toxicol.*, 36:83-106, 1996.

Simonsen et al., "Tetracyclic hydroxy acids," In *the Terpenes*, Cambridge University, Cambridge, 5:221-285, 1957.

Singh and Evans, "Nitric oxide, the biological mediator of the decade: fact or fiction?" *Eur. Respir. J.*, 10:699-707, 1997.

Singh et al., "Anti-inflammatory activity of oleanolic acid in rats and mice," *J. Pharm.Pharmacol.*, 44:456-458, 1992.

Sive et al., "Expression of chondrocyte markers by cells of normal and degenerate intervertebral discs," *Mol. Pathol.*, 55:91-97, 2002.

Snitman et al., "Synthetic approaches to taxodione synthesis of methyl 12-oxopodocarpa-5,9(11)-diene-8β-carboxylate," *Synth. Comm.*, 8:187-194, 1978.

Sonogashira et al., "A convenient synthesis of acetylenes: catalytic substitutions of acetylenic hydrogen with bromoakenes, iodoarenes, and bromopyridines," *Tetrahedron Lett.*, 4467-4470, 1975.

Sporn and Roberts, "Peptide growth factors and inflammation, tissue repair, and cancer," *J. Clin. Invest.*, 78:329-332, 1986.

Sporn et al., "Prospects for prevention and treatment of cancer with selective PPARγ modulators (SPARMs)," *Trends in Molecular Medicine*, 7(9):395-400, 2001.

Sporn et al., "Transforming growth factor-beta: biological function and chemical structure," *Science*, 233:532-534, 1986.

Stadheim et al., "The novel triterpenoid 2-cyano-3,12-dioxooleana-1,9-dien-28-oic acid (CDDO) potently enhances apoptosis induced by tumor necrosis factor in human leukemia cells," *J. Biol. Chem.*, 277:16448-16455, 2002.

Steadman's Medical Journal 23$^{rd}$ Edition, The Williams & Wilkins Company, p. 401, 1976.

Sterzycki, "Pyrodinium tosylate, a mild catalyst for formation and cleavage of dioxolane-type acetals," *Synthesis*, 724-725, 1979.

Stewart et al., "Risk of Alzheimer's disease and duration of NSAID use" *Neurology*, 48:626-632, 1997.

Strejan et al., "Suppression of chronic-relapsing experimental allergic encephalomyelitis in strain-13 guinea pigs by administration of liposome-associated myelin basic protein," *J. Neuroimmunol.*, 7 (1): 27, 1984.

Suh et al., "A novel synthetic oleanane triterpenoid, 2-cyano-3,12-dioxoolean-1,9-dien-28-oic acid, with potent differentiating, antiproliferative, and anti-inflammatory activity," *Cancer Res.*, 59(2):336-341, 1999.

Suh et al., "A novel synthetic oleanane triterpenoid, 2-cyano-3,12-dioxoolean-1,9-dien-28-oic acid (CDDO), induces cell differentiation in human myeloid leukemias," *Proceedings of the American Association for Cancer Research Annual Meeting*, 40:300, abstract # 1988, 1999.

Suh et al., "New triterpenoids as cancer preventive and anti-inflammatory agents," *Proceedings of the American Association for Cancer Research*, Abstract No. 1457, 38: 216, 1997.

Suh et al., "Novel triterpenoids suppress inducible nitric oxide synthase (iNOS) and inducible cyclooxygenase (COX-2) in mouse macrophages," *Cancer Research*, 58:717-723, 1998.

Suh et al., "Novel triterpenoids suppress inducible ntiric oxide synthase (iNOS) and inducible cyclooxygenase (COX-2)," *Proceedings of the American Association for Cancer Research Annual Meeting*, 39:266, 1998.

Suh et al., "Synthetic triterpenoids activate a pathway for apoptosis in AML cells involving downregulation of FLIP and sensitization to TRAIL," *Leukemia*, 17:2122-2129, 2003.

Suh et al, "Synthetic triterpenoids enhance transforming growth factor β/Smad signaling," *Cancer Res.*, 63:1371-1376, 2003.

Suh et al., "Triterpenoids CDDO and CDDO-Me Down-Regulate FLIP Expression and Sensitize AML Cells to Trail-Induced Apoptosis," *American Society of Hematology 43$^{rd}$ Annual Meeting and Exposition*, Abstract No. 498, 2001.

Sun et al., "The synthetic triterpenoid, CDDO, suppresses alloreactive T cell responses and reduces murine early acute graft-versus-host disease mortality," *Biology of Blood and Marrow Transplantation*, 13:521-529, 2007.

Supplementary European Search Report, issued in European Patent App. No. 01 989 130, mailed Aug. 9, 2007.

Supplementary European Search Report, issued in European Patent App. No. 03 729 681, mailed Aug. 3, 2006.

Sussan et al., "Disruption of Nrf2, a key inducer of antioxidant defenses, attenuates ApoE-mediated atherosclerosis in mice," *PLoS One*, 3 (11): 1-9, 2008.

Syftestad et al., "The in vitro chondrogenic response of limb-bud mesenchyme to a water-soluble fraction prepared from demineralized bone matrix," *Differentiation*, 29:230, 1985.

Tabe et al., "Chrmoatin-Mediated Transcriptional Activation with Novel Peroxisome Proliferator—Activated Receptor gamma(P-

PARgamma) Ligand 2-cyano-1,9-dien-28-oic Acid (CDDO) in Acute Promyelocytic Leukemia Cells," *Abstracts of the 44th Annual Meeting of the American Society of Hematology*, Abstract No. 2191, 2002.

Takabe et al., "Synthesis of lycosyl esters of oleanolic," *Carbohydrate Research*, 76:101-108, 1979, Database CAPLUS on STN AN:1980:42278.

Takahashi et al., "Increased expression of inducible and endothelial constitutive nitric oxide synthases in rat colon tumors induced by azoxymethane," *Cancer Res.*, 57:1233-1237, 1997.

Tamir and Tannebaum, "The role of nitric oxide (NO) in the carcinogenic process," *Biochim. Biophys. Acta*, 1288:F31-F36, 1996.

Tamm et al., "Expression and prognostic significance of IAP-family genes in human cancers and leukemias," *Blood*, 94(Suppl. 1):69a, Abstract # 298, 1999.

Tempero et al., "Randomized phase II comparison of dose-intense gemcitabine: thirty-minute infusion and fixed dose rate infusion in patients with pancreatic adenocarcinoma," *J. Clin. Oncol.*, 21 (18): 3402-3408, 2003.

Tenenbaum and Heersche, "Differentiation of osteoblasts and formation of mineralized bone in vitro," *Calcif. Tissue Int.*, 34:76, 1982.

Therasse et al., "New guidelines to evaluate the response to treatment in solid tumors. European Organization for Research and Treatment of Cancer, National Cancer Institute of the United States, National Cancer Institute of Canada," *J. Natl. Cancer Instit.*, 92 (3): 205, 2000.

Thimmulappa et al., "Nrf2 is a critical regulator of the innate immune response and survival during experimental sepsis," *J. Clinical Investigation*, 116 (4): 984-995, 2006.

Thimmulappa et al., "Nrf2-dependent protection from LPS induced inflammatory response and mortality by CDDO-imidazolide," *Biochem. Biophys. Res. Commun.*, 351:883-889, 2006.

Thimmulappa et al., "Preclinical evaluation of targeting the Nrf2 pathway by triterpenoids (CDDO-Im and CDDO-Me) for protection from LPS-induced inflammatory response and reactive oxygen species in human peripheral blood mononuclear cells and neutrophils," *Antioxidants & Redox Signaling*, 9:1-8, 2007.

Toriumi et al., "Mandibular reconstruction with a recombinant bone-inducing factor. Functional, histologic, and biomechanical evaluation," *Arch. Otolaryngol. Head Neck Surg.*, 117:1101-1112, 1991.

Torres et al., "Inflammation and nitric oxide production in skeletal muscle of type 2 diabetic patients," *Journal of Endocrinology*, 181:419-427, 2004.

Tran et al., "The synthetic triterpenoid CDDO-methyl ester modulates microglial activities, inhibits TNF production, and provides dopaminergic neuroprotection," *Journal of Neuroinflammation*, 5:1-14, 2008.

Tsai et al., "Monoclonal antibody to human osteosarcoma: a novel Mr 26,000 protein recognized by murine hybridoma TMMR-2," *Cancer Res.*, 50:152-161, 1990.

Tsao et al., "DRIP205 co-activator overexpression enhances PPARgamma-mediated differentiation of leukemia cells by CDDO," *Proc. Amer. Assoc. Cancer Res.*, 46:1855, 2005.

Tsao et al., "Targeted Induction of Apoptosis in Leukemias by PPARgammma Ligation," *American Society of Hematology 43rd Annual Meeting and Exposition*, Abstract No. 2381, 2001.

Tsujii and DuBois, "Alterations in cellular adhesion and apoptosis in epithelial cells overexpressing prostaglandin endoperoxide synthase 2," *Cell*, 83(3):493-501, 1995.

Tsujii et al., "Cyclooxygenases regulates angiogenesis induced by colon cancer cells," *Cell*, 93:705-716, 1998.

Turksen et al., "Isolation of monoclonal antibodies recognizing rat bone-associated molecules in vitro and in vivo," *J. Histochem. Cytochem.*, 40:1339-1352, 1992.

U.S. Appl. No. 12/352,473, filed Jan. 12, 2009.
U.S. Appl. No. 12/426,737, filed Apr. 20, 2009.
U.S. Appl. No. 12/426,778, filed Apr. 20, 2009.
U.S. Appl. No. 12/426,791, filed Apr. 20, 2009.
U.S. Appl. No. 12/426,832, filed Apr. 20, 2009.
U.S. Appl. No. 12/426,889, filed Apr. 20, 2009.
U.S. Appl. No. 60/955,939, filed Aug. 15, 2007.

Van Muiswinkel and Kuiperij, "The Nrf2-ARE signaling pathway: promising drug target to combat oxidative stress in neurodegenerative disorders," *Current Drug Target—CNS & Neurological Disorders*, 4:267-281, 2005.

Vazquez et al., "Human immunodeficiency virus type 1-induced macrophage gene expression includes the p21 gene, a target for viral regulation," *J. Viral.*, 79:4479-4491, 2005.

Veerman et al., "Antitumor activity of prolonged as compared with bolus administration of 2',2'-difluorodeoxycytidine in vivo against murine colon tumors," *Cancer Chemother. Pharmacol.*, 38 (4): 335-342, 1996.

Vodovotz et al., "Inducible nitric oxide synthase in tangle-bearing neurons of patients with Alzheimer's Disease," *The Journal of Experimental Medicine*, 184:1425-1433, 1996.

Vukicevic et al., "Stimulation of the expression of osteogenic and chondrogenic phenotypes in vitro by osteogenin," *Proc. Natl. Acad. Sci. USA*, 86:8793-7, 1989.

Walczak et al., "Tumoricidal activity of tumor necrosis factor-related apoptosis-inducing ligand in vivo", *Nature Medicine*, 5(2):157-163, 1999.

Walsh et al., "Monoclonal antibodies with selective reactivity against osteoblasts and osteocytes in human bone," *J. Bone Miner Res.*, 9:1687-1696, 1994.

Wang et al., "A novel synthetic triterpenoid, 2-cyano-3,12-dioxoolean-1,9-dien-28-oic acid (CDDO) induces adipocyte differentiation in 3T3-L1 cells," *Proceedings of the American Association for Cancer Research Annual Meeting*, 40:300, abstract # 1989, 1999.

Wang et al., "A synthetic Triterpenoid, 2-cyano-3,12-dioxooleana-1,9-dien-28-oic acid (CDDO), is a ligand for the peroxisome proliferator-activated receptor γ," *Mol. Endocrin.*, 14(10):1550-1556, 2000.

Wang et al., "Synthetic triterpenoid CDDO and its derivatives increase ceramides and are cytotoxic to pediatric acute lymphoblastic leukemia cell lines," *Proc. Am. Assoc. Cancer Res.*, 47: 4643, 2006.

Warrell et al., "Differentiation therapy of acute promyelocytic leukemia with tretinoin (all-trans-retinoic acid)," *N. Engl. J. Med.*, 324(20):1385-1393, 1991.

Williams et al., "Immunology of multiple sclerosis," *Clin. Neurosci.*, 2(3-4):229-245, 1994.

Woodley, "Liposomes for Oral Administration of Drugs," *Crit. Rev. Therapeutic Drug Carrier System*, 2(1):1-18, 1985.

Xie et al., "Differential expression patterns in human myeloblastic leukemia HL-60 and multidrug resistant HL-60/Dox cells analyzed by human cDNA expression array," *Blood*, 92 (Suppl 1):387a, Abstract #1600. 1998.

Yates et al., "Pharmacodynamic characterization of chemopreventive triterpenoids as exceptionally potent inducers of Nrf2-regulated genes," *Mol. Cancer Ther.*, 6:154-162, 2007.

Yates et al., "Potent protection against aflatoxin-induced tumorigenesis through induction of Nrf2-regulated pathways by the triterpenoid 1-[2-cyano-3-,12-dioxooleana-1,9(11)-dien-28-oyl]imidazole," *Cancer Res.*, 66:2488-2494, 2006.

Yore et al., "The synthetic triterpenoid 1-[2-cyano-3,12-dioxooleana-1,9(11)-dien-28-oyl]imidazole blocks nuclear factor-kappaB activation through direct inhibition of IkappaB kinase beta," *Mol. Cancer Ther.*, 5 (12): 3232-3239, 2006.

Yu and Kensler, "Nrf2 as a target for cancer chemoprevention," *Mutat. Res.*, 591 (1-2): 93-102, 2005.

Yue et al., "Depletion of intracellular glutathione contributes to JNK-mediated death receptor 5 upregulation and apoptosis induction by the novel synthetic triterpenoid methyl-2-cyano-3, 12-dioxooleana-1, 9-dien-28-oate (CDDO-Me).," *Cancer & Biology Therapy*, 5(5):492-497, 2006.

Zapata et al., "CDDO and CDDO-Im Reduce Tumor Burden in a Transgenic Mouse Model of CLL," *Blood*, 104:3477, 2004.

Zapata et al., "Triterpenoids show activity against leukemic cells in a transgenic mouse model of CLL," *Proc. Amer. Assoc. Cancer Res.*, 46:5179, 2005.

Zhang et al., "Synthetic triterpenoid CDDO as effective therapy for HER2-expressing resistant breast cancer," *Proc. Amer. Assoc. Cancer Res.*, Abstract No. 3799, 2004.

Zhang et al., "The novel synthetic oleanane triterpenoid CDDO (2-cyano-3, 12-dioxoolean-1, 9-dien-28-oic acid) induces apoptosis in Mycosis fungoides/Sézary syndrome cells," *J. Invest. Dermatol.*, 123:380-387, 2004.

Zhou et al., "Carbon monoxide suppresses bleomycin-induced lung fibrosis," *Am J Pathol.*, 166(1):27-37, 2005.

Zhou et al., "Physical stability of amorphous pharmaceuticals: Importance of configurational thermodynamic quantities and molecular mobility," *J. Pharmaceutical Sciences*, 91 (8): 1863-1872, 2002.

Zou et al., "c-Jun NH2-terminal kinase-mediated up-regulation of death receptor 5 contributes to induction of apoptosis by the novel synthetic triterpenoid methyl-2-cyano-3,12-dioxooleana-1, 9-dien-28-oate in human lung cancer cells," *Cancer Res.*, 64:7570-7578, 2004.

Office Communication issued in European Patent Application No. 07864553.8, dated Jun. 9, 2011.

* cited by examiner

SYNTHESIS AND BIOLOGICAL ACTIVITIES OF NEW TRICYCLIC-*BIS*-ENONES (TBES)

The present application is a continuation of application Ser. No. 11/941,820, filed Nov. 16, 2007 now U.S. Pat. No. 7,714,012, which claims the benefit of priority to U.S. Provisional Application No. 60/866,330, filed Nov. 17, 2006, the entire contents of each of which are being incorporated herein by reference in their entirety.

The U.S. Government owns rights in the application pursuant to funding from NIH and National Foundation for Cancer Research through NIH Grants CA-105294 and CA-078814.

BACKGROUND OF THE INVENTION

I. Field of the Invention

The present invention provides novel tricyclic-bis-enone derivatives (TBEs), as well as the process for the preparation of such TBEs, for prevention and/or treatment of cancer, Alzheimer's disease, Parkinson's disease, multiple sclerosis, amyotrophiclateral sclerosis, rheumatoid arthritis, inflammatory bowel disease, and other diseases whose pathogenesis is believed to involve excessive production of either nitric oxide (NO) or prostaglandins.

II. Description of Related Art

One of the major needs in clinical oncology is the development of effective and safe new agents for chemoprevention. In particular, there is a need for chemopreventative agents targeted at mechanisms known to be involved in the process of carcinogenesis. In recent years, there has been a resurgence of interest in the study of mechanisms of inflammation that relate to carcinogenesis and in the use of such mechanisms as the basis for development of new chemopreventative agents.

The concept that inflammation and carcinogenesis are related phenomena has been the patient of many studies that have attempted to link these two processes in a mechanistic fashion (Sporn and Roberts, 1986; Ohshima and Bartsch, 1994). The enzymes that mediate the constitutive synthesis of NO and prostaglandins from arginine and arachidonate, respectively, have relatively little significance for either inflammation or carcinogenesis. In contrast, inducible nitric oxide synthase (iNOS) and inducible cycloxygenase (COX-2) both have critical roles in the response of tissues to injury or infectious agents (Moncada et al., 1991; Nathan and Xie, 1994; Siebert and Masferrer, 1994; Tamir and Tannebaum, 1996). These inducible enzymes are essential components of the inflammatory process, the ultimate repair of injury, and carcinogenesis. While physiological activity of iNOS and COX-2 may provide a definite benefit to the organism, aberrant or excessive expression of either iNOS or COX-2 has been implicated in the pathogenesis of many disease processes, particularly in chronic degeneration of the central nervous system, carcinogenesis, septic shock, cardiomyopathy, rheumatoid arthritis, and other autoimmune diseases. Unresolved, smoldering inflammation is now understood to play an important role in the pathology of many diseases, including cardiovascular disease (e.g., atherosclerosis and heart failure), diabetes, renal failure, and respiratory diseases such as chronic obstructive pulmonary disease.

The need for new agents to prevent cancer is readily evident from the continuing high mortality rates for the common forms of epithelial cancer, such as carcinoma of the lung, colon, breast, and prostate. As genetic testing now can identify increasing numbers of people who are at high risk for the development of these cancers, it becomes increasingly important to discover new pharmacologic agents that can be used interventionally to prevent this outcome, well before the occurrence of malignant invasive disease. Therefore, it would be advantageous to provide compounds for use in the chemoprevention of cancer that are low in cost for large scale synthesis, and that are water soluble compounds, thus providing use of administration.

Ongoing efforts for the improvement of anti-inflammatory and antiproliferative activity of oleanolic acid analogues led to the discovery of 2-cyano-3,12-dioxooleana-1,9(11)-dien-28-oic acid (CDDO) and related compounds (Honda et al., 1997, 1998, 1999, 2000a, 2000b, 2002; Suh et al., 1998; 1999; Place et al., 2003).

It has been shown that TP-190 and 222 are potent inhibitors of NO production in mouse macrophages and RAW cells (Honda et al., 2000, 2002). TP-222 is orally potent against inflammatory bowel disease in SvEv129 Rag2−/− mice caused by oral infection with *Helicobacter hepaticus*. CDDO and several close analogues have also been shown to be potent inducers of apoptosis in cancer cells, with relatively low toxicity in normal tissue. Thus, in addition to their uses in preventing cancer and treating inflammatory diseases, these agents are useful for treating established cancer.

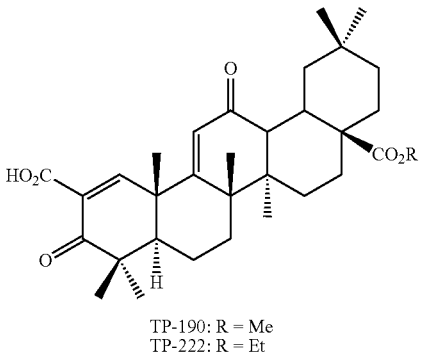

TP-190: R = Me
TP-222: R = Et

In connection with these investigations, it was found that tricyclic-bis-enone compounds (TBEs) with similar enone functionalities in rings A and C are also a novel class of inhibitors of nitric oxide (NO) production in mouse macrophages (Favaloro et al., 2002) and RAW cells. In particular, bis-cyano enone (±)-TBE-9 (see Table 1, below) is orally active in a preliminary in vivo inflammation model (Favaloro et al., 2002). In addition, (+)-TBE-9, having the opposite configuration to that of CDDO, shows 10 times higher inhibitory activity than (−)-TBE-9 on NO production in mouse macrophages. To the contrary, (−)-TBE-9 is active against MCF-7 mouse breast cancer cell lines, whilst (+)-TBE-9 is inactive (Honda et al., 2003). Therefore, the syntheses of optically active versions of new TBE for a comparison of the biological potency of both enantiomers is very important.

TABLE 1

Inhibitory activity of TBE compounds on NO production in primary mouse macrophages stimulated with interferon-γ

| Compound (racemic) | $IC_{50}$ (nM) |
|---|---|
| TBE-1 | 310 |
| TBE-2 | 480 |
| TBE-3 | 53 |
| TBE-4 | 75 |

TABLE 1-continued

Inhibitory activity of TBE compounds on NO production in primary mouse macrophages stimulated with interferon-γ

| Compound (racemic) | $IC_{50}$ (nM) |
|---|---|
| TBE-5 | 61 |
| CDDO | 0.5 |
| hydrocortisone | 10 |
| TBE-6 | 91 |
| TBE-7 | 1600 |
| TBE-8 | 61 |
| TBE-9 | 2.1 |
| TBE-10 | 19 |
| Oleanolic acid | >40,000 |

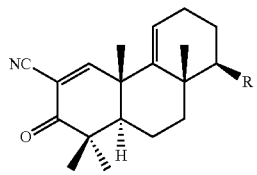

TBE-1: R = OH
TBE-2: R = OAc

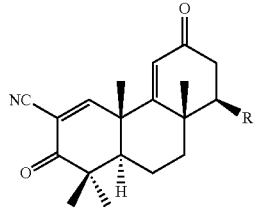

TBE-3: R = OAc
TBE-4: R = OH
TBE-10: R = H

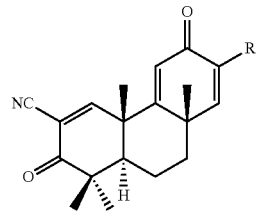

TBE-5: R = H
TBE-6: R = $CO_2Me$
TBE-7: R = $CO_2H$
TBE-8: R = $CONH_2$
TBE-9: R = CN

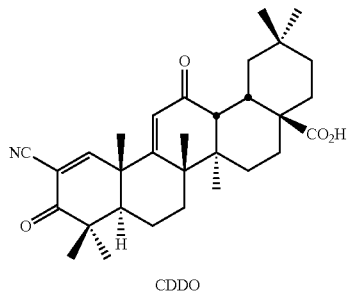

CDDO

Given the promising properties shown by the TBE compounds studied so far, it would be advantageous to provide additional TBE compounds, especially those with improved potency, pharmacokinetics, and water solubility.

SUMMARY OF THE INVENTION

Thus, to overcome deficiencies in the prior art, new TBE compounds were designed and prepared, some showing dramatically increased potency and other useful properties.

In accordance with the present invention, there is provided a compound having the structure Q1:

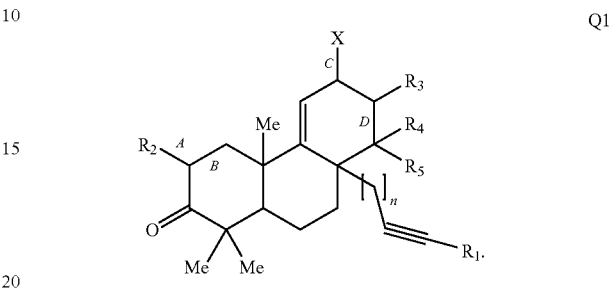

In certain embodiments, the groups $R_1$, $R_2$, $R_3$, $R_4$ and $R_5$ are each independently —H, hydroxy, amino, cyano, halo, nitro, mercapto, phosphate, sulfonic acid, sulfonate, or substituted or unsubstituted versions of $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkoxy, $C_1$-$C_{15}$-heteroaryloxy, $C_2$-$C_{15}$-heteroaralkyloxy, $C_1$-$C_{15}$-acyloxy, $C_1$-$C_{15}$-alkylamino, $C_2$-$C_{15}$-alkenylamino, $C_2$-$C_{15}$-alkynylamino, $C_6$-$C_{15}$-arylamino, $C_7$-$C_{15}$-aralkylamino, $C_1$-$C_{15}$-heteroarylamino, $C_2$-$C_{15}$-heteroaralkylamino, $C_2$-$C_{15}$-amido, $C_1$-$C_{15}$-alkylthio, $C_6$-$C_{15}$-arylthio, $C_7$-$C_{15}$-aralkylthio, $C_1$-$C_{15}$-heteroarylthio, $C_2$-$C_{15}$-heteroaralkylthio, $C_1$-$C_{15}$-acylthio, or $C_0$-$C_{15}$-silyl.

In certain embodiments, $R_1$, $R_2$, $R_3$, $R_4$ and $R_5$ are substituted or unsubstituted versions of alkyl, alkenyl, alkynyl, aryl, aralkyl, heteroaryl, heteroaralkyl, acyl, alkoxy, alkenyloxy, alkynyloxy, aryloxy, aralkoxy, heteroaryloxy, heteroaralkyloxy, acyloxy, alkylamino, alkenylamino, alkynylamino, arylamino, aralkylamino, heteroarylamino, heteroaralkylamino, amido, alkylthio, arylthio, aralkylthio, heteroarylthio, heteroaralkylthio, acylthio, or silyl.

In a non-limiting example, $R_1$, $R_2$, $R_3$, $R_4$ and $R_5$ are each independently —H, —$CH_3$, —$CH_2CH_3$, —$CH_2CH_2CH_3$, —$CH(CH_3)_2$, —$CH(CH_2)_2$, —$CH_2CH_2CH_2CH_3$, —$CH(CH_3)CH_2CH_3$, —$CH_2CH(CH_3)_2$, —$C(CH_3)_3$, —$SiH_3$, —$Si(CH_3)_3$, —$Si(CH_3)_2C(CH_3)_3$, —$CH_2C(CH_3)_3$, —$CH_2Si(CH_3)_3$, —$C_6H_5$, —$C_6H_4CH_3$, —$C_6H_4CH_2CH_3$, —$C_6H_4CH_2CH_2CH_3$, —$C_6H_4CH(CH_3)_2$, —$C_6H_4CH(CH_2)_2$, —$C_6H_3(CH_3)_2$, —$C_6H_3(CH_3)CH_2CH_3$, —CH=$CH_2$, —CH=$CHCH_3$, —CH=$CHCH_2CH_3$, —CH=$CHCH_2CH_2CH_3$, —CH=$CHCH(CH_3)_2$, —CH=$CHCH(CH)_2$, F, Cl, Br, I, —OH, —$OCH_3$, —$OCH_2CH_3$, —$OCH_2CH_2CH_3$, —$OCH(CH_3)_2$, —$OCH(CH_2)_2$, —$OCH_2CF_3$, —$OCOCH_3$, —$OC_6H_5$, —$NH_2$, —$NHCH_3$, —$NHCH_2CH_3$, —$NHCH_2CH_2CH_3$, —$NHCH(CH_3)_2$, —$NHCH(CH_2)_2$, —$N(CH_3)_2$, —$N(CH_3)CH_2CH_3$, —$N(CH_2CH_3)_2$, —$NHCOCH_3$, —$NHCO_2C(CH_3)_3$, —CH=CHF, —CH=CHCl, —CH=CHBr, —$CH_2F$, —$CH_2Cl$, —$CH_2Br$, —$CH_2OH$, —$CH_2OCH_3$, —$CH_2OCH_2CH_3$, —$CH_2OCH_2CH_2CH_3$, —$CH_2OCH(CH_3)_2$, —$CH_2OCH(CH_2)_2$, —$CH_2OCH_2CF_3$, —$CH_2OCOCH_3$, —$CH_2NH_2$, —$CH_2NHCH_3$, —$CH_2N(CH_3)_2$—$CH_2NHCH_2CH_3$, —$CH_2N(CH_3)CH_2CH_3$, —$CH_2NHCH_2CH_2CH_3$, —$CH_2NHCH(CH_3)_2$, —CH$_2$NHCH(CH$_2$)$_2$, —CH$_2$N(CH$_2$CH$_3$)$_2$, —CH$_2$CH$_2$F, —CH$_2$CH$_2$Cl, —CH$_2$CH$_2$Br, —CH$_2$CH$_2$I, —CH$_2$CH$_2$OH, CH$_2$CH$_2$OCOCH$_3$, —CH$_2$CH$_2$NH$_2$, —CH$_2$CH$_2$N(CH$_3$)$_2$, —CH$_2$CH$_2$NHCH$_2$CH$_3$, —CH$_2$CH$_2$N(CH$_3$)CH$_2$CH$_3$, —CH$_2$CH$_2$NHCH$_2$CH$_2$CH$_3$, —CH$_2$CH$_2$NHCH(CH$_3$)$_2$, —CH$_2$CH$_2$NHCH(CH$_2$)$_2$, —CH$_2$CH$_2$N(CH$_2$CH$_3$)$_2$, —CH$_2$CH$_2$NHCO$_2$C(CH$_3$)$_3$, —CH$_2$CH=CH$_2$, —CH$_2$CH=CHCH$_3$, —CH$_2$CH=CHCH$_2$CH$_3$, —CH$_2$CH=CHCH$_2$CH$_2$CH$_3$, —CH$_2$CH=CHCH(CH$_3$)$_2$, —CH$_2$CH=CHCH(CH$_2$)$_2$, —CF$_3$, —CN, —C≡CH, —C≡CCH$_3$, —C≡CSi(CH$_3$)$_3$, —CH=CH$_2$, —CH=CHCH$_3$, —COH, —COCH$_3$, —COCH$_2$CH$_3$, —COCH$_2$CH$_2$CH$_3$, —COCH(CH$_3$)$_2$, —COCH(CH$_2$)$_2$, —COCH$_2$CF$_3$, —COC$_6$H$_5$, —COC$_6$H$_4$CH$_3$, —COC$_6$H$_4$CH$_2$CH$_3$, —COC$_6$H$_4$CH$_2$CH$_2$CH$_3$, —COC$_6$H$_4$CH(CH$_3$)$_2$, —COC$_6$H$_4$CH(CH$_2$)$_2$, —COC$_6$H$_3$(CH$_3$)$_2$, —CO$_2$H, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$CH(CH$_2$)$_2$, —CONH$_2$, —CONHCH$_3$, —CONHCH$_2$CH$_3$, —CONHCH$_2$CH$_2$CH$_3$, —CONHCH(CH$_3$)$_2$, —CONHCH(CH$_2$)$_2$, —CON(CH$_3$)$_2$, —CON(CH$_2$CH$_3$)CH$_3$, —CON(CH$_2$CH$_3$)$_2$, —CONHCH$_2$CF$_3$, —C$_6$H$_4$CH=CH$_2$, —C$_6$H$_4$CH=CHCH$_3$, —C$_6$H$_4$F, —C$_6$H$_4$Cl, —C$_6$H$_4$Br, —C$_6$H$_4$I, —C$_6$H$_4$OH, —C$_6$H$_4$OCH$_3$, —C$_6$H$_4$OCH$_2$CH$_3$, —C$_6$H$_4$OCOCH$_3$, —C$_6$H$_4$OC$_6$H$_5$, —C$_6$H$_4$NH$_2$, —C$_6$H$_4$NHCH$_3$, —C$_6$H$_4$NHCH$_2$CH$_3$, —C$_6$H$_4$CH$_2$Cl, —C$_6$H$_4$CH$_2$Br, —C$_6$H$_4$CH$_2$OH, —C$_6$H$_4$CH$_2$OCOCH$_3$, —C$_6$H$_4$CH$_2$NH$_2$, —C$_6$H$_4$N(CH$_3$)$_2$, —C$_6$H$_4$CH$_2$CH$_2$Cl, —C$_6$H$_4$CH$_2$CH$_2$OH, —C$_6$H$_4$CH$_2$CH$_2$OCOCH$_3$, —C$_6$H$_4$CH$_2$CH$_2$NH$_2$, —C$_6$H$_4$CH$_2$CH=CH$_2$, —C$_6$H$_4$CF$_3$, —C$_6$H$_4$CN, —C$_6$H$_4$C≡CH, —C$_6$H$_4$C≡CCH$_3$, —C$_6$H$_4$C≡CSi(CH$_3$)$_3$, —C$_6$H$_4$COH, —C$_6$H$_4$COCH$_3$, —C$_6$H$_4$COCH$_2$CH$_3$, —C$_6$H$_4$COCH$_2$CF$_3$, —C$_6$H$_4$COC$_6$H$_5$, —C$_6$H$_4$CO$_2$H, —C$_6$H$_4$CO$_2$CH$_3$, —C$_6$H$_4$CONH$_2$, —C$_6$H$_4$CONHCH$_3$, —C$_6$H$_4$CON(CH$_3$)$_2$, —SH, —SCH$_3$, —SC$_6$H$_5$, —SCH$_2$C$_6$H$_5$, or —SCOCH$_3$.

In some embodiments, the group X is selected from the group consisting of —H and =O. In other embodiments, X is hydroxyl. The invention also contemplates that X is =S or =NR', wherein R' is —H, —OH, —NH$_2$, or —NHR", wherein R" is a substituted or unsubstituted version of C$_1$-C$_{15}$-alkyl or C$_6$-C$_{15}$-aryl.

The labels, A, B, C and D of structure Q1, independently signify a single- or a double-bond, provided that (1) when D is a double-bond, R$_4$ is absent, (2) when C is a double bond, X is =O, =NR, or =S, (3) when C is a single bond, X is —H or —OH, (4) when A is a double bond B is a single bond, (5) when B is a double bond A is a single bond.

The letter "n", in structure Q1 can be 0, 1, 2, 3, 4, 5, or 6.

In some aspects of the invention, the ketone group shown in structure Q1 may replaced by its enol tautomer. Similarly, in some embodiments, any ketone group implied or contemplated by the definition of structure Q1 may be found as its enol tautomer. For example, the ketone group when X is =O, can be as its enol tautomer.

In some embodiments, a pharmaceutically acceptable salt of structure Q1 is provided. In certain embodiments, hydrates of structure Q1 are provided. The invention also provides optical isomers of the compounds defined by structure Q1. In certain embodiments, the optical isomer of a compound defined by structure Q1 is substantially free from the other optical isomers. In other embodiments, two or more optical isomers are present in the same composition. In certain of these embodiments, two optical isomers are present is roughly equal amounts. In some embodiments, the invention provides for a racemic mixture of an enantiomeric pair of compounds defined by structure Q1.

In non-limiting embodiments, the invention provides for a set of compounds wherein B, C and D are double bonds, n is 0, and X is =O. In other embodiments, B and C are double bonds, n is 0, and X is =O. In some embodiments, neither A, B, C, nor D is a double bond. In some embodiments, only one of A, B, C, and D is a double bond. In other embodiments, only two of A, B, C, and D are double bonds, provided that when A is a double bond, B is not a double bond. In other embodiments, only three of A, B, C, and D are double bonds, provided that when A is a double bond, B is not a double bond.

The invention contemplates that any methyl group and any hydrogen atom shown or implied in structure Q1 can each independently be replaced with a —H, hydroxy, amino, cyano, halo, nitro, mercapto, or substituted or unsubstituted versions of C$_1$-C$_{15}$-alkyl, C$_2$-C$_{15}$-alkenyl, C$_2$-C$_{15}$-alkynyl, C$_6$-C$_{15}$-aryl, C$_7$-C$_{15}$-aralkyl, C$_1$-C$_{15}$-heteroaryl, C$_2$-C$_{15}$-heteroaralkyl, C$_1$-C$_{15}$-acyl, C$_1$-C$_{15}$-alkoxy, C$_2$-C$_{15}$-alkenyloxy, C$_2$-C$_{15}$-alkynyloxy, C$_6$-C$_{15}$-aryloxy, C$_7$-C$_{15}$-aralkoxy, C$_1$-C$_{15}$-heteroaryloxy, C$_2$-C$_{15}$-heteroaralkyloxy, C$_1$-C$_{15}$-acyloxy, C$_1$-C$_{15}$-alkylamino, C$_2$-C$_{15}$-alkenylamino, C$_2$-C$_{15}$-alkynylamino, C$_6$-C$_{15}$-arylamino, C$_7$-C$_{15}$-aralkylamino, C$_1$-C$_{15}$-heteroarylamino, C$_2$-C$_{15}$-heteroaralkylamino, C$_2$-C$_{15}$-amido, C$_1$-C$_{15}$-alkylthio, C$_6$-C$_{15}$-arylthio, C$_7$-C$_{15}$-aralkylthio, C$_1$-C$_{15}$-heteroarylthio, C$_2$-C$_{15}$-heteroaralkylthio, C$_1$-C$_{15}$-acylthio, or C$_0$-C$_{15}$-silyl group.

In certain examples, the invention provides that R$_1$ of structure Q1 is —CH$_3$, —CH$_2$CH$_3$, —Si(CH$_3$)$_3$, —Si(CH$_3$)$_2$C(CH$_3$)$_3$, —C$_6$H$_5$, —F, —Cl, —Br, —CH$_2$OH, —CH$_2$OCH$_3$, —CH$_2$OCH$_2$CH$_3$, —CH$_2$OCH$_2$CF$_3$, —CH$_2$OCOCH$_3$, —CH$_2$N(CH$_3$)$_2$, —CH$_2$CH$_2$NH$_2$, —CH$_2$CH$_2$NHCO$_2$C(CH$_3$)$_3$, —CN, —C≡CH, —C≡CCH$_3$, —C≡CSi(CH$_3$)$_3$, —CH=CH$_2$, —CH=CHCH$_3$, —COH, —COCH$_3$, —COCH$_2$CH$_3$, —COC$_6$H$_5$, —CO$_2$H, —CO$_2$CH$_3$, —CONH$_2$, —CONHCH$_3$, —CON(CH$_3$)$_2$, —CONHCH$_2$CH$_3$, —CON(CH$_2$CH$_3$)$_2$, —CONHCH$_2$CF$_3$,

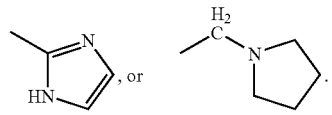

In some embodiments, —R$_2$ of structure Q1 is —H, —CN, —CO$_2$H, —CO$_2$CH$_3$, or =CHOH.

In certain embodiments, —R$_3$ of structure Q1 is —H, —CN, —CH$_2$N(CH$_3$)$_2$, —CH$_2$N(CH$_2$CH$_3$)$_2$,

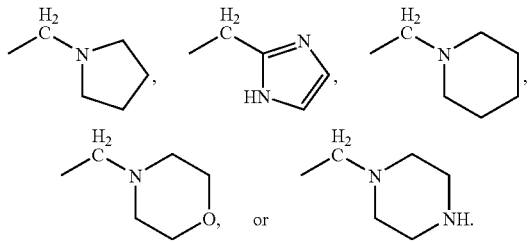

TABLE 2
Structures of TBE Compounds and Derivatives
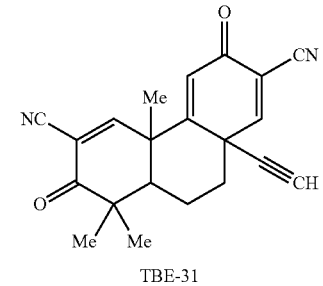
TBE-31
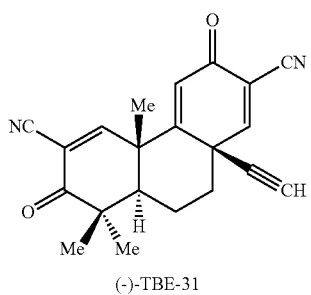
(−)-TBE-31
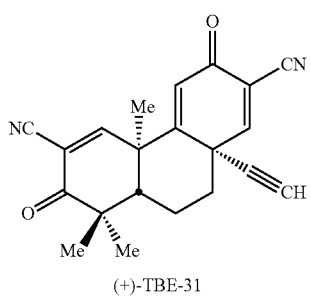
(+)-TBE-31
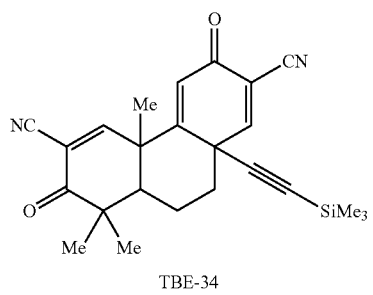
TBE-34
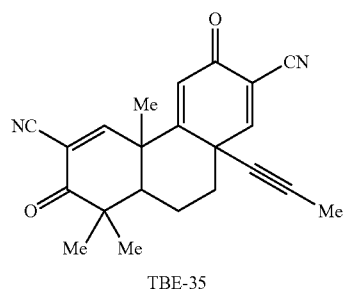
TBE-35
TABLE 2-continued
Structures of TBE Compounds and Derivatives
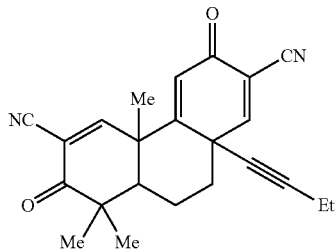
TBE-36
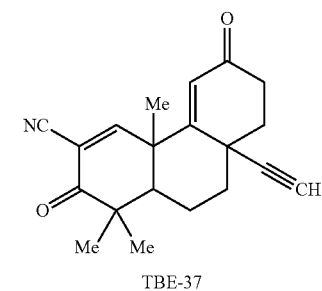
TBE-37
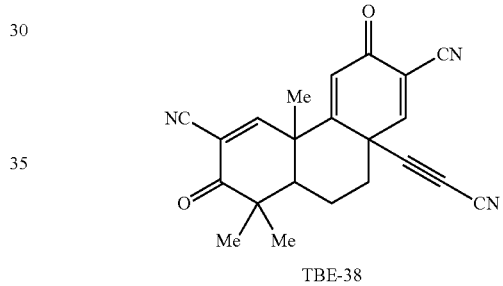
TBE-38
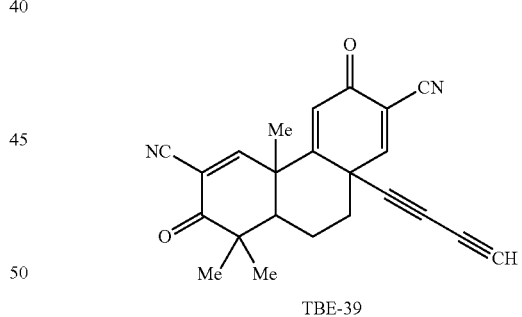
TBE-39
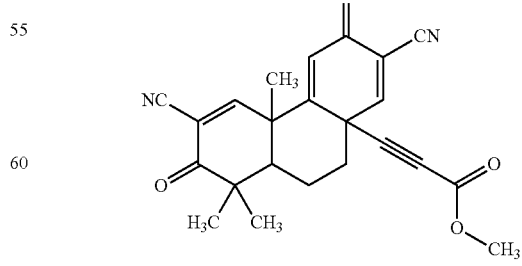
TBE-40

TABLE 2-continued

Structures of TBE Compounds and Derivatives

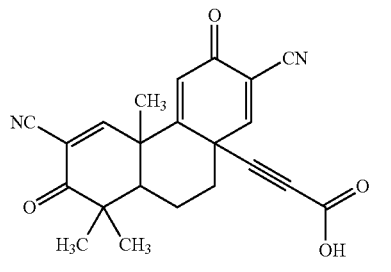

TBE-41

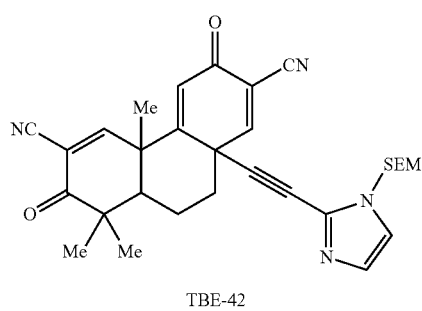

TBE-42

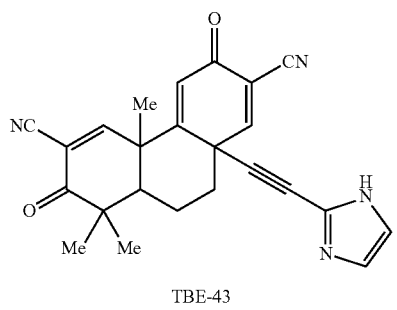

TBE-43

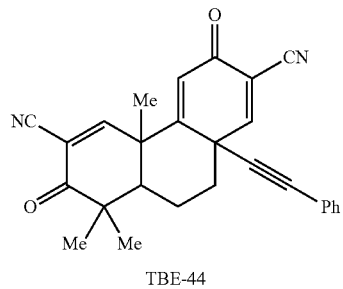

TBE-44

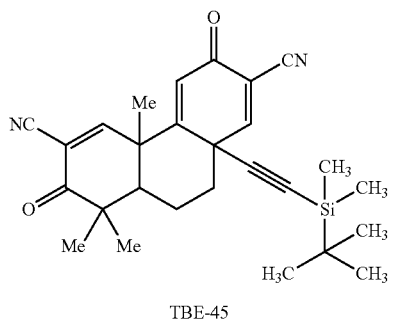

TBE-45

For example, the invention provides for the compound TBE-31, having the structure shown in Table 2, and pharma-ceutically acceptable salts, hydrates, and optical isomers thereof. In some of these embodiments, the TBE-31 compound is (−)-TBE-31, having the structure shown in Table 2. In some embodiments, (−)-TBE-31 is substantially free from other optical isomers. In other embodiments, (−)-TBE-31 is part of a composition containing other optical isomers. In some embodiments, the TBE-31 compound is (+)-TBE-31, having the structure shown in Table 2. In some embodiments, (+)-TBE-31 is substantially free from other optical isomers. In other embodiments, (+)-TBE-31 is part of a composition containing other optical isomers. In some embodiments, (+)-TBE-31 and (−)-TBE-31 form a racemic mixture.

In another non-limiting example, the invention provides for one or more of the compounds shown in Table 2, and pharmaceutically acceptable salts, hydrates, and optical isomers thereof. In some embodiments, the compound is a racemic mixture. In other embodiments, the compound is a single optical isomer, which is substantially free from other optical isomers. For example, TBE-45 comprises a tert-butyldimethylsilyl (TBS) group, which shows stability under acidic and basic conditions.

In other non-limiting examples, the invention provides for one or more of the TBE derivatives defined by the structures shown in Table 3, and pharmaceutically acceptable salts, hydrates, and optical isomers thereof. In some of these embodiments, the compound provided is a single optical isomer of one of the compounds in Table 3, substantially free from other optical isomers. In other embodiments, the invention provides for a racemic mixture of a compound shown in Table 3.

TABLE 3

Additional Structures of TBE Compounds and Derivatives

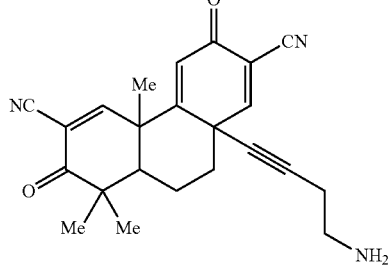

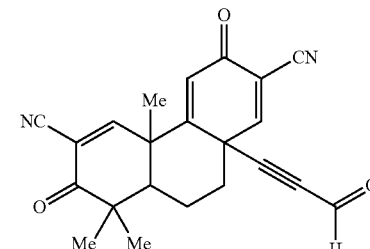

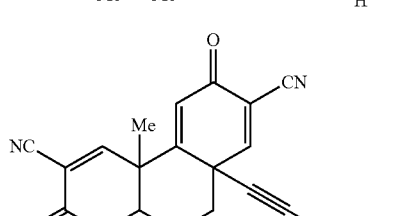

TABLE 3-continued

Additional Structures of TBE Compounds and Derivatives

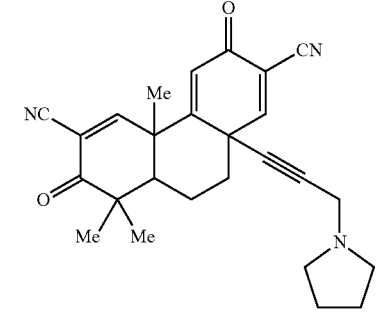

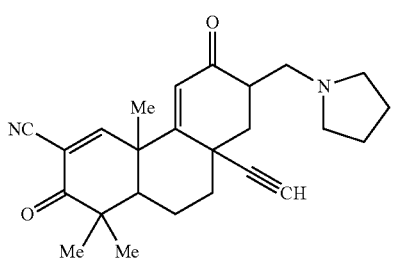

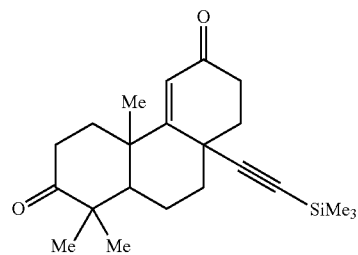

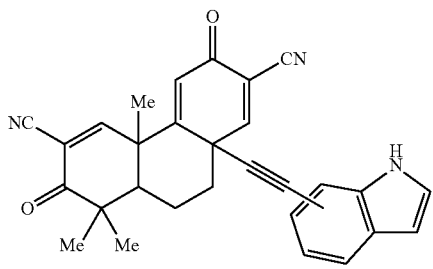

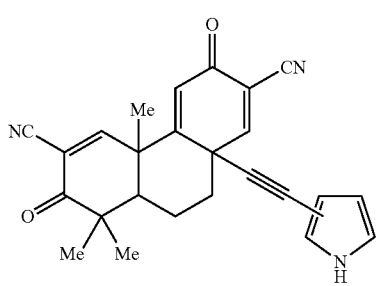

In certain embodiments, the invention provides for a TBE-derivative having the structure:

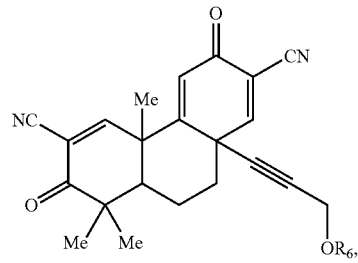

wherein $R_6$ is —H or a substituted or unsubstituted version of $C_1$-$C_{14}$-alkyl or $C_7$-$C_{14}$-aralkyl, $C_2$-$C_{14}$-heteroaralkyl, $C_1$-$C_{14}$-acyl, or $C_0$-$C_{14}$-silyl. In certain embodiments, a pharmaceutically acceptable salt, hydrate, or optical isomer of this structure is provided.

In some embodiments, the invention provides for a TBE-derivative having the structure:

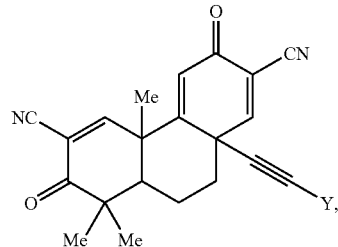

wherein Y is selected from the group consisting of —F, —Cl, —Br, and —I. In certain embodiments, a pharmaceutically acceptable salt, hydrate, or optical isomer of this structure is provided.

In certain embodiments, the invention provides for a TBE-derivative having the structure:

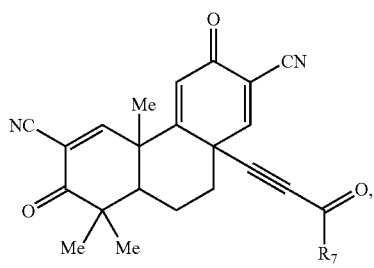

wherein $R_7$ is —H or a substituted or unsubstituted version of $C_1$-$C_{14}$-alkyl or $C_6$-$C_{14}$-aryl. In certain embodiments, a pharmaceutically acceptable salt, hydrate, or optical isomer of this structure is provided.

In certain embodiments, the invention provides for a TBE-derivative having the structure:

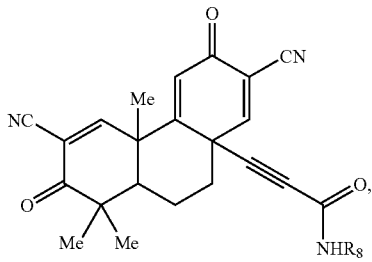

wherein $R_8$ is —H or a substituted or unsubstituted version of $C_1$-$C_{14}$-alkyl or $C_6$-$C_{14}$-aryl. In certain embodiments, a pharmaceutically acceptable salt, hydrate, or optical isomer of this structure is provided.

In certain embodiments, the invention provides for a TBE-derivative having the structure:

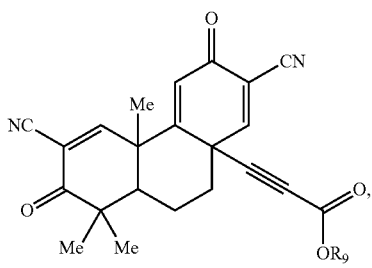

wherein $R_9$ is —H or a substituted or unsubstituted version of $C_1$-$C_{14}$-alkyl or $C_6$-$C_{14}$-aryl. In certain embodiments, a pharmaceutically acceptable salt, hydrate, or optical isomer of this structure is provided.

In certain embodiments, the invention provides for a TBE-derivative having the structure:

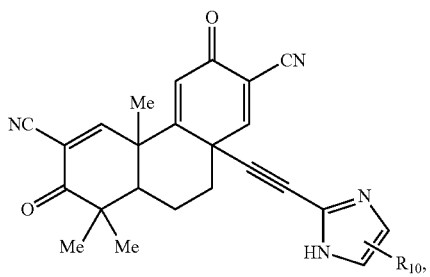

wherein $R_{10}$ is —H, hydroxy, amino, cyano, nitro, mercapto, or substituted or unsubstituted versions of $C_1$-$C_{12}$-alkyl, $C_2$-$C_{12}$-alkenyl, $C_2$-$C_{12}$-alkynyl, $C_6$-$C_{12}$-aryl, $C_7$-$C_{12}$-aralkyl, $C_1$-$C_{12}$-heteroaryl, $C_2$-$C_{12}$-heteroaralkyl, $C_1$-$C_{12}$-acyl, $C_1$-$C_{12}$-alkoxy, $C_2$-$C_{12}$-alkenyloxy, $C_2$-$C_{12}$-alkynyloxy, $C_6$-$C_{12}$-aryloxy, $C_7$-$C_{12}$-aralkoxy, $C_1$-$C_{12}$-heteroaryloxy, $C_2$-$C_{12}$-heteroaralkyloxy, $C_1$-$C_{12}$-acyloxy, $C_1$-$C_{12}$-alkylamino, $C_2$-$C_2$-alkenylamino, $C_2$-$C_{12}$-alkynylamino, $C_6$-$C_{12}$-arylamino, $C_7$-$C_{12}$-aralkylamino, $C_1$-$C_{12}$-heteroarylamino, $C_2$-$C_{12}$-heteroaralkylamino, $C_2$-$C_{12}$-amido, $C_1$-$C_{12}$-alkylthio, $C_6$-$C_{12}$-arylthio, $C_7$-$C_{12}$-aralkylthio, $C_1$-$C_{12}$-heteroarylthio, $C_2$-$C_{12}$-heteroaralkylthio, $C_1$-$C_{12}$-acylthio, or $C_0$-$C_{12}$-silyl. In certain embodiments, a pharmaceutically acceptable salt, hydrate, or optical isomer of this structure is provided.

In certain embodiments, the invention provides for a TBE-derivative having the structure:

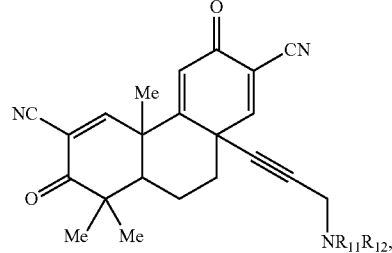

wherein either $R_{11}$ and $R_{12}$ are each independently —H or substituted or unsubstituted versions of $C_1$-$C_7$-alkyl or $C_6$-$C_7$-aryl, or $R_{11}$ and $R_{12}$, when taken together with the nitrogen atom to which they are attached, form a ring structure, having from 2 to 8 carbon atoms. In certain embodiments, a pharmaceutically acceptable salt, hydrate, or optical isomer of this structure is provided.

In certain embodiments, the invention provides for a TBE-derivative having the structure:

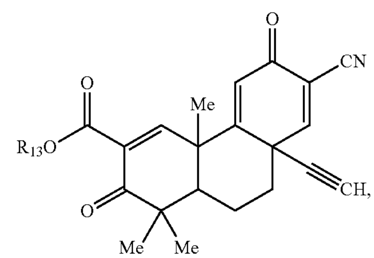

wherein $R_{13}$ is —H or a substituted or unsubstituted version of $C_1$-$C_{14}$-alkyl or $C_6$-$C_{14}$-aryl. In certain embodiments, a pharmaceutically acceptable salt, hydrate, or optical isomer of this structure is provided.

In certain embodiments, the invention provides for a TBE-derivative having the structure:

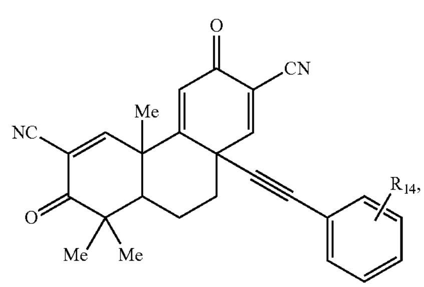

wherein $R_{14}$ is —H, hydroxy, amino, cyano, nitro, mercapto, or substituted or unsubstituted versions of $C_1$-$C_9$-alkyl, $C_2$-$C_9$-alkenyl, $C_2$-$C_9$-alkynyl, $C_6$-$C_9$-aryl, $C_7$-$C_9$-aralkyl, $C_1$-$C_9$-heteroaryl, $C_2$-$C_9$-heteroaralkyl, $C_1$-$C_9$-acyl, $C_1$-$C_9$-alkoxy, $C_2$-$C_9$-alkenyloxy, $C_2$-$C_9$-alkynyloxy, $C_6$-$C_9$-aryloxy, $C_7$-$C_9$-aralkoxy, $C_1$-$C_9$-heteroaryloxy, $C_2$-$C_9$-heteroaralkyloxy, $C_1$-$C_9$-acyloxy, $C_1$-$C_9$-alkylamino, $C_2$-$C_9$-alkenylamino, $C_2$-$C_9$-alkynylamino, $C_6$-$C_9$-arylamino, $C_7$-$C_9$-aralkylamino, $C_1$-$C_9$-heteroarylamino, $C_2$-$C_9$-heteroaralkylamino, $C_2$-$C_9$-amido, $C_1$-$C_9$-alkylthio, $C_6$-$C_9$-arylthio, $C_7$-$C_9$-aralkylthio, $C_1$-$C_9$-heteroarylthio, $C_2$-$C_9$- heteroaralkylthio, $C_1$-$C_9$-acylthio, or $C_0$-$C_9$-silyl. In certain embodiments, a pharmaceutically acceptable salt, hydrate, or optical isomer of this structure is provided.

In certain embodiments, the invention provides for a TBE-derivative having the structure:

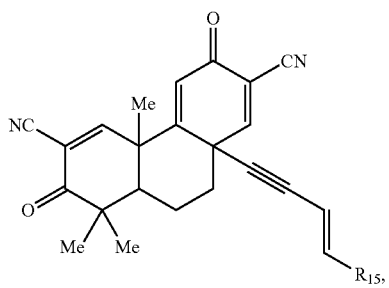

wherein $R_{15}$ is —H, hydroxy, amino, cyano, nitro, mercapto, or substituted or unsubstituted versions of $C_1$-$C_{13}$-alkyl, $C_2$-$C_{13}$-alkenyl, $C_2$-$C_{13}$-alkynyl, $C_6$-$C_{13}$-aryl, $C_7$-$C_{13}$-aralkyl, $C_1$-$C_{13}$-heteroaryl, $C_2$-$C_{13}$-heteroaralkyl, $C_1$-$C_{13}$-acyl, $C_1$-$C_{13}$-alkoxy, $C_2$-$C_{13}$-alkenyloxy, $C_2$-$C_{13}$-alkynyloxy, $C_6$-$C_{13}$-aryloxy, $C_7$-$C_{13}$-aralkoxy, $C_1$-$C_{13}$-heteroaryloxy, $C_2$-$C_{13}$-heteroaralkyloxy, $C_1$-$C_{13}$-acyloxy, $C_1$-$C_{13}$-alkylamino, $C_2$-$C_{13}$-alkenylamino, $C_2$-$C_{13}$-alkynylamino, $C_6$-$C_{13}$-arylamino, $C_7$-$C_{13}$-aralkylamino, $C_1$-$C_{13}$-heteroarylamino, $C_2$-$C_{13}$-heteroaralkylamino, $C_2$-$C_{13}$-amido, $C_1$-$C_{13}$-alkylthio, $C_6$-$C_{13}$-arylthio, $C_7$-$C_{13}$-aralkylthio, $C_1$-$C_{13}$-heteroarylthio, $C_2$-$C_{13}$-heteroaralkylthio, $C_1$-$C_{13}$-acylthio, or $C_0$-$C_{13}$-silyl.

In certain embodiments, a pharmaceutically acceptable salt, hydrate, or optical isomer of this structure is provided.

In certain embodiments, the invention provides for a TBE-derivative having the structure:

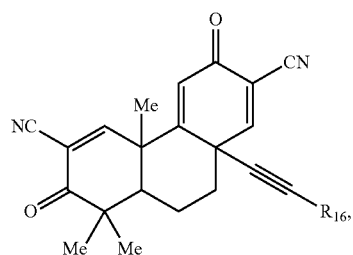

wherein $R_{16}$ is —H or a substituted or unsubstituted version of $C_1$-$C_{15}$-alkyl, $C_6$-$C_{15}$-aryl, or $C_1$-$C_{15}$-heteroaryl. In certain embodiments, a pharmaceutically acceptable salt, hydrate, or optical isomer of this structure is provided.

In some embodiments, the invention provides for the compound defined by the following structure:

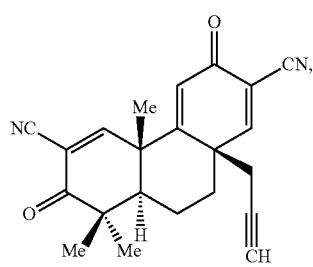

substantially free from other optical isomers, and pharmaceutically acceptable salts and hydrates thereof. In other embodiments, the compound is a racemic mixture.

In some embodiments, the invention provides for the compound defined by the following structure:

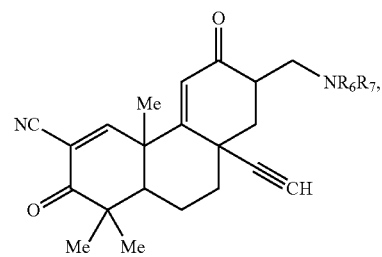

wherein either $R_6$ and $R_7$ are each independently H or substituted or unsubstituted versions of $C_1$-$C_7$-alkyl or $C_6$-$C_7$-aryl, or $R_6$ and $R_7$, when taken together with the nitrogen atom to which they are attached, form a ring structure, having from 2 to 8 carbon atoms, and pharmaceutically acceptable salts, hydrates, and optical isomers thereof.

In some embodiments, the invention provides for the compound defined by the following structure:

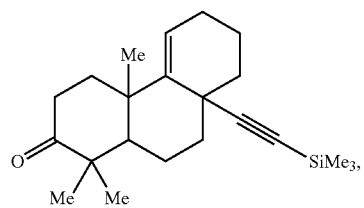

and pharmaceutically acceptable salts, hydrates, and optical isomers thereof.

In some embodiments, the invention provides for the compound defined by the structure Q2, shown below:

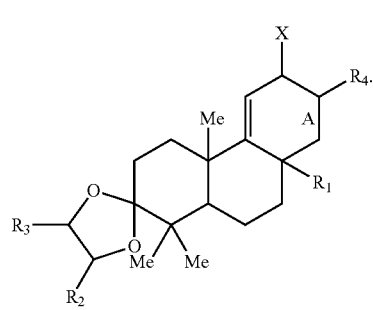

In some embodiments, the substituent X, shown in structure "Q2", is selected from the group consisting of —H, —OH and =O. In some embodiments, "A", shown in structure Q2, signifies a single-bond. In other embodiments, "A" signifies a double-bond.

In certain embodiments, $R_1$, shown in structure Q2, is a substituted or unsubstituted version of $C_2$-$C_{15}$-alkyl, $C_2$-$C_{15}$-alkenyl, $C_2$-$C_{15}$-alkynyl, $C_7$-$C_{15}$-aralkyl, $C_2$-$C_{15}$-heteroaralkyl, or $C_2$-$C_{15}$-acyl. In other embodiments, $R_1$ is —COH.

In certain examples, the invention provides that $R_1$ of structure Q2 is —CH$_3$, —CH$_2$CH$_3$, —CH$_2$OH, —CH$_2$OCH$_3$, —CH$_2$OCH$_2$CH$_3$, —CH$_2$OCH$_2$CF$_3$, —CH$_2$OCOCH$_3$, —CH$_2$N(CH$_3$)$_2$, —CH$_2$CH$_2$NH$_2$, —CH$_2$CH$_2$NHCO$_2$C(CH$_3$)$_3$, —CN, —C≡CCH$_3$, —C≡CSi(CH$_3$)$_3$, —CH=CH$_2$, —CH=CHCH$_3$, —COH, —COCH$_3$, —COCH$_2$CH$_3$, —COC$_6$H$_5$, —CO$_2$H, —CO$_2$CH$_3$, —CONH$_2$, —CONHCH$_3$, —CON(CH$_3$)$_2$, —CONHCH$_2$CH$_3$, —CON(CH$_2$CH$_3$)$_2$, —CONHCH$_2$CF$_3$, or

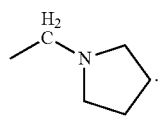

In some embodiments, $R_2$ and $R_3$, shown in structure Q2, are each independently —H or substituted or unsubstituted version of $C_1$-$C_{15}$-alkyl. In certain embodiments, $R_4$, shown in structure Q2, is either —H or —CN.

The invention further contemplates that $R_1$, $R_2$, $R_3$, or $R_4$ of structure Q2, can each independently be —H, —CH$_3$, —CH$_2$CH$_3$, —CH$_2$CH$_2$CH$_3$, —CH(CH$_3$)$_2$, —CH(CH$_2$)$_2$, —CH$_2$CH$_2$CH$_2$CH$_3$, —CH(CH$_3$)CH$_2$CH$_3$, —CH$_2$CH(CH$_3$)$_2$, —C(CH$_3$)$_3$, —CH$_2$C(CH$_3$)$_3$—CH$_2$Si(CH$_3$)$_3$, —CH=CH$_2$, —CH=CHCH$_3$, —CH=CHCH$_2$CH$_3$, —CH=CHCH$_2$CH$_2$CH$_3$, —CH=CHCH(CH$_3$)$_2$, —CH=CHCH(CH$_2$)$_2$, —CH=CHF, —CH=CHCl, —CH=CHBr, —CH$_2$F, —CH$_2$Cl, —CH$_2$Br, —CH$_2$OH, —CH$_2$OCH$_3$, —CH$_2$OCH$_2$CH$_3$, —CH$_2$OCH$_2$CH$_2$CH$_3$, —CH$_2$OCH(CH$_3$)$_2$, —CH$_2$OCH(CH$_2$)$_2$, —CH$_2$OCH$_2$CF$_3$, —CH$_2$OCOCH$_3$, —CH$_2$NH$_2$, —CH$_2$NHCH$_3$, —CH$_2$N(CH$_3$)$_2$, —CH$_2$NHCH$_2$CH$_3$, —CH$_2$N(CH$_3$)CH$_2$CH$_3$, —CH$_2$NHCH$_2$CH$_3$, —CH$_2$NHCH(CH$_3$)$_2$, —CH$_2$NHCH(CH$_2$)$_2$, —CH$_2$N(CH$_2$CH$_3$)$_2$, —CH$_2$CH$_2$F, —CH$_2$CH$_2$Cl, —CH$_2$CH$_2$Br, —CH$_2$CH$_2$I, —CH$_2$CH$_2$OH, CH$_2$CH$_2$OCOCH$_3$, —CH$_2$CH$_2$NH$_2$, —CH$_2$CH$_2$N(CH$_3$)$_2$, —CH$_2$CH$_2$NHCH$_2$CH$_3$, —CH$_2$CH$_2$N(CH$_3$)CH$_2$CH$_3$, —CH$_2$CH$_2$NHCH$_2$CH$_2$CH$_3$, —CH$_2$CH$_2$NHCH(CH$_3$)$_2$, —CH$_2$CH$_2$NHCH(CH$_2$)$_2$, —CH$_2$CH$_2$N(CH$_2$CH$_3$)$_2$, —CH$_2$CH$_2$NHCO$_2$C(CH$_3$)$_3$, —CH$_2$CH=CH$_2$, —CH$_2$CH=CHCH$_3$, —CH$_2$CH=CHCH$_2$CH$_3$, —CH$_2$CH=CHCH$_2$CH$_2$CH$_3$, —CH$_2$CH=CHCH(CH$_3$)$_2$, —CH$_2$CH=CHCH(CH$_2$)$_2$, —CF$_3$, —CN, —C≡CH, —C≡CCH$_3$, —C≡CSi(CH$_3$)$_3$, —CH=CH$_2$, —CH=CHCH$_3$, —COH, —COCH$_3$, —COCH$_2$CH$_3$, —COCH$_2$CH$_2$CH$_3$, —COCH(CH$_3$)$_2$, —COCH(CH$_2$)$_2$, —COCH$_2$CF$_3$, —COC$_6$H$_5$, —COC$_6$H$_4$CH$_3$, —COC$_6$H$_4$CH$_2$CH$_3$, —COC$_6$H$_4$CH$_2$CH$_2$CH$_3$, —COC$_6$H$_4$CH(CH$_3$)$_2$, —COC$_6$H$_4$CH(CH$_2$)$_2$, —COC$_6$H$_3$(CH$_3$)$_2$, —CO$_2$H, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$CH(CH$_2$)$_2$, —CONH$_2$, —CONHCH$_3$, —CONHCH$_2$CH$_3$, —CONHCH$_2$CH$_2$CH$_3$, —CONHCH(CH$_3$)$_2$, —CONHCH(CH$_2$)$_2$, —CON(CH$_3$)$_2$, —CON(CH$_2$CH$_3$)CH$_3$, —CON(CH$_2$CH$_3$)$_2$, or —CONHCH$_2$CF$_3$.

In some embodiments, the invention provides for compound 2, defined by the structure:

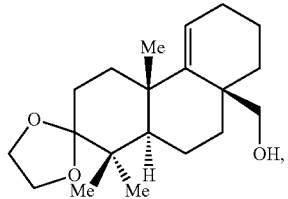

substantially free from other optical isomers. In other embodiments, the compound is part of a racemic mixture.

In some embodiments, the invention provides for compound 3, defined by the structure:

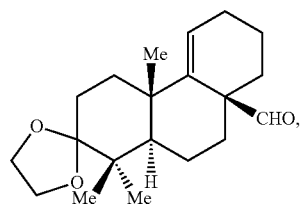

substantially free from other optical isomers. In other embodiments, the compound is part of a racemic mixture.

In another non-limiting example, the invention provides compound 4, having the structure:

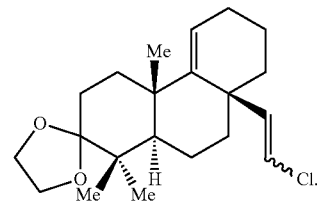

In some embodiments, either one of the two geometric isomers defined by the structure is substantially free from the other geometric isomer. In other embodiments, both geometric isomers are present in the same composition. In some embodiments, either one of the two geometric isomers is a single enantiomer, substantially free from the other enantiomer. In some embodiments, either one of the two geometric isomers is part of a racemic mixture.

In some embodiments, the invention provides for compound I, defined by the structure:

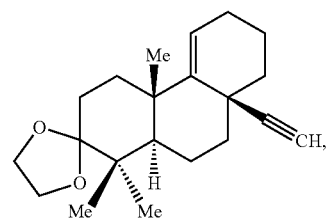

substantially free from other optical isomers. In other embodiments, the compound is part of a racemic mixture.

In some embodiments, the invention provides for compound 5, defined by the structure:

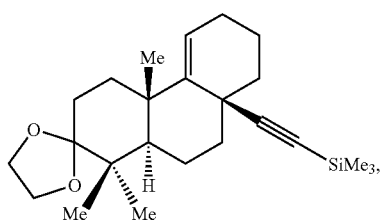

substantially free from other optical isomers. In other embodiments, the compound is part of a racemic mixture.

In some embodiments, the invention provides for the compound defined by the structure.

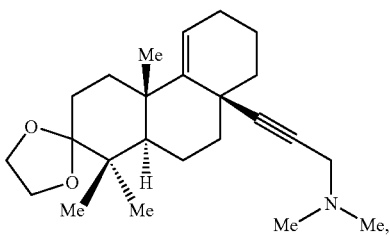

substantially free from other optical isomers. In other embodiments, the compound is part of a racemic mixture.

In some embodiments, the invention provides for the compound defined by the structure:

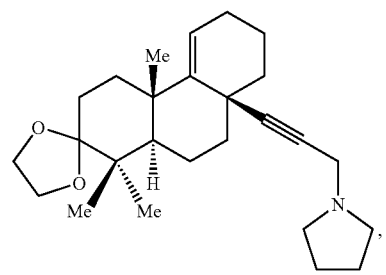

substantially free from other optical isomers. In other embodiments, the compound is part of a racemic mixture.

In some embodiments, the invention provides for compound 43, defined by the structure:

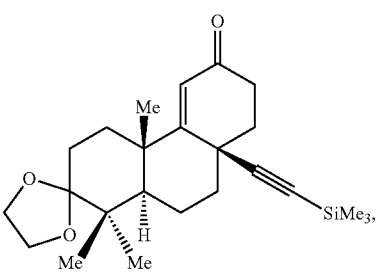

substantially free from other optical isomers. In other embodiments, the compound is part of a racemic mixture.

In some embodiments, the invention provides for compound 44, defined by the structure:

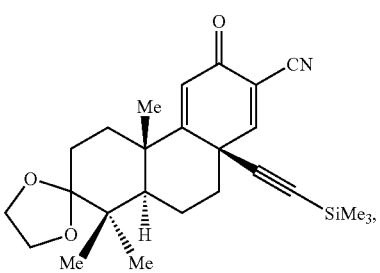

substantially free from other optical isomers. In other embodiments, the compound is part of a racemic mixture.

In some embodiments, the invention provides for the compound defined by the structure:

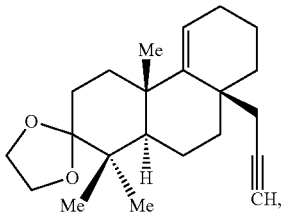

substantially free from other optical isomers. In other embodiments, the compound is part of a racemic mixture.

In some embodiments, the invention provides for the compound defined by the structure:

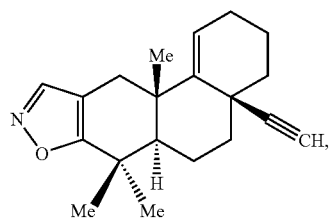

substantially free from other optical isomers. In other embodiments, the compound is part of a racemic mixture.

In certain embodiments, the invention provides a method of manufacturing compound I, by obtaining and oxidizing compound 2, using a Swern oxidation to form a first intermediate; then reacting the first intermediate with $Ph_3P(CH_2Cl)Cl$ and n-BuLi to form a second intermediate, and further reacting the second intermediate with MeLi to obtain compound I. In some embodiments, the method occurs in one discrete step. In other embodiments, the method occurs in 1, 2, 3, 4, 5, 6, 7, 8, 9, 10, or more discrete steps. In some embodiments the additional discrete steps can involve purification, work-up, neutralization, filtration, lyophilization, chromatography, washing, extraction, salt-exchange, protection, deprotection, sampling, and analysis.

In certain embodiments, the invention provides a method of manufacturing a compound having the structure Q1. In some of these embodiments, the method comprises obtaining and reacting compound I using alkyl-lithium chemistry to obtain a compound having the structure Q1. In some embodiments, the method occurs in one discrete step. In other embodiments, the method occurs in 1, 2, 3, 4, 5, 6, 7, 8, 9, 10, or more discrete steps. In some embodiments the additional discrete steps can involve purification, work-up, neutralization, filtration, lyophilization, chromatography, washing, extraction, salt-exchange, protection, deprotection, sampling, and analysis.

In another embodiment, the invention provides another method of obtaining a compound having the structure Q1. The method comprises obtaining compound I, and reacting said compound with an aryl halide or a vinyl halide using Sonogashira coupling to obtain the compound having the structure Q1. In some embodiments, the method occurs in one discrete step. In other embodiments, the method occurs in 1, 2, 3, 4, 5, 6, 7, 8, 9, 10, or more discrete steps. In some embodiments the additional discrete steps can involve purification, work-up, neutralization, filtration, lyophilization, chromatography, washing, extraction, salt-exchange, protection, deprotection, sampling, and analysis.

In further embodiments, the invention provides another method of obtaining a compound having the structure Q1. In certain of these embodiments, the method of obtaining a compound having the structure Q1, comprises obtaining compound I and reacting said compound with an aromatic iodo-substituted heterocyclic compound under Mannich-type conditions to obtain the compound having the structure Q1. In some embodiments, the method occurs in one discrete step. In other embodiments, the method occurs in 1, 2, 3, 4, 5, 6, 7, 8, 9, 10, or more discrete steps. In some embodiments, the additional discrete steps can involve purification, work-up, neutralization, filtration, lyophilization, chromatography, washing, extraction, salt-exchange, protection, deprotection, sampling, and analysis.

The present invention overcomes deficiencies in the art and provides an anti-cancer therapy that involves the administration of TBE-compounds, such as TBE-31 and TBE-34, as single-agent anticancer therapeutics. Also provided is an anti-cancer therapy that involves the combination of TBE-compounds, such as TBE-31 and TBE-34, with conventional chemotherapeutic compounds and/or with chemotherapeutic agents that inhibit cancer-promoting signaling pathways or activate different parts of apoptotic cascades.

The invention discloses a method of treating a patient having cancer comprising administering a therapeutically effective amount of a compound of this invention, such as those described above or throughout this specification. In some of these embodiments, the cancer is brain, lung, liver, spleen, kidney, lymph node, small intestine, pancreas, blood cell, bone, colon, stomach, bread, endometrium, prostate, testicle, ovary, central nervous system, skin, head and neck, esophagus, or bone marrow cancer. For example, in some embodiments, the cancer is epithelial cancer. In other embodiments, the cancer is lung, colon, breast or prostate cancer. In other embodiments, the cancer is colon cancer. In further embodiments, the patient has been identified as having a high risk for the development of cancer. In some embodiments, the compound is optically pure. For example, in some embodiments, the compound is predominantly the (+) enantiomer. In other embodiments, the compound is predominantly the (−) enantiomer. In other embodiments, the compound is a racemic mixture. In certain embodiments, the compound is administered with an aqueous solution. In some embodiments, the therapeutically effective amount is 0.1-1000 mg/kg. In further embodiments, an additional agent is administered to said patient.

The invention also discloses a method of treating a patient having an inflammatory disease, comprising administering a therapeutically effective amount of a compound of this invention, such as those described above or throughout this specification. In some embodiments, the inflammatory disease is rheumatoid arthritis, or inflammatory bowel disease. In some embodiments, the compound is optically pure. For example, in some embodiments, the compound is predominantly the (+) enantiomer. In other embodiments, the compound is predominantly the (−) enantiomer. In other embodiments, the compound is a racemic mixture. In certain embodiments, the compound is administered with an aqueous solution. In some embodiments, the therapeutically effective amount is 0.1-1000 mg/kg. In further embodiments, an additional agent is administered to said patient.

The invention also discloses a method of treating a patient having a neurodegenerative disease, comprising administering a therapeutically effective amount of a compound of this invention, such as those described above or throughout this specification. In some embodiments, the neurodegenerative disease is Alzheimer's disease, Parkinson's disease, multiple sclerosis or amyotrophic lateral sclerosis. In some embodiments, the compound is optically pure. For example, in some embodiments, the compound is predominantly the (+) enantiomer. In other embodiments, the compound is predominantly the (−) enantiomer. In other embodiments, the compound is a racemic mixture. In certain embodiments, the compound is administered with an aqueous solution. In some embodiments, the therapeutically effective amount is 0.1-1000 mg/kg. In further embodiments, an additional agent is administered to said patient.

The invention also discloses a method of treating a patient having a pathogenesis involving the excessive production of nitric oxide or prostaglandins, comprising administering a therapeutically effective amount of a compound of this invention, such as those described above or throughout this specification. In some embodiments, the compound is optically pure. For example, in some embodiments, the compound is predominantly the (+) enantiomer. In other embodiments, the compound is predominantly the (−) enantiomer. In other embodiments, the compound is a racemic mixture. In certain embodiments, the compound is administered with an aqueous solution. In some embodiments, the therapeutically effective amount is 0.1-1000 mg/kg. In further embodiments, an additional agent is administered to said patient. In certain embodiments, the prostaglandins are inflammatory prostaglandins.

The invention also discloses a method of treating a patient having a disorder characterized by the overexpression of iNOS or COX-2 gene, comprising administering a therapeutically effective amount of a compound of this invention, such as those described above or throughout this specification. In some embodiments, the compound is optically pure. For example, in some embodiments, the compound is predominantly the (+) enantiomer. In other embodiments, the compound is predominantly the (−) enantiomer. In other embodiments, the compound is a racemic mixture. In certain embodiments, the compound is administered with an aqueous solution. In some embodiments, the therapeutically effective amount is 0.1-1000 mg/kg. In further embodiments, an additional agent is administered to said patient.

The invention also discloses a method of modulating transcription or translation of iNOS or COX-2 genes in a patient, comprising administering a therapeutically effective amount of a compound of this invention, such as those described above or throughout this specification. In some embodiments, the compound is optically pure. For example, in some embodiments, the compound is predominantly the (+) enantiomer. In other embodiments, the compound is predominantly the (−) enantiomer. In other embodiments, the compound is a racemic mixture. In certain embodiments, the compound is administered with an aqueous solution. In some embodiments, the therapeutically effective amount is 0.1-1000 mg/kg. In further embodiments, an additional agent is administered to said patient.

The invention also discloses a method of modulating excessive nitric oxide or prostaglandin formation in a patient, comprising administering a therapeutically effective amount of a compound of this invention, such as those described above or throughout this specification. In some embodiments, the compound is optically pure. For example, in some embodiments, the compound is predominantly the (+) enantiomer. In other embodiments, the compound is predominantly the (−) enantiomer. In other embodiments, the compound is a racemic mixture. In certain embodiments, the compound is administered with an aqueous solution. In some embodiments, the therapeutically effective amount is 0.1-1000 mg/kg. In further embodiments, an additional agent is administered to said patient. In certain embodiments, the formation of inflammatory prostaglandins may be modulated.

In another aspect, there is disclosed a method for inducing cytotoxicity in a cell comprising contacting the cell with a compound of the present invention, such as those described above or throughout this specification, and a treatment selected from the group consisting of chemotherapy using a chemotherapeutic agent, radiotherapy, gene therapy, and surgery, wherein the compound and the treatment are provided in a combined amount effective to induce cytotoxicity in said cell. In a non-limiting example, the compound is 10a-ethynyl-4b,8,8-trimethyl-3,7-dioxo-3,4b,7,8,8a,9,10,10a-octahydrophenanthrene-2,6-dicarbonitrile (TBE-31) or (+)-(4bS,8aS,10aR)-10a-ethynyl-4-b,8,8-trimethyl-3,7-dioxo-3,4b,7,8,8a,9,10,10a-octahydrophenanthrene-2,6-dicarbonitrile ((+)-TBE-31), substantially free from other optical isomers.

In certain embodiments, the compound of this invention is contacted with the cell prior to contacting the cell with the chemotherapeutic agent. In other embodiments, a chemotherapeutic agent is contacted with the cell prior to contacting said cell with the compound.

In some embodiments, the cell is a cancer cell. In some of these embodiments, said cancer cell is a leukemic cell. In further of these embodiments, the leukemic cell is a blood cancer cell, a myeloid leukemia cell, a monocytic leukemia cell, a myelocytic leukemia cell, a promyelocytic leukemia cell, a myeloblastic leukemia cell, a lymphocytic leukemia cell, an acute myelogenous leukemic cell, a chronic myelogenous leukemia cell, a lymphoblastic leukemia cell, or a hairy cell leukemia cell.

In other embodiments, the cancer cell is a solid tumor cell. In certain of these embodiments, the solid tumor cell is a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, or a soft tissue cancer cell.

In some embodiments, the cell being cytotoxically induced is located in a human subject. In some of these embodiments, the compound of this invention is administered locally. In further of these embodiments, the compound is administered by direct intratumoral injection, wherein the compound is administered by injection into tumor vasculature. In other embodiments, the compound is administered systemically. In some of these embodiments, the compound is administered intravenously. In other embodiments, the compound is administered intra-arterially. In further embodiments, the compound is administered intra-peritoneally. In still further embodiments, the compound is administered orally. In certain embodiments, the compound is administered by contacting a cell during ex vivo purging.

For example, in some aspects, the chemotherapeutic agent used in combination with a compound of this invention is doxorubicin, decitabine, daunorubicin, dactinomycin, mitoxantrone, cisplatin, procarbazine, mitomycin, carboplatin, bleomycin, etoposide, teniposide, mechlroethamine, cyclophosphamide, ifosfamide, melphalan, chlorambucil, ifosfamide, melphalan, hexamethylmelamine, thiopeta, busulfan, carmustine, lomustine, semustine, streptozocin, dacarbazine, adriamycin, 5-fluorouracil (5FU), camptothecin, actinomycin-D, hydrogen peroxide, nitrosurea, plicomycin, tamoxifen, taxol, transplatinum, vincristin, vinblastin, TRAIL, dolastatin-10, bryostatin, annamycin, mylotarg, sodium phenylacetate, sodium butyrate, methotrexate, a cortocosteroid, or tacrolimus.

In other aspects, the chemotherapeutic agent is a retinoid. In some of these embodiments, the retinoid is selected from the group comprising all-trans-retinoic acid, 9-cis-retinoic acid, LG100268, LGD1069, fenretinide, CD437, a RAR-specific retinoic acid, and a RXR-specific retinoic acid. In some of these embodiments, the RXR-specific retinoic acid is LG100268.

In some embodiments, the cell being cytotoxically induced is contacted with a compound of this invention a second time. In further embodiments, the cell is contacted with the chemotherapeutic agent a second time. In certain embodiments, the compound of this invention and the chemotherapeutic agent are contacted with the cell at the same time.

In certain embodiments, the invention discloses a method of killing a tumor cell comprising contacting said tumor cell with a compound of this invention and a chemotherapeutic agent, wherein the compound of this invention and said chemotherapeutic agent are provided in a combined amount effective to kill said tumor cell. In some of these embodiments, the compound of this invention is 10a-ethynyl-4b,8,8-trimethyl-3,7-dioxo-3,4b,7,8,8a,9,10,10a-octahydrophenanthrene-2,6-dicarbonitrile (TBE-31). In other embodiments, the compound of this invention is (+)-(4bS,8aS,10aR)-10a-ethynyl-4b,8,8-trimethyl-3,7-dioxo-3,4b,7,8,8a,9,10,10a-octahydrophenanthrene-2,6-dicarbonitrile ((+)-TBE-31), substantially free from other optical isomers. In certain embodiments, the chemotherapeutic agent is a retinoid.

In some aspects of the invention, a method of inducing apoptosis in a tumor cell comprising contacting said tumor cell with a compound of this invention and a chemotherapeutic agent is disclosed. In some of these embodiments, the compound of this invention and said chemotherapeutic agent are provided in a combined amount effective to induce apoptosis of said tumor cell. In certain embodiments, the compound of this invention is 10a-ethynyl-4b,8,8-trimethyl-3,7-dioxo-3,4b,7,8,8a,9,10,10a-octahydrophenanthrene-2,6-dicarbonitrile (TBE-31). In other embodiments, the compound of this invention is (+)-(4bS,8aS,10aR)-10a-ethynyl-4b,8,8-trimethyl-3,7-dioxo-3,4b,7,8,8a,9,10,10a-octahydrophenanthrene-2,6-dicarbonitrile ((+)-TBE-31), substantially free from other optical isomers. In some embodiments, the chemotherapeutic agent is a retinoid.

In other aspects of the invention, a method of inducing differentiation in a tumor cell comprising contacting said tumor cell with a compound of this invention and a chemotherapeutic agent is provided. In certain of these embodiments, the compound of this invention and said chemotherapeutic agent are provided in a combined amount effective to induce the differentiation of the tumor cell. In certain of these embodiments, the compound of this invention is 10a-ethynyl-4b,8,8-trimethyl-3,7-dioxo-3,4b,7,8,8a,9,10,10a-octahydrophenanthrene-2,6-dicarbonitrile (TBE-31). In other of these embodiments, the compound of this invention is (+)-(4bS, 8aS,10aR)-10a-ethynyl-4b,8,8-trimethyl-3,7-dioxo-3,4b,7, 8,8a,9,10,10a-octahydrophenanthrene-2,6-dicarbonitrile ((+)-TBE-31), substantially free from other optical isomers. In some embodiments, the chemotherapeutic agent is a retinoid.

In another aspect of this invention, a method of treating cancer in a human patient, comprising administering a compound of this invention and a chemotherapeutic agent to said human patient, is provided. In some embodiments, the compound of this invention and said chemotherapeutic agent are provided in a combined amount effective to treat the cancer. In some of these embodiments, the compound of this invention is 10a-ethynyl-4b,8,8-trimethyl-3,7-dioxo-3,4b,7,8,8a, 9,10,10a-octahydrophenanthrene-2,6-dicarbonitrile (TBE-31). In other of these embodiments, the compound of this invention is (+)-(4bS,8aS,10aR)-10a-ethynyl-4b,8,8-trimethyl-3,7-dioxo-3,4b,7,8,8a,9,10,10a-octahydrophenanthrene-2,6-dicarbonitrile ((+)-TBE-31), substantially free from other optical isomers. In some of these embodiments, the chemotherapeutic agent is a retinoid.

In another aspect of the invention, a method of potentiating the effect of a chemotherapeutic agent on a tumor cell is provided, comprising contacting said tumor cell with a compound of this invention and a chemotherapeutic agent. In some of these embodiments, the compound of this invention is 10a-ethynyl-4b,8,8-trimethyl-3,7-dioxo-3,4b,7,8,8a,9,10, 10a-octahydrophenanthrene-2,6-dicarbonitrile (TBE-31). In other of these embodiments, the compound of this invention is (+)-(4bS,8aS,10aR)-10a-ethynyl-4b,8,8-trimethyl-3,7-dioxo-3,4b,7,8,8a,9,10,10a-octahydrophenanthrene-2,6-dicarbonitrile ((+)-TBE-31), substantially free from other optical isomers. In certain embodiments, the chemotherapeutic agent is a retinoid.

In a further aspect of the invention, a method of inhibiting growth of a tumor cell is disclosed, comprising contacting said tumor cell with a compound of this invention and a chemotherapeutic agent wherein the compound of this invention and the chemotherapeutic agent are provided in a combined amount effective to inhibit growth of said tumor cell. In some of these embodiments, the compound of this invention is 10a-ethynyl-4b,8,8-trimethyl-3,7-dioxo-3,4b,7,8,8a,9,10, 10a-octahydrophenanthrene-2,6-dicarbonitrile (TBE-31). In other of these embodiments, the compound of this invention is (+)-(4bS,8aS,10aR)-10a-ethynyl-4b,8,8-trimethyl-3,7-dioxo-3,4b,7,8,8a,9,10,10a-octahydrophenanthrene-2,6-dicarbonitrile ((+)-TBE-31), substantially free from other optical isomers. In certain embodiments, the chemotherapeutic agent is a retinoid.

The invention further discloses a method of inducing apoptosis in a lymphoid cell that expresses Bcl-2 comprising contacting said lymphoid cell with a compound of this invention and an immunosupressive agent. In some of these embodiments, the Bcl-2 is endogenous. In other of these embodiments, the Bcl-2 is exogenous. In certain embodiments, the Bcl-2 is expressed by an expression vector that comprises a nucleic acid that encodes Bcl-2 under the control of a promoter active in the lymphoid cell. In some embodiments, the lymphoid cell is a T-cell. In further embodiments, the lymphoid cell is a cancer cell. In some of these embodiments, the lymphoid cell is located in a human. In certain aspects, the immunosupressive agent is a corticosteroid. In certain embodiments, the immunosupressive agent is a tacrolimus. The invention further provides in some embodiments, that the lymphoid cell is further contacted with a chemotherapeutic agent.

Therefore, provided in the invention is a method for inducing cytotoxicity in a cell comprising contacting the cell with a TBE-compound and a chemotherapeutic agent, wherein the combination of the TBE-compound with the chemotherapeutic agent is effective in inducing cytotoxicity in the cell. The TBE-compound is TBE-31 or TBE-34.

In one embodiment of the method, the TBE-compound is contacted with the cell prior to contacting the cell with the chemotherapeutic agent. In another embodiment of the method, the chemotherapeutic agent is contacted with the cell prior to contacting the cell with TBE-31.

In other embodiments of the method, the cell is a cancer cell. In some aspects the cancer cell is a leukemic cell. In more specific aspects, the leukemic cell is a blood cancer cell, a myeloid leukemia cell, a monocytic leukemia cell, a myelocytic leukemia cell, a promyelocytic leukemia cell, a myeloblastic leukemia cell, a lymphocytic leukemia cell, an acute myelogenous leukemic cell, a chronic myelogenous leukemic cell, a lymphoblastic leukemia cell, a hairy cell leukemia cell.

In yet other embodiments, the cancer cell is a solid tumor cell. In specific aspects, the solid tumor cell is a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, a soft tissue cancer cell.

In one embodiment of the method, the cell is located in a human subject. In one embodiment, the TBE-compound may be administered locally. Therefore, the compound may be administered by intratumoral injection and/or by injection into tumor vasculature.

In another embodiment of the method, the TBE-compound may be administered systemically. In other specific aspects of this embodiment, the TBE-compounds may be administered intravenously, intra-arterially, intra-peritoneally and/or orally. TBE-31 may be administered at dosages in the range of 5-30 mg/kg intravenously (i.v.) or 5-100 mg/kg orally. Thus, 5, 10, 15, 20, 25, or 30 mg/kg of TBE-31 may be administered by i.v. or 5, 10, 15, 20, 25, 30, 35, 40, 45, 50, 55, 60, 65, 70, 75, 80, 85, 90, 95, or 100 mg/kg TBE-31 may be administered orally. TBE-31-Me may be administered in the range of 5-100 mg/kg intravenously or 5-100 mg/kg orally for 3-30 days. Thus, 5, 10, 15, 20, 25, 30, 35, 40, 45, 50, 55, 60, 65, 70, 75, 80, 85, 90, 95, or 100 mg/kg of TBE-31 may be administered by i.v. or, 5, 10, 15, 20, 25, 30, 35, 40, 45, 50, 55, 60, 65, 70, 75, 80, 85, 90, 95, or 100 mg/kg of TBE-31 may be administered orally. The skilled artisan will appreciate that these dosages are only guidelines and a physician will determine exact dosages at the time of administration factoring in other conditions such as age, sex, disease, etc. of the patient.

In one embodiment, the chemotherapeutic agent may be one or more of the listed chemotherapeutics including, doxorubicin, daunorubicin, dactinomycin, mitoxantrone, cisplatin, procarbazine, mitomycin, carboplatin, bleomycin, etoposide, teniposide, mechlroethamine, cyclophosphamide, ifosfamide, melphalan, chlorambucil, ifosfamide, melphalan, hexamethylmelamine, thiopeta, busulfan, carmustine, lomustine, semustine, streptozocin, dacarbazine, adriamycin, 5-fluorouracil (5FU), camptothecin, actinomycin-D, hydrogen peroxide, nitrosurea, plicomycin, tamoxifen, taxol, transplatinum, vincristin, vinblastin, mylotarg, dolastatin-10, bryostatin and methotrexate. However, one of ordinary skill in the art will appreciate that the invention is not limited to these chemotherapeutic agents and may involve the use of other DNA damaging agents as well.

In yet other embodiments, the chemotherapeutic agent is a retinoid. The retinoid may be all-trans-retinoic acid (ATRA), 9-cis-retinoic acid, LG100268, LGD1069 (Targretin, bexarotene), fenretinide [N-(4-hydroxyphenyl)retinamide, 4-HPR], CD437 or any RXR- or RAR-specific retinoic acid. In one specific embodiment, the RXR-specific retinoic acid is LG100268. In some embodiments, the retinoids may be administered as liposomal formulations. These liposomal formulations may be administered intravenously or through other routes as well, for example a liposomal formulation of ATRA is administered a range of 10-100 mg/m$^2$/day intravenously. Thus, one may administer 10, 20, 25, 30, 35, 40, 45, 50, 55, 60, 65, 70, 75, 80, 85, 90, 95, or 100 mg/m$^2$/day of a liposomal formulation of ATRA. In one specific embodiment, 90 mg/m$^2$/day of ATRA as a liposomal formulation is intravenously. In other embodiments, the retinoids may be administered orally. For example, ATRA may be administered in the range of 10-100 mg/m$^2$/day. Thus, one may administer 10, 20, 25, 30, 35, 40, 45, 50, 55, 60, 65, 70, 75, 80, 85, 90, 95, or 100 mg/m$^2$/day of ATRA. In one specific embodiment, ATRA may be administered at 45 mg/m$^2$/day orally daily. In another example, 9-cis-Retinoid acid may be administered in the range of 20-150 mg/m$^2$ twice a day orally. Thus, one may administer 20, 25, 30, 35, 40, 45, 50, 55, 60, 65, 70, 75, 80, 85, 90, 95, 100, 105, 110, 115, 120, 125, 130, 135, 140, 145, or 150 mg/m$^2$ of 9-cis-retinoid. LG100268 may be effective in a dose range of 5-50 mg/kg. Thus, 5, 10, 15, 20, 25, 30, 35, 40, 45, to 50 mg/kg of LG100268 may be administered. LGD1069 (Targretin, bexarotene) capsules are contemplated for the topical treatment of cutaneous lesions in patients with cutaneous T-cell lymphoma (CTCL) who have refractory or resistant disease after other therapies. The dose ranges of these capsules are 300-400 mg/m$^2$/day orally. Thus, 300, 350, 400 mg/m$^2$/day may be used. LGD1069 gel at 1% may also be used for the topical treatment of cutaneous lesions in patients with CTCL (Stage (1A and 1B) who have refractory or resistant disease after other therapies; two to four times daily. Fenretinide [N-(4-hydroxyphenyl)retinamide, 4-HPR] is contemplated useful at 25-600 mg daily and the administration in some embodiments may be continuous. Thus, 25, 30, 35, 40, 45, 50, 55, 60, 65, 70, 75, 80, 85, 90, 95, 100, 120, 140, 160, 180, 200, 220, 240, 260, 280, 300, 320, 340, 360, 380, 400, 420, 440, 460, 480, 500, 520, 540, 560, 580, 600 mg may be administered daily. Of course, the skilled artisan will understand that while these dosage ranges provide useful guidelines appropriate adjustments in the dosage depending on the needs of an individual patient factoring in disease, gender, age and other general health conditions will be made at the time of administration to a patient by a trained physician.

In some embodiments of the method, the cell is contacted with the TBE-compound a second time. In yet other embodiments, the cell may be contacted with the chemotherapeutic agent a second time. In still other aspects of this method, the TBE-compound and the chemotherapeutic agent can be contacted with the cell at the same time.

One embodiment of the method, further comprising tumor resection in conjunction with the TBE-compound based combination therapy. The tumor resection may occurs prior to the contacting. Thus, the contacting can comprises treating a resected tumor bed with the TBE-compound and the chemotherapeutic agent. In other aspects, the tumor resection occurs after the contacting. In still other aspects, the contacting occurs both before and after the tumor resection.

The invention also provides methods of killing a tumor cell comprising contacting the tumor cell with a TBE-compound and a chemotherapeutic agent, wherein the combination of said TBE-compound with said chemotherapeutic agent, induces killing of said tumor cell.

The invention also provides methods of inducing apoptosis in a tumor cell comprising contacting said tumor cell with a TBE-compound and a chemotherapeutic agent, wherein the combination of said TBE-compound with said chemotherapeutic agent, induces apoptosis of said tumor cell. The TBE-compound is TBE-31 or TBE-34. In some embodiments of this method, the chemotherapeutic agent is a retinoid.

Also provided are methods for inducing differentiation in a tumor cell comprising contacting the tumor cell with a TBE-compound and a chemotherapeutic agent, wherein the combination of the TBE-compound with the chemotherapeutic agent, induces the differentiation of the tumor cell.

Further provided are methods for treating cancer in a human patient comprising administering a TBE-compound and a chemotherapeutic agent to the human patient, wherein the combination of the TBE-compound with the chemotherapeutic agent, is effective to treat the cancer.

The invention also describes methods of potentiating the effect of a chemotherapeutic agent on a tumor cell comprising contacting the tumor cell with a TBE-compound and the chemotherapeutic agent.

In addition, the invention provides methods of inhibiting growth of a tumor cell comprising contacting the tumor cell with a TBE-compound and a chemotherapeutic agent.

In all these methods, the TBE-compound can be TBE-31, TBE-34, or any of the compounds of this invention, disclosed above and throughout this specification. In some embodiments, the chemotherapeutic agent is a retinoid. In some specific aspects, the retinoids are all-trans-retinoic acid (ATRA), 9-cis-retinoic acid, LG100268, LGD1069 (Targretin, bexarotene), fenretinide [N-(4-hydroxyphenyl)retinamide, 4-HPR], CD437 or any RXR- or RAR-specific retinoic acid. In additional embodiments, other chemotherapeutics described above and elsewhere in the specification may also be used.

Also provided are various tricyclic-bis-enone compositions effective for inhibiting IFN-γ-induced NO production in macrophages or RAW cells, said composition having an IC$_{50}$ value of at least less than about 0.7 µM. The compositions may have an IC$_{50}$ value of at least less than about 0.1, 0.05, 0.01, 0.005, or 0.001 µM, be optically pure, be predominantly the (+) enantiomer, predominantly the (−) enantiomer, or a racemic mixture. The composition may be water soluble.

Following longstanding patent law convention, the word "a" and "an", when used in conjunction with the word comprising, mean "one or more" in this specification, including the claims.

BRIEF DESCRIPTION OF THE DRAWINGS

The following drawings form part of the present specification and are included to further demonstrate certain aspects of the present invention. The invention may be better understood by reference to one of these drawings in combination with the detailed description of specific embodiments presented herein.

FIG. 1 shows that a series of TBEs are extremely potent inhibitors of the growth of both human myeloma cells and human leukemia cells. Of the TBEs tested in this study, TBE-31 is by far the most potent, equivalent to that of CDDO itself (TP-151) in the 8226 myeloma cells, and more potent than CDDO in the U937 leukemia cells. CDDO is presently in clinical trial for treatment of acute myelogenous leukemia. TP-235 is the imidazolide derivative of CDDO.

FIG. 2 shows that TBE-31 is a potent inducer of heme oxygenase in U937 cells. None of the other TBEs that were tested provided significant induction of heme oxygenase. For comparison of TBE-31 with the triterpenoids, note that TBE-31 is markedly more potent than TP-151 (CDDO), and almost as potent as TP-235, which is the imidazolide derivative of CDDO.

FIG. 3 shows that TBE-31 is an orally active agent. The level of induction with TBE-31 is again comparable to that found with CDDO-Imidazolide, a very potent triterpenoid agent for induction of heme oxygenase-1.

FIG. 4 shows that TBE-31 strongly induces CD11b at 100 nM. Although the potency is comparable to that of CDDO-Im at 10 and 30 nM, it is more potent than CDDO-Im at 100 nM.

DESCRIPTION OF ILLUSTRATIVE EMBODIMENTS

I. The Present Invention

Figure 1:
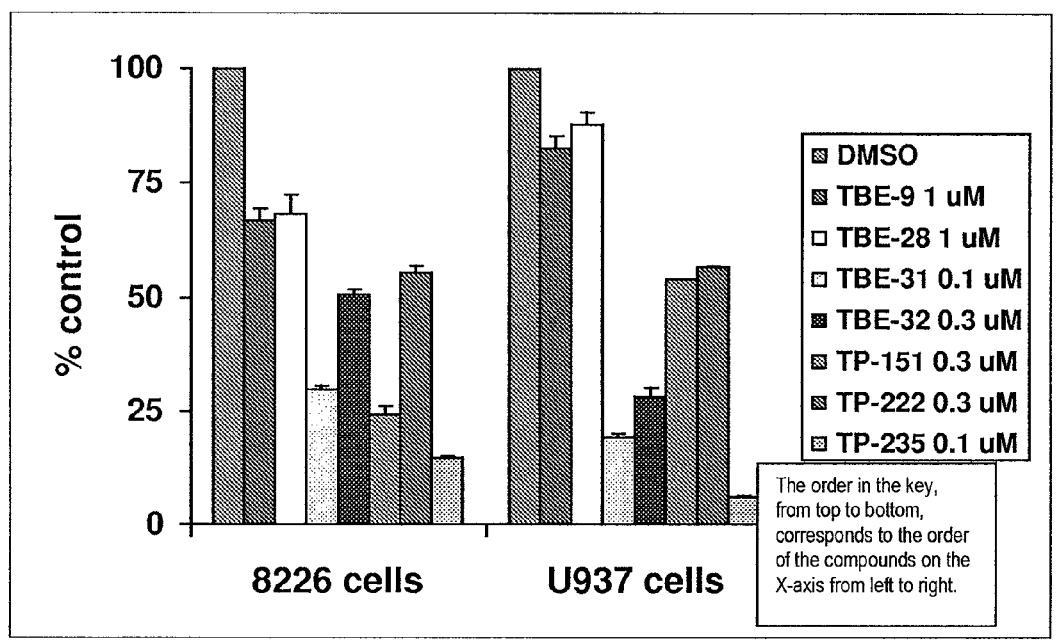
FIG. 1. TBEs inhibit proliferation of RMPI 8226 human myeloma cells and U937 human leukemia cells. Cells were treated with TBEs and triterpenoids for 3-4 days and counted by Coulter counter.

Within the past few years, there has been increasing interest in the development of selective COX-2 and iNOS inhibitors for prevention of cancer, especially in the colon. The approach described herein involves the synthesis and use of novel tricyclic-bis-enones (TBEs), especially those modified in the C-8a position, to block the formation of the enzymes COX-2 and iNOS. The novel TBEs show higher levels of activity in suppressing the expression of the COX-2 and iNOS genes, and thus for the treatment of cancer. In addition, the present invention overcomes deficiencies in the art by providing new target compounds to create novel cancer chemopreventative and anti-inflammatory agents. Novel methods for the synthesis of TBEs also are provided.

II. Definitions

As used herein, the term "amino" means —$NH_2$; the term "nitro" means —$NO_2$; the term "halo" designates —F, —Cl, —Br or —I; the term "mercapto" means —SH; the term "cyano" means —CN; the term "silyl" means —$SiH_3$, and the term "hydroxy" means —OH.

The term "substituted," when used to modify a class of organic radicals (e.g. alkyl, aryl, acyl, etc.), means that one or more than one hydrogen atom of that radical has been replaced by a heteroatom, or a heteroatom containing group. Specific substituted organic radicals are defined more fully below.

The term "unsubstituted," when used to modify a class of organic radicals (e.g. alkyl, aryl, acyl, etc.) means that none of the hydrogen atoms of that radical have been replaced with a heteroatom or a heteroatom containing group. Substitution of a hydrogen atom with a carbon atom, or a group consisting of only carbon and hydrogen atoms, is not sufficient to make a group substituted. For example, the group $-C_6H_4C\equiv CH$ is an example of an unsubstituted aryl group, while $-C_6H_4F$ is an example of a substituted aryl group. Specific unsubstituted organic radicals are defined more fully below.

The term "unsubstituted $C_n$-alkyl" refers to a radical, having a linear or branched, cyclic or acyclic structure, further having no carbon-carbon double or triple bonds, further having a total of n carbon atoms, all of which are nonaromatic, 3 or more hydrogen atoms, and no heteroatoms. For example, an unsubstituted $C_1$-$C_{10}$-alkyl has 1 to 10 carbon atoms. The term "alkyl" includes straight-chain alkyl groups, branched-chain alkyl groups, cycloalkyl (alicyclic) groups, alkyl substituted cycloalkyl groups, and cycloalkyl substituted alkyl groups. The groups, $-CH_3$, $-CH_2CH_3$, $-CH_2CH_2CH_3$, $-CH(CH_3)_2$, $-CH(CH_2)_2$, $-CH_2CH_2CH_2CH_3$, $-CH(CH_3)CH_2CH_3$, $-CH_2CH(CH_3)_2$, $-C(CH_3)_3$, and $-CH_2C(CH_3)_3$, are all examples of unsubstituted alkyl groups.

The term "substituted $C_n$-alkyl" refers to a radical, having a single saturated carbon atom as the point of attachment, no carbon-carbon double or triple bonds, further having a linear or branched, cyclic or acyclic structure, further having a total of n carbon atoms, all of which are nonaromatic, 0, 1, or more than one hydrogen atom, at least one heteroatom, wherein each heteroatom is independently selected from the group consisting of N, O, F, Cl, Br, I, Si, P, and S. For example, a substituted $C_1$-$C_{10}$-alkyl has 1 to 10 carbon atoms. The following groups are all examples of substituted alkyl groups: trifluoromethyl, $-CH_2F$, $-CH_2Cl$, $-CH_2Br$, $-CH_2OH$, $-CH_2OCH_3$, $-CH_2OCH_2CH_3$, $-CH_2OCH_2CH_2CH_3$, $-CH_2OCH(CH_3)_2$, $-CH_2OCH(CH_2)_2$, $-CH_2OCH_2CF_3$, $-CH_2OCOCH_3$, $-CH_2NH_2$, $-CH_2NHCH_3$, $-CH_2N(CH_3)_2$, $-CH_2NHCH_2CH_3$, $-CH_2N(CH_3)CH_2CH_3$, $-CH_2NHCH_2CH_2CH_3$, $-CH_2NHCH(CH_3)_2$, $-CH_2NHCH(CH_2)_2$, $-CH_2N(CH_2CH_3)_2$, $-CH_2CH_2F$, $-CH_2CH_2Cl$, $-CH_2CH_2Br$, $-CH_2CH_2I$, $-CH_2CH_2OH$, $CH_2CH_2OCOCH_3$, $-CH_2CH_2NH_2$, $-CH_2CH_2N(CH_3)_2$, $-CH_2CH_2NHCH_3$, $-CH_2CH_2N(CH_3)CH_2CH_3$, $-CH_2CH_2NHCH_2CH_3$, $-CH_2CH_2NHCH(CH_3)_2$, $-CH_2CH_2NHCH(CH_2)_2$, $-CH_2CH_2N(CH_2CH_3)_2$, $-CH_2CH_2NHCO_2C(CH_3)_3$, and $-CH_2Si(CH_3)_3$.

The term "unsubstituted $C_n$-alkenyl" refers to a radical, having a linear or branched, cyclic or acyclic structure, further having at least one carbon-carbon double bond, a total of n carbon atoms, all of which are nonaromatic, 3 or more hydrogen atoms, and no heteroatoms. For example, an unsubstituted $C_2$-$C_{10}$-alkenyl has 2 to 10 carbon atoms. Unsubstituted alkenyl groups include: $-CH=CH_2$, $-CH=CHCH_3$, $-CH=CHCH_2CH_3$, $-CH=CHCH_2CH_2CH_3$, $-CH=CHCH(CH_3)_2$, $-CH=CHCH(CH_2)_2$, $-CH_2CH=CH_2$, $-CH_2CH=CHCH_3$, $-CH_2CH=CHCH_2CH_3$, $-CH_2CH=CHCH_2CH_2CH_3$, $-CH_2CH=CHCH(CH_3)_2$, and $-CH_2CH=CHCH(CH_2)_2$.

The term "substituted $C_n$-alkenyl" refers to a radical, having a single nonaromatic carbon atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one heteroatom, wherein each heteroatom is independently selected from the group consisting of N, O, F, Cl, Br, I, Si, P, and S. For example, a substituted $C_2$-$C_{10}$-alkenyl has 2 to 10 carbon atoms. The groups, $-CH=CHF$, $-CH=CHCl$ and $-CH=CHBr$, are examples of substituted alkenyl groups.

The term "unsubstituted $C_n$-alkynyl" refers to a radical, having a linear or branched, cyclic or acyclic structure, further having at least one carbon-carbon triple bond, a total of n carbon atoms, all of which are nonaromatic, at least one hydrogen atom, and no heteroatoms. For example, an unsubstituted $C_2$-$C_{10}$-alkynyl has 2 to 10 carbon atoms. The groups, $-C\equiv CH$ and $-C\equiv CCH_3$, are examples of unsubstituted alkynyl groups.

The term "substituted $C_n$-alkynyl" refers to a radical, having a single nonaromatic carbon atom as the point of attachment and at least one nonaromatic carbon-carbon triple bond, further having a linear or branched, cyclic or acyclic structure, and having a total of n carbon atoms, 0, 1, or more than one hydrogen atom, and at least one heteroatom, wherein each heteroatom is independently selected from the group consisting of N, O, F, Cl, Br, I, Si, P, and S. For example, a substituted $C_2$-$C_{10}$-alkynyl has 2 to 10 carbon atoms. The group, $-C\equiv CSi(CH_3)_3$, is an example of a substituted alkynyl group.

The term "unsubstituted $C_n$-aryl" refers to a radical, having a single carbon atom as a point of attachment, wherein the carbon atom is part of an aromatic ring structure containing only carbon atoms, further having a total of n carbon atoms, 5 or more hydrogen atoms, and no heteroatoms. For example, an unsubstituted $C_6$-$C_{10}$-aryl has 6 to 10 carbon atoms. Examples of unsubstituted aryl groups include phenyl, methylphenyl, di(methyl)phenyl, $-C_6H_4CH_2CH_3$, $-C_6H_4CH_2CH_2CH_3$, $-C_6H_4CH(CH_3)_2$, $-C_6H_4CH(CH_2)_2$, $-C_6H_3(CH_3)CH_2CH_3$, $-C_6H_4CH=CH_2$, $-C_6H_4CH=CHCH_3$, $-C_6H_4C\equiv CH$, and $-C_6H_4C\equiv CCH_3$. Aryl groups also include polycyclic fused aromatic groups such as naphthyl, quinolyl, indolyl, and the like.

The term "substituted $C_n$-aryl" refers to a radical, having a single carbon atom as point of attachment, wherein the carbon atom is part of an aromatic ring structure containing only carbon atoms, further having a total of n aromatic or non-aromatic carbon atoms, 0, 1, or more than one hydrogen atom, and at least one nonaromatic heteroatom, wherein each heteroatom is independently selected from the group consisting of N, O, F, Cl, Br, I, Si, P, and S. For example, a substituted $C_6$-$C_{10}$-aryl has 6 to 10 carbon atoms. The groups, $-C_6H_4F$, $-C_6H_4Cl$, $-C_6H_4Br$, $-C_6H_4I$, $-C_6H_4OH$, $-C_6H_4OCH_3$, $-C_6H_4OCH_2CH_3$, $-C_6H_4OCOCH_3$, $-C_6H_4OC_6H_5$, $-C_6H_4NH_2$, $-C_6H_4NHCH_3$, $-C_6H_4NHCH_2CH_3$, $-C_6H_4CH_2Cl$, $-C_6H_4CH_2Br$, $-C_6H_4CH_2OH$, $-C_6H_4CH_2OCOCH_3$, $-C_6H_4CH_2NH_2$, $-C_6H_4N(CH_3)_2$, $-C_6H_4CH_2CH_2Cl$, $-C_6H_4CH_2CH_2OH$, $-C_6H_4CH_2CH_2OCOCH_3$, $-C_6H_4CH_2CH_2NH_2$, $-C_6H_4CH=CH_2$, $-C_6H_4CF_3$, $-C_6H_4CN$, $-C_6H_4C\equiv CSi(CH_3)_3$, $-C_6H_4COH$, $-C_6H_4COCH_3$, $-C_6H_4COCH_2CH_3$, $-C_6H_4COCH_2CF_3$, $-C_6H_4COC_6H_5$, $-C_6H_4CO_2H$, $-C_6H_4CO_2CH_3$, $-C_6H_4CONH_2$, $-C_6H_4CONHCH_3$, and $-C_6H_4CON(CH_3)_2$ are examples of substituted aryl groups.

The term "unsubstituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 7 or more hydrogen atoms, and no heteroatoms. For example, an unsubstituted $C_7$-$C_{10}$-aralkyl has 7 to 10 carbon atoms. An "aralkyl" includes an alkyl substituted with an aryl group. Examples of unsubstituted aralkyls include phenylmethyl (benzyl) and phenylethyl.

The term "substituted $C_n$-aralkyl" refers to a radical, having a single saturated carbon atom as the point of attachment, further having a total of n carbon atoms, wherein at least 6 of the carbon atoms form an aromatic ring structure containing only carbon atoms, 0, 1, or more than one hydrogen atom, and at least one heteroatom, wherein each heteroatom is independently selected from the group consisting of N, O, F, Cl, Br, I, Si, P, and S. For example, a substituted $C_7$-$C_{10}$-aralkyl has 7 to 10 carbon atoms.

The term "unsubstituted $C_n$-heteroaryl" refers to a radical, having either a single aromatic carbon atom or a single aromatic hetero atom as the point of attachment, further having a total of n carbon atoms, at least one hydrogen atom, and at least one heteroatom, wherein at least one of the carbon atoms and all of the heteroatoms are incorporated into one or more aromatic ring structures, further wherein each heteroatom is independently selected from the group consisting of N, O, F, Cl, Br, I, Si, P, and S. For example, an unsubstituted $C_1$-$C_{10}$-heteroaryl has 1 to 10 carbon atoms. For example, the term "heteroaryl" includes those groups derived from the compounds: pyrrole, furan, thiophene, imidazole, oxazole, isoxazole, thiazole, isothiazole, triazole, pyrazole, pyridine, pyrazine, pyridazine, pyrimidine, and the like.

The term "substituted $C_n$-heteroaryl" refers to a radical, having either a single aromatic carbon atom or a single aromatic heteroatom as the point of attachment, further having a total of n carbon atoms, at least one hydrogen atom, and at least two heteroatoms, wherein at least one of the carbon atoms and at least one of the heteroatoms are incorporated into one or more aromatic ring structures, further wherein at least one of the heteroatoms is not part of the one or more aromatic ring structures, further wherein each heteroatom is independently selected from the group consisting of N, O, F, Cl, Br, I, Si, P, and S. For example, an substituted $C_1$-$C_{10}$-heteroaryl has 1 to 10 carbon atoms.

The term "unsubstituted $C_n$-heteroaralkyl" refers to a radical, having a single saturated carbon atom as the point of attachment, further having a total of n carbon atoms, at least three hydrogen atoms, and at least one heteroatom, wherein at least one of the carbon atoms and all of the heteroatoms form an aromatic ring structure, further wherein each heteroatom is independently selected from the group consisting of N, O, F, Cl, Br, I, Si, P, and S. For example, an unsubstituted $C_2$-$C_{10}$-heteroaralkyl has 2 to 10 carbon atoms.

The term "substituted $C_n$-heteroaralkyl" refers to a radical having a single saturated carbon atom as the point of attachment, further having a total of n carbon atoms, 0, 1, or more than one hydrogen atom, and at least two heteroatoms, wherein at least one of the carbon atoms and at least one of the heteroatoms are incorporated into one or more aromatic ring structures, further wherein at least one of the heteroatoms is not part of an aromatic ring structure, further wherein each heteroatom is independently selected from the group consisting of N, O, F, Cl, Br, I, Si, P, and S. For example, a substituted $C_2$-$C_{10}$-heteroaralkyl has 2 to 10 carbon atoms.

The term "unsubstituted $C_n$-acyl" refers to a radical, having a single carbon atom of a carbonyl group as the point of attachment, further having a linear or branched, cyclic or acyclic structure, further having a total of n carbon atoms, 1 or more hydrogen atoms, a total of one oxygen atom, and no additional heteroatoms. For example, an unsubstituted $C_1$-$C_{10}$-acyl has 1 to 10 carbon atoms. The groups, —COH, —COCH$_3$, —COCH$_2$CH$_3$, —COCH$_2$CH$_2$CH$_3$, —COCH(CH$_3$)$_2$, —COCH(CH$_2$)$_2$, —COC$_6$H$_5$, —COC$_6$H$_4$CH$_3$, —COC$_6$H$_4$CH$_2$CH$_3$, —COC$_6$H$_4$CH$_2$CH$_2$CH$_3$, —COC$_6$H$_4$CH(CH$_3$)$_2$, —COC$_6$H$_4$CH(CH$_2$)$_2$, and —COC$_6$H$_3$(CH$_3$)$_2$, are examples of unsubstituted acyl groups.

The term "substituted $C_n$-acyl" refers to a radical, having a single carbon atom as the point of attachment, the carbon atom being part of a carbonyl group, further having a linear or branched, cyclic or acyclic structure, further having a total of n carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a substituted $C_1$-$C_{10}$-acyl has 1 to 10 carbon atoms. The term substituted acyl includes carbamoyl, thiocarboxylate, and thiocarboxylic acid groups. The groups, —COCH$_2$CF$_3$, —CO$_2$H, —CO$_2$CH$_3$, —CO$_2$CH$_2$CH$_3$, —CO$_2$CH$_2$CH$_2$CH$_3$, —CO$_2$CH(CH$_3$)$_2$, —CO$_2$CH(CH$_2$)$_2$, —CONH$_2$, —CONHCH$_3$, —CONHCH$_2$CH$_3$, —CONHCH$_2$CH$_2$CH$_3$, —CONHCH(CH$_3$)$_2$, —CONHCH(CH$_2$)$_2$, —CON(CH$_3$)$_2$, —CON(CH$_2$CH$_3$)CH$_3$, —CON(CH$_2$CH$_3$)$_2$ and —CONHCH$_2$CF$_3$, are examples of substituted acyl groups.

The term "unsubstituted $C_n$-alkoxy" refers to a group, having the structure —OR, in which R is an unsubstituted $C_n$-alkyl, as that term is defined above. Unsubstituted alkoxy groups include: —OCH$_3$, —OCH$_2$CH$_3$, —OCH$_2$CH$_2$CH$_3$, —OCH(CH$_3$)$_2$, and —OCH(CH$_2$)$_2$.

The term "substituted $C_n$-alkoxy" refers to a group, having the structure —OR, in which R is a substituted $C_n$-alkyl, as that term is defined above. For example, —OCH$_2$CF$_3$ is a substituted alkoxy group.

The term "unsubstituted $C_n$-alkenyloxy" refers to a group, having the structure —OR, in which R is an unsubstituted $C_n$-alkenyl, as that term is defined above.

The term "substituted $C_n$-alkenyloxy" refers to a group, having the structure —OR, in which R is a substituted $C_n$-alkenyl, as that term is defined above.

The term "unsubstituted $C_n$-alkynyloxy" refers to a group, having the structure —OR, in which R is an unsubstituted $C_n$-alkynyl, as that term is defined above.

The term "substituted $C_n$-alkenyloxy" refers to a group, having the structure —OR, in which R is a substituted $C_n$-alkynyl, as that term is defined above.

The term "unsubstituted $C_n$-aryloxy" refers to a group, having the structure —OAr, in which Ar is an unsubstituted $C_n$-aryl, as that term is defined above. An example of an unsubstituted aryloxy group is —OC$_6$H$_5$.

The term "substituted $C_n$-aryloxy" refers to a group, having the structure —OAr, in which Ar is a substituted $C_n$-aryl, as that term is defined above.

The term "unsubstituted $C_n$-aralkyloxy" refers to a group, having the structure —OAr, in which Ar is an unsubstituted $C_n$-aralkyl, as that term is defined above.

The term "substituted $C_n$-aralkyloxy" refers to a group, having the structure —OAr, in which Ar is a substituted $C_n$-aralkyl, as that term is defined above.

The term "unsubstituted $C_n$-heteroaryloxy" refers to a group, having the structure —OAr, in which Ar is an unsubstituted $C_n$-heteroaryl, as that term is defined above.

The term "substituted $C_n$-heteroaryloxy" refers to a group, having the structure —OAr, in which Ar is a substituted $C_n$-heteroaryl, as that term is defined above.

The term "unsubstituted $C_n$-heteroaralkyloxy" refers to a group, having the structure —OAr, in which Ar is an unsubstituted $C_n$-heteroaralkyl, as that term is defined above.

The term "substituted $C_n$-heteroaralkyloxy" refers to a group, having the structure —OAr, in which Ar is a substituted $C_n$-heteroaralkyl, as that term is defined above.

The term "unsubstituted $C_n$-acyloxy" refers to a group, having the structure —OAc, in which Ac is an unsubstituted $C_n$-acyl, as that term is defined above. An unsubstituted acyloxy group includes alkylcarbonyloxy and arylcarbonyloxy groups. For example, —OCOCH$_3$ is an example of an unsubstituted acyloxy group.

The term "substituted $C_n$-acyloxy" refers to a group, having the structure —OAc, in which Ac is a substituted $C_n$-acyl, as that term is defined above. A substituted acyloxy group includes alkoxycarbonyloxy, aryloxycarbonyloxy, carboxylate, alkylcarbonyl, alkoxycarbonyl, aminocarbonyl, and alkylthiocarbonyl groups.

The term "unsubstituted $C_n$-alkylamino" refers to a radical, having a single nitrogen atom as the point of attachment, further having one or two saturated carbon atoms attached to the nitrogen atom, further having a linear or branched, cyclic or acyclic structure, containing a total of n carbon atoms, all of which are nonaromatic, 4 or more hydrogen atoms, a total of 1 nitrogen atom, and no additional heteroatoms. For example, an unsubstituted $C_1$-$C_{10}$-alkylamino has 1 to 10 carbon atoms. An alkylamino group includes dialkylamino groups. An unsubstituted alkylamino group would include —NHCH$_3$, —NHCH$_2$CH$_3$, —NHCH$_2$CH$_2$CH$_3$, —NHCH(CH$_3$)$_2$, —NHCH(CH$_2$)$_2$, —NHCH$_2$CH$_2$CH$_2$CH$_3$, —NHCH(CH$_3$)CH$_2$CH$_3$, —NHCH$_2$CH(CH$_3$)$_2$, —NHC(CH$_3$)$_3$, —N(CH$_3$)$_2$, —N(CH$_3$)CH$_2$CH$_3$, —N(CH$_2$CH$_3$)$_2$, N-pyrrolidinyl, and N-piperidinyl.

The term "substituted $C_n$-alkylamino" refers to a radical, having a single nitrogen atom as the point of attachment, further having one or two saturated carbon atoms attached to the nitrogen atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a substituted $C_1$-$C_{10}$-alkylamino has 1 to 10 carbon atoms.

The term "unsubstituted $C_n$-alkenylamino" refers to a radical, having a single nitrogen atom as the point of attachment, further having a linear or branched, cyclic or acyclic structure, containing at least one carbon-carbon double bond, a total of n carbon atoms, all of which are nonaromatic, 4 or more hydrogen atoms, a total of one nitrogen atom, and no additional heteroatoms. For example, an unsubstituted $C_2$-$C_{10}$-alkenylamino has 2 to 10 carbon atoms. An alkenylamino group includes dialkenylamino and alkyl(alkenyl)amino groups.

The term "substituted $C_n$-alkenylamino" refers to a radical, having a single nitrogen atom as the point of attachment and at least one nonaromatic carbon-carbon double bond, but no carbon-carbon triple bonds, further having a linear or branched, cyclic or acyclic structure, further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a substituted $C_2$-$C_{10}$-alkenylamino has 2 to 10 carbon atoms.

The term "unsubstituted $C_n$-alkynylamino" refers to a radical, having a single nitrogen atom as the point of attachment, further having a linear or branched, cyclic or acyclic structure, containing at least one carbon-carbon triple bond, a total of n carbon atoms, all of which are nonaromatic, at least one hydrogen atoms, a total of one nitrogen atom, and no additional heteroatoms. For example, an unsubstituted $C_2$-$C_{10}$-alkynylamino has 2 to 10 carbon atoms. An alkynylamino group includes dialkynylamino and alkyl(alkynyl)amino groups.

The term "substituted $C_n$-alkynylamino" refers to a radical, having a single nitrogen atom as the point of attachment, further having at least one nonaromatic carbon-carbon triple bond, further having a linear or branched, cyclic or acyclic structure, and further having a total of n carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a substituted $C_2$-$C_{10}$-alkynylamino has 2 to 10 carbon atoms.

The term "unsubstituted $C_n$-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 6 or more hydrogen atoms, a total of one nitrogen atom, and no additional heteroatoms. For example, an unsubstituted $C_6$-$C_{10}$-arylamino has 6 to 10 carbon atoms. An arylamino group includes diarylamino and alkyl(aryl)amino groups.

The term "substituted $C_n$-arylamino" refers to a radical, having a single nitrogen atom as the point of attachment, further having at least one aromatic ring structure attached to the nitrogen atom, wherein the aromatic ring structure contains only carbon atoms, further having a total of n carbon atoms, 0, 1, or more hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a substituted $C_6$-$C_{10}$-arylamino has 6 to 10 carbon atoms.

The term "unsubstituted $C_n$-aralkylamino" refers to a radical, having a single nitrogen atom as the point of attachment, further having one or two saturated carbon atoms attached to the nitrogen atom, further having a total of n carbon atoms, wherein at least 6 of the carbon atoms form an aromatic ring structure containing only carbon atoms, 8 or more hydrogen atoms, a total of one nitrogen atom, and no additional heteroatoms. For example, an unsubstituted $C_7$-$C_{10}$-aralkylamino has 7 to 10 carbon atoms. An aralkylamino group includes diaralkylamino, alkyl(aralkyl)amino, and aryl(aralkyl)amino groups.

The term "substituted $C_n$-aralkylamino" refers to a radical, having a single nitrogen atom as the point of attachment, further having at least one or two saturated carbon atoms attached to the nitrogen atom, further having a total of n carbon atoms, wherein at least 6 of the carbon atoms form an aromatic ring structure containing only carbon atoms, 0, 1, or more than one hydrogen atom, and at least one additional heteroatom, that is, in addition to the nitrogen atom at the point of attachment, wherein each additional heteroatom is independently selected from the group consisting of N, O, F, Cl, Br, I, Si, P, and S. For example, a substituted $C_7$-$C_{10}$-aralkylamino has 7 to 10 carbon atoms.

The term "unsubstituted $C_n$-heteroarylamino" refers to a radical, having a single nitrogen atom as the point of attachment, further having a total of n carbon atoms, at least one hydrogen atom, and at least one additional heteroatom, in addition to the nitrogen atom at the point of attachment, wherein at least one of the carbon atoms and all of the additional heteroatoms are incorporated into one or more aromatic ring structures, further wherein each additional heteroatom is independently selected from the group consisting of N, O, F, Cl, Br, I, Si, P, and S. For example, an unsubstituted $C_1$-$C_{10}$-heteroarylamino has 1 to 10 carbon atoms. A heteroarylamino group includes alkyl(heteroaryl)amino and aryl(heteroaryl)amino groups.

The term "substituted $C_n$-heteroarylamino" refers to a radical, having a single nitrogen atom as the point of attachment, further having a total of n carbon atoms, at least one hydrogen atom, at least two additional heteroatoms, that is, in addition to the nitrogen atom at the point of attachment, wherein at least one of the carbon atoms and at least one of the additional heteroatoms are incorporated into one or more aromatic ring structures, further wherein at least one of the additional heteroatoms is not part of the one or more aromatic ring structures, further wherein each additional heteroatom is independently selected from the group consisting of N, O, F, Cl, Br, I, Si, P, and S. For example, an substituted $C_1$-$C_{10}$-heteroarylamino has 1 to 10 carbon atoms.

The term "unsubstituted $C_n$-heteroaralkylamino" refers to a radical, having a single nitrogen atom as the point of attachment, further having one or two saturated carbon atoms attached to the nitrogen atom, further having a total of n carbon atoms, at least three hydrogen atoms, at least one additional heteroatom, wherein at least one of the carbon atoms and all of the additional hetero atoms form an aromatic ring structure, further wherein each additional heteroatom is independently selected from the group consisting of N, O, F, Cl, Br, I, Si, P, and S. For example, an unsubstituted $C_2$-$C_{10}$-heteroaralkylamino has 2 to 10 carbon atoms. A heteroaralkylamino group includes alkyl(heteroaralkyl)amino and aryl(heteroaralkyl)amino groups.

The term "substituted $C_n$-heteroaralkylamino" refers to a radical, having a single nitrogen atom as the point of attachment, further having one or two saturated carbon atoms attached to the nitrogen atom, further having a total of n carbon atoms, 0, 1, or more than one hydrogen atom, at least two additional heteroatoms, that is, in addition to the nitrogen atom at the point of attachment, wherein at least one of the carbon atoms and at least one of the additional heteroatoms are incorporated into one or more aromatic ring structures, further wherein at least one of the heteroatoms is not part of an aromatic ring structure, further wherein each heteroatom is independently selected from the group consisting of N, O, F, Cl, Br, I, Si, P, and S. For example, a substituted $C_2$-$C_{10}$-heteroaralkylamino has 2 to 10 carbon atoms.

The term "unsubstituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n carbon atoms, 1 or more hydrogen atoms, a total of one oxygen atom, a total of one nitrogen atom, and no additional heteroatoms. For example, an unsubstituted $C_1$-$C_{10}$-amido has 1 to 10 carbon atoms. A amido group includes N-alkyl-amido, N-aryl-amido, N-aralkyl-amido, acylamino, alkylcarbonylamino, arylcarbonylamino, and ureido groups. The group, —$NHCOCH_3$, is an example of an unsubstituted amido group.

The term "substituted $C_n$-amido" refers to a radical, having a single nitrogen atom as the point of attachment, further having a carbonyl group attached via its carbon atom to the nitrogen atom, further having a linear or branched, cyclic or acyclic structure, further having a total of n aromatic or non-aromatic carbon atoms, 0, 1, or more than one hydrogen atom, at least one additional heteroatom in addition to the oxygen of the carbonyl group, wherein each additional heteroatom is independently selected from the group consisting of N, O, F, Cl, Br, I, Si, P, and S. For example, a substituted $C_1$-$C_{10}$-amido has 1 to 10 carbon atoms. The group, —$NHCO_2C(CH_3)_3$, is an example of an substituted amido group.

The term "unsubstituted $C_n$-alkylthio" refers to a group, having the structure —SR, in which R is an unsubstituted $C_n$-alkyl, as that term is defined above. The group, —$SCH_3$, is an example of an unsubstituted alkylthio group.

The term "substituted $C_n$-alkylthio" refers to a group, having the structure —SR, in which R is a substituted $C_n$-alkyl, as that term is defined above.

The term "unsubstituted $C_n$-alkenylthio" refers to a group, having the structure —SR, in which R is an unsubstituted $C_n$-alkenyl, as that term is defined above.

The term "substituted $C_n$-alkenylthio" refers to a group, having the structure —SR, in which R is a substituted $C_n$-alkenyl, as that term is defined above.

The term "unsubstituted $C_n$-alkynylthio" refers to a group, having the structure —SR, in which R is an unsubstituted $C_n$-alkynyl, as that term is defined above.

The term "substituted $C_n$-alkenylthio" refers to a group, having the structure —SR, in which R is a substituted $C_n$-alkynyl, as that term is defined above.

The term "unsubstituted $C_n$-arylthio" refers to a group, having the structure —SAr, in which Ar is an unsubstituted $C_n$-aryl, as that term is defined above. The group, —$SC_6H_5$, is an example of an unsubstituted arylthio group.

The term "substituted $C_n$-arylthio" refers to a group, having the structure —SAr, in which Ar is a substituted $C_n$-aryl, as that term is defined above.

The term "unsubstituted $C_n$-aralkylthio" refers to a group, having the structure —SAr, in which Ar is an unsubstituted $C_n$-aralkyl, as that term is defined above. The group, —$SCH_2C_6H_5$, is an example of an unsubstituted aralkyl group.

The term "substituted $C_n$-aralkylthio" refers to a group, having the structure —SAr, in which Ar is a substituted $C_n$-aralkyl, as that term is defined above.

The term "unsubstituted $C_n$-heteroarylthio" refers to a group, having the structure —SAr, in which Ar is an unsubstituted $C_n$-heteroaryl, as that term is defined above.

The term "substituted $C_n$-heteroarylthio" refers to a group, having the structure —SAr, in which Ar is a substituted $C_n$-heteroaryl, as that term is defined above.

The term "unsubstituted $C_n$-heteroaralkylthio" refers to a group, having the structure —SAr, in which Ar is an unsubstituted $C_n$-heteroaralkyl, as that term is defined above.

The term "substituted $C_n$-heteroaralkylthio" refers to a group, having the structure —SAr, in which Ar is a substituted $C_n$-heteroaralkyl, as that term is defined above.

The term "unsubstituted $C_n$-acylthio" refers to a group, having the structure —SAc, in which Ac is an unsubstituted $C_n$-acyl, as that term is defined above. The group, —$SCOCH_3$, is an example of an unsubstituted acylthio group.

The term "substituted $C_n$-acylthio" refers to a group, having the structure —SAc, in which Ac is a substituted $C_n$-acyl, as that term is defined above.

The term "unsubstituted $C_n$-alkylsilyl" refers to a radical, having a single silicon atom as the point of attachment, further having one, two, or three saturated carbon atoms attached to the silicon atom, further having a linear or branched, cyclic or acyclic structure, containing a total of n carbon atoms, all of which are nonaromatic, 5 or more hydrogen atoms, a total of 1 silicon atom, and no additional heteroatoms. For example, an unsubstituted $C_1$-$C_{10}$-alkylsilyl has 1 to 10 carbon atoms.

An alkylsilyl group includes dialkylamino groups. The groups, —Si(CH$_3$)$_3$ and —Si(CH$_3$)$_2$C(CH$_3$)$_3$, are examples of unsubstituted alkylsilyl groups.

The term "substituted C$_n$-alkylsilyl" refers to a radical, having a single silicon atom as the point of attachment, further having at least one, two, or three saturated carbon atoms attached to the silicon atom, no carbon-carbon double or triple bonds, further having a linear or branched, cyclic or acyclic structure, further having a total of n carbon atoms, all of which are nonaromatic, 0, 1, or more than one hydrogen atom, and at least one additional heteroatom, that is, in addition to the silicon atom at the point of attachment, wherein each additional heteroatom is independently selected from the group consisting of N, O, F, Cl, Br, I, Si, P, and S. For example, a substituted C$_1$-C$_{10}$-alkylsilyl has 1 to 10 carbon atoms.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like. Other suitable salts are known to one of ordinary skill in the art.

Suitable pharmaceutically acceptable salts may also be formed by reacting the agents of the invention with an organic base such as methylamine, ethylamine, ethanolamine, lysine, ornithine and the like. Other suitable salts are known to one of ordinary skill in the art.

Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable and as long as the anion or cation does not contribute undesired qualities or effects. Further, additional pharmaceutically acceptable salts are known to those skilled in the art, and may be used within the scope of the invention. Additional examples of pharmaceutically acceptable salts and their methods of preparation and use are presented in Pharmaceutical Salts: Properties, Selection and Use—A Handbook, by C. G. Wermuth and P. H. Stahl, Verlag Helvetica Chimica Acta, 2002, which is incorporated herein by reference.

As used herein, the term "patient" is intended to include living organisms in which certain conditions as described herein can occur. Examples include humans, monkeys, cows, sheep, goats, dogs, cats, mice, rats, and transgenic species thereof. In a preferred embodiment, the patient is a primate. In an even more preferred embodiment, the primate is a human. Other examples of subjects include experimental animals such as mice, rats, dogs, cats, goats, sheep, pigs, and cows. The experimental animal can be an animal model for a disorder, e.g., a transgenic mouse with an Alzheimer's-type neuropathology. A patient can be a human suffering from a neurodegenerative disease, such as Alzheimer's disease, or Parkinson's disease.

As used herein, the term "IC$_{50}$" refers to an inhibitory dose which is 50% of the maximum response obtained.

As used herein, the term "water soluble" means that the compound dissolves in water at least to the extent of 0.010 mole/liter or is classified as soluble according to literature precedence.

As used herein, predominantly one enantiomer means that the compound contains at least 95% of one enantiomer, or more preferably at least 98% of one enantiomer, or most preferably at least 99% of one enantiomer. For example, a compound may contain 99% (+)-TBE-31 and 1% (−)-TBE-31.

As used herein the specification, "a" or "an" may mean one or more. As used herein in the claim(s), when used in conjunction with the word "comprising" or "having," the words "a" or "an" may mean one or more than one. As used herein "another" may mean at least a second or more.

Other abbreviations used herein are as follows: DMSO, dimethyl sulfoxide; iNOS, inducible nitric oxide synthase; COX-2, cyclooxygenase-2; NGF, nerve growth factor; IBMX, isobutylmethylxanthine; FBS, fetal bovine serum; GPDH, glycerol 3-phosphate dehydrogenase; RXR, retinoid X receptor; TGF-β, transforming growth factor-β; IFN-γ, interferon-γ; LPS, bacterial endotoxic lipopolysaccharide; TNF-α, tumor necrosis factor-α; IL-1β, interleukin-1β; GAPDH, glyceraldehyde-3-phosphate dehydrogenase; MTT, 3-[4,5-dimethylthiazol-2-yl]-2,5-diphenyltetrazolium bromide; TCA, trichloroacetic acid; HO-1, inducible heme oxygenase.

III. Synthesis of TBEs

Although triterpenoids are widely used for medicinal purposes in many Asian countries, this class of molecules has not had an impact on the practice of Western medicine. Triteipenoids are formed in nature by the cyclization of squalene with the retention of all 30 carbon atoms in molecules such as oleanolic acid (OA) and ursolic acid (UA). Although OA and UA are known to have numerous pharmacological activities, including chemoprevention of cancer and anti-inflammatory activity in experimental animals, the potency of these naturally occurring molecules is relatively weak. Chemical synthesis of new steroid analogs has provided many useful derivatives that are more potent and specific than the natural parent structures. With this as a model, and considering the known anti-inflammatory and anticarcinogenic activities of OA and UA (Huang et al., 1994; Nishino et al., 1988; Hirota et al., 1990; Singh et al., 1992), the inventors have synthesized and characterized a series of synthetic triterpenoid analogs as potential inhibitors of inflammation and carcinogenesis, using inhibition of NO production induced by interferon-γ in mouse macrophages (iNOS assay) as a preliminary screening assay system (Ding et al., 1990; Bogdan et al., 1992).

TBEs can be synthesized from cheap commercially available reagents. Novel TBEs with various functionalities at various positions can be designed rationally as shown in Example 1. Water-soluble TBEs can be designed and synthesized as described below. Water solubility is possible because the hydrophobic part of TBEs is smaller than that of triterpenoids. The use of water-soluble compounds would reduce undesirable pharmacokinetics, limitations of administration methods, and considerable difficulty in developing formulations for clinical use.

In certain embodiments of this invention, the C-8a position of TBE-compounds (see below) were modified. Insertion of functionalities at C-8a should improve the potency and pharmacokinetics because the balance between hydrophilicity and hydrophobicity is shifted. Also, one can obtain water-soluble compounds by the insertion of appropriate functionalities. Although some biologically active natural products have functionalities at the same position [e.g., anti-tumor quassinoids (Cassady et al., 1980)], CDDO analogs, with functionalities at the same position, cannot be synthesized from oleanolic acid with ease.

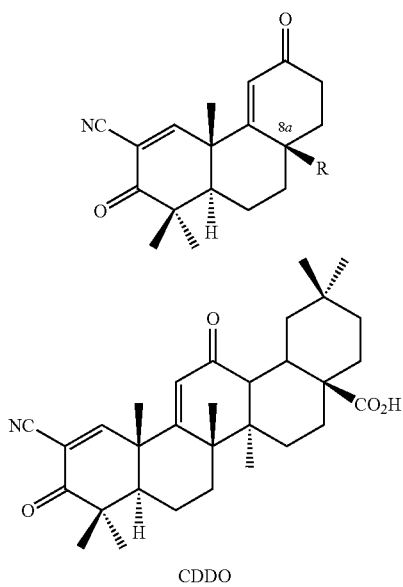

CDDO

The inventors have synthesized various C-8a functionalized TBE compounds using the simple tricycles 1a-1c, shown below, as starting materials, whose efficient synthesis has been established in Honda et al., 2005, which is incorporated herein by reference.

1a: R = CO₂H
1b: R = CO₂Me
1c: R = CH₂OH

A. Synthesis of (±)-TBE-31 and 34 in Racemic Form

Intermediate I is a key intermediate for the synthesis of various TBE-31 analogs. Scheme 1 shows the synthesis of Common Intermediate I.

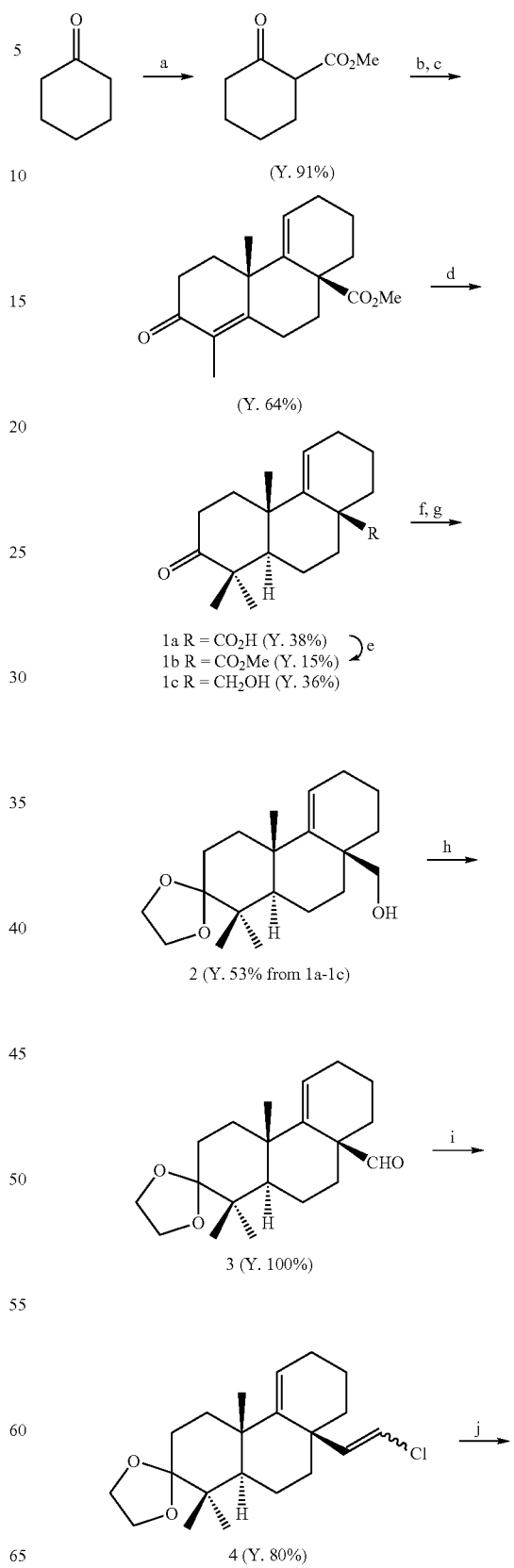

-continued

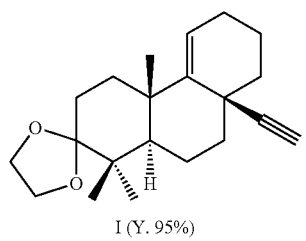

I (Y. 95%)

(a) Me₂CO₃, NaH, KH, THF; (b) 3-chloro-2-pentanone, Na, MeOH; (c) Cs₂CO₃, Me₂SO₄, DMF; (d) Li, NH₃, H₂O, CH₃I; (e) CH₂N₂, Et₂O, THF; (f) EG, PPTS, PhH; (g) LAH, Et₂O; (h) Swern oxidation; (i) Ph₃PCH₂Cl₂, n-BuLi, THF, HMPA; (j) MeLi, THF; aq NH₄Cl.

Compounds 1a-1c were obtained from cyclohexanone according to the method of Honda et al. 2005, which is incorporated herein by reference. Without separation, a mixture of 1a-1c was converted to a mixture of 1b and 1c with ethereal diazomethane. Compound 2 was obtained from the mixture of 1b and 1c by protection of their carbonyl groups with ethylene glycol (EG) in the presence of pyridinium p-toluenesulfonate (PPTS) in benzene (PhH) (Sterzycki, 1979), followed by LiAlH₄ reduction (53% yield from the mixture of 1a-1c). Swern oxidation (DMSO and oxalyl chloride, Omura and Swern, 1978) of 2 gave 3 in quantitative yield. Compound 4 was prepared in 80% yield as a mixture of E/Z chlorovinyl isomers by Wittig reaction on 3 with (chloromethyl)triphenylphosphonium chloride (Mella et al., 1988). Dehydrochlorination of 4 with methyl lithium, followed by quenching the acetylide with aqueous NH₄Cl solution afforded the common intermediate I in 95% yield (21% overall yield from cyclohexanone) (Mella et al., 1988). Noteworthy is that 100 g of I can be made from 160 g of cyclohexanone by this sequence.

TBE-31 and 34 in racemic form were synthesized from I by the sequence shown in Scheme 2.

-continued

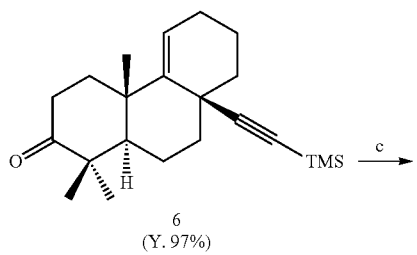

6
(Y. 97%)

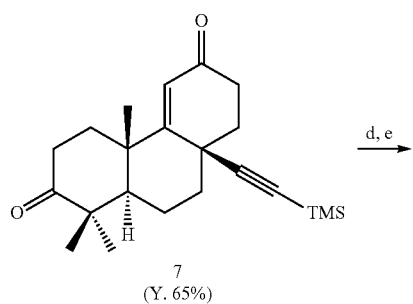

7
(Y. 65%)

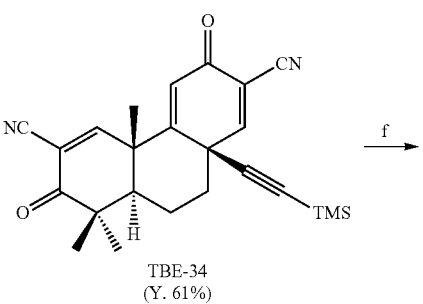

TBE-34
(Y. 61%)

(a) MeLi, THF; TMSCl; (b) aq. HCl, MeOH; (c) CrO₃, t-BuOOH, CH₂Cl₂; (d) p-TsCN, LDA, THF; (e) DDQ, PhH; (f) TBAF, THF

Scheme 2

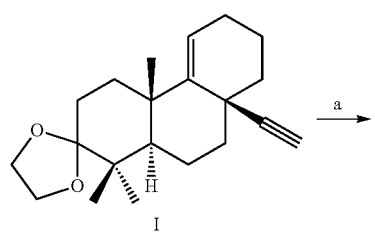

I

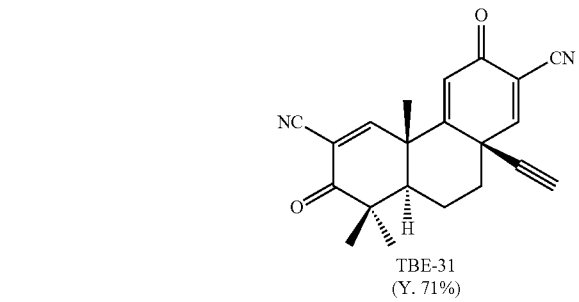

TBE-31
(Y. 71%)

(a) MeLi, THF; TMSCl; (b) aq. HCl, MeOH; (c) CrO₃, t-BuOOH, CH₂Cl₂; (d) p-TsCN, LDA, THF; (e) DDQ, PhH; (f) TBAF, THF

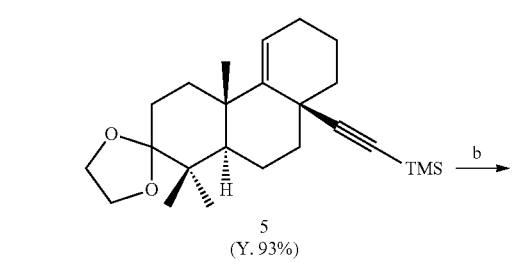

5
(Y. 93%)

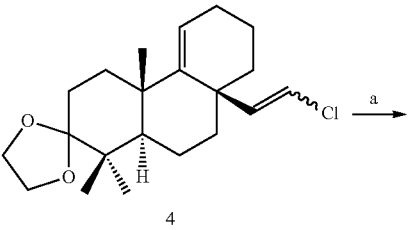

4

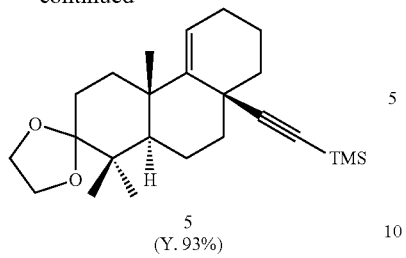

5
(Y. 93%)

Treatment of lithium acetylide of I with chlorotrimethylsilane (TMSCl) gave 5 in 93% yield. Deketalization of 5 afforded 6 in 97% yield. Enone 7 was prepared in 65% yield by a chromium-mediated allylic oxidation of 6 (Muzart, 1987). TBE-34 was obtained in 61% yield by double cyanation of 7 with lithium diisopropylamide (LDA) and p-toluenesulfonyl cyanide (p-TsCN) (Kahne et al., 1981), followed by 2,3-dichloro-5,6-dicyanobenzoquinone (DDQ) oxidation (36% overall yield from I). The TMS group was removed by tetra(n-butyl)ammonium fluoride (TBAF) (Cai et al., 1995) to give TBE-31 in 71% yield (25% overall yield from I). Also, intermediate 5 was directly made in 93% yield from 4 using Corey's method (Corey et al., 1973) without going through intermediate I.

B. Synthesis of Optically Active (−)- and (+)-TBE-31 and 34

Optically active (−)- and (+)-TBE-31 and 34 were synthesized by the sequence shown in Scheme 3.

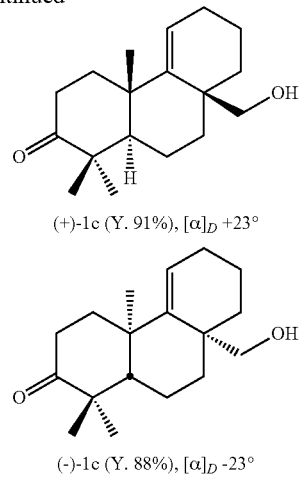

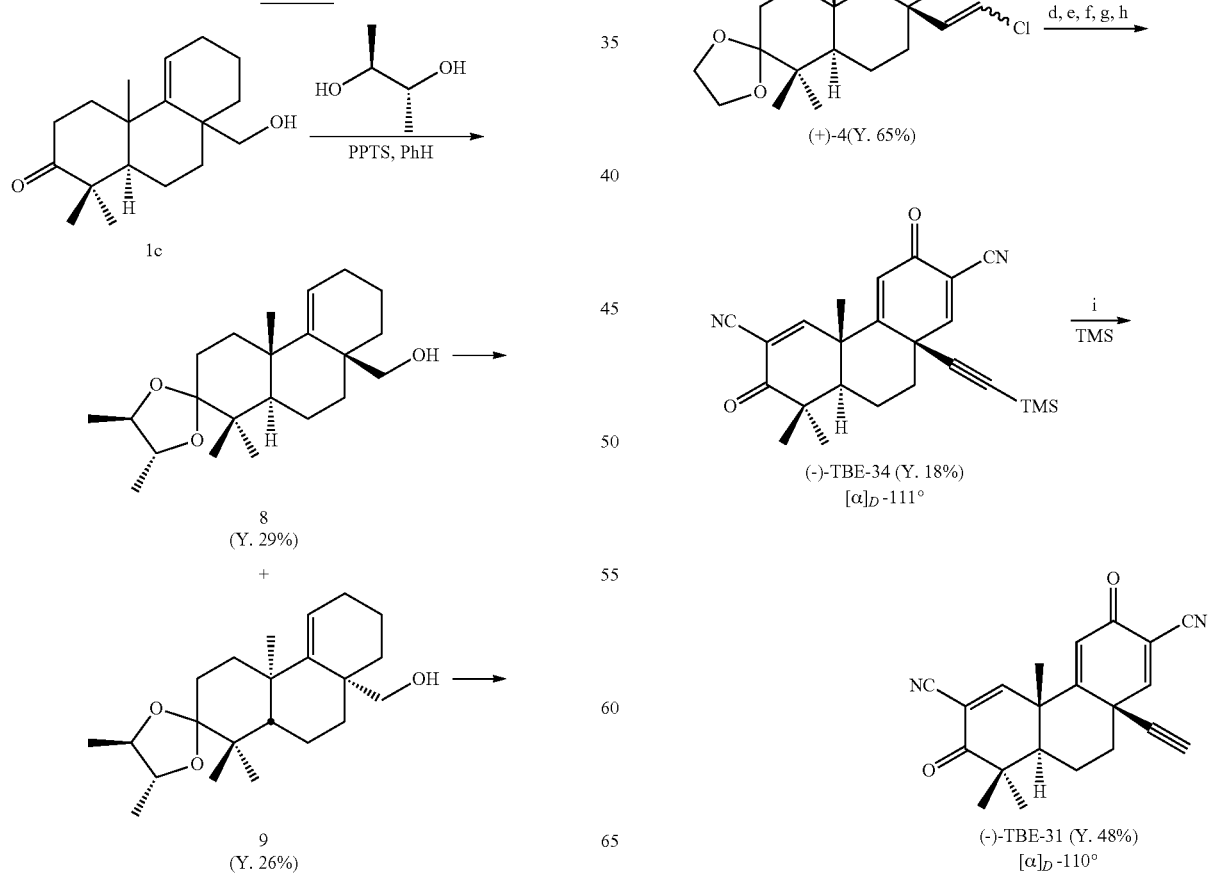

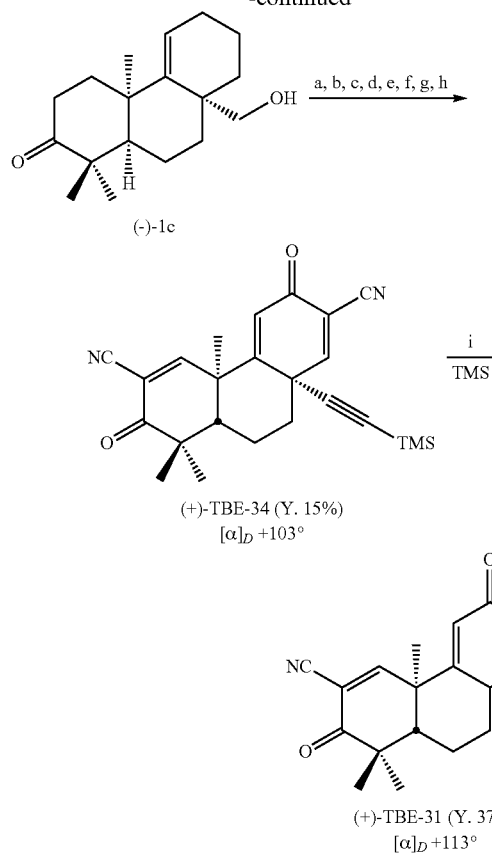

(a) EG, PPTS, PhH; (b) Swern oxidation; (c) Ph₃PCH₂Cl₂, n-BuLi, THF, HMPA; (d) MeLi, THF; TMSCl; (e) aq. HCl, MeOH; (f) CrO₃, t-BuOOH, CH₂Cl₂; (g) p-TsCN, LDA, THF; (h) DDQ, PhH; (i) TBAF, THF The resolution of alcohol 1c was carried out in the manner described by Grieco (Grieco and Speake, 1998). Treatment of 1c with the chiral diol, (−)-(R,R)-2,3-butanediol afforded the pair of diastereomers 8 and 9. Separation of the two diastereomers was achieved by iterative flash column chromatography to give diastereomer 8 (including 8% of 9) in 29% yield and diastereomer 9 (including 10% of 8) in 26% yield. The diastereomeric purity was determined by $^1$H NMR (300 MHz, CDCl₃) using the integration values of the methyl signals (δ 0.92 and 0.88 of 8, and 0.96 and 0.86 of 9) for the two diasteromers.

Diastereomer 8 was then treated with acidic methanol and the resulting ketone (+)-1c was obtained in 91% yield. Similarly, the other diastereomer 9 gave (−)-1c in 88% yield under the same conditions. Based on the diastereomeric purity, we concluded that (+)-1c includes 8% of (−)-1c (enantiomeric excess (ee), 84%) and (−)-1c includes 10% of (+)-1c (ee, 80%). The CD values for the two enantiomers (+)-1c and (−)-1c are $\Delta_{288}$=+0.22, and $\Delta_{288}$=−0.22 respectively. Based on these CD values and application of the octant rule (Charney, 1979), we have determined that (+)-1c has the same configuration as that of CDDO and (−)-1c has the opposite configuration.

Enantiomer (+)-1c was treated with ethylene glycol and PPTS to give the protected ketone, which was subjected to Swern oxidation with oxalyl chloride and dimethyl sulfoxide. A Wittig reaction of the resulting aldehyde with (chloromethyl) triphenylphosphonium chloride afforded the alkenyl chloride (+)-4 in 65% yield. Treatment of (+)-4 with methyl lithium and quenching of the resulting anion by TMSCl gave the TMS protected acetylene. Deprotection of the ketal group was followed by a chromium mediated allylic oxidation with t-butyl hydroperoxide which afforded the enone. Double cyanation of the enone with LDA and p-TsCN gave the dinitrile intermediate, which was oxidized by DDQ in benzene to give the desired compound (−)-TBE-34 in 18% yield. Removal of the TMS group was achieved by treatment of (−)-TBE-34 with TBAF to give (−)-TBE-31 in 48% yield.

(+)-TBE-34 was obtained from (−)-1c in 15% yield by the same procedure used to obtain (−)-TBE-34 from (+)-1c. Removal of the TMS group from (+)-TBE-34 with TBAF afforded the desired (+)-TBE-31 in 37% yield.

C. Design and Synthesis of New TBE-31 Analogs Using Alkyl Lithium

As shown below, TBE-31 analogs having the structure III, shown below, can be synthesized from compounds having the structure II, also shown below, which is obtained from compound I using alkyl lithium (n-BuLi, MeLi and so on) and R₁X (nucleophilic substitution). TBE-34 (intermediate of TBE-31), TBE-35, 36, 38, and 39 have been prepared in this fashion.

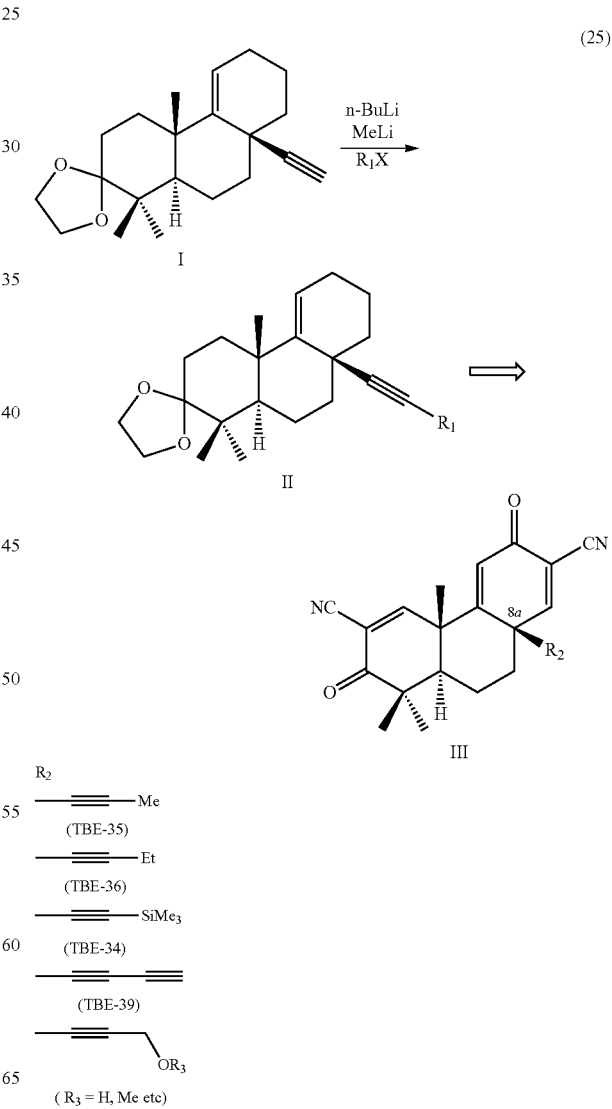

-continued

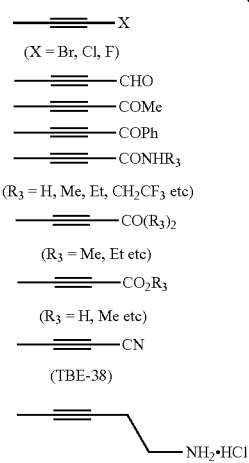

The specific synthetic methods of obtaining TBE-35, 36, 38, and 39 are shown in Schemes 4-7, respectively.

Scheme 4 shows the synthesis of TBE-35 from I.

Scheme 4

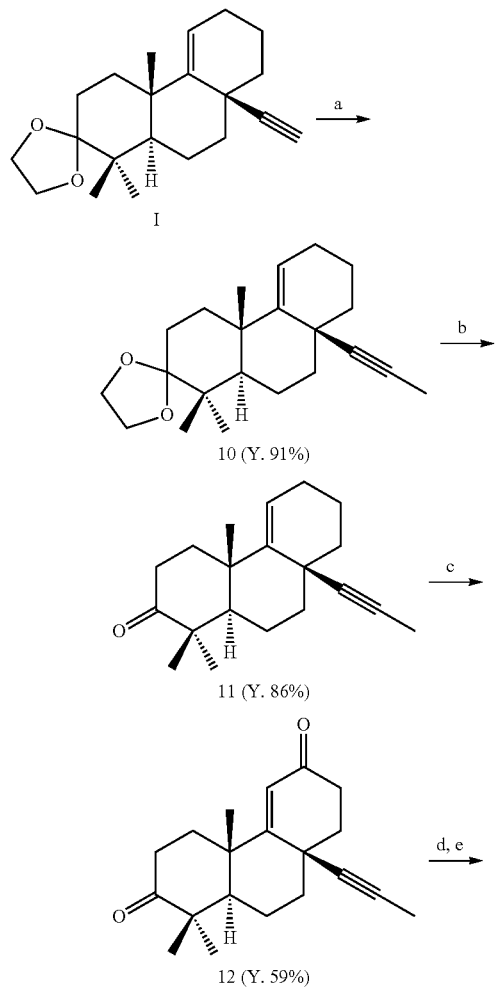

-continued

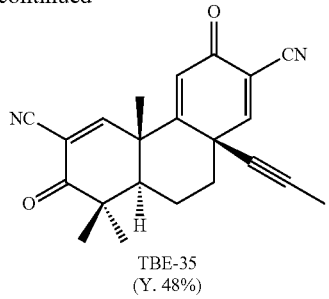

TBE-35
(Y. 48%)

(a) MeLi, THF; MeI; (b) aq. HCl, MeOH; (c) CrO₃, t-BuOOH, CH₂Cl₂; (d) p-TsCN, LDA, THF; (e) DDQ, PhH.

Insertion of the methyl group into the acetylene moiety was achieved by treating the intermediate I with methyl lithium and trapping the resulting anion with methyl iodide, to give 10 in 91% yield. The ketal 10 was subjected to acidic conditions to give the ketone 11 in 86% yield. Allylic oxidation of 11 afforded the enone 12 (59% yield). Double cyanation of 12 with LDA and p-TsCN gave the dinitrile, which was reacted with DDQ in benzene to give the desired compound TBE-35 in 48% (22% overall yield from I).

Scheme 5 shows the synthesis of TBE-36 from I.

Scheme 5

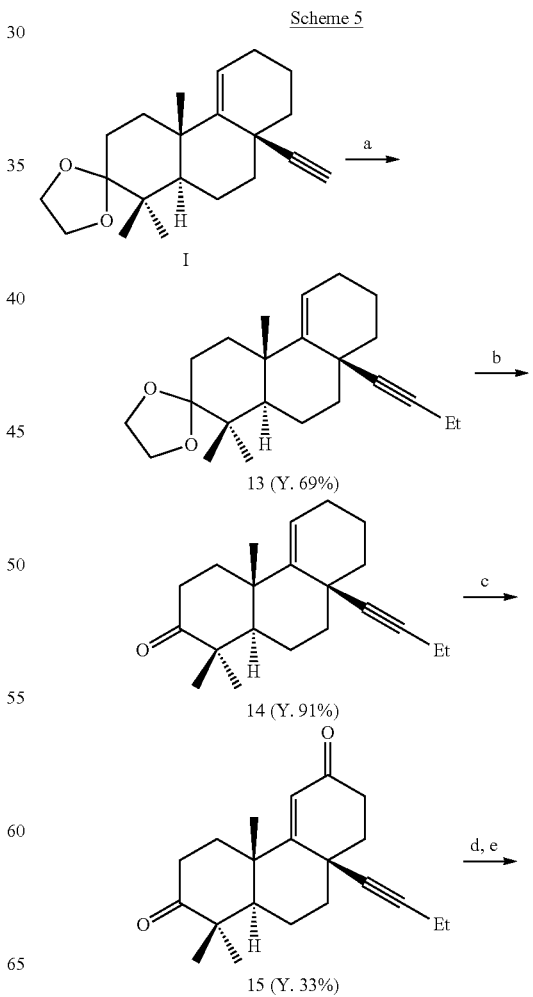

51
-continued

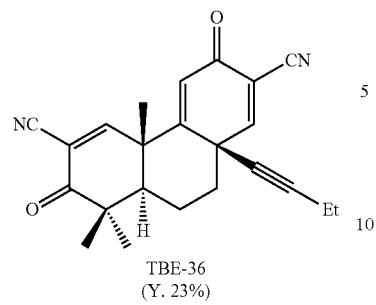

TBE-36
(Y. 23%)

(a) MeLi, THF; EtI; (b) aq. HCl, MeOH; (c) CrO₃, t-BuOOH, CH₂Cl₂; (d) p-TsCN, LDA, THF; (e) DDQ, PhH.

Reaction of compound I with MeLi and iodoethane gave the ethyl acetylene 13 in 69% yield. Compound 13 was treated with aqueous HCl solution to give the ketone 14 in 91% yield. Allylic oxidation of 14 afforded the diketone 15 in 33% yield. Treatment of 15 with LDA and p-TsCN gave the dinitrile intermediate, which was subjected to oxidation by DDQ in benzene to give the desired compound TBE-36 in 23% yield (5% overall yield from I).

Scheme 6 shows the synthesis of TBE-38 from I.

52
-continued

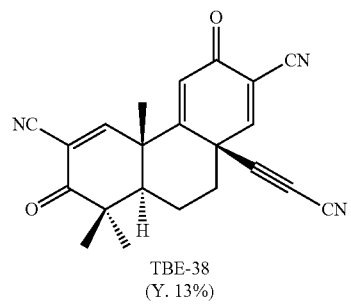

TBE-38
(Y. 13%)

(a) n-BuLi, THF; PhOCN; (b) aq. HCl, MeOH; (c) CrO₃, t-BuOOH, CH₂Cl₂; (d) p-TsCN, LDA, THF; (e) DDQ, PhH.

Treatment of lithium acetylide of I with phenyl cyanate (PhOCN) afforded 16 in 64% yield (Murray et al., 1980). Deketalization of 16 gave 17 in 96% yield. Allylic oxidation of 17 gave 18 in 53% yield. Double cyanation of 18, followed by DDQ oxidation gave TBE-38 in 13% yield (4% overall yield from I).

Scheme 7 shows the synthesis of TBE-39 from I.

Scheme 6

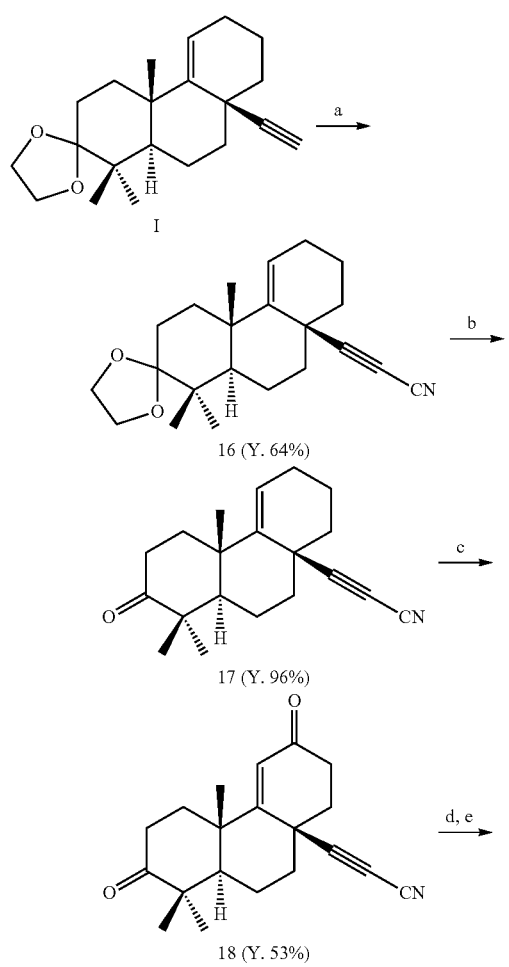

Scheme 7

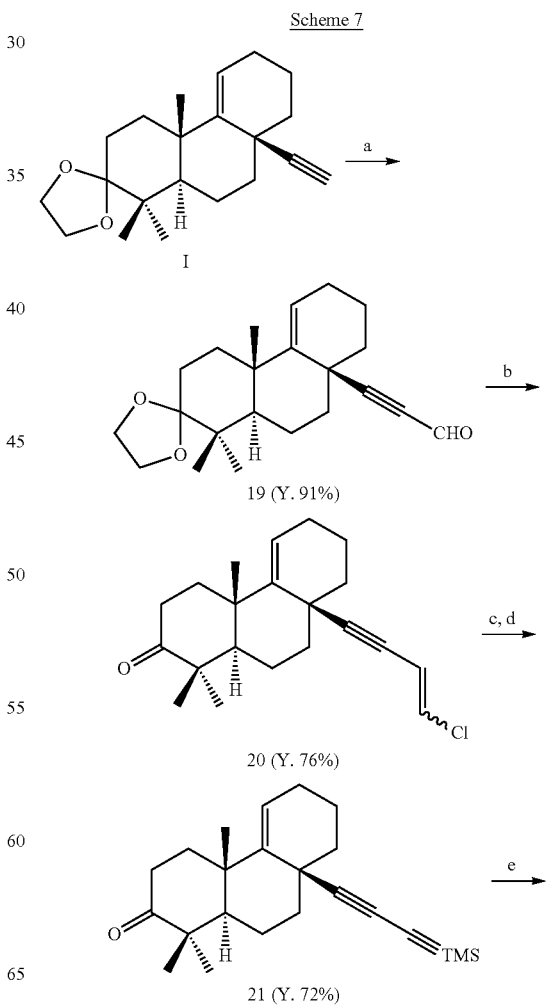

53

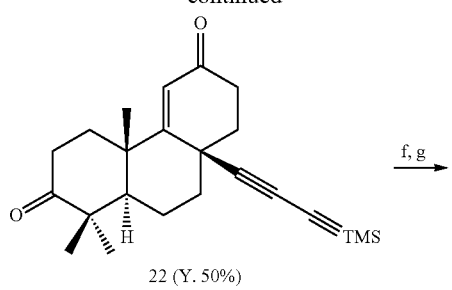

22 (Y. 50%)

f, g

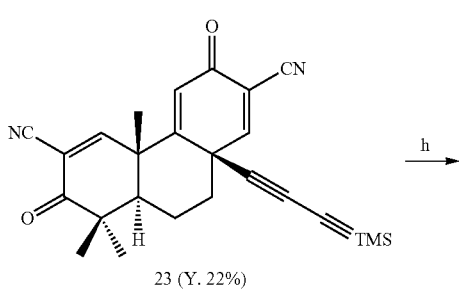

23 (Y. 22%)

h

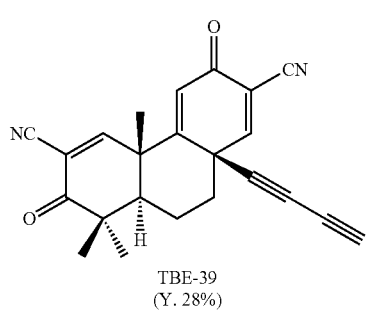

TBE-39
(Y. 28%)

(a) n-BuLi, BF₃Et₂O, DMF, THF; (b) Ph₃PCH₂Cl₂, n-BuLi, HMPA, THF;
(c) MeLi, THF, TMSCl; (d) aq. HCl, MeOH; (e) CrO₃, t-BuOOH, CH₂Cl₂;
(f) p-TsCN, LDA, THF; (g) DDQ, PhH; (h) TBAF, THF.

The aldehyde 19 was obtained by the formylation of alkyne I with dimethylformamide and boron triflouride etherate in 91% yield (Iguchi et al, 1993). The Wittig reaction of aldehyde 19 with (chloromethyl)triphenylphosphonium chloride gave the alkenyl chloride 20 in 76% yield. Treatment of 20 with methyl lithium and quenching of the resulting anion with TMSCl yielded the TMS protected alkyne. Treatment of this alkyne with aqueous HCl solution afforded the ketone 21 in 72% yield. Allylic oxidation of 21 gave the enone 22 in 50% yield. Double cyanation of 22 with p-TsCN gave the dinitrile intermediate, which was subsequently oxidized with DDQ to give the bis-enone 23 in 22% yield. Removal of the TMS group with TBAF gave the desired compound TBE-39 in 28% yield (2% overall yield from I).

As an amine hydrochloride, compound 25, shown below, would be water-soluble, making this compound very interesting. The synthetic plan is shown in Scheme 8.

54

Scheme 8

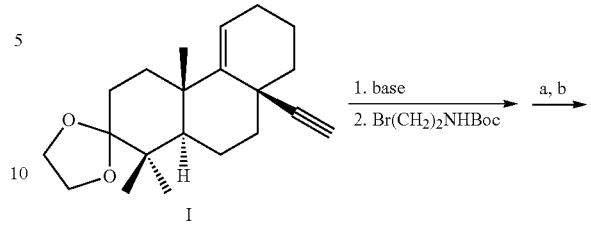

I 1. base
2. Br(CH₂)₂NHBoc a, b

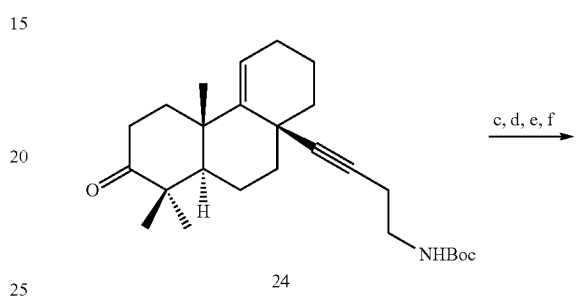

24 c, d, e, f

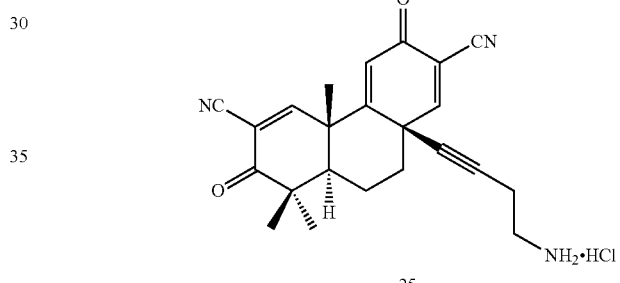

25

(a) PPTS, acetone; (b) Boc₂O; (c) CrO₃, t-BuOOH, CH₂Cl₂; (d) p-TsCN, LDA, THF; (e) DDQ, PhH; (f) HCl Compound 24 can be synthesized by treatment of acetylide of I with commercially available Br(CH₂)₂NHBoc, followed by deketalization and subsequent protection with Boc₂O. Compound 25 can be obtained from 24 by the same sequence (allylic oxidation, double cyanation, and DDQ oxidation) as for other TBEs, followed by deprotection with HCl.

D. Design and Synthesis of New TBE-31 Analogs Using Sonogashira Coupling

Sonogashira coupling of acetylene with aryl halide and/or vinyl halide using palladium complex (e.g. PdCl₂(PPh₃)₂) and CuI is a very useful reaction for the synthesis of various acetylene derivatives (Sonogashira et al., 1975). Compounds having structure III can be synthesized by Sonogashira coupling, as shown in Scheme 9. Also, it is possible to synthesize compounds having the structure III, directly from TBE-31. Sonogashira coupling provides a more convergent synthetic approach, allowing for the exploration of various compounds having the structure III.

Scheme 9
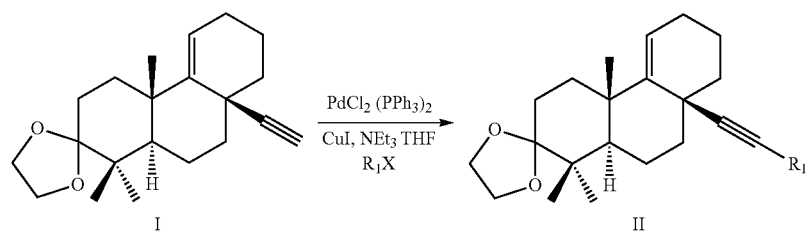
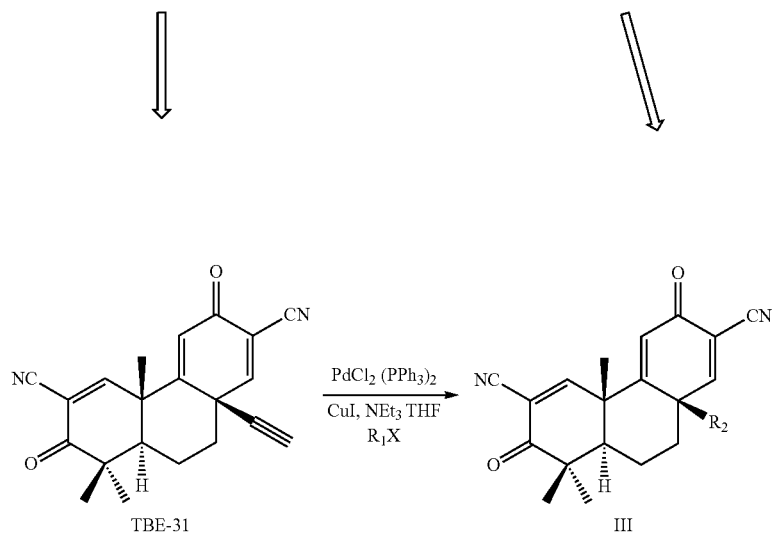
($R_1$ = aryl, vinyl, X = halogen)
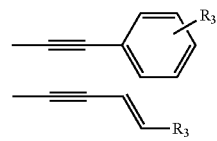
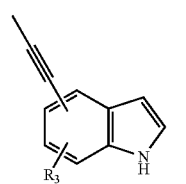
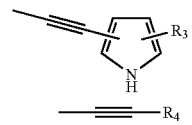
($R_4$ = aromatic heterocycles)
The synthetic plan of compound 29 is shown in Scheme 10. Compound 26 was successfully synthesized in 64% yield from I using Sonogashira coupling. Deketalization of 26 can give 27. Allylic oxidation of 27 can afford enone 28. Double cyanation of 28, followed by DDQ oxidation can give compound 29.

Scheme 10
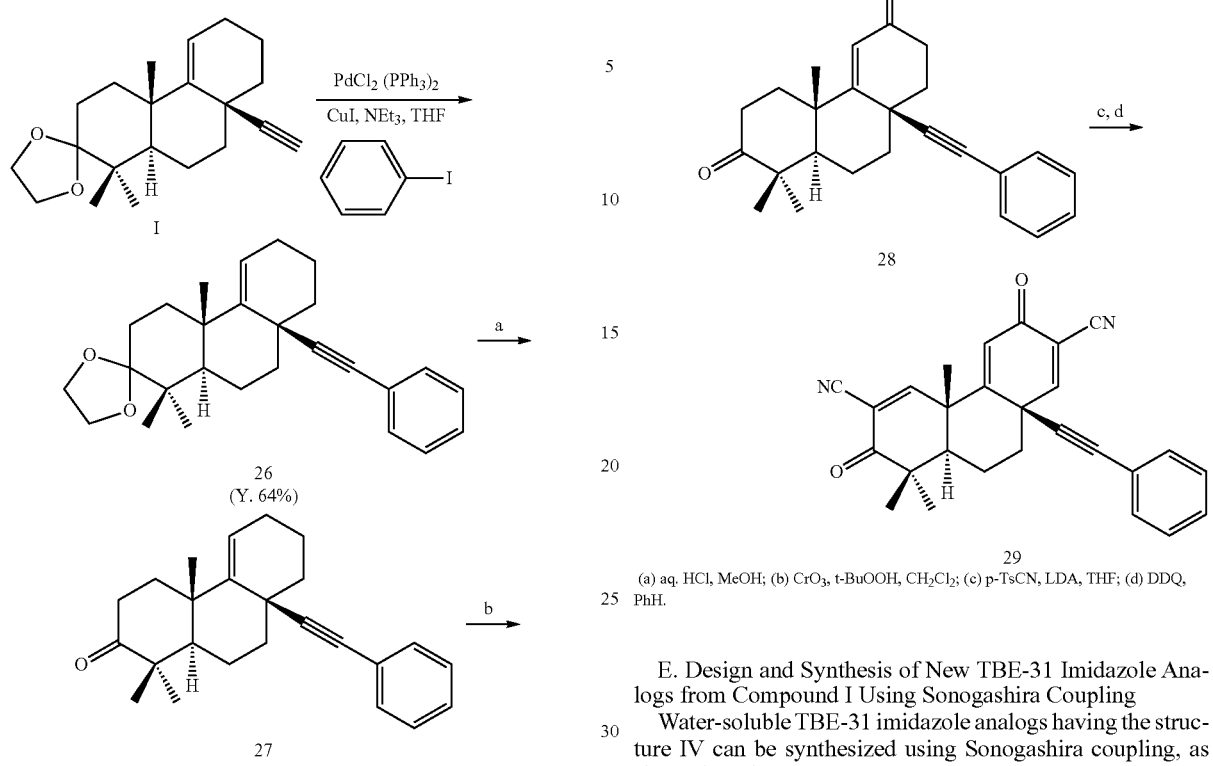
(a) aq. HCl, MeOH; (b) CrO₃, t-BuOOH, CH₂Cl₂; (c) p-TsCN, LDA, THF; (d) DDQ, PhH.
E. Design and Synthesis of New TBE-31 Imidazole Analogs from Compound I Using Sonogashira Coupling
Water-soluble TBE-31 imidazole analogs having the structure IV can be synthesized using Sonogashira coupling, as shown in Scheme 11.
Scheme 11
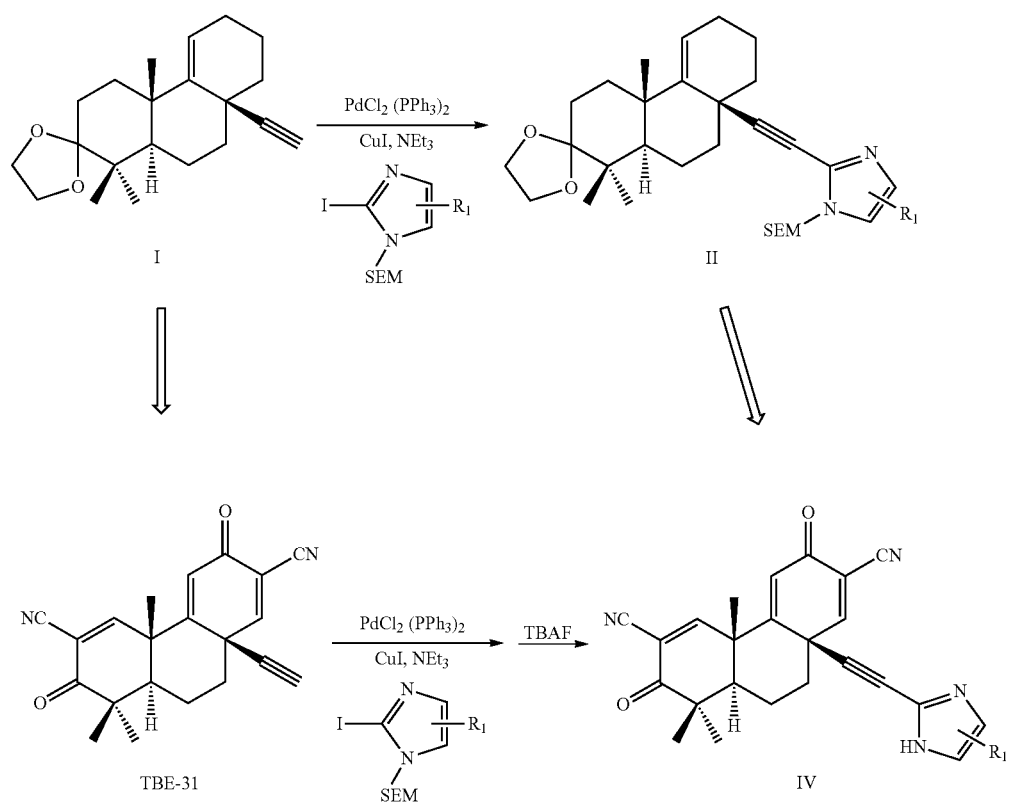

The synthetic plan of compound 34 is shown in Scheme 12. Imidazole hydrochloride 34 is expected to be water-soluble. Compounds 30 was synthesized in 73% yield from I by Sonogashira coupling using iodo-SEM-imidazole (Paul et al. 2002). Deketalization of 30 gave 31 in 70% yield. Allylic oxidation of 31 can give 32. Double cyanation of 32, followed by DDQ oxidation can afford 33. The desired compound 34 can be obtained by removal of SEM group of 33.

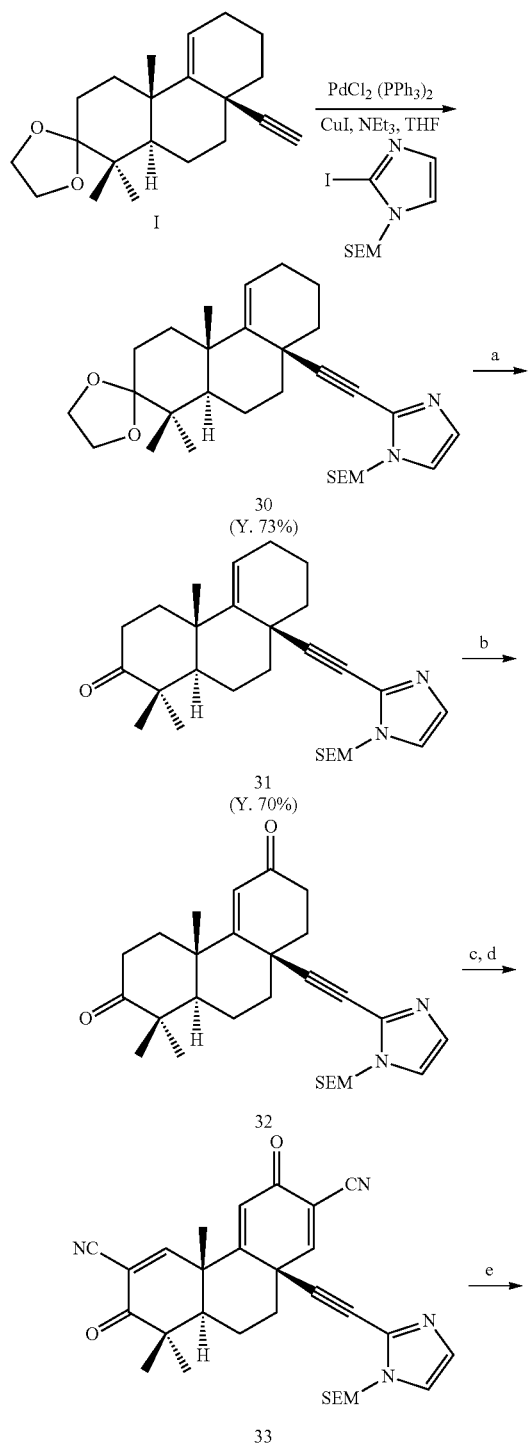

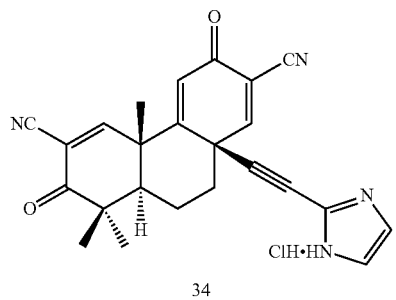

(a) aq. HCl, MeOH; (b) CrO₃, t-BuOOH, CH₂Cl₂; (c) p-TsCN, LDA, THF; (d) DDQ, PhH; (e) TBAF, THF.

F. Design and Synthesis of New TBE-31 Analogs from Compound I Using Mannich Reactions Water-soluble TBE-31 analogs with amino side chains (38, 42, and so on) can be synthesized using Mannich reactions. Analogs 38 and 42 can be synthesized by the sequence shown in Schemes 13 and 14.

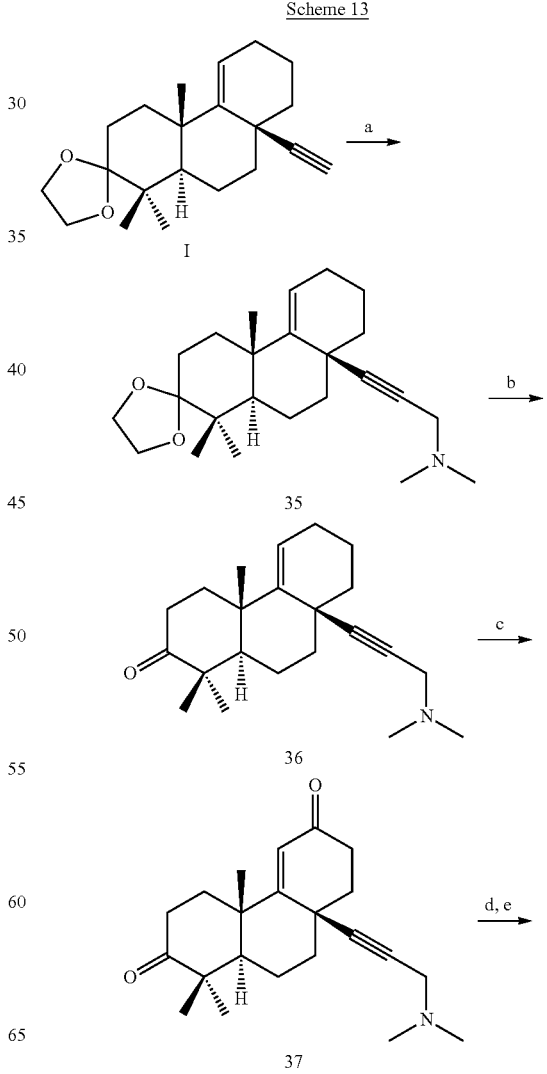

-continued

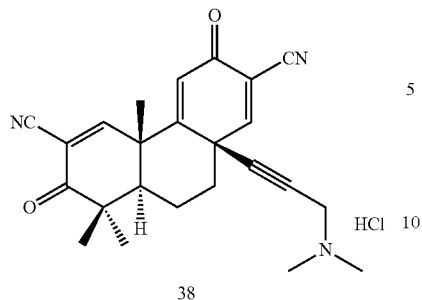

38

(a) (Me$_2$N)$_2$CH$_2$, CuCl, THF; (b) aq. HCl, MeOH; (c) CrO$_3$, t-BuOOH, CH$_2$Cl$_2$; (d) p-TsCN, LDA, THF; (e) DDQ, PhH; HCl, dioxane.

The Mannich reaction of I with bis(dimethylamino)methane (Amstutz et al., 1987; Chung et al., 1990) under the catalysis of CuCl in refluxing THF can afford 35. Compound 38 can be obtained from 35 by the same sequence as for other TBEs.

Scheme 14

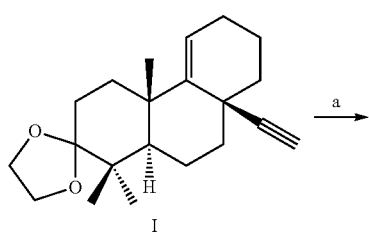

I

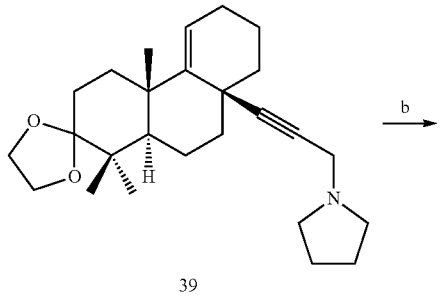

39

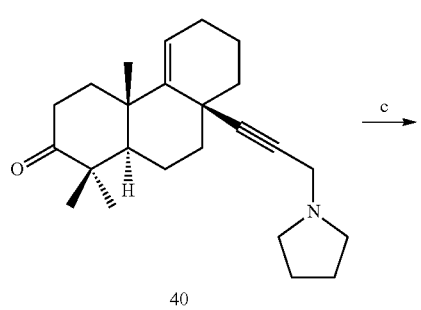

40

-continued

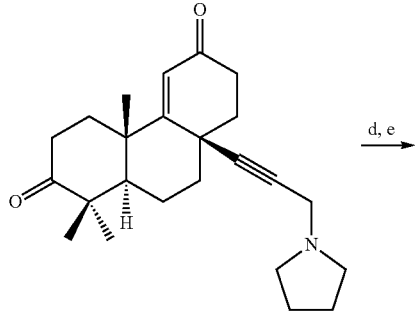

41

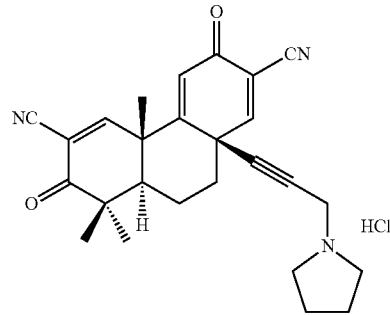

42

(a) HCHO, pyrrolidine, CuCl, THF; (b) aq. HCl, MeOH; (c) CrO$_3$, t-BuOOH, CH$_2$Cl$_2$; (d) p-TsCN, LDA, THF; (e) DDQ, PhH; HCl, dioxane.

Compound 39 can be synthesized by the Mannich reaction using formaldehyde and pyrrolidine under the catalysis of CuCl. Compound 42 can be obtained from 39 by the same sequence as for other TBEs.

G. Design and Synthesis of New TBE-31 Analogs with a Carboxyl Group in Ring A

Compound 48 can be synthesized by the sequence shown in Scheme 15.

Scheme 15

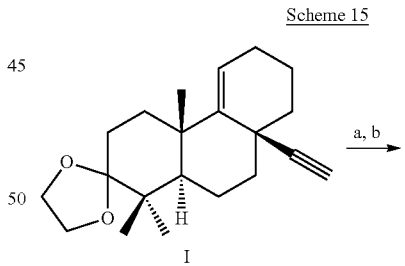

I

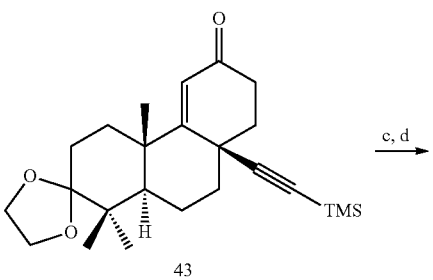

43

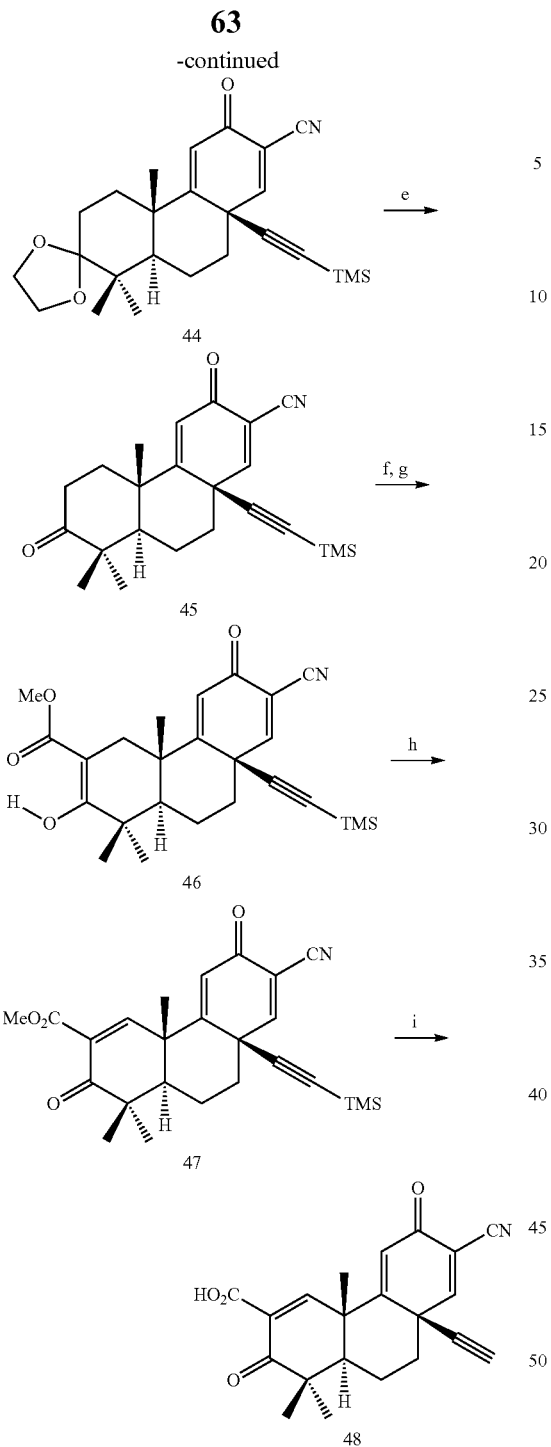

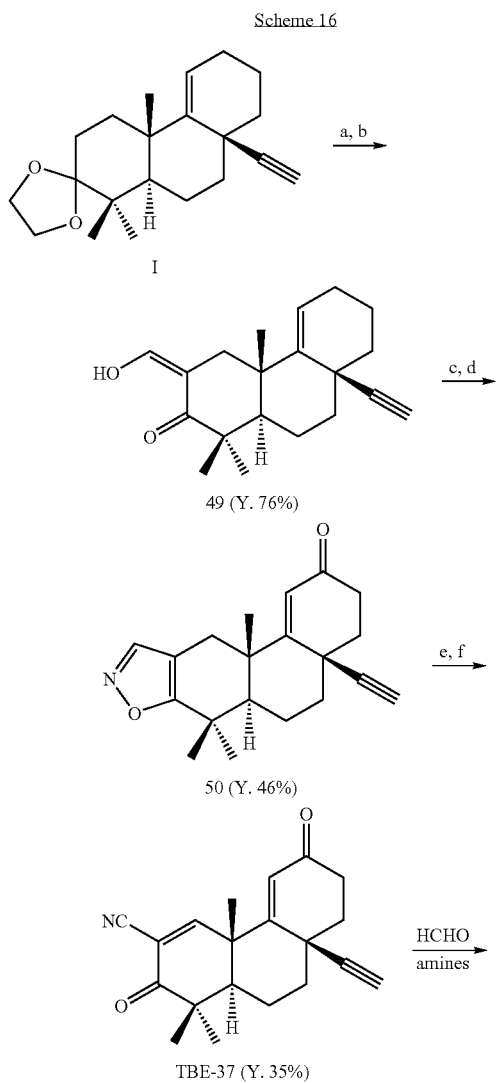

(a) MeLi, LDA, THF; TMSCl; (b) CrO₃, t-BuOOH, CH₂Cl₂; (c) p-TsCN, LDA, THF; (d) DDQ, PhH; (e) PPTS, acetone; (f) Stiles' reagent, DMF; (g) CH₂N₂; (h) PhSeCl, pyr., H₂O₂; (i) K₂CO₃.

Compound 43 can be synthesized by treatment of acetylide of I with TMSCl, followed by allylic oxidation. Cyanation of 43, followed by DDQ oxidation can afford 44. After removal of ketal of 44, 46 can be obtained from 45 by Stiles' reagent (Finkbeiner et al., 1963), followed by methylation. Addition of phenylselenyl chloride (PhSeCl), followed by oxidation/elimination with H₂O₂ can give 47 (Liotta et al., 1981). The desired compound 48 can be prepared by treatment of 47 with K₂CO₃-MeOH-water (Cai et al., 1995).

H. Design and Synthesis of New TBE-31 Analogs Containing Amino Side Chains from Compound I A series of analogs with a C-8a alkyne group and C-7 amino side chains having general formula V (Scheme 16) was designed for the following reasons. In many cases, amine side chains like pyrrolidine, piperidine, imidazole etc. affect biological properties, e.g., potency and pharmacokinetics of the parent compounds. Also, salts of these amines would be soluble in water. Thirdly, because one Michael acceptor is diminished in these analogs in comparison with TBE-31 analogs, side effects and/or toxicity, which might be caused by Michael acceptors, may be reduced. They can be synthesized from TBE-37 by Mannich reactions with amines and formaldehyde under basic or acidic conditions. TBE-37 was synthesized from I. Compound 49 was obtained in 76% yield from I by deketalization, followed by formylation with ethyl formate in the presence of sodium methoxide in benzene (Clinton et al., 1961). Treatment of 49 with hydroxylamine (Johnson et al., 1945), followed by allylic oxidation gave 50 in 46% yield. TBE-37 was prepared by cleavage of the isoxazole of 50 with sodium methoxide (Johnson et al., 1945), followed by DDQ oxidation (12% overall yield from I).

Scheme 16

-continued

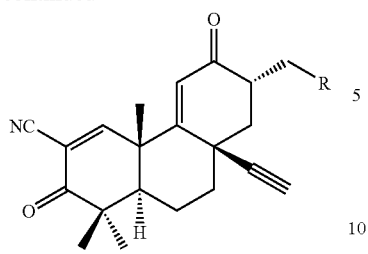

V:R = NMe$_2$, NEt$_2$

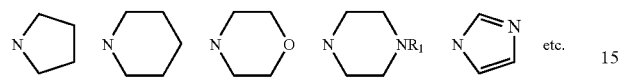

I. The Design and Synthesis of Compound 60 Using Kowalski Ester Homologation

Compound 60, shown below, which has a three carbon chain including the terminal acetylene group at C-8a (contrast with TBE-31, which has a two carbon chain) can be made using the Kowalski method (Kowalski et al., 1992), shown in Scheme 17. Ketalization of 1b can give 51. Compound 51 can be converted to 52 by the Kowalski method. Compound 54 can be obtained from 52 by LiAlH$_4$ reduction, followed by Swern oxidation. Compound 60 can be synthesized via intermediate VI from 54 by the same sequence as for TBE-31. Intermediate VI is a key intermediate as well as I.

Scheme 17

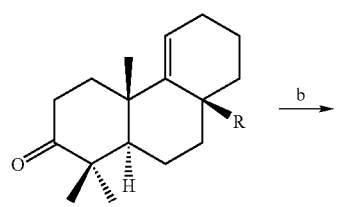

1a R = CO$_2$H  
1b R = CO$_2$Me   } a

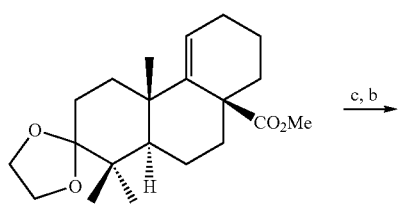

51

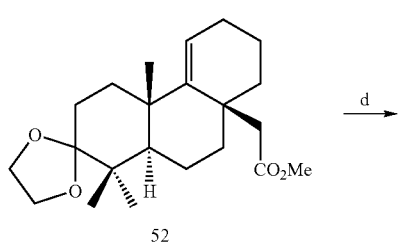

52

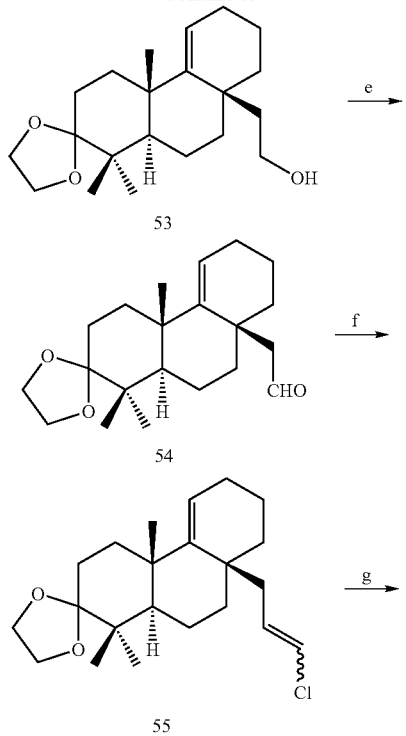

53

54

55

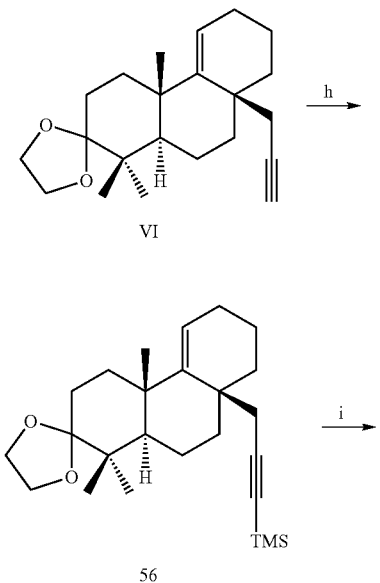

VI

56

57

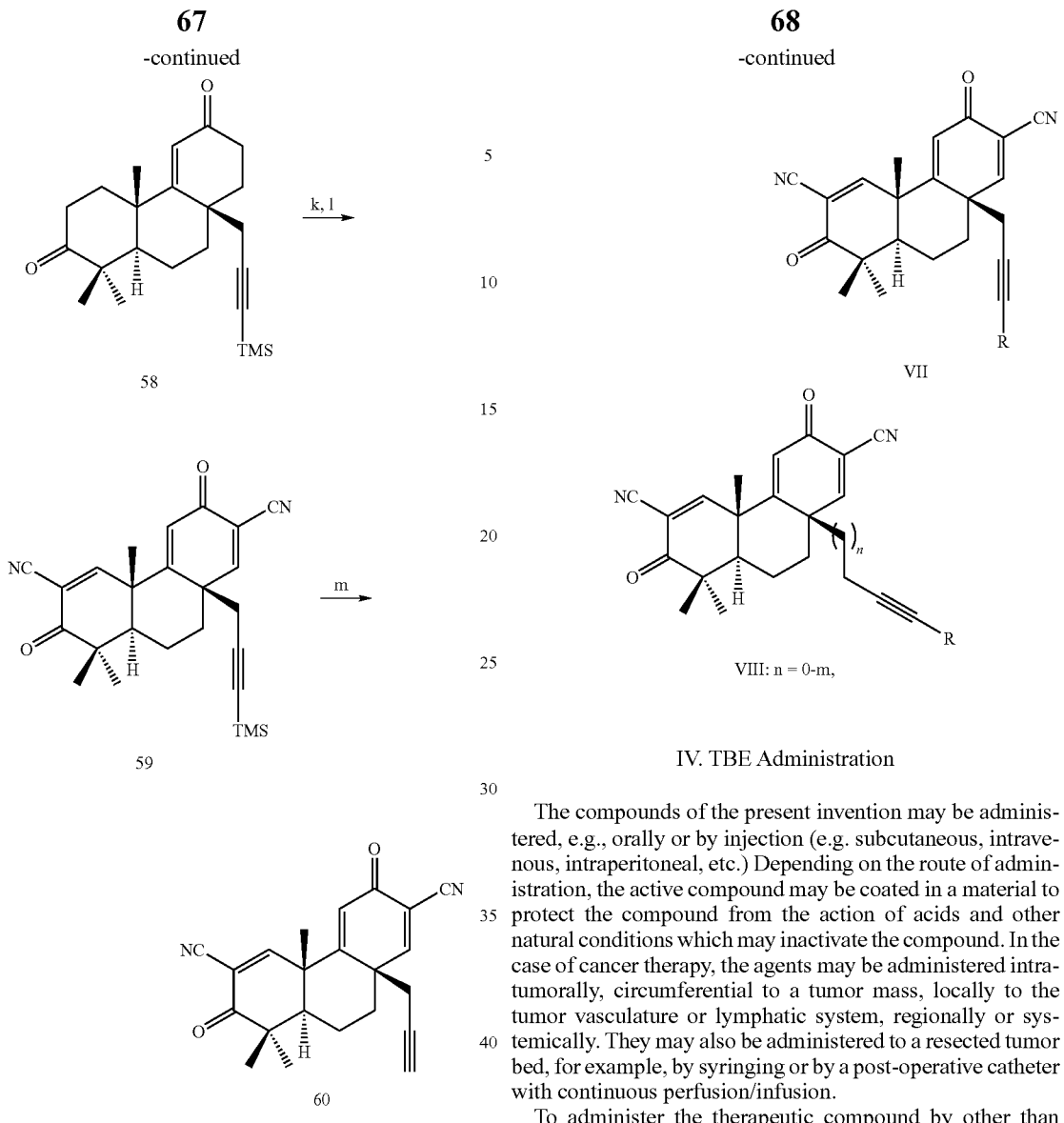

(a) CH₂N₂, Et₂O, THF; (b) ethylene glycol, PPTS, PhH; (c) CH₂Br₂, LiTMP; LiHMDS; s-BuLi; n-BuLi; MeOH, HCl (Kowalski method); (d) LAH, Et₂O; (e) Swern oxidation; (f) Ph₃PCH₂Cl₂, n-BuLi, THF, HMPA; (g) MeLi, THF; aq NH₄Cl; (h) MeLi, THF; TMSCl; (i) aq. HCl, MeOH; (j) CrO₃, t-BuOOH, CH₂Cl₂; (k) p-TsCN, LDA, THF; (l) DDQ, PhH; (m) TBAF, THF Various analogs of compound VII can be prepared from compound VI using the same procedure as used for TBE-31 analogs (Scheme 18). Also, if one were to repeat the Kowalski method for 51, one can synthesize analogs shown in general formula VIII.

Scheme 18

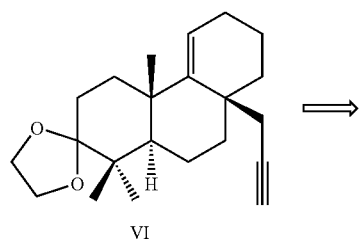

VI

IV. TBE Administration

The compounds of the present invention may be administered, e.g., orally or by injection (e.g. subcutaneous, intravenous, intraperitoneal, etc.) Depending on the route of administration, the active compound may be coated in a material to protect the compound from the action of acids and other natural conditions which may inactivate the compound. In the case of cancer therapy, the agents may be administered intratumorally, circumferential to a tumor mass, locally to the tumor vasculature or lymphatic system, regionally or systemically. They may also be administered to a resected tumor bed, for example, by syringing or by a post-operative catheter with continuous perfusion/infusion.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

Compounds of the invention may also be formulated for local administration, e.g., for topical administration to the skin or mucosa, for topical administration to the eye, for delivery to the lungs by inhalation, or by incorporation into a biocompatible matrix for controlled release to a specified site over an extended period of time (e.g., as an active ingredient in a drug-eluting cardiac stent). In certain cases significant systemic concentrations may also be achieved by these routes of administration (e.g., via pulmonary or transmucosal delivery).

Active compounds are administered at a therapeutically effective dosage sufficient to treat a condition associated with a condition in a patient. A "therapeutically effective amount" preferably reduces the amount of symptoms of the condition in the infected patient by at least about 20%, more preferably by at least about 40%, even more preferably by at least about 60%, and still more preferably by at least about 80% relative to untreated subjects. For example, the efficacy of a compound can be evaluated in an animal model system that may be predictive of efficacy in treating the disease in humans, such as the model systems shown in the examples and drawings.

V. TBE Uses and Mechanisms

These TBE compounds of the present invention have utility for prevention and treatment of cancer, inflammation, Alzheimer's disease, Parkinson's disease, multiple sclerosis, amyotrophic lateral sclerosis, rheumatoid arthritis, and inflammatory bowel disease, all other diseases whose pathogenesis is believed to involve excessive production of either nitric oxide or prostaglandins, and pathologies involving oxidative stress alone or oxidative stress exacerbated by inflammation.

The practice of the present invention will employ, unless otherwise indicated, conventional techniques of cell biology, cell culture, molecular biology, microbiology, recombinant DNA, medicine, pharmacology and immunology, which are within the skill of the art. Such techniques are explained fully in the literature. See, for example, Sambrook et al., 1989; Ausubel et al., 1994; Glover, 1985; Gait, 1984; U.S. Pat. No. 4,683,195; Hames and Higgins, 1985; Mayer and Walker, 1988; Weir and Blackwell, 1986.

A. Use of TBEs for the Treatment and Prevention of Cancer

In particular, the present invention may be applied to therapy of such cancers as breast, prostate, lung (SCLC and NSCLC), brain, head & neck, esophagus, trachea, stomach, colon, rectum, uterus, cervix, prostate, liver, pancreas, skin, blood and lymphatic system, testes and ovary. The compounds of this invention may be applied as a single-agent for the treatment of cancer or they may be applied to treat cancer in combination with other agents or methods of treatment. For example, FIG. 1 shows that a series of TBEs are potent inhibitors of the growth of both human myeloma cells and human leukemia cells.

The invention contemplates that the compounds of the present invention, will function, through one or more of the mechanisms described below and throughout this application to induce apoptosis in tumor cells, induce differentiation, inhibit cancer cell proliferation, inhibit inflammatory response, and/or function in a chemopreventative capacity.

Further disclosed herein are the synthesis and biological activities of new TBE compounds that have important properties including: (1) the ability to induce apoptosis and differentiate both malignant and non-malignant cells, (2) activity at sub-micromolar or nanomolar levels as an inhibitor of proliferation of many malignant or premalignant inhibitors of proliferation of many malignant or premalignant cells, (3) significantly greater activity than most compounds in suppressing the de novo synthesis of the inflammatory enzyme inducible nitric oxide synthase (iNOS), (4) the ability to inhibit NF-κB activation, (5) the ability to induce heme oxygenase-1 (HO-1) (6) water solubility, and (7) cheap production. TBEs also are important for the development of new chemopreventative agents, as well as relevant to therapy of malignancy itself.

i. Inhibition of iNOS or COX-2 Expression

The aberrant or excessive expression of either iNOS or cyclooxygenase-2 (COX-2) has been implicated in the pathogenesis of many disease processes, including carcinogenesis in the colon. Thus, overexpression of the gene for COX-2 is an early and central event in colon carcinogenesis (Prescott and White, 1996; Dubois et al., 1996). Mice with defects in the APC (adenomatous polyposis coli) gene develop large numbers of intestinal polyps at an early age, and marked elevations in COX-2 enzyme levels have been found in these polyps. These animal findings correlate with the finding of elevated levels of COX-2 mRNA and protein in many human primary colon cancers and colon cancer cell lines (Prescott and White, 1996), and it is believed that this elevation in COX-2 leads to a suppression of apoptosis, which would ordinarily lead to death of preneoplastic cells (Tsujii and DuBois, 1995).

The functional relevance of COX-2 to intestinal tumorigenesis has been demonstrated by knockout of the COX-2 gene and the subsequent mating of mice bearing this knockout with polyp-forming mice bearing lesions in the APC gene; the COX-2 knockout caused a dramatic diminution in the number of polyps in the offspring (Oshima et al., 1996). Furthermore, treatment of experimental animals with either selective COX-2 inhibitors or non-selective COX-1/COX-2 inhibitors has been reported to be a potent approach to chemoprevention of intestinal cancer (Marnett, 1992; Oshima et al., 1996; Boolbol et al., 1996; Reddy et al., 1996; Sheng et al., 1997).

As for the role of iNOS in carcinogenesis, it is clear that NO is a potent mutagen (Tamir and Tannebaum, 1996), and that nitric oxide can also activate COX-2 (Salvemini et al., 1994). Furthermore, there is a marked increase in iNOS in rate colon tumors induced by the carcinogen, azoxymethane (Takahashi et al., 1997).

A series of synthetic triterpenoid (TP) analogs of oleanolic acid have been shown to be powerful inhibitors of cellular inflammatory processes, such as the induction by IFN-γ of inducible nitric oxide synthase (iNOS) and of cyclooxygenase 2 in mouse macrophages. See Honda et al., 2000a; Honda et al., 2000b, and Honda et al., 2002, which are all incorporated herein by reference.

The current invention discloses TBE compounds that have the property of significantly greater activity than most compounds in suppressing the synthesis of the inflammatory enzyme iNOS. Given the structural similarities between TPs and TBEs, the inventors contemplate that the TBEs of the present invention will also serve to inhibit expression of the COX-2 enzyme.

ii. Inhibition of NF-κB

Numerous studies by others have suggested an important role of in regulating genes involved in apoptosis, proliferation, and metastasis (Baeuerle et al., 1996; Baldwin, 1996; Bargou et al., 1997; Barnes et al., 1997; Ghosh et al., 1998; Barkett et al., 1999; Pahl et al., 1999; Rayet et al., 1999; Huang et al., 2000). Aberrant expression of genes of the NF-κB complex has been found in many human tumors and has been shown to suppress apoptosis and promote proliferation and it is also linked with inflammation. For example, NF-κB can prevent programmed necrosis by inducing genes encoding antioxidant proteins (Luo et al., 2005). Many cancer cells, of either epithelial or hematopoietic origin, use NF-κB to achieve resistance to anticancer drugs, radiation, and death cytokines. It has been suggested that NF-κB activity may lead to enhancement of the cell cycle by its ability to activate cyclin D1 (Guttridge et al., 1999; Hinz et al., 1999; Joyce et al., 1999). Inhibition of IKK-driven NF-κB activation offers a strategy for treatment of different malignancies and can convert inflammation-induced tumor growth to inflammation-induced tumor regression. Luo et al., 2005, is incorporated herein by reference.

Synthetic triterpenoids have been shown to be potent inhibitors of NF-κB. For example, as reported by Shishodia et al., 2006, CDDO-Me modulates nuclear factor κB (NF-κB) activity and NF-κB-regulated gene expression. Using human leukemia cell lines and patient samples, it was shown that CDDO-Me potently inhibits both constitutive and inducible NF-κB activated by tumor necrosis factor (TNF), interleukin (IL)-1β, phorbol ester, okadaic acid, hydrogen peroxide, lipopolysaccharide, and cigarette smoke. NF-κB suppression occurred through inhibition of IκBα kinase activation, IκBα phosphorylation, IκBα degradation, p65 phosphorylation, p65 nuclear translocation, and NF-κB-mediated reporter gene transcription. This inhibition was shown to correlate with suppression of NF-κB-dependent genes involved in anti-apoptosis (IAP2, cFLIP, TRAF1, survivin, and bcl-2), proliferation (cyclin d1 and c-myc), and angiogenesis (VEGF, cox-2, and mmp-9). CDDO-Me was also shown to potentiate the cytotoxic effects of TNF and chemotherapeutic agents. Overall, the results suggest that CDDO-Me inhibits NF-κB through inhibition of IκBα kinase, leading to the suppression of expression of NF-κB-regulated gene products and enhancement of apoptosis induced by TNF and chemotherapeutic agents. Shishodia et al., 2006, is incorporated herein by reference.

The present invention contemplates that the compounds of this invention, in particular the TBEs of the present invention, will function, through a mechanism described above and throughout this application to modulate nuclear factor κB (NF-κB) activity and NF-κB-regulated gene expression. There are important structural similarities between CDDO-Me and many of the TBEs of the present invention. For example, many of the TBEs of the present invention, such as TBE-31 and TBE-34, have A- and C-rings containing α,β-unsaturated carbonyl moieties in the same position as CDDO-Me. Therefore, it is contemplated that TBE will inhibit both constitutive and inducible NF-κB activated by tumor necrosis factor (TNF), interleukin (IL)-1β, phorbol ester, okadaic acid, hydrogen peroxide, lipopolysaccharide, and cigarette smoke. Moreover, the inventors contemplate that NF-κB suppression will occur through inhibition of IκBα kinase activation, IκBα phosphorylation, IκBα degradation, p65 phosphorylation, p65 nuclear translocation, and/or NF-κB-mediated reporter gene transcription. Furthermore, the invention contemplates that the compounds of this invention will potentiate the cytotoxic effects of TNF and other chemotherapeutic agents. Also, the inventors contemplate that the compounds of this invention may inhibit NF-κB through inhibition of IκBα kinase, leading to the suppression of expression of NF-κB-regulated gene products and enhancement of apoptosis induced by TNF and other chemotherapeutic agents. Given all the processes that suppression of NF-κB and NF-κB-regulated gene products are thought to mediate, the invention contemplates that the compounds of this invention will be useful not only for apoptotic activity, but also for antiproliferative, anti-invasive, anti-angiogenic, antimetastatic, and anti-inflammatory activity.

Triterpenoids, such as CDDO and the C-28 methyl ester CDDO-Me, have also been shown induce apoptosis of human tumor cells by disruption of the cell's redox balance (Ahmad et al., 2006; Ikeda et al., 2003). It was shown that CDDO and CDDO-Me block TNF-α-induced targeting of NF-κB p65 to the nucleus. In the same study, it was also shown that CDDO-Me also blocks TNF-α-induced phosphorylation of IκBα.

The results also showed that CDDO-Me inhibits IκBα kinase β (IKKβ) activity in cells. Furthermore, supporting a direct mechanism, CDDO-Me was shown to inhibit recombinant IKKβ activity in vitro. The results also demonstrate that (i) CDDO and CDDO-Me form adducts with IKKβ, but not IKKβ with mutation of Cys-179 to Ala, and (ii) CDDO-Me inhibits IKKβ by a mechanism dependent on oxidation of Cys-179. These findings, as reported in Ahmad et al., 2006, indicate that CDDO and CDDO-Me directly block IKKβ activity and thereby the NF-κB pathway by interacting with Cys-179 in the IKKβ activation loop. Both Ahmad et al., 2006 and Ikeda et al., 2003 are incorporated herein by reference.

The invention contemplates that the compounds of this invention will induce apoptosis of human tumor cells by disruption of the cell's redox balance. It is known that the A-ring of triterpenoids contains an α,β-unsaturated carbonyl moiety that can form reversible adducts with reactive thiol groups in dithiotreitol (DTT) or with specific cysteine-rich protein targets (Ahmad et al., 2006; Ikeda et al., 2003). There are important structural similarities between synthetic triterpenoids, such as CDDO and CDDO-Me and many of the TBEs of the present invention. For example, many of the TBEs of the present invention, such as TBE-31 and TBE-34, have an A-ring containing an α,β-unsaturated carbonyl moiety in the same position as CDDO and CDDO-Me. TBEs may therefore block TNF-α-induced targeting of NF-κB p65 to the nucleus. Furthermore, the invention contemplates that the compounds of this invention will block TNF-α-induced phosphorylation of IκBα. Moreover, it is contemplated that the compounds of this invention will inhibit IκBα kinase β (IKKβ) activity in cells. In addition, the compounds of this invention may inhibit recombinant IKKβ activity in vitro. The compounds of this invention may function to directly block IKKβ activity and thereby the NF-κB pathway by interacting with Cys-179 in the IKKβ activation loop.

iii. Activation of JNK Pathway

CDDO-Me has also been shown to induces a c-Jun N-terminal kinase (JNK)-mediated DR5 expression and apoptosis (Yue et al., 2006; Zou et al., 2004). It is also known that death receptor (DR) 4 or 5, on binding to its ligand, tumor necrosis factor-related apoptosis-inducing ligand (TRAIL), triggers apoptosis via activating the caspase-8-mediated caspase cascade (Zou et al., 2004). Certain anticancer drugs have been shown to up-regulate the expression of these receptors and thereby induce apoptosis or enhance TRAIL-induced apoptosis. For example, it has been shown that methyl-2-cyano-3, 12-dioxooleana-1,9-dien-28-oate (CDDO-Me) activates the extrinsic DR-mediated apoptotic pathway in human lung cancer cells (Yue et al., 2006a). In that study, it was found that CDDO-Me not only activates caspase-8 but also induces expression of DRs, particularly DR5, in a p53-independent mechanism. The studies showed that DR5 up-regulation is required for induction of apoptosis by CDDO-Me and for enhancement of TRAIL-induced apoptosis by CDDO-Me. CDDO-Me rapidly activated c-Jun NH2-terminal kinase (JNK) before DR up-regulation and caspase-8 activation. These results show that activation of JNK pathway results in CDDO-Me-induced DR up-regulation, caspase-8 activation, and apoptosis. The study concluded that CDDO-Me induces apoptosis via JNK-mediated DR up-regulation in human lung cancer cells. A related study determined that the mechanism by which CDDO-Me induces JNK activation is through depletion of intracellular GSH.

The present invention contemplates that the compounds of this invention will activate the JNK pathway via the mechanism described in Yue et al., 2006 and Zou et al., 2004, which are both incorporated herein by reference. There are important structural similarities between CDDO-Me and many of the TBEs of the present invention. For example, many of the TBEs of the present invention contain two enone functional groups in the same positions shown to be critical in the study of CDDO-analogs tested in Dinkova-Kostova et al., 2005. The compounds of this invention may also act in concert to both inhibit the NF-κB pathway and induce the JNK pathway. Through this combination of effects, the compounds of this invention are expected to be powerful and selective inducers of apoptosis in cancer cells.

iv. Induction of Phase 2 Response

A series of synthetic triterpenoid (TP) analogs of oleanolic acid have also been shown to be potent inducers of the phase 2 response, that is elevation of NAD(P)H-quinone oxidoreductase and heme oxygenase 1, which is a major protector of cells against oxidative and electrophile stress. See Dinkova-Kostova et al., 2005. Like previously identified phase 2 inducers, the TP analogs were shown to use the antioxidant response element-Nrf2-Keap1 signaling pathway. The high potency of TP analogs in inducing the phase 2 response and blocking inflammation was shown to depend on the presence of enone functional groups at critical positions in rings A and C of the TP structure. The TP analogs, in addition to blocking inflammation and promoting differentiation, were shown to exhibit another very important protective property: the induction of the phase 2 response.

The present invention contemplates that the compounds of this invention will also be inducers of the phase 2 response, thereby protecting cells against oxidative and electrophile stress. There are important structural similarities between TPs and TBEs. For example, many of the TBEs of the present invention contain two enone functional group in the same positions shown to be critical for the TP compounds tested in Dinkova-Kostova et al., 2005, which is incorporated herein by reference. The TBE compounds of this invention may therefore also use the antioxidant response element-Nrf2-Keap1 signaling pathway to induce the phase 2 response.

v. Activation Nrf2 and Chemoprevention

As discussed above, synthetic triterpenoid analogs of oleanolic acid are potent inducers of the phase 2 response as well as inhibitors of inflammation. It has also been shown that the triterpenoid, 1-[2-cyano-3-,12-dioxooleana-1,9(11)-dien-28-oyl]imidazole (CDDO-Im), is a highly potent chemopreventive agent that inhibits aflatoxin-induced tumorigenesis in rat liver (Yates et al., 2006). Microarray analysis using wild-type and Nrf2 knockout mice confirmed that many phase 2 and antioxidant genes are induced in an Nrf2-dependent manner in mouse liver following treatment with CDDO-Im. It was shown that low-micromole doses of CDDO-Im induce cytoprotective genes, inhibit DNA adduct formation, and dramatically block hepatic tumorigenesis. The potency of CDDO-Im in vivo highlights the chemopreventive promise of targeting Nrf2 pathways with triterpenoids. Yates et al., 2006 is incorporated herein by reference.

Another study has reported that the synthetic triterpenoid CDDO and its derivative CDDO-Im are multifunctional molecules with potent antiproliferative, differentiating, and anti-inflammatory activities (Liby et al., 2005). Treatment with CDDO-Im was shown in this study to elevate protein levels of Nrf2, a transcription factor previously shown to bind ARE sequences, and increase expression of a number of antioxidant and detoxification genes regulated by Nrf2. The triterpenoids also reduced the formation of reactive oxygen species in cells challenged with tert-butyl hydroperoxide, but this cytoprotective activity was absent in Nrf2 deficient cells. Liby et al., 2005 is incorporated herein by reference.

The inventors contemplate that the compounds of the present invention can be used to inhibit tumorigenesis by inducing cytoprotective genes, inhibit DNA adduct formation, and block hepatic tumorigenesis. Especially the TBE compounds of the present invention may function to elevate protein levels of Nrf2 and increase expression of a number of antioxidant and detoxification genes regulated by Nrf2. The invention contemplates that the TBE compounds of this invention will reduce the formation of reactive oxygen species in cells challenged by oxidative stress. The TBEs of the present invention may function using the mechanism described by Liby et al., 2005, or a related mechanism.

There are important structural similarities between CDDO-Im and TBEs. For example, CDDO-Im and the TBEs of the present invention contain two enone functional groups at the same positions. One or both of these enone groups make the compounds susceptible to Michael-addition reactions, which may be responsible for the chemopreventive properties of CDDO-Im and other synthetic triterpenoids. One or both enone groups may also be responsible for many of the other properties of synthetic triterpenoids. Given the structural similarities between CDDO compounds and TBEs, the inventors contemplate that the TBE compounds of this invention will have the same or related chemopreventative properties. Furthermore, given that activation of Nrf2 is also reported to be beneficial in models of neurodegenerative disease and respiratory disease, the inventors contemplate that the TBE compounds of the present invention will be effective in treating these pathologies.

vi. Cell Differentiation Effects

The inventors contemplate that the TBEs of the present invention will effect cell differentiating and may therefore serve as useful compounds for the treatment of cancer. The TBEs of the present invention have structural similarities to CDDO, including two enone moieties. CDDO has been reported to have potent differentiating activities, and has been identified as a ligand for the peroxisome proliferator-activated receptor γ (PPARγ). See Wang et al., 2006, which is incorporated herein by reference. That study showed that CDDO induces adipocytic differentiation in 3T3-L1 cells. Based on the structural similarities of CDDO and the TBEs of the present invention, especially the common enone functionalities, the inventors contemplate that the compounds of the present invention will effect cell differentiation through a similar or related mechanism.

B. Induction of HO-1 and Treatment of Disorders Caused by Oxidative Stress and/or Inflammation Induction of HO-1, in particular, is known to be therapeutic in animal models of many different diseases, including myocardial infarction, renal failure, transplant failure and rejection, stroke, cardiovascular disease, and autoimmune disease.

The inventors contemplate the use of the compounds of this invention for treating a subject having a condition caused by elevated levels of oxidative stress in one or more tissues. The oxidative stress may be accompanied by either acute or chronic inflammation. The oxidative stress may be caused by acute exposure to an external agent such as ionizing radiation or a cytotoxic chemotherapy agent (e.g., doxorubicin), by trauma or other acute tissue injury, by ischemia/reperfusion injury, by poor circulation or anemia, by localized or systemic hypoxia or hyperoxia, or by other abnormal physiological states such as hyperglycemia or hypoglycemia.

In animal models of many such conditions, stimulating expression of inducible heme oxygenase (HO-1) has been shown to have a significant therapeutic effect (e.g., Sacerdoti et al., 2005; Abraham & Kappas, 2005; Bach, 2006; Araujo et al., 2003; Liu et al., 2006; Ishikawa et al., 2001; Kruger et al., 2006; Satoh et al., 2006; Zhou et al., 2005; Morse and Choi, 2005; Morse and Choi, 2002.). This enzyme breaks free heme down into iron, carbon monoxide (CO), and biliverdin (which is subsequently converted to the potent antioxidant molecule, bilirubin). It was shown that at nanomolar concentrations, CDDO and CDDO-Im rapidly increase the expression of the cytoprotective heme oxygenase-1 (HO-1) enzyme in vitro and in vivo. See Liby et al., 2005. Transfection studies using a series of reporter constructs showed that activation of the human HO-1 promoter by the triterpenoids requires an antioxidant response element (ARE), a cyclic AMP response element, and an E Box sequence. Inactivation of one of these response elements alone was shown to partially reduce HO-1 induction, but mutations in all three sequences entirely eliminated promoter activity in response to the triterpenoids. As described below, compounds of the invention are potent inducers of HO-1 expression (see e.g. FIGS. 2, 3 and 9).

Therefore, the compounds of this invention, especially given the their structural similarities with the potent CDDO compounds, may be useful in preventing or treating tissue damage or organ failure resulting from oxidative stress exacerbated by inflammation. Examples of diseases that fall in this category include: heart failure, liver failure, transplant failure and rejection, renal failure, pancreatitis, fibrotic lung diseases (cystic fibrosis and COPD, among others), diabetes (including complications), atherosclerosis, ischemia-reperfusion injury, glaucoma, stroke, autoimmune disease, macular degeneration, and muscular dystrophy. In the case of organ failure, the compounds of this invention may be usefully applied in treating either acute or chronic failure.

Accordingly, in pathologies involving oxidative stress alone or oxidative stress exacerbated by inflammation, treatment may comprise administering to a subject a therapeutically effective amount of a compound of this invention, such as those described above or throughout this specification. Treatment may be administered preventively, in advance of a predictable state of oxidative stress (e.g., organ transplantation or the administration of radiation therapy to a cancer patient), or it may be administered therapeutically in settings involving established oxidative stress and inflammation.

The invention contemplates that the compounds of this invention can also be generally applied to the treatment of inflammatory conditions, such as sepsis, dermatitis, autoimmune disease and osteoarthritis. Other conditions that may be treatable with the compounds of this invention include inflammatory pain and neuropathic pain. The effects here would most likely rely on induction of Nrf2 and inhibition of NF-κB. The compounds of this invention have also been shown to induce HO-1, which is mediated by Nrf2. See for example, FIGS. 2, 3 and 9.

C. Treatment of Neurological Disease

Figure 10:
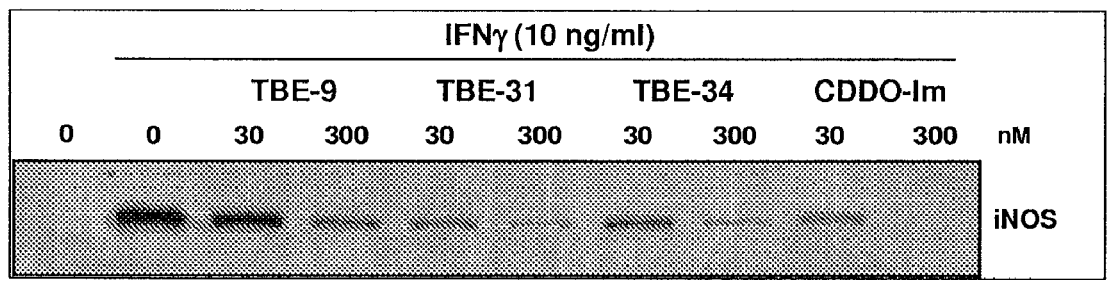
FIG. 10. TBEs inhibit the induction of iNOS in RAW cells stimulated with IFNγ. Cells were incubated with TBEs and CDDO-Im (30-300 nM) and IFN-γ (10 ng/ml) for 24 hours. Total cell lysates were analyzed by SDS-PAGE, probed with iNOS antibody, and developed by ECL. TBE-31 and CDDO-Im, at 30 nM, show similar inhibitory potency in this assay. TBE-34 is nearly equivalent in potency to both compounds.
Figure 11:
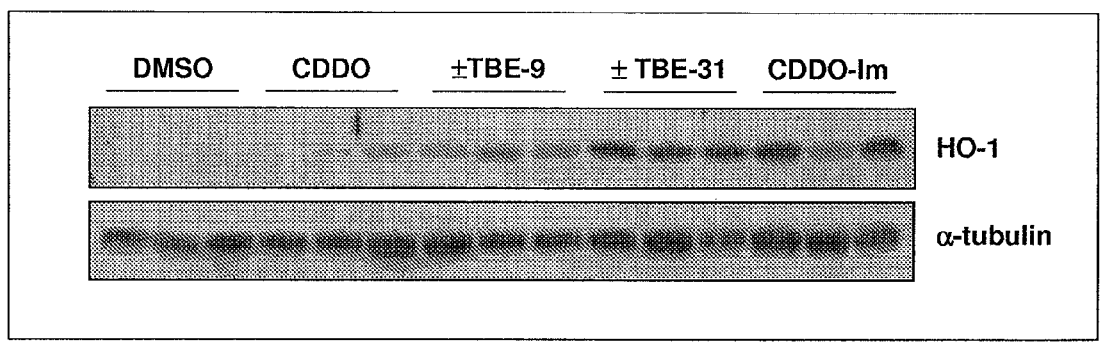
FIG. 11. TBE-31 is a potent inducer of heme oxygenase-1 in liver. Male CD-1 mice (3 per group) were gavaged with 1 µmol TBEs, CDDO or CDDO-Im in DMSO. Six hours later, livers were harvested and homogenized. Lysates were separated by SDS-PAGE, probed with HO-1 antibodies, and developed by ECL.
Figure 12:
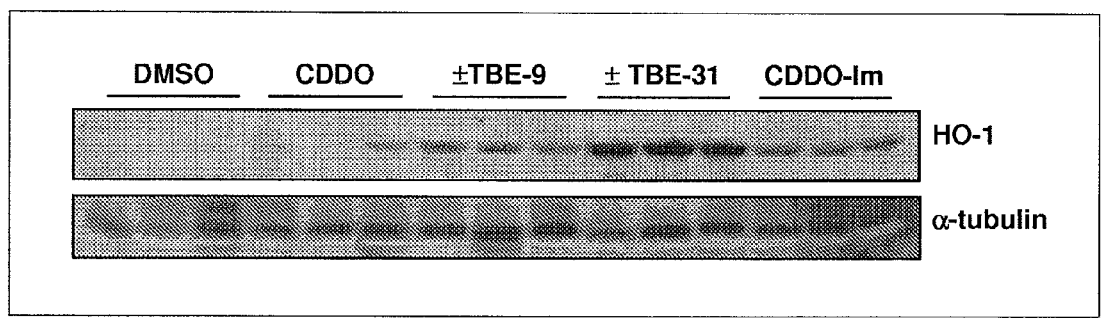
FIG. 12. TBE-31 induces heme oxygenase-1 in stomach. Male CD-1 mice (3 per group) were gavaged with 1 µmol TBEs, CDDO or CDDO-Im in DMSO. Six hours later, stomachs were harvested and homogenized. Lysates were separated by SDS-PAGE, probed with HO-1 antibodies, and developed by ECL.
Figure 13:
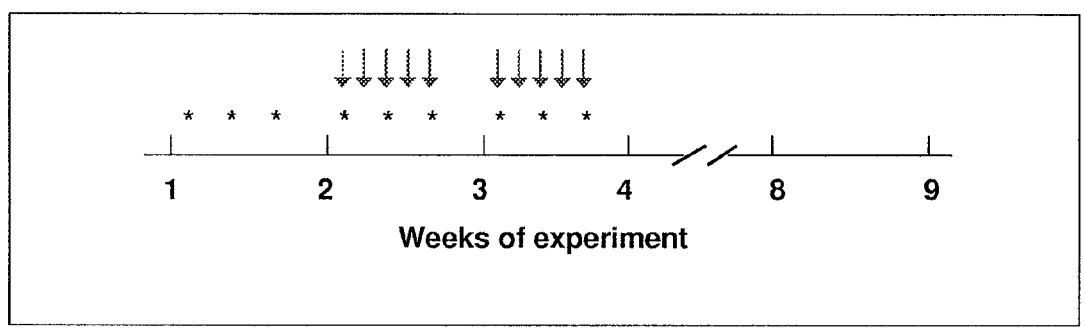
FIG. 13. Protocol for evaluating TBE-31 as an inhibitor of aflatoxin-induced tumorigenesis in male F344 rats. Asterisks (*) indicate administration of 0.3, 1, 10, 30, or 60 µmol TBE-31/kg body weight or CDDO-Im (10 µmmol/kg body weight) by gavage at 8:00 am. Arrows (↓) indicate administration of 25 µg aflatoxin B1 per rat by gavage at 2:00 pm.
Figure 14:
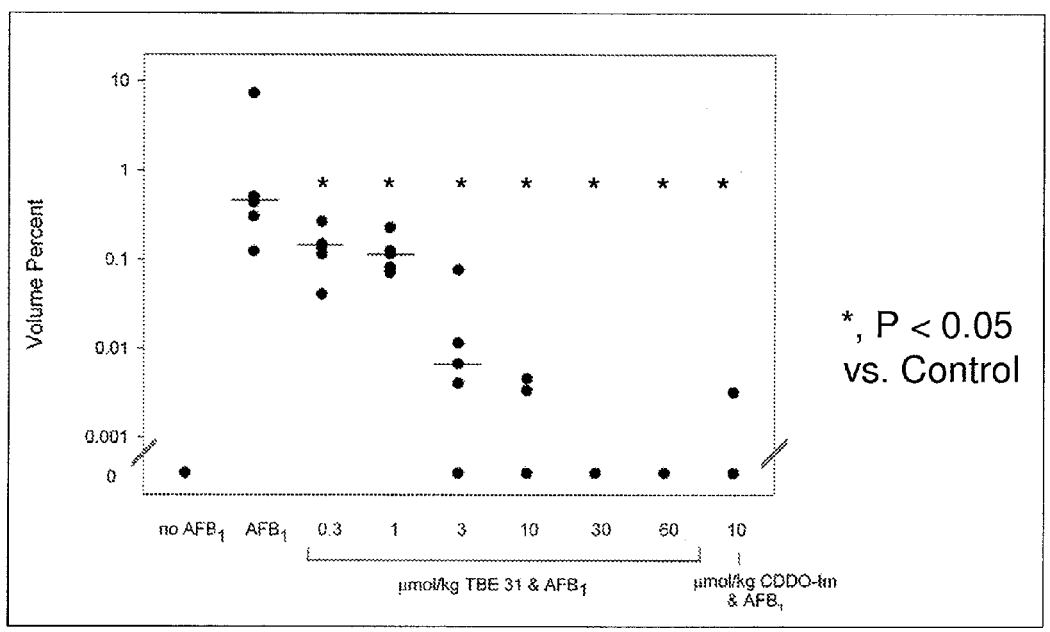
FIG. 14. TBE-31 reduces the formation of preneoplastic foci in the livers of rats challenged with aflatoxin. Male F344 rats (n=4 per group) were gavaged with TBEs or CDDO-Im and aflatoxin as shown above. Livers were harvested 5 weeks after the final dose of drug and aflatoxin, and liver sections were stained for expression of GST-P positive foci and analyzed by light microscopy. The number of foci per unit tissue area and their areas were evaluated, and the volume percent of liver occupied by GST-P positive foci then calculated. Asterisks (*) indicate P<0.05 vs. Control.

Multiple sclerosis (MS) is known to be an inflammatory condition of the central nervous system (Williams et al., 1994; Merrill and Benvenist, 1996; Genain and Nauser, 1997). Inflammatory, oxidative, or immune mechanisms may be involved in the pathogenesis of Alzheimer's disease (AD), Parkinson's disease (PD), amyotrophiclateral sclerosis (ALS), and MS (Bagasra et al., 1995; McGeer and McGeer, 1995; Simonian and Coyle, 1996; Kaltschmidt et al., 1997). Both reactive astrocytes and activated microglia have been implicated in causation of neurodegenerative disease (NDD) and neuroinflammatory disease (NID); there has been a particular emphasis on microglia as cells that synthesize both NO and prostaglandins as products of the respective enzymes, iNOS and COX-2. De novo formation of these enzymes may be driven by inflammatory cytokines such as interferon-γ or interleukin-1. In turn, excessive production of NO may lead to inflammatory cascades and/or oxidative damage in cells and tissues of many organs, including neurons and oligodendrocytes of the nervous system, with consequent manifestations in AD and MS, and possible PD and ALS (Coyle and Puttfarcken, 1993; Beal, 1996; Merrill and Benvenist, 1996; Simonian and Coyle, 1996; Vodovotz et al., 1996). Epidemiologic data indicate that chronic use of NSAID's which block synthesis of prostaglandins from arachidonate, markedly lower the risk for development of AD (McGeer et al., 1996; Stewart et al., 1997). Thus, agents that block formation of NO and prostaglandins, may be used in approaches to prevention and treatment of NDD. The inventors contemplate that the compounds of this invention, which have been shown to block the synthesis of iNOS (see FIGS. 5 and 10), will be useful in treating the neurological diseases described above.

VI. Combination Therapy

In addition to being used as a monotherapy, the TBE's of the present invention will also find use in combination therapies. Such combination therapies may include the use of anti-inflammatory agents generally, or inhibitors of COX-2 and/or iNOS. Alternatively, the combination may be include a second anti-cancer therapy, as discussed in detail below.

An "anti-cancer" agent is capable of negatively affecting cancer in a patient, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the TBE and the other agent(s) at the same time. This may be achieved by contacting the cell with a single composition or pharmacological formulation that includes both agents, or by contacting the cell with two distinct compositions or formulations, at the same time, wherein one composition includes the TBE and the other includes the second agent(s).

Alternatively, the TBE therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and the TBE would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, TBE therapy is "A" and the secondary agent, such as radio- or chemotherapy, is "B":

Administration of the TBE compounds of the present invention to a patient will follow general protocols for the administration of chemotherapeutics, taking into account the toxicity, if any, of the drug. It is expected that the treatment cycles would be repeated as necessary. It also is contemplated that various standard therapies, as well as surgical intervention, may be applied in combination with the described hyperproliferative cell therapies.

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present invention, it is contemplated that TBE therapy could be used similarly in conjunction with chemotherapeutic, radiotherapeutic, or immunotherapeutic intervention, in addition to other pro-apoptotic or cell cycle regulating agents, as discussed below.

A. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristin, vinblastin and methotrexate, or any analog or derivative variant of the foregoing.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

It has been shown that CDDO-Me can enhance the tumor-killing effect of radiation while simultaneously protecting normal tissue from radiation damage. This result is consistent

```
A/B/A    B/A/B    B/B/A    A/A/B    A/B/B    B/A/A    A/B/B/B    B/A/B/B

B/B/B/A    B/B/A/B    A/A/B/B    A/B/A/B    A/B/B/A    B/B/A/A

Figure 9:
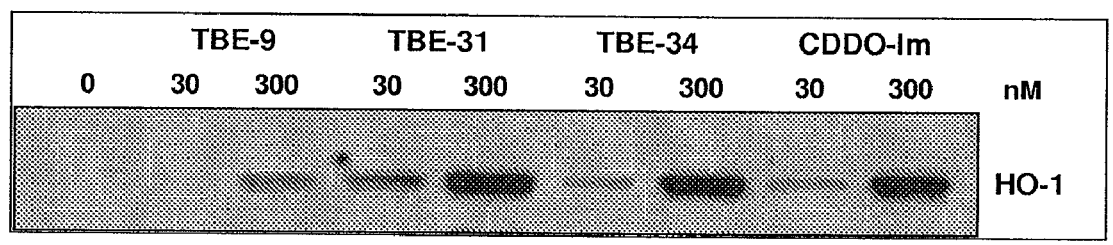
FIG. 9. TBEs induce HO-1 in RAW cells. Cells were incubated with TBEs and CDDO-Im (30-300 nM) for 24 hours. Total cell lysates were analyzed by SDS-PAGE, probed with HO-1 antibodies, and developed by ECL. TBE-31, at 30 nM, is higher inducer than CDDO-Im, which is the most potent compound amongst semi-synthetic triterpenoid analogues in this assay. TBE-34, at 30 and 300 nM, shows similar potency to that of CDDO-Im.

B/A/B/A    B/A/A/B    A/A/A/B    B/A/A/A    A/B/A/A    A/A/B/A
``` with the anti-cancer effects and the protective effects against radiation-induced mucositis and chemotherapy-related toxicities other models shown in many animal models. These protective effects may be due to the Nrf2 activation and NF-κB inhibition. The compounds of this invention have also been shown to activate Nrf2. For example, the induction of HO-1, as shown for example in FIG. 9, is mediated by Nrf2. Therefore, the compounds of this invention, may be useful in enhancing the tumor-killing effect of radiation while simultaneously protecting normal tissue from radiation damage.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with TBE therapy. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p9'7), gp68, TAG-72, HMFG, Sialyl Lewis Antigen, MucA, MucB, PLAP, estrogen receptor, laminin receptor, erb B and p155.

D. Gene Therapy

In yet another embodiment, the secondary treatment is a secondary gene therapy in which a therapeutic polynucleotide is administered before, after, or at the same time a TBE. Therapeutic genes may include an antisense version of an inducer of cellular proliferation (sometimes called an oncogene), an inhibitor of cellular proliferation (sometimes called a tumor suppressor), or an inducer of programmed cell death (sometimes called a pro-apoptotic gene).

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that, as has been reported for triterpenoids such as CDDO, the compounds of the present invention, given their structural similarities, may upregulate the expression of cell surface receptors involved in apoptotic signaling (e.g., DR4 and DR5) and may therefore have additive or synergistic effects in combination with ligands for these receptors (e.g., TRAIL; see Hyer et al., 2005, which is incorporated herein by reference). The upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increasing intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

G. Anti-Inflammatory Agents

It is contemplated that other anti-inflammatory agents will be used in conjunction with the TBE derivatives of the current invention. Other COX inhibitors may be used, including arylcarboxylic acids (salicylic acid, acetylsalicylic acid, diflunisal, choline magnesium trisalicylate, salicylate, benorylate, flufenamic acid, mefenamic acid, meclofenamic acid and triflumic acid), arylalkanoic acids (diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin and sulindac) and enolic acids (phenylbutazone, oxyphenbutazone, azapropazone, feprazone, piroxicam, and isoxicam. (U.S. Pat. No. 6,025, 395)

Histamine H2 receptor blocking agents may also be used in conjunction with the TBE derivatives of the current invention, including cimetidine, ranitidine, famotidine and nizatidine.

H. Anti-Cholinesterase Inhibitors

Treatment with acetylcholinesterase inhibitors such as tacrine, donepizil, metrifonate and rivastigmine for the treatment of Alzheimer's and other disease in conjunction with the TBE derivatives of the present invention is contemplated. Other acetylcholinesterase inhibitors may be developed which may be used once approved include rivastigmine and metrifonate. Acetylcholinesterase inhibitors increase the amount of neurotransmitter acetylcholine at the nerve terminal by decreasing its breakdown by the enzyme cholinesterase.

I. Estrogen Replacement Therapy

Estrogen replacement therapy (ERT) can be used in conjunction with the TBE derivatives of the current invention for the treatment of Alzheimer's and other diseases. Estrogen is an excellent neuroprotective agent and effects multiple pathways that are involved in the pathogenesis of diseases that also involve excessive production of either nitric oxide (NO) or prostaglandins.

J. MAO-B Inhibitors

MAO-B Inhibitors such as selegilene (Eldepryl or Deprenyl) may be used in conjunction with the TBE derivatives of the current invention. Selegilene is used for Parkinson's disease and irreversibly inhibits monoamine oxidase type B (MAO-B). Monoamine oxidase is an enzyme that inactivates the monoamine neurotransmitters norepinephrine, serotonin and dopamine.

K. Pharmaceutical Agents for MS

Common drugs for multiple sclerosis (MS) that can be used in combination with the triterpenoid derivatives include immunosuppressive drugs such as azathioprine (Imuran), cladribine (Leustatin), and Cyclophosphamide (Cytoxan).

L. Supplements

Dietary and nutritional supplements with reported benefits for treatment or prevention of Parkinson's, Alzheimer's, multiple sclerosis, amyotrophiclateral sclerosis, rheumatoid arthritis, inflammatory bowel disease, and all other diseases whose pathogenesis is believed to involve excessive production of either nitric oxide (NO) or prostaglandins, such as acetyl-L-carnitine, octacosanol, evening primrose oil, vitamin B6, tyrosine, phenylalanine, vitamin C, L-dopa, or a combination of several antioxidants may be used in conjunction with the TBE derivatives of the current invention.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of TBEs

General Experimental Procedures

Optical rotations were measured with a Jasco DIP-370 digital polarimeter. $^1$H and $^{13}$C NMR spectra were recorded at 300 MHz or 75 MHz on a Fourier transform spectrometer, respectively. The chemical shifts are reported in δ (ppm) using the δ 7.27 signal of CHCl$_3$ and the δ 2.05 signal of acetone-d$_6$ ($^1$H NMR), and the δ 77.23 signal of CDCl$_3$ and the δ 39.52 signal of DMSO-d$_6$ ($^{13}$C NMR) as internal standards. Low-resolution mass spectra and high-resolution MS data were obtained by ESI+ method unless otherwise stated. Elemental analyses were performed by Atlantic Microlab Inc., Norcross, Ga., USA. TLC was performed by precoated plates with silica gel 60 F$_{254}$. Flash column chromatography was done with silica gel (230-400 mesh). Anhydrous THF and CH$_2$Cl$_2$ were prepared by a solvent purification system with alumina. All other solvents (analytical grade) including anhydrous solvents and reagents were used as received. All experiments were performed under a nitrogen atmosphere unless otherwise stated.

Synthesis of Compound I

Compound I was synthesized according to the following procedures:

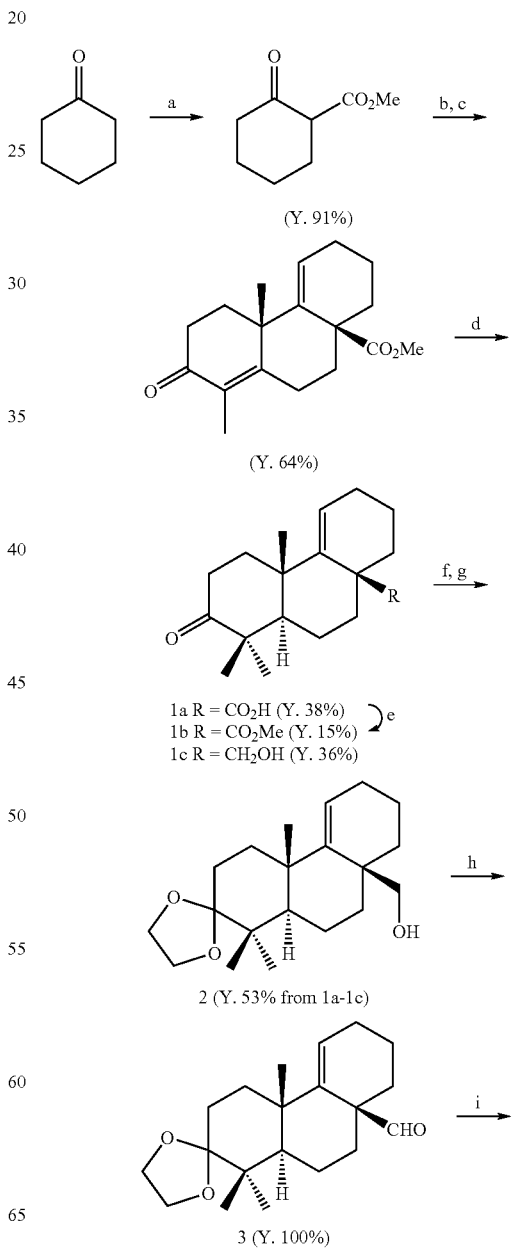

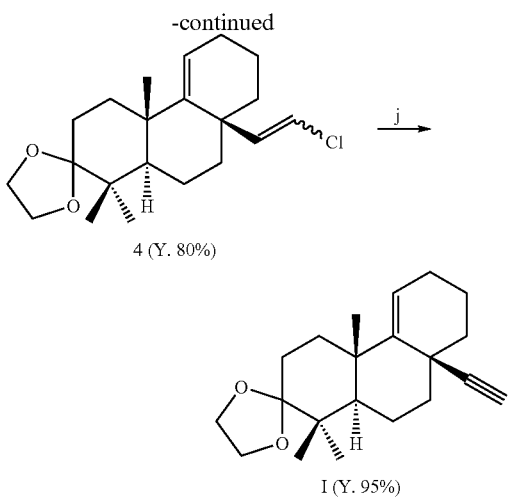

4 (Y. 80%)

I (Y. 95%)

(a) Me$_2$CO$_3$, NaH, KH, THF; (b) 3-chloro-2-pentanone, Na, MeOH; (c) Cs$_2$CO$_3$, Me$_2$SO$_4$, DMF; (d) Li, NH$_3$, H$_2$O, CH$_3$I; (e) CH$_2$N$_2$, Et$_2$O, THF; (f) EG, PPTS, PhH; (g) LAH, Et$_2$O; (h) Swern oxidation; (i) Ph$_3$PCH$_2$Cl$_2$, n-BuLi, THF, HMPA; (j) MeLi, THF; aq NH$_4$Cl.

Synthesis of 2-carbomethoxycyclohexanone: To sodium hydride (60% oil dispersion, 10 g) was added a solution of dimethyl carbonate (18.02 g, 200 mmol) in dry THF (50 mL). The mixture was stirred at reflux temperature (100° C.), and then, a solution of cyclohexanone (7.8 g, 80 mmol) in dry THF (20 mL) was added dropwise to the mixture using a syringe pump. After two minutes of addition, potassium hydride (30% oil dispersion, 0.9 g) was added to initiate the reaction. The addition of cyclohexanone was continued over a period of 1 h. The mixture was refluxed and stirred for an additional 30 min after complete addition of cyclohexanone, when the reaction mixture lumped. It was cooled down in an ice bath for 20 min. The mixture was hydrolyzed by the slow addition of 3M aqueous acetic acid (75 mL), then poured into brine (100 mL) and extracted with CH$_2$Cl$_2$ (150 mL×4). The combined organic layers were dried over MgSO$_4$ and filtered. The filtrate was evaporated in vacuo to give a thick yellow liquid (17.2 g). The liquid was distilled under reduced pressure to give 2 (11.3 g, 91%) as a colorless liquid [bp 38-43° C. (0.05-0.075 mm Hg, bath temp: 75-78° C.)]. See Ruest et al., 1976.

Synthesis of tricyclic methyl ester: To dry methanol (129 mL) was added sodium metal (6.6 g) in an ice bath. After the sodium was completely dissolved in methanol, 2-carbomethoxycyclohexanone (11.31 g, 72 mmol) was added. The container of 2-carbomethoxycyclohexanone was washed with dry methanol (8 mL, 4 mL×2, total 16 mL), and then the washings were added to the reaction mixture. The mixture was heated under reflux. Then, to the mixture was added 1-chloro-3-pentanone (23 mL) using a syringe pump under reflux over 13 h. After the complete addition, the mixture was stirred under reflux for an additional 4 h. After removal of methanol in vacuo, 5% aqueous HCl solution (about 100 mL) was added to acidify the mixture. The acidic mixture was extracted with CH$_2$Cl$_2$ (200 mL, 100 mL, 50 mL×2, total 400 mL). The extract was washed with 5% aqueous NaOH solution (100 mL, 50 mL×5, total 350 mL). The basic solution was acidified with 10% aqueous HCl solution (about 130 mL) to give a precipitate. It was extracted with CH$_2$Cl$_2$ (100 mL×3). The extract was washed with brine (100 mL×1), dried over MgSO$_4$ and filtered. The filtrate was evaporated in vacuo to give tricyclic acid (19.9 g, quantitative) as a pale yellow oil. This material was used for the next reaction without further purification (Kerwin et al., 1987).

To a solution of tricyclic acid (14.8 g, 54 mmol) in dry DMF (390 mL) was added dimethylsulfate (7.7 mL, 80.4 mmol) and Cs$_2$CO$_3$ (26.2 g, 80.4 mmol) successively. The mixture was stirred at room temperature overnight. The reaction mixture was poured into water (900 mL). The aqueous mixture was extracted with ethyl acetate (EtOAc) (300 mL×4). The extract was washed with brine (200 mL×3), dried over MgSO$_4$ and filtered. The filtrate was evaporated in vacuo to give a yellow crystalline solid (14.3 g). The solid was recrystallized from hot diethyl ether (100 mL) five times to give a total of 5.9 g of tricyclic methyl ester as cream colored crystals. The mother liquor gave a crystalline solid (6.92 g). The solid was purified by flash column chromatography (hexanes/EtOAc 3:1) to give tricyclic methyl ester as a crystalline solid (4.12 g). Total amount of 4 obtained was 10.02 g (64%).

Synthesis of compounds 1a-1c: To liquid ammonia (100 mL) was added lithium (600 mg, 86 mmol, 7.2 eq, sliced ribbon). The solution was stirred at −78° C. for 15 min. Compound 4 (3.5 g, 12 mmol) and water (218 mg, 12 mmol, 1 eq) in THF (47 mL) were added dropwise and the mixture was stirred under reflux at −33° C. (bp of ammonia) (with the aid of a CCl$_4$ bath) for 1 h. The mixture was cooled to −78° C. and isoprene (approx. 1.25 mL) was injected until the blue color disappeared turning the solution cloudy white. To this mixture were successively added THF (17.5 mL) and iodomethane (17.5 mL) dropwise. The reaction mixture was stirred under reflux at −33° C. for 1 h. After removal of the ammonia with the aid of a nitrogen stream, 10% aqueous HCl solution (2×60 mL, 2×30 mL) was added to the mixture to acidify. The acidic mixture was extracted with CH$_2$Cl$_2$ (4×50 mL). The combined organic extracts were washed with brine (2×25 mL), dried over MgSO$_4$, filtered and concentrated in vacuo to give a mixture of 1a-1c (3.8 g, 1a:1b:1c=2:1:2) as an oil. This mixture was used for the next reaction. The method of Honda et al. 2005 is incorporated herein by reference.

Synthesis of compound 2: A mixture 1a-1c (7.5 g) was dissolved in THF (140 mL), then a solution of diazomethane in ether was added till the solution turned a permanent bright yellow color. The mixture was evaporated in vacuo to give a mixture of 1b and 1c (7.6 g, 1b:1c=3:2).

A mixture of 1b and 1c (7.6 g), ethylene glycol (EG) (36.5 mL) and pyridinium p-toluenesulfonate (PPTS) (1.4 g) in dry benzene (140 mL) was vigorously refluxed at 110° C. under N$_2$ with a Dean-Stark apparatus for 5 h. The organic layer was separated and washed with saturated aqueous NaHCO$_3$ solution (50 mL×2), and brine (50 mL×1), then dried over MgSO$_4$ and filtered. The filtrate was evaporated in vacuo to give a mixture of ketalized 1b and 2 (7.96 g, ketalized 1b:2=3:2). The mixture was used for the next step.

To a solution of a mixture of ketalized 1b and 2 [7.72 g including about 4.5 g of ketalized 1b (ca. 13 mmol)] in dry ether was added LiAlH$_4$ (2.05 g, 54 mmol) in an ice bath. The mixture was stirred at room temperature for 5.5 h. The reaction mixture was quenched with water (4.75 mL), 40% aqueous NaOH solution (3.4 mL), and water (6.75 mL), successively in that order. A grayish white precipitate was formed and filtered off. The filtrate was washed with saturated aqueous NH$_4$Cl solution (×1), then dried over MgSO$_4$ and filtered. The filtrate was evaporated in vacuo to give a fluffy colorless solid (6.1 g). The solid was purified by flash column chromatography (hexanes/EtOAc 3:1) to give 2 as a colorless solid (3.46 g, 53% yield from a mixture of 1a-1c).

Synthesis of compound 3: To dry CH$_2$Cl$_2$ (37.5 mL) in a pre-dried round bottomed flask under N$_2$ was added oxalyl chloride (1.4 mL, 16.5 mmol). The solution was cooled to −78° C. for 20 min. A solution of DMSO (2.55 mL, 35.9 mmol) in CH$_2$Cl$_2$ (7.5 mL) was added slowly to the reaction flask. The reaction mixture was stirred at −78° C. for 10 min. Then a solution of 2 (4.79 g, 15.0 mmol) in CH$_2$Cl$_2$ (15 mL) was added slowly over 5 min. The reaction mixture was stirred for 20 min at −60° C., then triethylamine (10.5 mL, 74.8 mmol) was added slowly at that temperature. The cooling bath was removed and water (50 mL) was added at room temperature. Stirring was continued for 10 min, and then the organic layer was separated. The aqueous layer was extracted with CH$_2$Cl$_2$ (75 mL×4). The organic layers were combined and washed with 5% aqueous HCl solution (100 mL×1), water (100 mL×1), saturated aqueous Na$_2$CO$_3$ solution (100 mL×1), water (100 mL×1), then dried over MgSO$_4$ and filtered. The filtrate was evaporated in vacuo to give 3 (4.85 g, quantitative) as a crystalline colorless solid. This material was used for the next reaction without further purification.

Synthesis of compound 4: To a suspension of (chloromethyl)-triphenylphosphonium chloride (17.6 g, 50.7 mmol) in THF (54 mL) was added n-BuLi (30.2 mL, 1.6 M in hexane) dropwise in an ice bath under N$_2$. To the mixture was added hexamethylphosphoramide (HMPA) (8.3 mL). The mixture was stirred at room temperature for 20 min. To the mixture was added a solution of 3 (3.85 g, 12.1 mmol) in THF (54 mL) at room temperature. The mixture was stirred at room temperature for 50 min. To the mixture was added saturated aqueous NH$_4$OH solution (120 mL). The aqueous mixture was extracted with CH$_2$Cl$_2$-Et$_2$O (1:2, 75 mL×4). The extract was washed with brine (100 mL×2), then dried over MgSO$_4$ and filtered. The filtrate was evaporated to give a brown residue (17.13 g). The residue was washed with hexanes/EtOAc (10:1) and filtered through a glass filter. The solid residue in the filter was washed several times with hexanes/EtOAc (7:1-160 mL, 5:1-120 mL, 4:1-150 mL). The solid residue was checked by TLC and no product was present in it. The filtrates were combined and evaporated in vacuo to give a yellow residue (10 g). The residue was purified by flash column chromatography (hexanes/EtOAc 10:1) to give 4 (E-isomer:Z-isomer=1:4) as a colorless oil (3.38 g, 80%).

Synthesis of key intermediate I: To a solution of 4 (1.34 g, 3.82 mmol) in dry THF (10 mL) was added methyl lithium solution (1.6 M in hexanes, 9.73 mL) dropwise in an ice bath. The mixture was stirred at room temperature for 18 h. To the reaction mixture was added saturated aqueous NH$_4$Cl (50 mL) solution dropwise in an ice bath. The aqueous mixture was extracted with CH$_2$Cl$_2$-Et$_2$O (1:2, 75 mL×3). The extract was washed with brine (100 mL×2), then dried over MgSO$_4$ and filtered. The filtrate was evaporated in vacuo to give I (1.14 g, 95%) as a crystalline solid: $^1$H NMR (CDCl$_3$) δ 5.48 (1H, t, J=3.67 Hz), 3.97 (4H, m), 2.15 (1H, s), 1.36, 1.00, 0.86 (each 3H, s); $^{13}$C NMR (CDCl$_3$) δ 147.9, 119.2, 113.3, 93.0, 68.8, 65.1, 65.0, 52.0, 43.2, 42.6, 41.0, 40.4, 35.5, 35.2, 27.3, 26.2, 23.3, 23.2, 20.3, 19.6, 19.2; MS (ESI+) m/z 315 [M+H]+; HRMS (ESI+) calcd for C$_{21}$H$_{30}$O$_2$+H, 315.2324, found 315.2335.

Synthesis of (±)-TBE-31 and 34 in Racemic Form

TBE-31 and 34 in racemic form were synthesized from 4 by the following procedures:

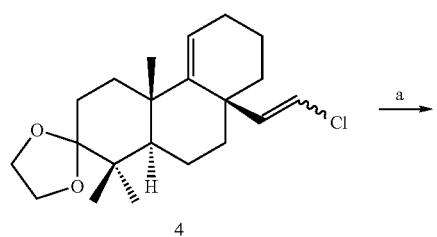

4

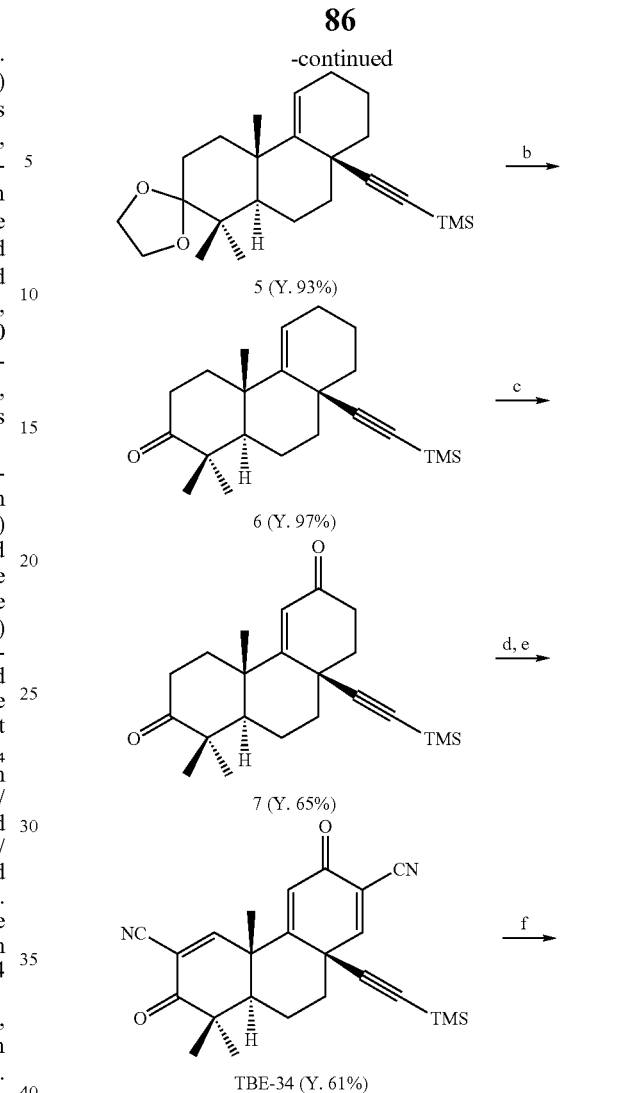

5 (Y. 93%)

6 (Y. 97%)

7 (Y. 65%)

TBE-34 (Y. 61%)

TBE-31 (Y. 71%)

(a) MeLi, THF; TMSCl; (b) aq. HCl, MeOH; (c) CrO$_3$, t-BuOOH, CH$_2$Cl$_2$; (d) p-TsCN, LDA, THF; (e) DDQ, PhH; (f) TBAF, THF

Synthesis of compound 5: To a solution of 4 (370 mg, 1.05 mmol) in THF (30 mL) was added methyl lithium solution (8.82 mL) dropwise in an ice bath. The mixture was stirred at room temperature for 18 h. To the reaction mixture was added chlorotrimethylsilane (TMSCl) (1.5 mL) dropwise in an ice bath. The mixture was stirred at room temperature for 15 min. To the mixture was added water (30 mL). The aqueous mixture was extracted with CH$_2$Cl$_2$-Et$_2$O (1:2, 35 mL×3). The extract was washed with saturated aqueous NaHCO$_3$ solution (×1) and brine (×1), then dried over MgSO$_4$ and filtered. The filtrate was evaporated to give 5 as a white crystalline solid (383 mg, 93%).

Synthesis of compound 6: To a solution of 5 (3.58 g, 9.26 mmol) in MeOH (710 mL) was added 10% aqueous HCl solution (145 mL). The mixture was stirred at room temperature for 10 min. The reaction mixture was carefully neutralized with triethylamine (approx. 50 mL). Most of the solvent methanol was evaporated and to the residue was added water (500 mL). The aqueous mixture was extracted with EtOAc (150 mL×4). The extract was washed with water (×1), saturated aqueous NaHCO$_3$ solution (×1), and brine (×1), then it was dried over MgSO$_4$ and filtered. The filtrate was evaporated to give 6 as a white solid (3.07 g, 97%). This material was used for the next reaction without further purification.

Synthesis of compound 7: To a solution of 6 (2.19 g, 6.39 mmol) in dry CH$_2$Cl$_2$ (35 mL), 70% t-BuOOH (9.1 mL) and CrO$_3$ (0.83 g, 8.3 mmol) were added successively in an ice bath. The mixture was stirred at room temperature for 45 min. The reaction mixture was diluted with CH$_2$Cl$_2$-Et$_2$O (1:2, 200 mL). It was washed with 5% aqueous NaOH solution (×1), 5% aqueous HCl solution (×1), saturated aqueous NaHCO$_3$ solution (×2), and brine (×1), then dried over MgSO$_4$ and filtered. The filtrate was evaporated to give a brown residue (2.35 g). The residue was purified by flash column chromatography (φ5 cm, h 15 cm, hexanes/EtOAc 2.5:1) to give 7 as a white solid (1.48 g, 65%).

Synthesis of TBE-34: To a solution of 7 (174 mg, 0.49 mmol) in THF (5.4 mL) was added lithium diisopropylamide (LDA) (0.68 mL) at −78° C. The mixture was allowed to reach room temperature over 20 min. Then, it was cooled to −78° C. (10 min). To the mixture was added a solution of p-toluenesulfonyl cyanide (p-TsCN) (371 mg) in THF (4.1 mL). The mixture was stirred at −78° C. for 30 min. To the reaction mixture was added saturated NH$_4$OH solution (2.9 mL). The mixture was allowed to reach room temperature (15 min). The mixture was acidified with 10% aqueous HCl solution. The acidic mixture was extracted with EtOAc (25 mL×3). The extract was washed with saturated NaHCO$_3$ solution (×2) and brine (×1), then dried over MgSO$_4$, and filtered. The filtrate was evaporated to give a residue (248 mg).

A mixture of the residue (248 mg) and 2,3-dichloro-5,6-dicyanobenzoquinone (DDQ) (217 mg) in anhydrous benzene (13 mL) was heated under reflux for 10 min. The insoluble matter was removed by filtration through a pipette plugged with cotton. The filtrate was concentrated in vacuo to give a residue (302 mg). The residue was purified by flash column chromatography (φ3 cm, h 15 cm, hexanes/EtOAc 2.5:1) to give TBE-34 as a crystalline solid (120.6 mg, 61%): $^1$H NMR (CDCl$_3$) δ 7.91 (1H, s), 7.41 (1H, s), 6.25 (1H, s), 2.48 (1H, dt, J=12.8 and 2.9 Hz), 2.24 (1H, m), 1.97 (1H, m), 1.82 (3H, s), 1.62 (2H, m), 1.26, 1.21 (each 3H, s), 0.19 (9H, s); $^{13}$C NMR (CDCl$_3$) δ 195.8, 178.8, 162.4, 160.6, 160.1, 122.3, 115.2, 114.2, 114.1, 113.2, 99.8, 94.6, 51.5, 45.38, 45.35, 40.6, 40.3, 26.3, 22.6, 21.8, 19.1, −0.4; MS (ESI+) m/z 403 [M+H]+; HRMS (ESI+) calcd for C$_{24}$H$_{26}$N$_2$O$_2$Si+H, 403.1842, found 403.1834. Anal. Calcd for C$_{24}$H$_{26}$N$_2$O$_2$Si: C, 71.61; H, 6.51; N, 6.96. Found: C, 71.29; H, 6.71; N, 6.77.

Synthesis of TBE-31: To the solid starting material TBE-34 (468 mg, 1.16 mmol), was added a solution of tetra(n-butyl)ammonium fluoride (TBAF) (955 mg, 3.65 mmol) in THF (8.5 mL). The mixture was stirred at room temperature for 15 min. The reaction mixture was diluted with EtOAc (100 mL). It was washed with saturated aqueous NaHCO$_3$ solution (50 mL×2). The basic washings were extracted with EtOAc (50 mL×2). The combined organic layers were washed with brine (×1), dried over MgSO$_4$, filtered and evaporated to give a pale yellow solid (408 mg). The crude product was purified by flash column chromatography (φ3 cm, h 15 cm). The column was eluted with a 1.5:1 mixture of hexanes and EtOAc. The pure TBE-31 (273 mg, 71%) was obtained as a white crystalline solid: $^1$H NMR (CDCl$_3$) δ 7.92 (1H, s), 7.44 (1H, s), 6.28 (1H, s), 2.63 (1H, s), 2.53 (1H, dt, J=12.8 and 3.1 Hz), 2.28 (1H, m), 1.99 (1H, m), 1.84 (3H, s), 1.64 (2H, m), 1.27, 1.22 (each 3H, s); $^{13}$C NMR (CDCl$_3$) δ 195.9, 178.6, 162.5, 160.3, 160.0, 122.5, 115.2, 114.4, 114.2, 113.0, 79.6, 77.0, 51.4, 45.4, 45.3, 40.2, 39.5, 26.3, 22.7, 21.8, 19.0; MS (FAB) m/z 331 [M+H]+; HRMS (FAB) calcd for C$_{21}$H$_{18}$N$_2$O$_2$+H, 331.1447, found 331.1434. Anal. Calcd for C$_{21}$H$_{18}$N$_2$O$_2$.1/4H$_2$O: C, 75.32; H, 5.57; N, 8.36. Found: C, 75.54; H, 5.47; N, 8.25.

Racemic TBE-31 may also be synthesized from Compound I using the method shown here:

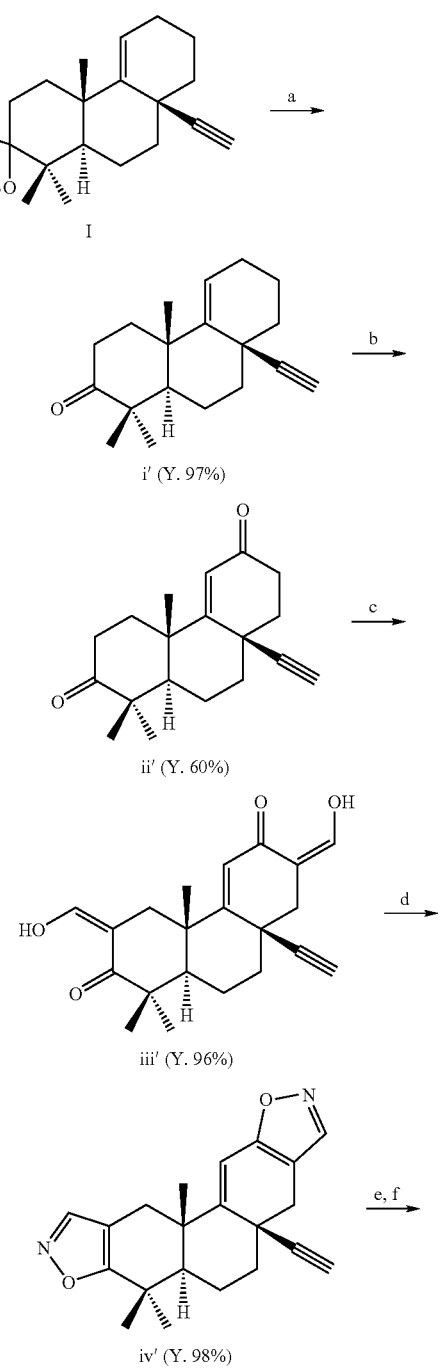

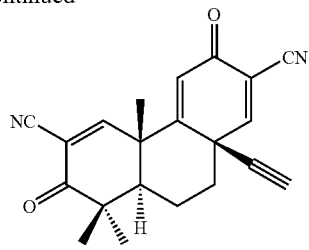

TBE-31 (Y. 55%, overall Y. 30% from I)

(a) aq. HCl, MeOH; (b) CrO₃, t-BuOOH, CH₂Cl₂; (c) HCO₂Et, NaOMe, PhH; (d) NH₂OH·HCl, aq EtOH; (e) NaOMe, MeOH, Et₂O; (f) PhSeCl, pyr., CH₂Cl₂.

To a warm solution of I (600 mg, 1.91 mmol) in methanol (145 mL) was added 10% aqueous HCl (28 mL) slowly. The reaction mixture was stirred at RT for 10 min (TLC check 5 min). Most of the methanol was removed by evaporation. The residue was dissolved in EtOAc (125 mL) and brine (75 mL) was added. The solution was extracted with EtOAc (×3). The combined organic layers were washed with sat. NaHCO₃ (×2) and brine (×1), then dried over MgSO₄, filtered and evaporated to give a brown oil (499 mg, 97%). The product was used for the next step without further purification.

To a solution of i' (499 mg, 1.84 mmol) in dry CH₂Cl₂ (10.1 mL) was added t-butyl hydroperoxide (2.6 mL, 70% in H₂O) at 0° C. To the mixture was added CrO₃ (240 mg, 2.4 mmol), also at 0° C. The mixture was stirred at RT for 150 min. It was then diluted with CH₂Cl₂.Et₂O (1:2, 100 mL). The solution was washed with 5% aq. NaOH (×3). The basic washings were extracted with CH₂Cl₂.Et₂O (1:2, ×3). The combined organic layers were washed with 5% aq. HCl (×3), sat. NaHCO₃ (×3), and brine (×2). The solution was then dried over MgSO₄, filtered and evaporated to give a brown residue (580 mg). The residue was purified by f.c.c (φ3 cm, h 15 cm) with a mixture of Hex:EtOAc (2:1) as the eluant. The product was obtained as a white crystalline solid (315 mg, 60%).

To a solution of ii' (50 mg, 0.176 mmol) in dry benzene (0.8 mL) was added ethyl formate (145.1 mg, 1.96 mmol) and sodium methoxide (105.8 mg, 1.96 mmol). The mixture was stirred at RT for 60 min under argon. The mixture was diluted with CH₂Cl₂.Et₂O (1:2, 30 mL). The solution was washed with sat. NH₄Cl (×2), and the aqueous washings were extracted with CH₂Cl₂.Et₂O (1:2, ×3). The combined organic layers were washed with brine (×2), dried over MgSO₄, filtered and evaporated to give a yellow oil iii' (58 mg, 96%). To a solution of iii' (58 mg, 0.17 mmol) in 2.8 mL ethanol was added a solution of hydroxylamine hydrochloride (191 mg, 2.75 mmol) in H₂O (0.6 mL). The mixture was refluxed at 105° C. for 65 min. The solvent was removed by evaporation, and the residue was diluted with H₂O (10 mL). The mixture was extracted with EtOAc (15 mL×3). The extract was washed with brine (×3), dried over MgSO₄, filtered and evaporated to give a purple residue iv' (56 mg, 98%).

To a solution of sodium methoxide (298 mg) in dry methanol (3.9 mL) was added a solution of iv' (56 mg) in dry methanol (2.6 mL). Dry ether (2.0 mL) was added and the reaction mixture was stirred at RT for 60 min. It was diluted with EtOAc (30 mL), and the mixture was washed with 5% HCl (×2), sat. NaHCO₃ (×2), and brine (×2), then dried over MgSO₄, filtered and evaporated to give dinitrile as a pink residue (40 mg, 71%).

To a solution of phenylselenylchloride (3.33 g) in dry CH₂Cl₂ (81 mL) was added a solution of dry pyridine (1.51 g, 1.54 mL) in dry CH₂Cl₂ (28 mL) in an ice bath. The mixture was stirred at 0-4° C. for 20 min, then a solution of dinitrile (1.455 g, 4.35 mmol) in dry CH₂Cl₂ (32 mL) was added slowly in the ice bath. The mixture was stirred at 0-4° C. for 60 min. The mixture was washed with 10% aq. HCl (30 mL×2). To the mixture was added 30% H₂O₂ (3.4 mL) in the ice bath. After 10 min of stirring, 30% H₂O₂ (2 mL) was added 4 times at 10 min intervals (total 11.4 mL). The mixture was stirred at 0-4° C. for 20 min after the last addition of H₂O₂. The mixture was washed with H₂O (×2), sat. NaHCO₃ (×2) and brine (×2), then dried over MgSO₄. The solution was filtered and evaporated to give a residue (1.5 g). The residue was purified by f.c.c (φ3 cm, h 15 cm) with a mixture of Hex:EtOAc (1:1) as the eluant. The product was further purified by washing it twice with cold ether, and pure TBE-31 was obtained as white crystals (1.1 g, 77%)

Synthesis of Optically Active (−)- and (+)-TBE-31 and 34

Optically active (−)- and (+)-TBE-31 and 34 were synthesized by the following procedures:

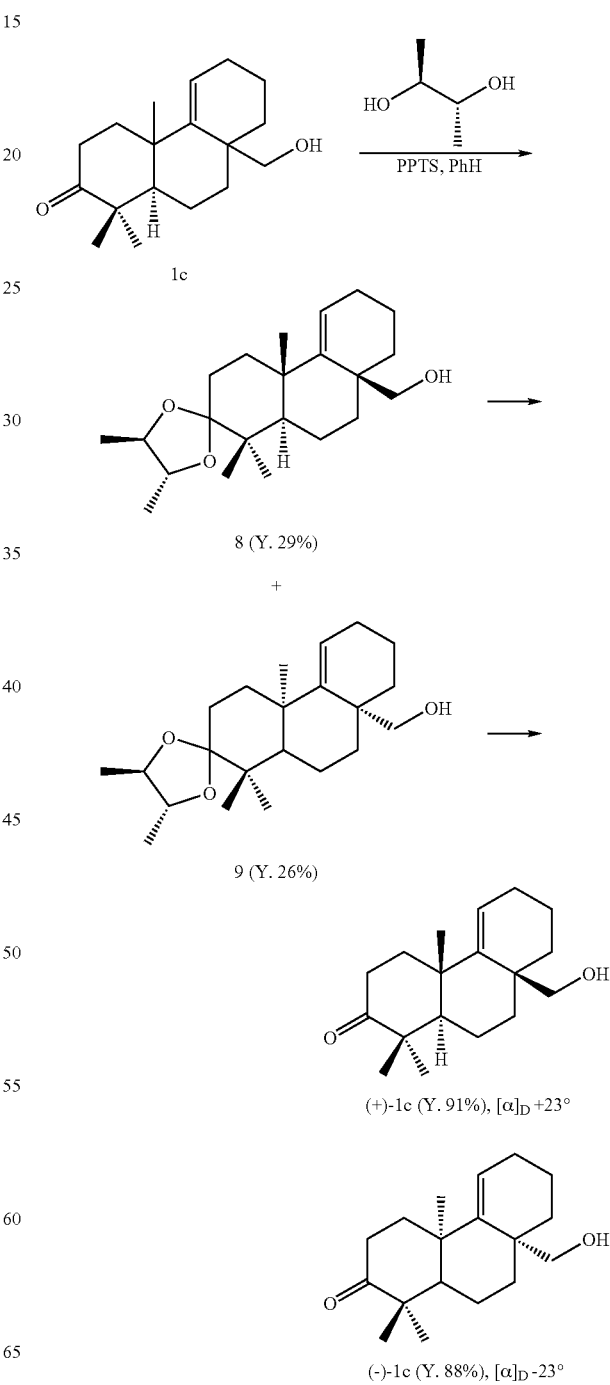

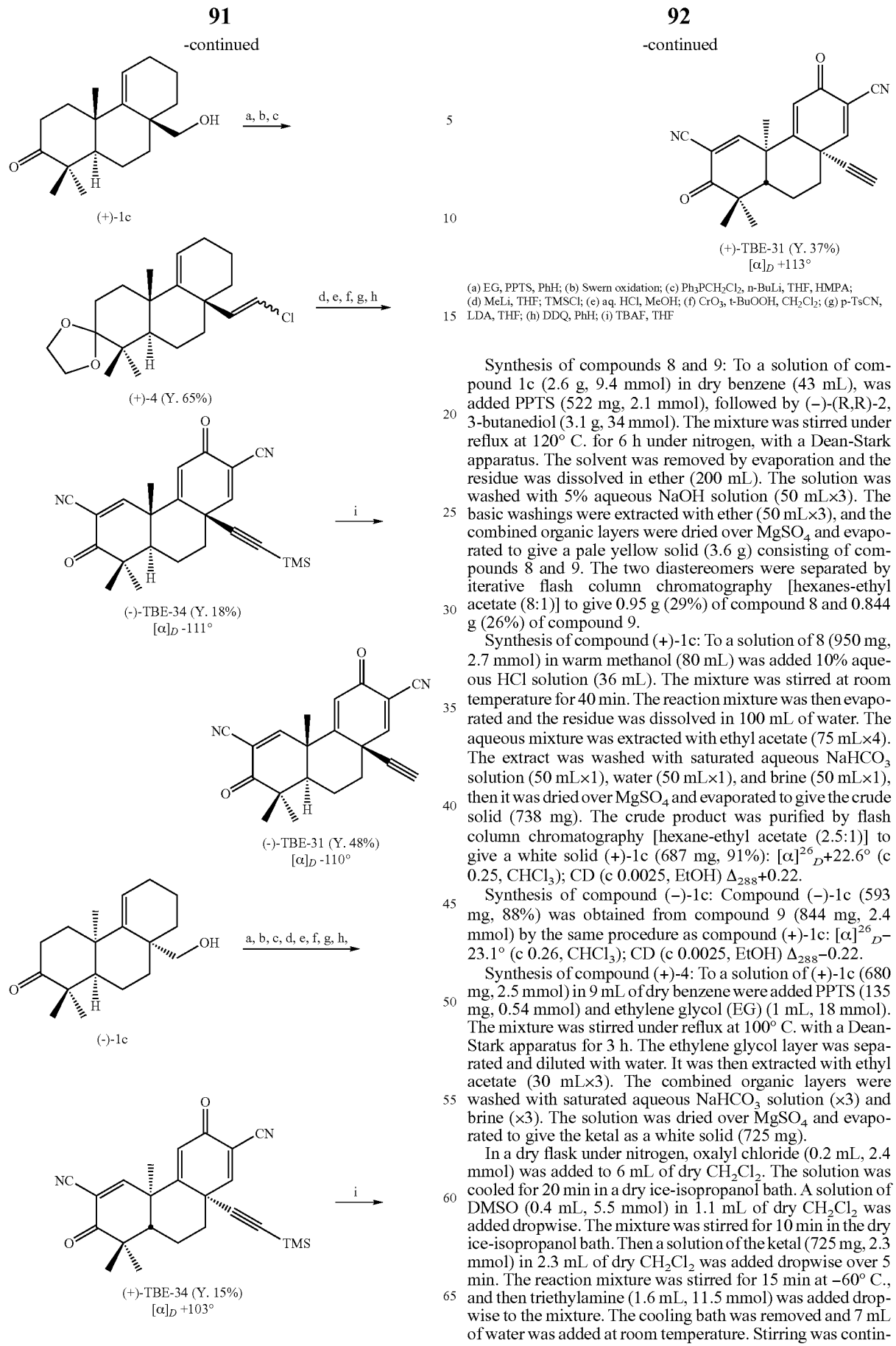

(a) EG, PPTS, PhH; (b) Swern oxidation; (c) Ph₃PCH₂Cl₂, n-BuLi, THF, HMPA; (d) MeLi, THF; TMSCl; (e) aq. HCl, MeOH; (f) CrO₃, t-BuOOH, CH₂Cl₂; (g) p-TsCN, LDA, THF; (h) DDQ, PhH; (i) TBAF, THF Synthesis of compounds 8 and 9: To a solution of compound 1c (2.6 g, 9.4 mmol) in dry benzene (43 mL), was added PPTS (522 mg, 2.1 mmol), followed by (−)-(R,R)-2,3-butanediol (3.1 g, 34 mmol). The mixture was stirred under reflux at 120° C. for 6 h under nitrogen, with a Dean-Stark apparatus. The solvent was removed by evaporation and the residue was dissolved in ether (200 mL). The solution was washed with 5% aqueous NaOH solution (50 mL×3). The basic washings were extracted with ether (50 mL×3), and the combined organic layers were dried over MgSO₄ and evaporated to give a pale yellow solid (3.6 g) consisting of compounds 8 and 9. The two diastereomers were separated by iterative flash column chromatography [hexanes-ethyl acetate (8:1)] to give 0.95 g (29%) of compound 8 and 0.844 g (26%) of compound 9.

Synthesis of compound (+)-1c: To a solution of 8 (950 mg, 2.7 mmol) in warm methanol (80 mL) was added 10% aqueous HCl solution (36 mL). The mixture was stirred at room temperature for 40 min. The reaction mixture was then evaporated and the residue was dissolved in 100 mL of water. The aqueous mixture was extracted with ethyl acetate (75 mL×4). The extract was washed with saturated aqueous NaHCO₃ solution (50 mL×1), water (50 mL×1), and brine (50 mL×1), then it was dried over MgSO₄ and evaporated to give the crude solid (738 mg). The crude product was purified by flash column chromatography [hexane-ethyl acetate (2.5:1)] to give a white solid (+)-1c (687 mg, 91%): $[\alpha]^{26}_D$+22.6° (c 0.25, CHCl₃); CD (c 0.0025, EtOH) $\Delta_{288}$+0.22.

Synthesis of compound (−)-1c: Compound (−)-1c (593 mg, 88%) was obtained from compound 9 (844 mg, 2.4 mmol) by the same procedure as compound (+)-1c: $[\alpha]^{26}_D$−23.1° (c 0.26, CHCl₃); CD (c 0.0025, EtOH) $\Delta_{288}$−0.22.

Synthesis of compound (+)-4: To a solution of (+)-1c (680 mg, 2.5 mmol) in 9 mL of dry benzene were added PPTS (135 mg, 0.54 mmol) and ethylene glycol (EG) (1 mL, 18 mmol). The mixture was stirred under reflux at 100° C. with a Dean-Stark apparatus for 3 h. The ethylene glycol layer was separated and diluted with water. It was then extracted with ethyl acetate (30 mL×3). The combined organic layers were washed with saturated aqueous NaHCO₃ solution (×3) and brine (×3). The solution was dried over MgSO₄ and evaporated to give the ketal as a white solid (725 mg).

In a dry flask under nitrogen, oxalyl chloride (0.2 mL, 2.4 mmol) was added to 6 mL of dry CH₂Cl₂. The solution was cooled for 20 min in a dry ice-isopropanol bath. A solution of DMSO (0.4 mL, 5.5 mmol) in 1.1 mL of dry CH₂Cl₂ was added dropwise. The mixture was stirred for 10 min in the dry ice-isopropanol bath. Then a solution of the ketal (725 mg, 2.3 mmol) in 2.3 mL of dry CH₂Cl₂ was added dropwise over 5 min. The reaction mixture was stirred for 15 min at −60° C., and then triethylamine (1.6 mL, 11.5 mmol) was added dropwise to the mixture. The cooling bath was removed and 7 mL of water was added at room temperature. Stirring was continued for 10 min, and then the organic layer was separated. The aqueous layer was extracted with $CH_2Cl_2$ (30 mL×3). The combined organic layers were washed successively with 5% aqueous HCl solution, water, diluted aqueous $Na_2CO_3$ solution and water. The solution was dried over $MgSO_4$ and evaporated to give the aldehyde as an off-white solid (631 mg).

To a suspension of (chloromethyl)triphenylphosphonium chloride (3 g, 8.6 mmol) in 9 mL of dry THF was added n-BuLi (5 mL, 1.6 M in hexane) dropwise in an ice bath under $N_2$. To the mixture was added HMPA (1.4 mL). The mixture was stirred at room temperature for 20 min. To the mixture was added a solution of the aldehyde (630 mg, 2.3 mmol) in THF (9 mL) at room temperature. The mixture was stirred at room temperature for 50 min. To the mixture was added saturated aqueous $NH_4Cl$ solution (60 mL). The aqueous mixture was extracted with $CH_2Cl_2$-$Et_2O$ (1:2, 40 mL×4). The extract was washed with brine (×2), then dried over $MgSO_4$ and filtered. The filtrate was evaporated to give a brown residue. The residue was washed with a mixture of hexanes-ethyl acetate (10:1), and filtered through a glass filter. The solid residue in the filter was washed several times with hexanes-ethyl acetate (10:1-110 mL, 7:1-80 mL, 5:1-60 mL, 4:1-50 mL). The filtrates were combined and evaporated to give a crude yellow solid (2.5 g). The crude product was purified by flash column chromatography [hexanes-ethyl acetate (10:1)] to give the product (+)-4 (556 mg, 65% from (+)-1c). $[\alpha]^{26}_D$+5.9° (c 0.44, $CHCl_3$).

(−)-TBE-34 (103 mg, 18%) was synthesized from (+)-4 by the same procedure as for (±)-TBE-34. $[\alpha]^{25}_D$−111° (c 0.43, $CHCl_3$).

(−)-TBE-31 (37 mg, 48%) was synthesized from (−)-TBE-34 by the same procedure as for (±)-TBE-31. $[\alpha]^{25}_D$−110° (c 0.72, $CHCl_3$).

(+)-TBE-34 (112 mg, 15%) was synthesized from (−)-1c by the same procedure as for (−)-TBE-34. $[\alpha]^{25}_D$+103° (c 0.85, $CHCl_3$).

(+)-TBE-31 (29 mg, 37%) was synthesized from (+)-TBE-34 by the same procedure as for (−)-TBE-31. $[\alpha]^{26}_D$+113° (c 0.72, $CHCl_3$)

Synthesis of TBE-35 from Compound I Using Methyl Lithium

TBE-35 was synthesized from Compound I using the following procedures

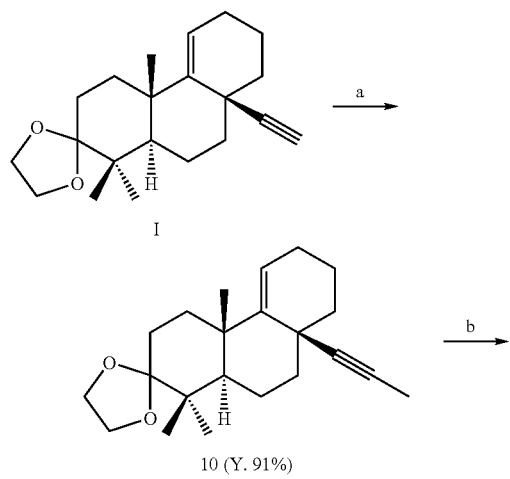

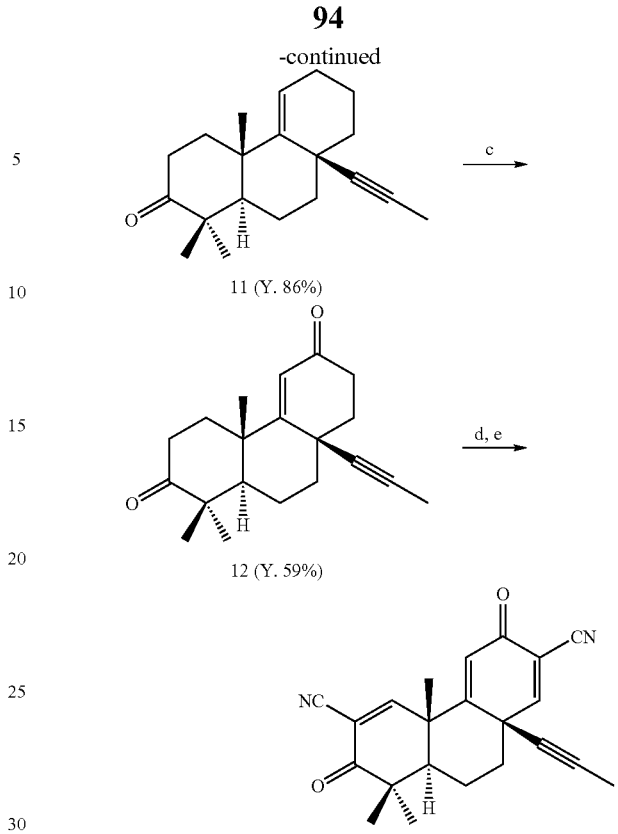

(a) MeLi, THF; MeI; (b) aq. HCl, MeOH; (c) $CrO_3$, t-BuOOH, $CH_2Cl_2$; (d) p-TsCN, LDA, THF; (e) DDQ, PhH.

Synthesis of compound 10: To a solution of I (40 mg, 0.13 mmol) in dry THF was added methyl lithium (1.6 M in hexanes, 0.75 mL) dropwise in an ice bath. The mixture was stirred at room temperature for 30 min, and then methyl iodide (0.25 mL, 4 mmol) was added dropwise to the reaction mixture. The mixture was stirred at room temperature for 20 min and then water (30 mL) was added. The aqueous mixture was extracted with $CH_2Cl_2$.$Et_2O$ (1:2, 15 mL×3). The extract was washed with saturated aqueous $NaHCO_3$ solution (30 mL×1) and brine (30 mL×1), then dried over $MgSO_4$ and evaporated in vacuo to give a colorless oil 10 (38 mg, 91%).

Synthesis of compound 11: To a solution of 10 (200 mg, 0.61 mmol) in warm methanol (46 mL) was added 10% aqueous HCl solution (9.5 mL). The mixture was stirred at room temperature for 15 min. The reaction mixture was evaporated and to the residue were added brine (25 mL) and ethyl acetate (10 mL). The aqueous mixture was extracted with ethyl acetate (50 mL×3). The extract was washed with saturated aqueous $NaHCO_3$ solution (50 mL×1), and brine (50 mL×1), then it was dried over $MgSO_4$ and evaporated to give 11 as a colorless oil (149 mg, 86%).

Synthesis of compound 12: To a solution of 11 (138 mg, 0.48 mmol) in dry $CH_2Cl_2$ (3 mL), 70% aqueous t-BuOOH solution (0.69 mL) and $CrO_3$ (63 mg, 0.63 mmol) were added successively in an ice bath. The mixture was stirred at room temperature for 45 min. The reaction mixture was diluted with $CH_2Cl_2$-$Et_2O$ (1:2, 30 mL). It was washed with 5% aqueous NaOH solution (15 mL×1), 5% aqueous HCl solution (15 mL×1), saturated aqueous $NaHCO_3$ solution (15 mL×2), and brine (15 mL×1), then dried over $MgSO_4$ and evaporated to give a brown residue (151 mg). The residue was purified by flash column chromatography [hexanes-ethyl acetate (1.5:1)] to give the product 12 as an amorphous white solid (85 mg, 59%).

Synthesis of (±)-TBE-35: To a solution of 12 (70 mg, 0.24 mmol) in dry THF (2 mL) was added LDA (2 M in THF/heptane, 0.27 mL) at −78° C. The mixture was stirred at room temperature for 20 min. Then, it was cooled at −78° C. for 10 min. To the mixture was added a cloudy solution of p-TsCN (149 mg, 0.82 mmol) in THF (1.9 mL). The mixture was stirred at −78° C. for 30 min. To the reaction mixture was added saturated aqueous NH$_4$OH solution (1.2 mL). The mixture was allowed to reach room temperature. The mixture was acidified with 10% aqueous HCl solution. The acidic mixture was extracted with ethyl acetate (30 mL×3). The extract was washed with saturated aqueous NaHCO$_3$ solution (30 mL×2) and brine (30 mL×1), then dried over MgSO$_4$, and evaporated to give a residue (113 mg).

The residue was dissolved in anhydrous benzene (6 mL) and to the solution was added DDQ (103 mg, 0.46 mmol). The mixture was heated under reflux at 100° C. for 10 min. The insoluble matter was removed by filtration and the filtrate was evaporated to give a brown residue (126 mg). The residue was purified by flash column chromatography [hexanes-ethyl acetate (2:1)] to give TBE-35 as a white solid (39 mg, 48%): $^1$H NMR (CDCl$_3$) δ 7.91 (1H, s), 7.40 (1H, s), 6.22 (1H, s), 2.42 (1H, dt, J=3.11 and 12.8 Hz), 2.22 (1H, ddd, J=3.30, 12.8 and 26.7 Hz), 1.96-1.91 (2H, m), 1.88, 1.81 (each 3H, s), 1.58 (1H, ddd, J=12.8, 12.8 and 4.03 Hz), 1.26, 1.21 (each 3H, s); $^{13}$C NMR (CDCl$_3$) δ196.0, 179.0, 162.8, 161.4, 161.1, 121.9, 115.1, 114.3, 113.5, 113.3, 85.1, 74.7, 51.5, 45.3, 45.2, 40.1, 39.8, 26.4, 22.6, 21.8, 19.0, 4.0; MS (ESI+) m/z 345 [M+H]; HRMS (ESI+) calcd for C$_{22}$H$_{20}$N$_2$O$_2$+H, 345.1603, found 345.1597. Anal. Calcd for C$_{22}$H$_{20}$N$_2$O$_2$.1/4H$_2$O: C, 75.73; H, 5.92; N, 8.03. Found: C, 75.74; H, 5.86; N, 7.84.

Synthesis of TBE-36 Using Methyl Lithium

TBE-36 was synthesized from compound I, using the following procedures:

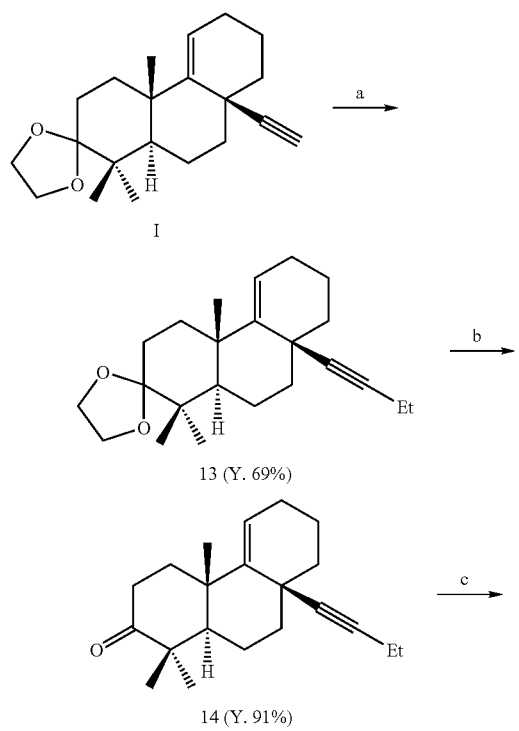

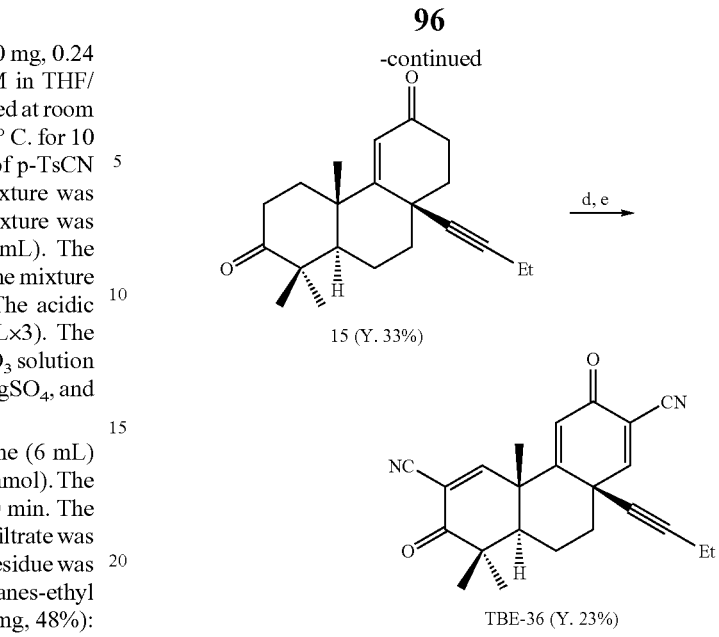

(a) MeLi, THF; EtI; (b) aq. HCl, MeOH; (c) CrO$_3$, t-BuOOH, CH$_2$Cl$_2$; (d) p-TsCN, LDA, THF; (e) DDQ, PhH.

Synthesis of compound 13: To a solution of I (252 mg, 0.80 mmol) in 15 mL of dry THF was added methyl lithium (1.6M in hexanes, 4.7 mL) dropwise in an ice bath. The mixture was stirred at room temperature for 30 min, and then iodoethane (1.95 mL, 4 mmoles) was added dropwise to the reaction mixture. The mixture was stirred at room temperature for 20 min and then water (50 mL) was added. The aqueous mixture was extracted with CH$_2$Cl$_2$-Et$_2$O (1:2, 30 mL×3). The extract was washed with saturated aqueous NaHCO$_3$ solution (30 mL×1) and brine (30 mL×1), then dried over MgSO$_4$ and evaporated in vacuo to give a colorless oil (268 mg). This oil was purified by flash column chromatography [hexanes-ethyl acetate (9:1)] to give compound 13 (189 mg, 69%).

Synthesis of compound 14: To a solution of 13 (56 mg, 0.16 mmol) in warm methanol (13 mL) was added 10% aqueous HCl solution (2.6 mL). The mixture was stirred at room temperature for 10 min. The reaction mixture was evaporated and to the residue were added brine (20 mL) and ethyl acetate (10 mL). The aqueous mixture was extracted with ethyl acetate (30 mL×3). The extract was washed with saturated aqueous NaHCO$_3$ solution (30 mL×1), and brine (30 mL×1), then it was dried over MgSO$_4$ and evaporated to give a colorless oil 14 (45 mg, 91%).

Synthesis of compound 15: To a solution of 14 (45 mg, 0.15 mmol) in dry CH$_2$Cl$_2$ (2 mL), 70% aqueous t-BuOOH solution (0.23 mL) and CrO$_3$ (21 mg, 0.21 mmol) were added successively in an ice bath. The mixture was stirred at room temperature for 45 min. The reaction mixture was diluted with CH$_2$Cl$_2$-Et$_2$O (1:2, 30 mL). It was washed with 5% aqueous NaOH solution (15 mL×1), 5% aqueous HCl solution (15 mL×1), saturated aqueous NaHCO$_3$ solution (15 mL×2), and brine (15 mL×1), then dried over MgSO$_4$ and evaporated to give a brown residue (78 mg). The residue was purified by flash column chromatography [hexanes-ethyl acetate (1.5:1)] to give the product 15 as a white solid (15 mg, 33%).

Synthesis of (±)-TBE-36: To a solution of 15 (38 mg, 0.12 mmol) in dry THF (2 mL) was added LDA (2 M in THF/heptane, 0.15 mL) at −78° C. The mixture was stirred at room temperature for 20 min. Then, it was cooled at −78° C. for 10 min. To the mixture was added a cloudy solution of p-TsCN (81 mg, 0.45 mmol) in THF (1.3 mL). The mixture was stirred at −78° C. for 30 min. To the reaction mixture was added saturated aqueous NH₄OH solution (1 mL). The mixture was allowed to reach room temperature. The mixture was acidified with 10% aqueous HCl solution. The acidic mixture was extracted with ethyl acetate (20 mL×3). The extract was washed with saturated aqueous NaHCO₃ solution (20 mL×2) and brine (20 mL×1), then dried over MgSO₄, and evaporated to give a residue (47 mg).

The residue was dissolved in anhydrous benzene (2.4 mL) and to the solution was added DDQ (42 mg, 0.18 mmol). The mixture was heated under reflux at 100° C. for 10 min. The insoluble matter was removed by filtration and the filtrate was evaporated to give a brown residue (69 mg). The residue was purified by flash column chromatography [hexanes-ethyl acetate (2:1)] and further purified by preparative TLC [CH₂Cl₂-MeOH (40:1)] to give TBE-36 as a white solid (10 mg, 23%): ¹H NMR (CDCl₃) δ 7.90 (1H, s), 7.40 (1H, s), 6.22 (1H, s), 2.43 (1H, dt, J=2.92 and 12.8 Hz), 2.25 (2H, q, J=7.50 Hz), 1.95 (1H, m), 1.82 (3H, s), 1.58 (1H, ddd, J=12.8, 12.8 and 4.03 Hz), 1.27, 1.21 (each 3H, s), 1.15 (3H, t, J=7.50 Hz); ¹³C NMR (CDCl₃) δ 195.8, 178.9, 162.5, 161.3, 161.0, 122.0, 115.2, 114.2, 113.7, 113.3, 90.6, 75.0, 51.7, 45.4, 45.3, 40.3, 39.8, 26.4, 22.8, 21.9, 19.1, 13.3, 12.8; MS (ESI+) m/z 359 [M+H]; HRMS (ESI+) calcd for C₂₃H₂₂N₂O₂+H 359.1760, found 359.1755.

Synthesis of TBE-38 Using n-Butyl Lithium

TBE-38 was synthesized from compound I, using the following procedures:

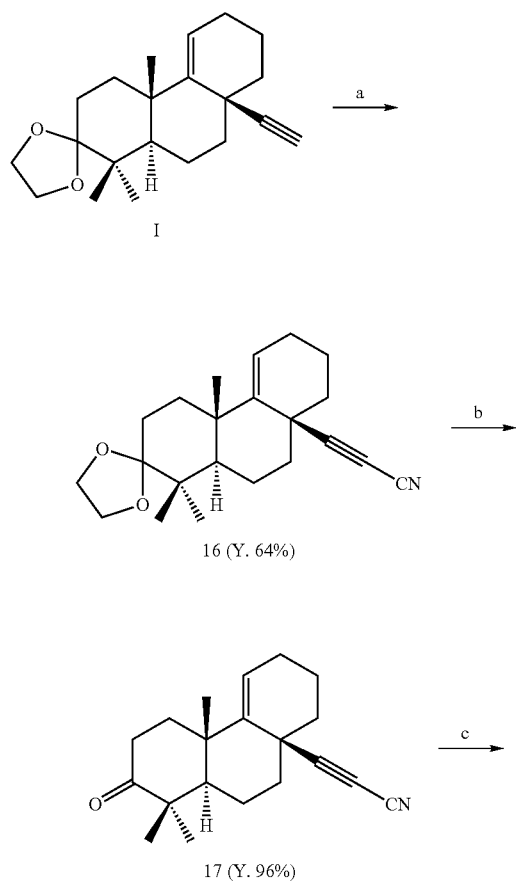

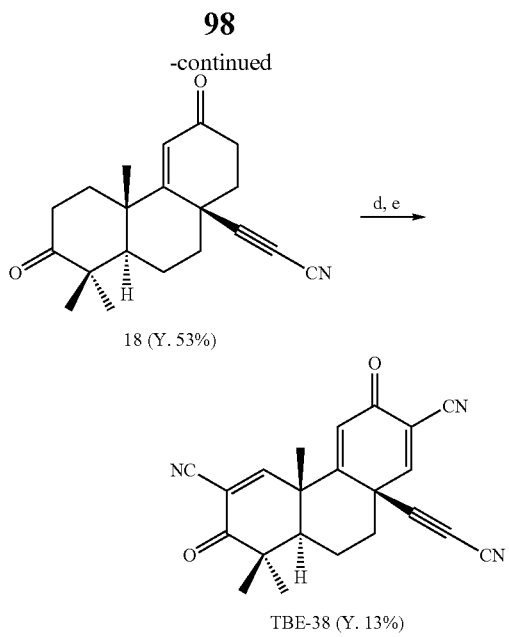

(a) n-BuLi, THF; PhOCN; (b) aq. HCl, MeOH; (c) CrO₃, t-BuOOH, CH₂Cl₂; (d) p-TsCN, LDA, THF; (e) DDQ, PhH.

Synthesis of compound 16: To a solution of I (350 mg, 1.1 mmol) in 5 mL of dry THF, cooled to −70° C., was added n-BuLi (1.6 M in hexanes, 1.4 mL, 2.2 mmol) dropwise over 5 min, followed by freshly prepared phenyl cyanate (0.14 mL, 1.2 mmol) also dropwise over 5 min. The reaction mixture was stirred at −70° C. to −60° C. for 30 min. Then, it was allowed to reach −40° C. over 30 min. It was stirred at −40° C. to −30° C. for 30 min, then allowed to reach room temperature over 30 min. After stirring for an additional 60 min at room temperature, the reaction mixture was poured into 30 mL of 3 M aqueous NaOH solution. The aqueous layer was separated and extracted with ether (50 mL×3). The organic layers were washed with 3 M aqueous NaOH solution (30 mL×2) and brine (30 mL×2), then dried over MgSO₄ and evaporated to give a yellow residue. Purification of the residue by flash column chromatography [hexanes-ethyl acetate (5:1)] gave compound 16 (241 mg, 64%).

Synthesis of compound 17: To a solution of 16 (232 mg, 0.68 mmol) in warm methanol (40 mL) was added 10% aqueous HCl solution (11 mL) at room temperature. The mixture was stirred at room temperature for 10 min. Then it was neutralized with triethylamine. The solvent was removed by evaporation, and to the residue was added 40 mL of brine. The aqueous solution was extracted with ethyl acetate (30 mL×3). The extract was washed with saturated NaHCO₃ solution (30 mL×1) and brine (30 mL×1), then it was dried over MgSO₄ and evaporated to give a white solid 17 (201 mg, 96%).

Synthesis of compound 18: To a solution of 17 (192 mg, 0.65 mmol) in dry CH₂Cl₂ (2 mL) was added 70% aqueous t-BuOOH solution (1 mL) dropwise in an ice bath, followed by CrO₃ (92 mg, 0.92 mmol), also in the ice bath. The mixture was stirred at room temperature for 1 h. The reaction mixture was diluted with CH₂Cl₂-Et₂O (1:2, 50 mL) and washed with 5% aqueous NaOH solution (25 mL×1), 5% aqueous HCl solution (25 mL×1), saturated NaHCO₃ solution (25 mL×1), and brine (25 mL×1). The solution was then dried over MgSO₄ and evaporated to give a brown residue. The residue was purified by flash column chromatography [hexanes-ethyl acetate (2.5:1)] to give a white solid 18 (106 mg, 53%).

Synthesis of (±)-TBE-38: To a solution of 18 (98 mg, 0.32 mmol) in dry THF (5 mL) was added LDA (2 M in THF/heptane, 0.38 mL, 0.76 mmol) at −78° C. The mixture was stirred at room temperature for 20 min. Then, it was cooled at −78° C. for 10 min. To the mixture was added a cloudy solution of p-TsCN (209 mg, 1.1 mmol) in dry THF (3.4 mL). The mixture was stirred at −78° C. for 30 min. To the reaction mixture was added saturated aqueous NH$_4$OH solution (2.6 mL). The mixture was allowed to reach room temperature. It was acidified with 10% aqueous HCl solution. The mixture was extracted with ethyl acetate (40 mL×3). The extract was washed with saturated NaHCO$_3$ solution (×2) and brine (×2), and then dried over MgSO$_4$ and evaporated to give a yellow residue (147 mg).

The residue was dissolved in anhydrous benzene (9 mL) and DDQ (146 mg, 0.64 mmol) was added. The mixture was heated under reflux for 15 min at 100° C. The insoluble matter was removed by filtration, and the filtrate was evaporated in vacuo to give a brown residue. The crude residue was purified by flash column chromatography [hexane-ethyl acetate (1.5:1)], followed by trituration with CDCl$_3$ to give (±)-TBE-38 as a white solid (15 mg, 13%): $^1$H NMR (acetone-d$_6$): δ 8.48 (1H, s), 7.98 (1H, s), 6.62 (1H, s), 2.48-2.33 (1H, m), 2.86-2.48 (4H, m), 1.91, 1.25, 1.22, (each 3H, s). $^{13}$C NMR (DMSO-d$_6$): δ 179.3, 164.2, 158.9, 158.2, 124.4, 116.3, 115.5, 115.3, 113.9, 105.2, 82.2, 61.1, 51.2, 46.1, 45.9, 40.5, 39.9, 26.2, 22.5, 21.9, 19.8, 13.9; MS (ESI+) m/z 357 [M+H]; HRMS (ESI+) calcd for C$_{22}$H$_{17}$N$_3$O$_2$+H, 356.1399, found 356.1402. Anal. Calcd for C$_{22}$H$_{17}$N$_3$O$_2$.1/10CH$_2$Cl$_2$: C, 72.95; H, 4.76; N, 11.55. Found: C, 73.22; H, 4.72; N, 11.17.

Synthesis of TBE-39 Using n-Butyl Lithium

TBE-39 was synthesized from compound I, using the following procedures:

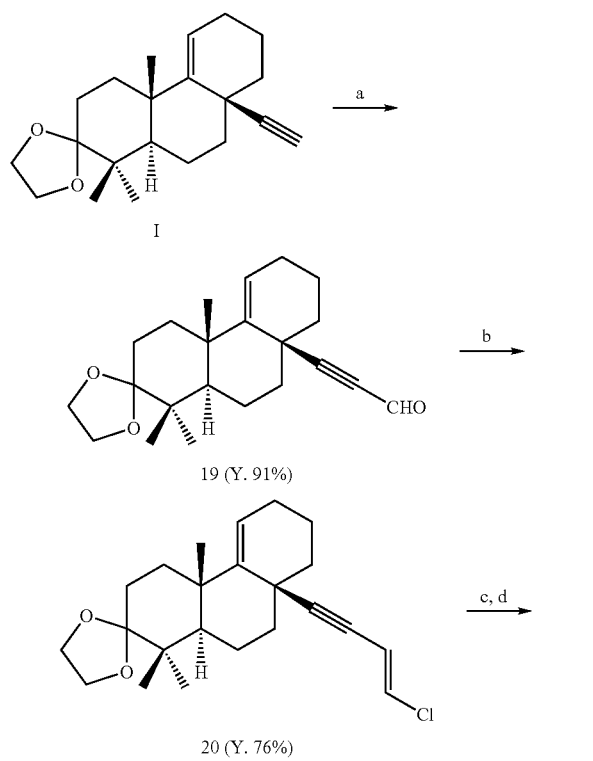

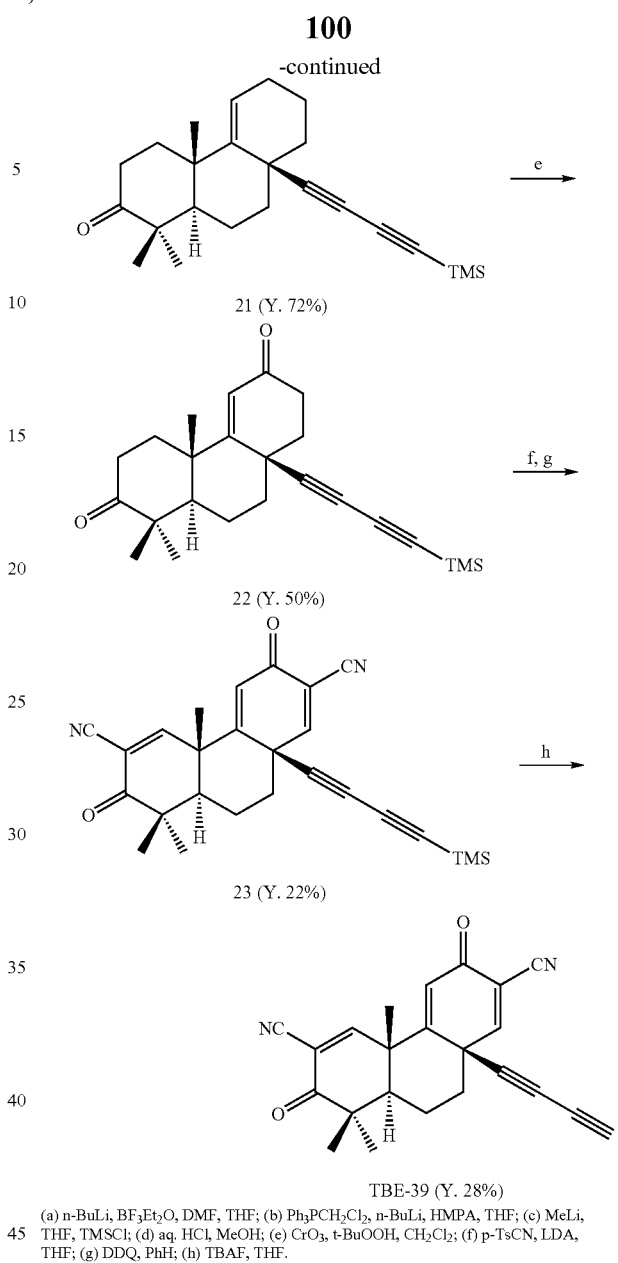

TBE-39 (Y. 28%)

(a) n-BuLi, BF$_3$Et$_2$O, DMF, THF; (b) Ph$_3$PCH$_2$Cl$_2$, n-BuLi, HMPA, THF; (c) MeLi, THF, TMSCl; (d) aq. HCl, MeOH; (e) CrO$_3$, t-BuOOH, CH$_2$Cl$_2$; (f) p-TsCN, LDA, THF; (g) DDQ, PhH; (h) TBAF, THF.

Synthesis of compound 19: To a stirred solution of compound I (628 mg, 2 mmol) in 14 mL of dry THF at −78° C., was added n-BuLi (1.6 M in hexanes, 1.51 mL, 2.4 mmol) under an argon atmosphere, and the reaction mixture was stirred for 30 min at −78° C. After addition of boron triflouride etherate (0.29 mL), the mixture was stirred for 10 min at −78° C., and then dry DMF (0.31 mL, 4 mmol) was added. The reaction mixture was stirred for 50 min. The mixture was diluted with CH$_2$Cl$_2$-Et$_2$O (1:2, 50 mL), and washed successively with saturated aqueous NH$_4$Cl solution, saturated aqueous NaHCO$_3$ solution, water and brine. The solution was then dried over MgSO$_4$, and evaporated to give a residue (708 mg). Purification of this residue by flash column chromatography [hexanes-ethyl acetate (8:1)] afforded compound 19 (620 mg, 91%) as a white solid.

Synthesis of compound 20: To a suspension of (chloromethyl)-triphenylphosphonium chloride (4.76 g, 13.7 mmol) in THF (14 mL) was added n-BuLi (1.6 M in hexane, 8.2 mL, 13.1 mmol) dropwise in an ice bath under N$_2$. To the mixture was added HMPA (2.4 mL). The mixture was stirred at room temperature for 20 min. To the mixture was added a solution of aldehyde 19 (798 mg, 2.3 mmol) in THF (14 mL) at room temperature. The mixture was stirred at room temperature for 50 min. To the mixture was added saturated NH$_4$OH solution (100 mL). The aqueous mixture was extracted with CH$_2$Cl$_2$-Et$_2$O (1:2, 50 mL×4). The extract was washed with brine (×2), then dried over MgSO$_4$ and filtered. The filtrate was evaporated to give a brown residue (4.56 g). The residue was washed with a mixture of hexanes-ethyl acetate (10:1), and filtered through a glass filter. The solid residue in the filter was washed several times with hexanes-ethyl acetate (10:1-110 mL, 7:1-80 mL, 5:1-120 mL). The filtrates were combined and evaporated to give a crude yellow solid (3.4 g). The crude product was purified by flash column chromatography [hexanes-ethyl acetate (10:1)] to give the product 20 as a colorless oil (667 mg, 76%).

Synthesis of compound 21: To a solution of 20 (570 mg, 1.52 mmol) in dry THF (43 mL) was added methyl lithium solution (1.6 M in hexanes, 12.7 mL, 20.3 mmol) dropwise in an ice bath. The mixture was stirred at room temperature for 17 h. To the reaction mixture was added TMSCl (2.2 mL, 17.2 mmol) dropwise in an ice bath. The mixture was stirred at room temperature for 30 min. To the mixture was added water (50 mL). The aqueous mixture was extracted with CH$_2$Cl$_2$-Et$_2$O (1:2, 50 mL×3). The extract was washed with saturated NaHCO$_3$ solution (×1) and brine (×1), then dried over MgSO$_4$ and evaporated to give a white solid (603 mg). To a solution of the solid (664 mg, 1.62 mmol) in warm MeOH (511 mL) was added 10% HCl (24 mL). The mixture was stirred at room temperature for 10 min. The reaction mixture was carefully neutralized with triethylamine to pH 7. The solvent methanol was evaporated and to the resulting residue was added water (150 mL). The aqueous mixture was extracted with ethyl acetate (75 mL×4). The extract was washed with water (×1), saturated aqueous NaHCO$_3$ solution (×1), and brine (×1), then it was dried over MgSO$_4$ and evaporated to give a crude solid (2.66 g). The crude product was purified by flash column chromatography [hexanes-ethyl acetate (7:1)] to give the product 21 as a white crystalline solid (441 mg, 72%).

Synthesis of compound 22: To a solution of 21 (430 mg, 1.17 mmol) in dry CH$_2$Cl$_2$ (6.5 mL), 70% aqueous t-BuOOH solution (1.8 mL) and CrO$_3$ (170 mg, 1.7 mmol) were added successively in an ice bath. The mixture was stirred at room temperature for 45 min. The reaction mixture was diluted with CH$_2$Cl$_2$-Et$_2$O (1:2, 60 mL). It was washed with 5% aqueous NaOH solution (×1), 5% aqueous HCl solution (×1), saturated aqueous NaHCO$_3$ solution (×2), and brine (×1), then dried over MgSO$_4$ and evaporated to give a brown residue (522 mg). The residue was purified by flash column chromatography [hexanes-ethyl acetate (2:1)] to give the product 22 as a white solid (225 mg, 50%).

Synthesis of compound 23: To a solution of 22 (100 mg, 0.26 mmol) in dry THF (2.9 mL) was added LDA (2 M in THF/heptane, 0.37 mL, 0.74 mmol) at −78° C. The mixture was stirred at room temperature for 20 min. Then, it was cooled at −78° C. for 10 min. To the mixture was added a cloudy solution of p-TsCN (199 mg, 1.1 mmol) in dry THF (2.2 mL). The mixture was stirred at −78° C. for 30 min. To the reaction mixture was added saturated aqueous NH$_4$OH solution (1.6 mL). The mixture was allowed to reach room temperature. The mixture was acidified with 10% aqueous HCl solution. The acidic mixture was extracted with ethyl acetate (30 mL×3). The extract was washed with saturated aqueous NaHCO$_3$ solution (×2) and brine (×1), then dried over MgSO$_4$, and filtered. The filtrate was evaporated to give a residue (145 mg).

The residue was dissolved in anhydrous benzene (7 mL) and DDQ (119 mg, 0.52 mmol) was added. The mixture was heated under reflux at 100° C. for 10 min. The insoluble matter was removed by filtration and the filtrate was evaporated to give a brown residue (319 mg). The residue was purified by flash column chromatography [hexanes-ethyl acetate (2:1)] to give a white solid (54 mg). The solid was further purified by trituration with hexanes-ethyl acetate (5:1) to give compound 23 as a white solid (25 mg, 22%).

Synthesis of (±)-TBE-39: To the solid starting material 23 (36 mg, 0.08 mmol), was added a solution of TBAF (69 mg, 3.65 mmol) in THF (0.8 mL). The mixture was stirred at room temperature for 15 min. The reaction mixture was diluted with ethyl acetate (45 mL). It was washed with saturated aqueous NaHCO$_3$ solution (×2). The basic washings were extracted with ethyl acetate (20 mL×2). The combined organic layers were washed with brine (×1), dried over MgSO$_4$ and evaporated to give a yellow residue (27.2 mg). The crude product was purified by flash column chromatography [hexanes-ethyl acetate (1.5:1)]. The pure product TBE-39 (8.5 mg, 28%) was obtained as a white solid: $^1$H NMR (CDCl$_3$) δ 7.89 (1H, s), 7.41 (1H, s), 6.28 (1H, s), 2.55 (1H, dt, J=3.11 and 12.8 Hz), 2.34 (1H, s), 1.82, 1.59, 1.27, 1.22 (each 3H, s). $^{13}$C NMR (CDCl$_3$): δ 178.2, 161.8, 159.5, 158.2, 122.7, 115.5, 115.0, 114.0, 112.8, 77.4, 72.4, 71.1, 70.8, 66.6, 5.1.5, 45.3, 45.1, 40.1, 39.8, 26.3, 22.6, 21.8, 19.2; MS (ESI+) m/z 355 [M+H]; HRMS (ESI+) calcd for C$_{23}$H$_{18}$N$_2$O$_2$+H, 355.1447, found 355.1458.

Synthesis of Compounds 26 from Compound I Using Sonogashira Coupling

Compound 26 was successfully synthesized in 64% yield from 1 using the Sonogashira coupling procedure shown here:

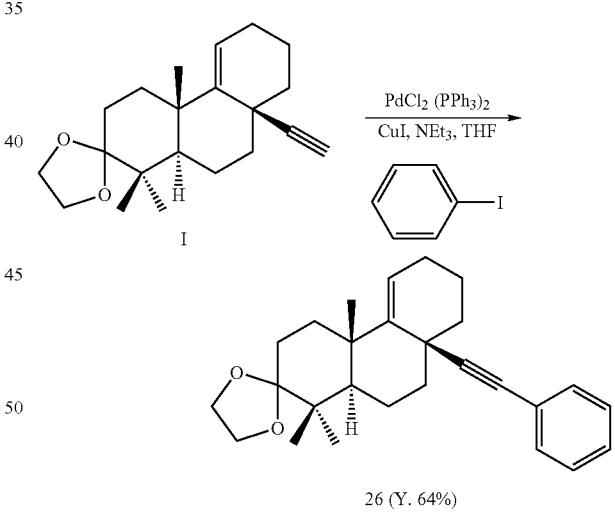

26 (Y. 64%)

To a stirred mixture of iodobenzene (62 mg, 0.3 mmol), copper iodide (2.4 mg, 0.01 mmol), and Pd(PPh$_3$)$_2$Cl$_2$ (4.2 mg, 0.01 mmol) in 0.3 mL of dry THF was added triethylamine (61 mg, 0.6 mmol) under a nitrogen atmosphere. A solution of compound I (100 mg, 0.32 mmol) in 0.8 mL of dry THF was added dropwise over 30 min. The mixture was stirred at room temperature for 16 h, and then diluted with CH$_2$Cl$_2$-Et$_2$O (1:2, 20 mL). The mixture was neutralized with 5% aqueous. HCl solution, and then diluted with 25 mL of water. The aqueous mixture was extracted with CH$_2$Cl$_2$-Et$_2$O (1:2, 25 mL×3), and the extract was washed with saturated aqueous NaHCO$_3$ solution (×1) and brine (×1). The solution was dried over MgSO₄ and filtered through Celite®. The filtrate was evaporated to give a brown residue (124 mg). Purification of the residue by flash column chromatography [hexanes-ethyl acetate (8.5:1)] afforded compound 26 (79 mg, 64%) as white crystals.

Synthesis of Compound 31 from Compound I Using Sonogashira Coupling

Compound 31 was synthesized by Sonogashira coupling between I and iodo-SEM-imidazole, followed by deketalization with aqueous HCl solution. The procedures are shown here.

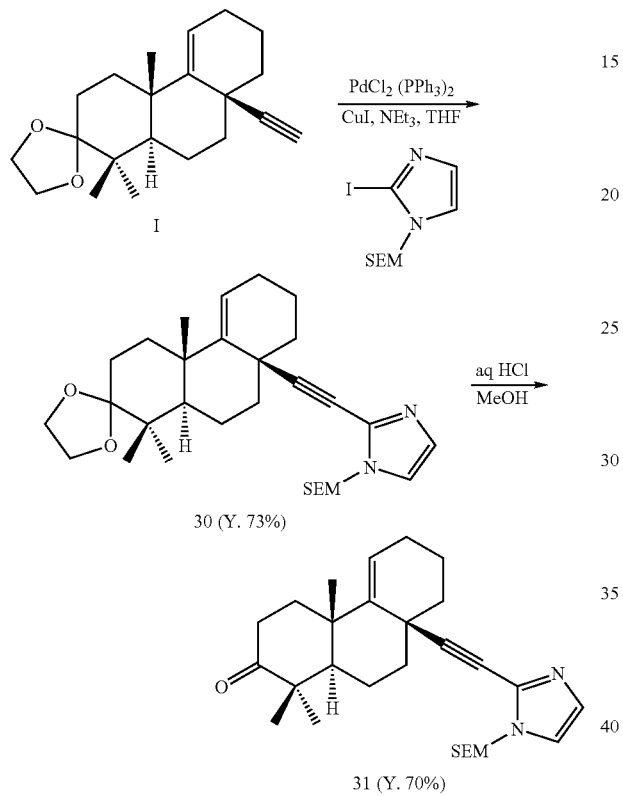

Synthesis of compound 30: To a mixture of iodo-SEM-imidazole (550 mg, 1.70 mmol), Pd(PPh₃)₂Cl₂ (57 mg, 0.08 mmol), and CuI (11 mg, 0.06 mmol) was added triethylamine (6.8 mL) under Ar. The mixture was degassed by Ar. To the mixture was added I (solid, 492 mg, 1.56 mmol). The mixture was degassed bt Ar, again. The mixture was stirred at 60° C. overnight. After removal of insoluble matter, the filtrate was evaporated in vacuo to give a residue (995 mg). A solution of the residue in methylene chloride was filtered through short Celite® column for removing Pd stuff. The filtrate was evaporated in vacuo to afford a residue (951 mg). The residue was purified by flash column chromatography (φ3 cm, h 15 cm, hexanes/EtOAc 2:1) to give 30 as a viscous oil (587 mg, 73%).

Synthesis of compound 31: To a solution of 30 (36.7 mg, 0.072 mmol) in methanol (5 mL) was added 10% aqueous HCl solution (1 mL). The mixture was stirred at room temperature for 10 min. Triethylamine was added to the mixture until the mixture was neutralized. The solvent was evaporated in vacuo. The resultant mixture was diluted with water. The aqueous mixture was extracted with EtOAc (10 mL×3). The extract was washed with brine (×2), dried over MgSO₄, and filtered. The filtrate was evaporated in vacuo to give 31 as a viscous oil (23.5 mg, 70%).

Synthesis of TBE-37 from Compound I

TBE-37 was synthesized from I using the procedure shown here:

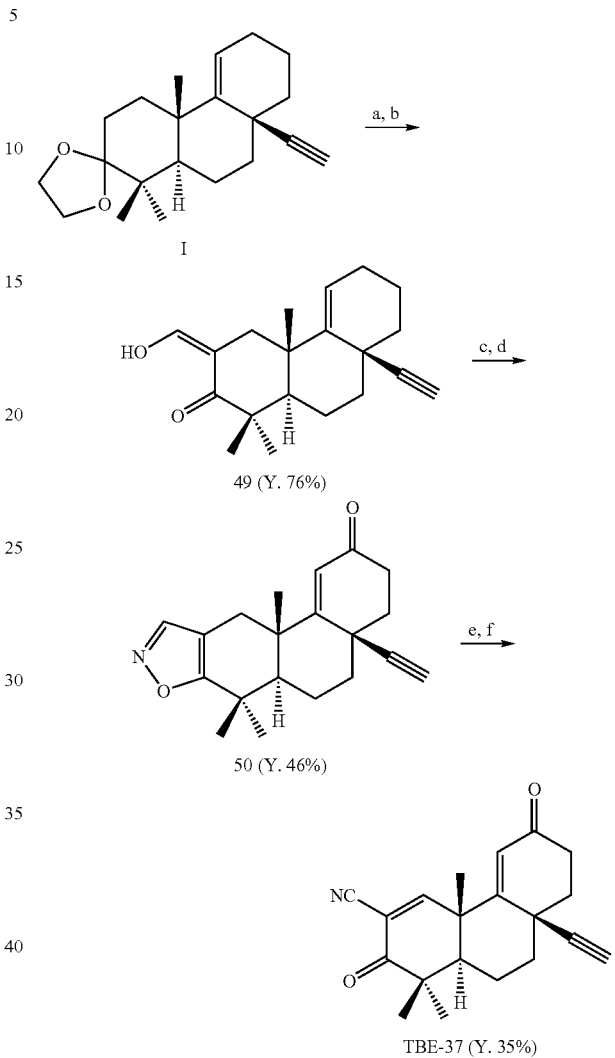

Synthesis of compound 49: To a solution of I (291 mg, 0.93 mmol) in warm methanol (67 mL) was added 10% aqueous HCl solution (13.5 mL). The mixture was stirred at room temperature for 10 min. The reaction mixture was evaporated and to the residue were added brine (50 mL) and ethyl acetate (20 mL). The aqueous mixture was extracted with ethyl acetate (40 mL×3). The extract was washed with saturated aqueous NaHCO₃ solution (40 mL×1), and brine (40 mL×1), then it was dried over MgSO₄ and evaporated to give a colorless oil (209 mg).

The oil (195 mg, 0.72 mmol) was dissolved in anhydrous benzene (3.3 mL), and to this solution were added ethyl formate (305 mg, 4.1 mmol) and sodium methoxide (222 mg, 4.1 mmol) successively. The mixture was stirred at room temperature for 75 min, and then it was diluted with CH₂Cl₂-Et₂O (1:2, 30 mL). The organic layer was washed with saturated aqueous NH₄Cl solution. The washings were extracted with CH₂Cl₂-Et₂O (1:2, 30 mL×3). The combined organic layers were washed with brine (40 mL×2) and dried over MgSO₄. The solution was evaporated in vacuo to give an orange residue (189 mg). The residue was purified by flash column chromatography [hexanes-ethyl acetate (3:1)] to give a pale orange solid 49 (195 mg, 76%).

Synthesis of compound 50: To a solution of 49 (189 mg, 0.63 mmol) in ethanol (9.5 mL) was added a solution of hydroxylamine hydrochloride (328 mg, 4.7 mmol) in water (1 mL). The mixture was refluxed at 105° C. for 1 h. The mixture was evaporated and diluted with water. The aqueous mixture was extracted with ethyl acetate (40 mL×3). The organic layer was washed with brine (40 mL×3) and dried over $MgSO_4$. The solution was evaporated to give a residue (154 mg) which was purified by flash column chromatography [hexanes-ethyl acetate (5:1)] to give a white solid (131 mg).

This solid (128 mg, 0.43 mmol) was dissolved in 2 mL of dry $CH_2Cl_2$ and a solution of 70% aqueous t-BuOOH solution (0.65 mL) was added dropwise at 0° C. To the mixture was added $CrO_3$ (60 mg, 0.6 mol), also at 0° C. The mixture was stirred at room temperature for 1 h, and then diluted with $CH_2Cl_2$-$Et_2O$ (1:2, 30 mL). The mixture was washed with 5% aqueous NaOH solution (15 mL×3). The basic washings were extracted with $CH_2Cl_2$-$Et_2O$ (1:2, 30 mL×3). The combined organic layers were washed with 5% aqueous HCl solution (30 mL×2), saturated $NaHCO_3$ solution (30 mL×2) and brine (30 mL×1). The solution was dried over $MgSO_4$, and evaporated to give a brown residue. The residue was purified by flash column chromatography [hexanes-ethyl acetate (1.5:1)] to give compound 50 (89 mg, 46%).

Synthesis of (±)-TBE-37: To a solution of sodium methoxide (463 mg, 8.6 mmol) in dry methanol (6 mL) was added a solution of compound 50 (86 mg, 0.28 mmol) in dry methanol (4 mL). Dry ether (3 mL) was added and the mixture was stirred at room temperature for 1.5 h. The reaction mixture was diluted with 40 mL of ethyl acetate, and washed with 5% aqueous HCl solution (20 mL×2), saturated aqueous $NaHCO_3$ solution (20 mL×2), and brine (20 mL×2). The solution was dried over $MgSO_4$ and evaporated to give a white solid (81 mg).

The solid (81 mg, 0.26 mmol) was dissolved in 1,4-dioxane (6 mL) and DDQ (81 mg, 0.36 mmol) was added. The mixture was stirred at room temperature for 1.5 h. The reaction mixture was evaporated and the resulting residue was dissolved in $CH_2Cl_2$. The insoluble matter was removed by filtration and the filtrate was evaporated to give a yellow solid (203 mg). After purification of this crude solid by flash column chromatography [hexanes-ethyl acetate (1:1)], followed by preparative TLC [$CH_2Cl_2$-MeOH (30:1)], 30 mg (35%) of TBE-37 was obtained as a white solid: $^1$H NMR (CDCl$_3$) δ 7.97 (1H, s), 5.99 (1H, s), 2.85 (1H, ddd, J=16.0, 16.0 and 4.52 Hz), 2.35 (1H, s), 1.72 (3H, s), 1.58 (1H, ddd, J=13.4, 13.4 and 4.03 Hz), 1.25, 1.18 (each 3H, s); $^{13}$C NMR (CDCl$_3$) δ 198.8, 196.5, 163.4, 162.5, 123.2, 114.7, 114.5, 86.1, 72.2, 49.7, 45.2, 44.3, 41.7, 39.4, 35.9, 34.4, 26.5, 24.7, 21.9, 19.4; MS (ESI+) m/z 308 [M+H]; HRMS (ESI+) calcd for $C_{20}H_{21}NO_2$+H, 308.1651, found 308.1646. Anal. Calcd for $C_{20}H_{21}NO_2$·1/4H$_2$O: C, 77.02; H, 6.95; N, 4.49. Found: C, 77.14; H, 6.92; N, 4.48.

Synthesis of TBE-45

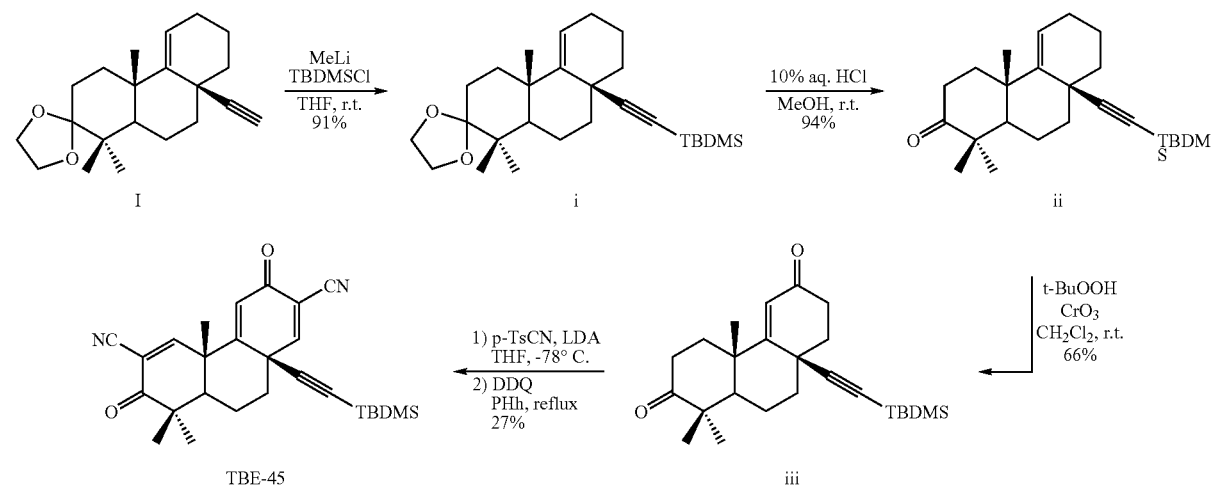

To a stirred solution of I (2.13 mmol, 670 mg) in dry THF (21 mL) was added, at 0° C. under N$_2$, MeLi (1.6M in hexanes, 10 eq, 21 mmol, 13 mL). The yellow mixture was stirred at room temperature for 30 min under N$_2$ and then a solution of TBDMSCl (12 eq, 25.6 mmol, 3.86 g) in dry THF (21 mL) was added dropwise at room temperature. The mixture was stirred at room temperature for 45 min under N$_2$. After addition of H$_2$O (25 mL), the mixture was extracted with CH$_2$Cl$_2$/Et$_2$O: 1/2 (3×35 mL). The combined organic layers were washed with a saturated NaHCO$_3$ aqueous solution (1×35 mL) and with brine (1×35 mL), dried over MgSO$_4$ and filtered. The filtrate was concentrated under reduced pressure to give 1.22 g of crude product as a white solid. The crude was purified by flash column chromatography (Hexanes/EtOAc: 10/1) to afford i (830 mg, 91%) as a white solid.

A suspension of i (1.90 mmol, 814 mg) in MeOH (110 mL) was warmed up and heated at 60° C. until complete dissolution. The heating was stopped and 22 mL of a 10% HCl aqueous solution was added to the mixture. After stirring at room temperature for 15 min, the mixture was neutralized with Et$_3$N and MeOH was removed under reduced pressure. 30 mL of H$_2$O were added to the residue and the resulting aqueous mixture was extracted with EtOAc (3×110 mL). The combined organic layers were washed with a saturated NaHCO$_3$ aqueous solution (1×100 mL) and with brine (1×100 mL), dried over MgSO$_4$ and filtered. The filtrate was concentrated under reduce pressure to give 810 mg of crude product as a pale yellow solid. The crude was purified by flash column chromatography (Hexanes/EtOAc: 10/1) to afford ii (685 mg, 94%) as a white solid.

To a stirred solution of ii (1.75 mmol, 675 mg) in dry $CH_2Cl_2$ (11 mL) was successively added, at 0° C. under $N_2$, t-BuOOH (70% in water, 10 eq, 17.5 mmol, 2.4 mmol) and $CrO_3$ (1.3 eq, 2.28 mmol, 228 mg). The dark red mixture was stirred at room temperature and under $N_2$ for 3 h. After dilution in $CH_2Cl_2/Et_2O$: 1/2 (90 mL), the organic layer was successively washed with a 5% NaOH aqueous solution (1×20 mL), with a 5% HCl aqueous solution (1×20 mL), with a saturated $NaHCO_3$ aqueous solution (1×20 mL) and with brine (1×20 mL), dried over $MgSO_4$ and filtered. The filtrate was concentrated under reduced pressure to give 830 mg of crude product as a dark red thick oil. The crude was purified by flash column chromatography (Hexanes/EtOAc: 5/1) to afford iii (465 mg, 66%) as a white solid.

To a stirred solution of iii (1.14 mmol, 444 mg) in dry THF (10 mL) was added, at −78° C. under $N_2$, LDA (2M in THF/heptane, 2.3 eq, 2.62 mmol, 1.3 mL). The yellow mixture was stirred at room temperature under $N_2$ for 20 min and then cooled to −78° C. for 10 min. A cloudy solution of p-TsCN⁻ (3.4 eq, 3.88 mmol, 703 mg) in dry THF (9 mL) was added and the mixture was stirred at −78° C. for 30 min under $N_2$. After addition of a saturated $NH_4Cl$ aqueous solution (5.7 mL), the mixture was allowed to reach room temperature and was acidified with a 10% HCl aqueous solution. The acidic mixture was extracted with EtOAc (3×50 mL). The combined organic layers were washed with a saturated $NaHCO_3$ aqueous solution (1×50 mL) and with brine (1×50 mL), dried over $MgSO_4$ and filtered. The filtrate was concentrated under reduced pressure to give a brown oil residue (700 mg). This residue was dissolved in anhydrous benzene (35 mL) and DDQ (2.18 mmol, 495 mg) was added to the solution. The red mixture was stirred at 100° C. for 10 min under $N_2$. The reaction mixture was cooled to room temperature. The insoluble matter was removed by filtration through cotton and the filtrate was concentrated under reduced pressure to give 710 mg of crude product as a brown residue. The crude was purified by flash column chromatography (Hexanes/EtOAc: 3/1) to give 286 mg of a beige solid. This solid was purified a second time by flash column chromatography ($CH_2Cl_2$/MeOH: 40/1) to give 249 mg of an off-white solid. This solid was recrystallized from Hexanes/EtOAc: 5/1 to afford TBE-45 (138 mg, 27%) as a white solid.

NMR data for TBE-45: $^1H$ NMR (CDCl$_3$, 500 MHz) δ0.12 (s, 3H), 0.13 (s, 3H), 0.93 (s, 9H), 1.21 (s, 3H), 1.27 (s, 3H), 1.63 (ddd, 1H, J 3.5, 13.0, 13.0 Hz), 1.96-1.99 (m, 1H), 2.24 (ddd, 1H, J 3.5, 13.0, 16.5 Hz), 2.48 (td, J 3.5, 13.0 Hz), 6.26 (s, 1H), 7.42 (s, 1H), 7.91 (s, 1H); $^{13}C$ (CDCl$_3$, 500 MHz) δ195.8, 178.7, 162.3, 160.5, 160.0, 122.3, 115.2, 114.2, 114.1, 113.2, 100.5, 93.2, 51.5, 45.3, 40.7, 40.5, 26.3, 26.2, 22.8, 21.8, 19.1, 16.8, −4.7, −4.8 ppm.

Example 2

Inhibitory Activity of C-8a Functionalized TBEs

The inventors have synthesized various C-8a functionalized TBE compounds and evaluated the potency for inhibition of NO production in RAW cells (see Tables 4-6, below). Based on these results, the inventors found the interesting structure-activity relationship that less polar and electron-releasing groups show higher potency. Particularly, (±)-TBE-31 having C-8a alkyne group is extremely potent at one nanomolar concentrations. The potency is higher than CDDO and equal to TP-225, which has the highest potency amongst semi-synthetic triterpenoids in the same assay (Honda et al., 2002).

TABLE 4

Inhibitory activity of C-8a functionalized TBE-10 analogs on NO production in RAW cells stimulated with interferon-γ

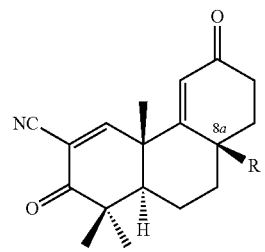

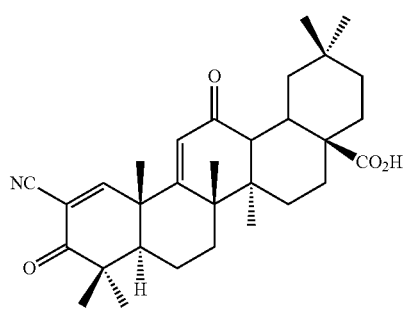

CDDO

| Compound (racemic) | R | IC$_{50}$ (nM) |
| --- | --- | --- |
| TBE-14 | CN | 64 |
| TBE-21 | CHO | 83 |
| TBE-20 | CO$_2$H | 83 |
| TBE-12 | CO$_2$Me | 287 |
| TBE-19 | CO$_2$SEM | 152 |
| TBE-18 | CONH$_2$ | <10,000 |
| TBE-16 | CH$_2$NH$_2$•HCl | 237 |
| TBE-15 | CH$_2$NHBoc | 64 |
| TBE-17 | CH$_2$F | 363 |
| TBE-22 | CH$_2$OAc | 85 |
| TBE-23 | CH$_2$OMe | 40 |
| TBE-13 | CH$_2$OH | 353 |
| TBE-10 | CH$_3$ | 22 |
| TBE-25 | CH$_2$CH$_3$ | 27 |
| TBE-9 | | 7 |
| CDDO | | 6 |
| hydroocortisone | | 61 |

TABLE 5

Inhibitory activity of C-8a functionalized TBE-9 analogs on NO production in RAW cells stimulated with interferon-γ

[Chemical structure of C-8a functionalized TBE-9 analog with R group, showing NC, O, and H substituents]

[Chemical structure of TP-225, showing NC, O, H, and CN substituents]

TP-225

| Compounds (racemic) | R | IC$_{50}$ (nM) |
|---|---|---|
| TBE-9 | CH$_3$ | 30 |
| TBE-26 | CN | 100 |
| TBE-28 | CH$_2$CH$_3$ | 10 |
| TBE-30 | CH=CH$_2$ | 10 |
| TBE-31 | CH≡CH | 1 |
| TBE-34 | C≡CH—TMS | 3 |
| TBE-35 | C=C—CH$_3$ | 5 |
| TBE-36 | C=C—CH$_2$CH$_3$ | 20 |
| TBE-38 | C=C—CN | 4 |
| TBE-39 | C=C—C=H | 3 |
| CDDO | | 20 |
| TP-225 | | 1 |

The inventors have found that TBE-34, a TBE-31 analog which is an intermediate for a synthesis of TBE-31, and TBE-39 show nearly equivalent potency to that of TBE-31 for inhibition against NO production in RAW cells (Table 5). TBE-34 is also nearly equivalent in potency to TBE-31 for induction of heme oxygenase (HO)-1 (see FIG. 9) and inhibition of inducible nitric oxide synthase (iNOS) in RAW cells (see FIG. 10). These results were unexpected, given that TBE-34 has an acetylene group with a bulky trimethylsilyl (TMS) substituent. While the inventors cannot rule out that TBE-34 may be converted to TBE-31 in living cells, that possibility is very low because the cleavage of the TMS group requires basic, acidic, or conditions involving the presence of tetrabutylammonium fluoride.

TABLE 6

Inhibitory activity of optically active TBE-31 and 34 on NO production in RAW cells stimulated with interferon-γ

[Chemical structure of (+)-enantiomer]

(+)-enantiomer

[Chemical structure of (−)-enantiomer]

(−)-enantiomer

| Compounds | R | IC$_{50}$ (nM) |
|---|---|---|
| (±)-TBE-31 | C≡CH | 1 |
| (+)-TBE-31 | C≡CH | 1 |
| (−)-TBE-31 | C≡CH | 3 |
| (±)-TBE-34 | C≡CH—TMS | 3 |
| (+)-TBE-34 | C≡CH—TMS | 2 |
| (−)-TBE-34 | C≡CH—TMS | 3 |

Interestingly and importantly, (+)-TBE-31 and 34 having the opposite configuration to those of triterpenoids show higher potency than (−)-TBE-31 and 34. These results are consistent with our previous results (Honda et al., 2003).

TBEs Inhibited Proliferation of RMPI 8226 Human Myeloma Cells and U937 Human Leukemia Cells Cells were treated with triterpenoids and TBEs for 3-4 days and counted by Coulter counter. FIG. 1 shows that a series of TBEs are extremely potent inhibitors of the growth of both human myeloma cells and human leukemia cells. Of the TBEs tested in this study, TBE-31 is by far the most potent, equivalent to that of CDDO itself (TP-151) in the 8226 myeloma cells, and more potent than CDDO in the U937 leukemia cells. CDDO is presently in clinical trial for treatment of acute myelogenous leukemia. TP-235 is the imidazolide derivative of CDDO.

TBE-31 was a Potent Inducer of Heme Oxygenase-1 in U937 Cells in Culture

Figure 2:
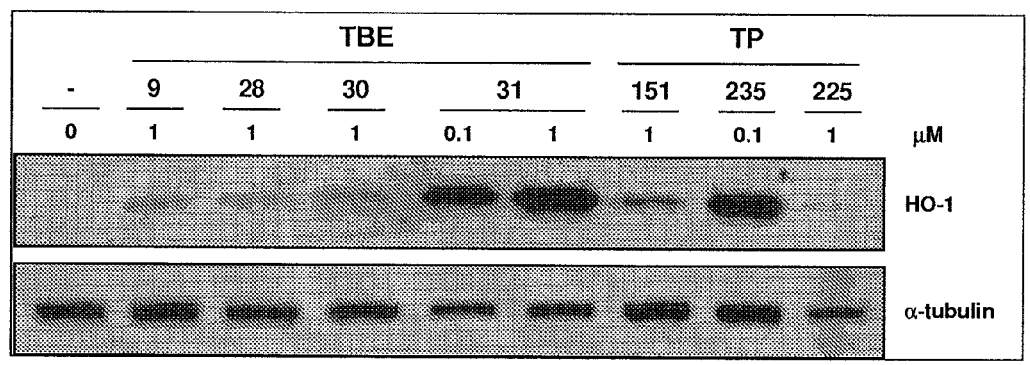
FIG. 2. TBE-31 is a potent inducer of heme oxygenase-1 in U937 cells in culture. Cells were incubated with TBEs and triterpenoids (0.1-1 µM) for 7 hours. Total cell lysates were analyzed by SDS-PAGE, probed with an HO-1 antibody, and developed by ECL.

Cells were incubated with triterpenoids or TBEs (0.1-1 μM) for 7 hours. Total cell lysates were analyzed by SDS-PAGE, probed with an HO-1 antibody, and developed by ECL. FIG. 2 shows that TBE-31 is a potent inducer of heme oxygenase in U937 cells. None of the other TBEs that were tested provided significant induction of heme oxygenase. For comparison of TBE-31 with the triterpenoids, one notes that TBE-31 is markedly more potent than TP-151 (CDDO), and almost as potent as TP-235, which is the imidazolide derivative of CDDO.

Figure 3:
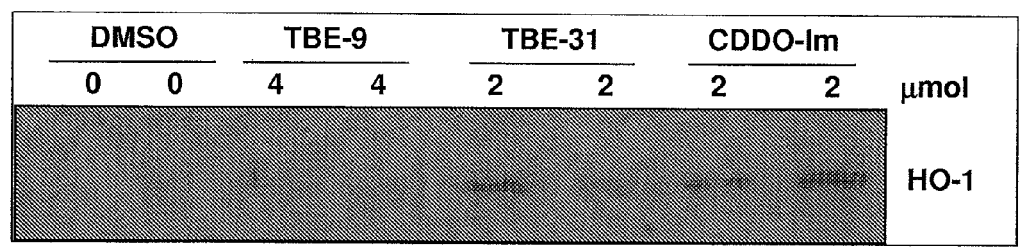
FIG. 3. TBE-31 is a potent inducer of heme oxygenase-1 in vivo when given by gavage. CD-1 mice (2 per group) were gavaged with TBEs or CDDO-Im in DMSO. After 6 h, livers were harvested and homogenized. Lysates were separated by SDS-PAGE, probed with HO-1 antibodies, and developed by ECL.

TBE-31 was a Potent Inducer of Heme Oxygenase-1 In Vivo when Given by Gavage CD-1 mice (2 per group) were gavaged with TBEs or CDDO-Im in DMSO. After 6 h, livers were harvested and homogenized. Lysates were separated by SDS-PAGE, probed with HO-1 antibodies, and developed by ECL. FIG. 3 shows that TBE-31 is an orally active agent. The level of induction with TBE-31 is again comparable to that found with CDDO-Imidazolide, a very potent triterpenoid agent for induction of heme oxygenase-1.

TBE-31 Induces CD11b Expression in U937 Cells

Figure 4:
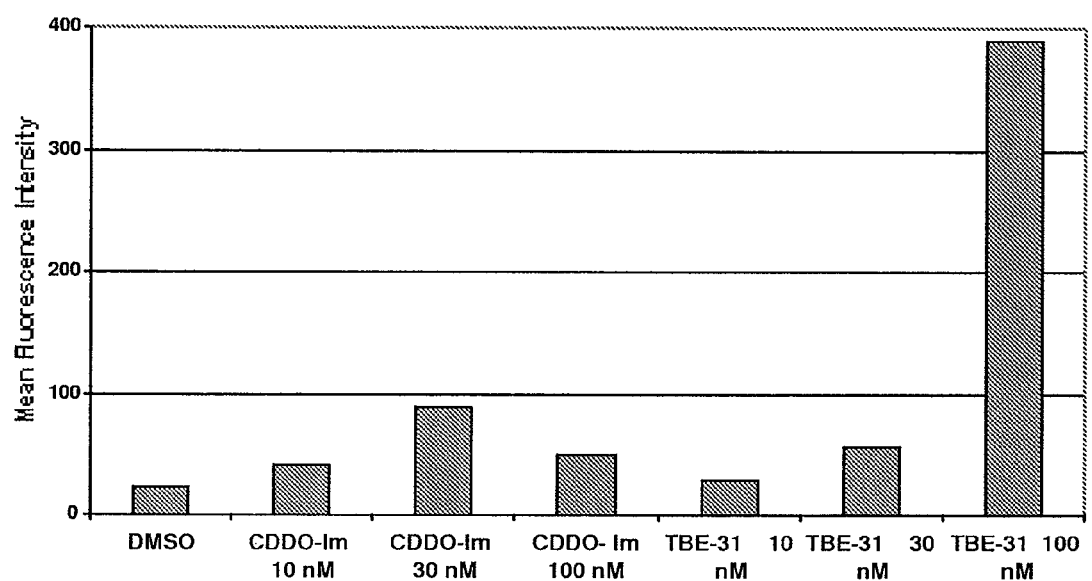
FIG. 4. TBE-31 induces CD11b expression in U937 cells. Cells were incubated with CDDO-Im or TBE-31 (10-100 nM) for 4 days. CD11b expression was measured by FACS analysis. Induction of CD11b is a marker of leukemia cell differentiation.

Cells were incubated with CDDO-Im or TBE-31 (10-100 nM) for 4 days. CD11b expression was measured by FACS analysis. Induction of CD11b is a marker of leukemia cell differentiation. FIG. 4 shows that TBE-31 strongly induces CD11b at 100 nM. Although the potency is comparable to that of CDDO-Im at 10 and 30 nM, it is more potent than CDDO-Im at 100 nM.

TBEs Inhibit iNOS in Raw Cells Stimulated with Interferon-γ

Figure 5:
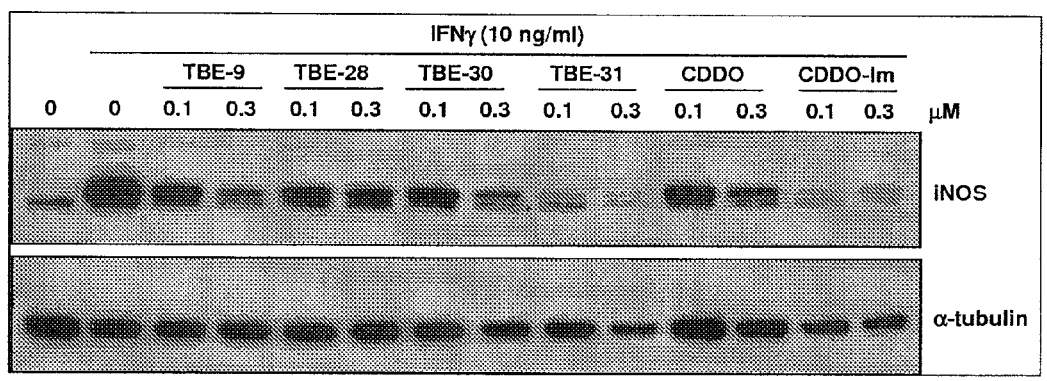
FIG. 5. TBEs inhibit iNOS in RAW cells stimulated with interferon-γ. Cells were incubated with TBEs and triterpenoids (0.1-0.3 µM) and IFN-γ (10 ng/ml) for 24 hours. Total cell lysates were analyzed by SDS-PAGE, probed with an iNOS antibody, and developed by ECL. The data in FIG. 5 show that TBE-31 is a potent suppressor of induction of iNOS in the mouse macrophage-like cell line, RAW 264.7. TBE-31 is significantly more potent than CDDO, and almost as potent as CDDO-Imidazolide (CDDO-Im). These data have important implications for the potential use of TBE-31 to suppress inflammation in a wide variety of diseases.

Cells were incubated with triterpenoids (0.1-0.3 mM) and IFNg (10 ng/ml) for 24 hours. Total cell lysates were analyzed by SDS-PAGE, probed with an iNOS antibody, and developed by ECL. The data in FIG. 5 show that TBE-31 is a potent suppressor of induction of iNOS in the mouse macrophage-like cell line, RAW 264.7. TBE-31 is significantly more potent than CDDO, and almost as potent as CDDO-Imidazolide (CDDO-Im).

TBEs Inhibit Proliferation of Jurkat Cells

Figure 6:
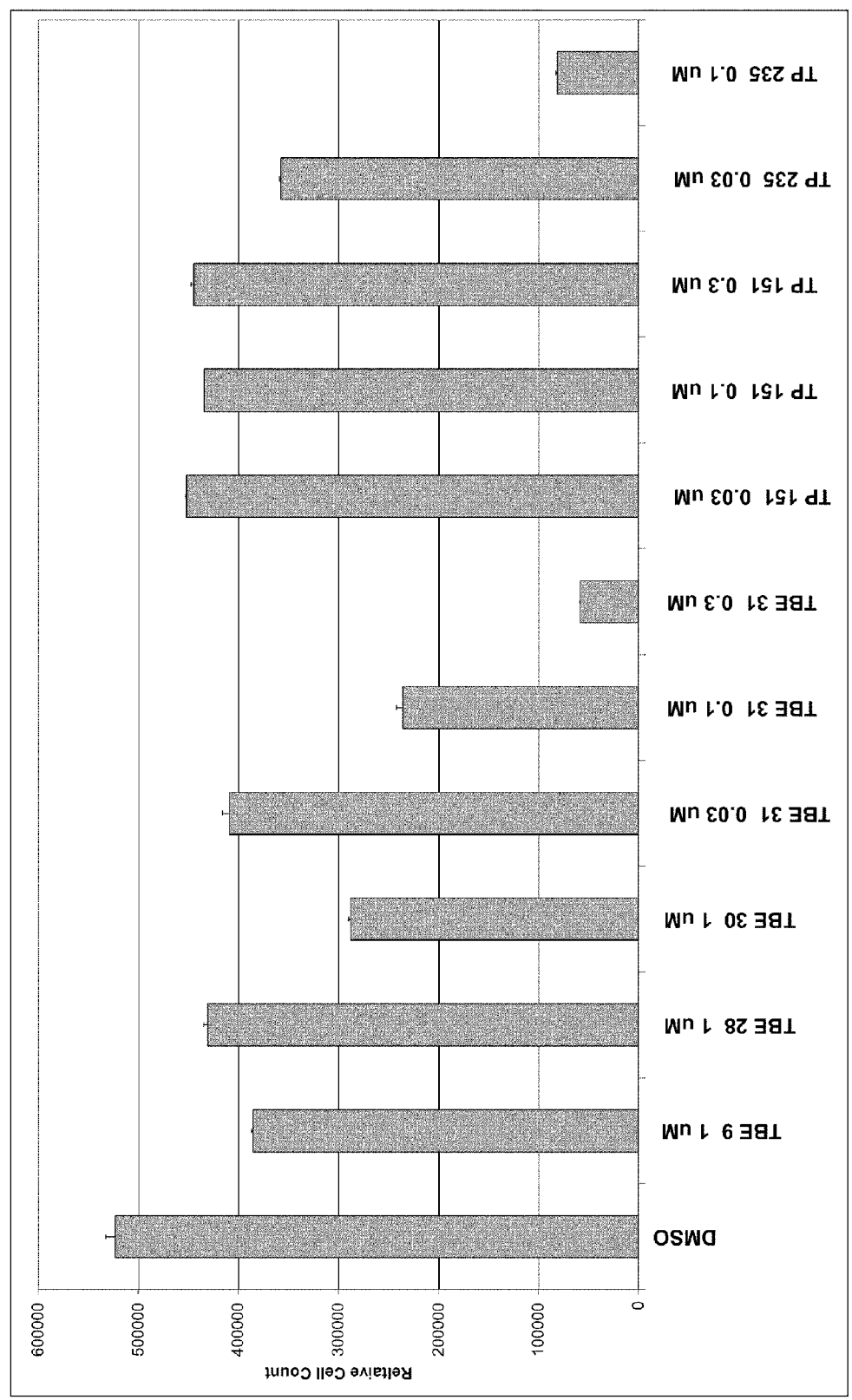
FIG. 6. TBEs inhibit proliferation of Jurkat cells. Cells were treated with TBEs and triterpenoids for 3-4 days and counted by Coulter counter. Jurkat cells are a T-cell leukemia, and this FIG. shows that TBE-31 is extremely active, more so than CDDO (TP-151), in controlling the growth of a malignancy originating from T-cells. Thus, it is to be expected that TBEs may have useful activities in regulation of lymphocyte, as well as macrophage, function.

Cells were treated with TBEs for 3-4 days and counted by Coulter counter. Jurkat cells are a T-cell leukemia, and FIG. 6 shows that TBE-31 is extremely active, more so than CDDO (TP-151), in controlling the growth of a malignancy originating from T-cells.

TBE-31 Induces Apoptosis in A549 Human Lung Cancer Cells

Figure 7:
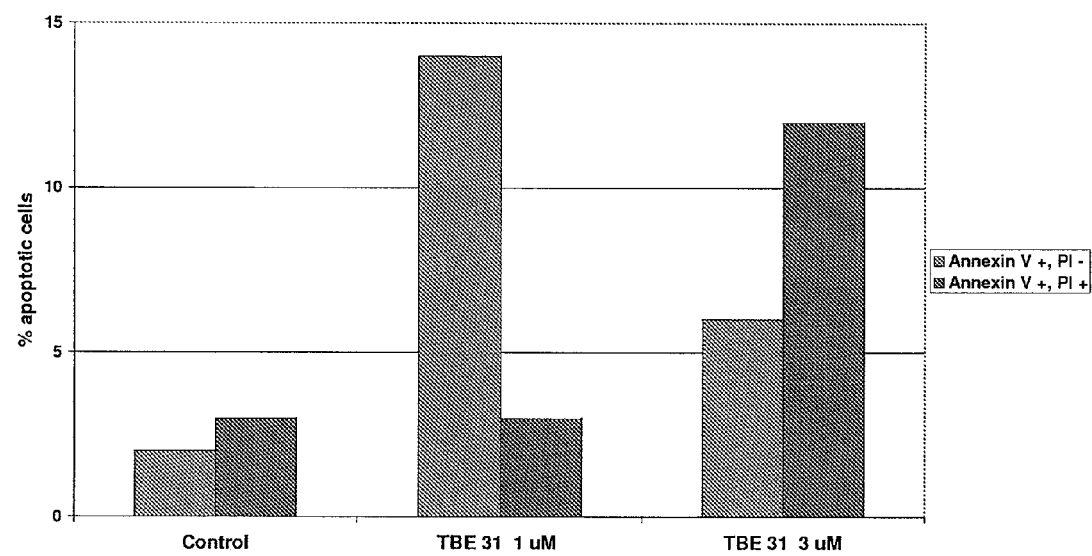
FIG. 7. TBE-31 induces apoptosis in A549 human lung cancer cells. Cells were treated with TBE-31 for 24 h. A549 is a classic human lung cancer cell line. This FIG. shows that TBE-31 can induce both early and late apoptosis.

Cells were treated for 24 h. A549 is a classic human lung cancer cell line. FIG. 7 shows that TBE-31 can induce both early and late apoptosis.

Induction of Apoptosis in U937 Cells by TBEs

Figure 8:
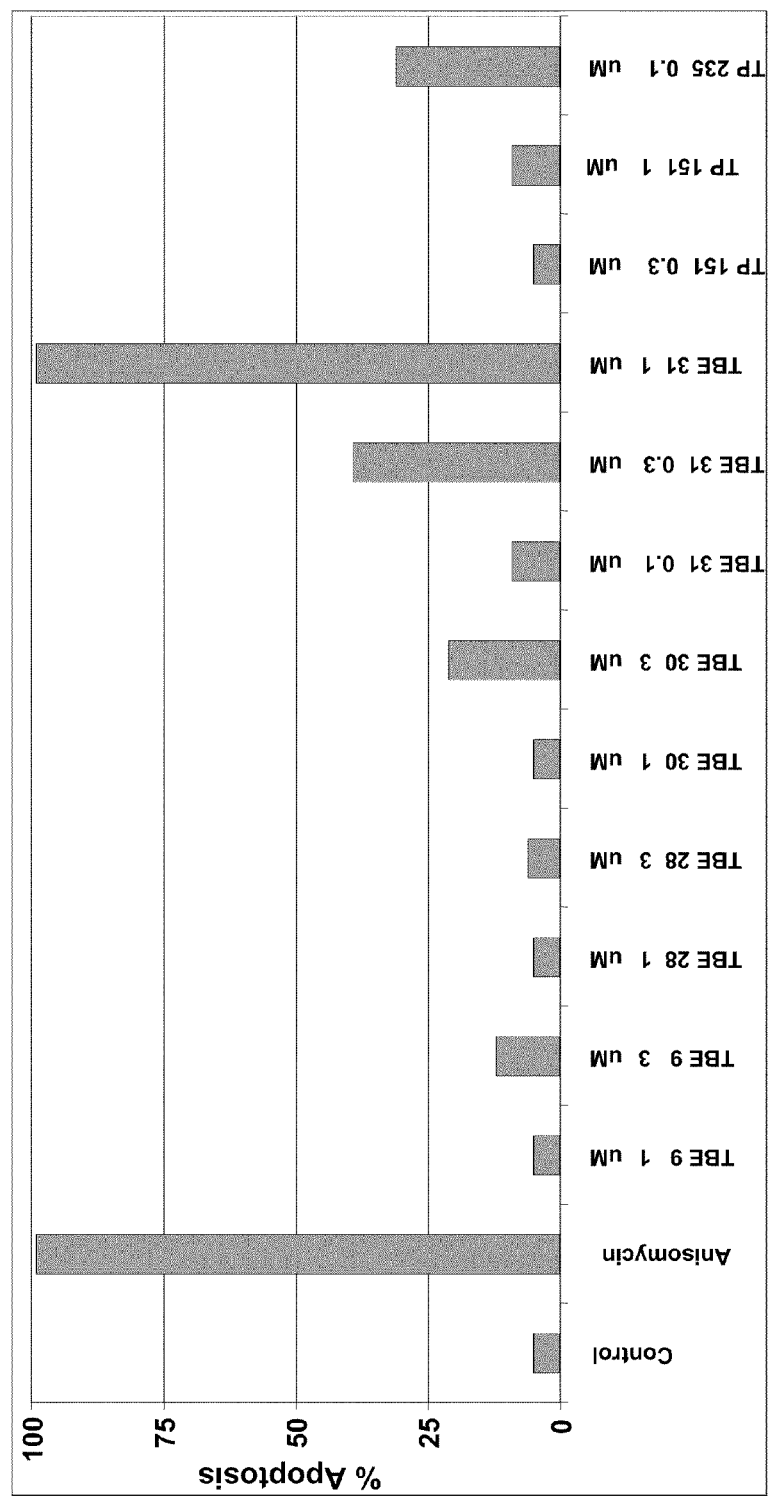
FIG. 8. Induction of apoptosis in U937 cells by TBEs. Cells were treated with TBEs and triterpenoids for 24 hours. Apoptosis was measured by Annexin V. TBE-31 is the most active of the TBEs, and is markedly more active than CDDO (TP-151).

Cells were treated for 24 hours. Apoptosis was measured by Annexin V. TBE-31 is the most active of the TBEs, as shown in FIG. 8, and is markedly more active than CDDO (TP-151).

TBEs Induce HO-1 in RAW Cells

Cells were incubated with TBEs (30-300 nM) for 24 hours. Total cell lysates were analyzed by SDS-PAGE, probed with HO-1 antibodies, and developed by ECL (see FIG. 9). TBE-31, at 30 nM, is higher inducer than CDDO-Im, which is the most potent compound amongst semi-synthetic triterpenoid analogues in this assay. TBE-34, at 30 and 300 nM, shows similar potency to that of CDDO-Im.

TBEs Inhibit the Induction of iNOS in Raw Cells Stimulated with IFNγ

Cells were incubated with TBEs (30-300 nM) and IFNγ (10 ng/ml) for 24 hours. Total cell lysates were analyzed by SDS-PAGE, probed with iNOS antibody, and developed by ECL. TBE-31 and CDDO-Im, at 30 nM, show similar inhibitory potency in this assay. TBE-34 is nearly equivalent in potency to both compounds.

Example 3

Biological Evaluation In Vitro and In Vivo of TBEs

A Prophetic Example

Standard methodology already in place in the laboratory (Suh et al., 1998, 1999) will be used to evaluate the biological activity of newly synthesized TBEs using suppression of de novo synthesis of iNOS and COX-2 as endpoints. Briefly, primary mouse macrophages or RAW264.7 cells will be cultured under standard conditions and stimulated with either interferon-γ or lipopolysaccharide (LPS). TBEs are added to cell cultures at the same time as inducers. Nitric oxide production in cell culture supernatants is measured as nitrite accumulation by the Griess reaction. Analysis of levels of iNOS protein in lysates of primary macrophages or RAW cells is done by Western blot analysis, while levels of iNOS mRNA are done by routine Northern blot analysis. Prostaglandin E2 production is measured with a commercially available ELISA assay kit, and COS-2 protein and mRNA levels are measured by routine Western and Northern blot analysis, respectively.

Assays are available to show activity in suppressing inflammation in vivo (ip, po and iv). The simplest assay for this purpose is to demonstrate that a new TBE can block the activation of macrophages (induced by interferon-γ) in the peritoneal cavity of mice. Mice will be injected ip with thioglycollate to stimulate the formation of macrophages, and these will be activated by ip injection of interferon-γ. A second in vivo system in which to text TBEs for suppression of macrophage activation is the granulomatous hepatitis model that has been used by Nathan and colleagues (Nicholson et al., 1999; MacMicking et al., 1995). In this model, mice are injected ip with heat killed bacteria (*Propionibacterium acnes*), which results in the recruitment and activation of macrophages in the liver to form a granulomatous lesion. If such mice are challenged with LPS a week after injection with *Propionibacterium acnes*, they show a greatly enhanced response to LPS, as can be measured by high serum levels of nitrate plus nitrite (products of iNOS activity). The inventors will use TBEs to block the original formation of lesions in the liver as well as to block the response of activated liver macrophages to LPS. A third in vivo test is to evaluate the potency of TBEs against lethal inflammation of C57BL/6 mice caused by oral infection with *Toxoplasma gondii*. This model has been used by Dr. Kasper, Department of Medicine and Microbiology, Dartmouth Medical School, and colleagues (for example, Khan et al., 1997; Lee et al., 1999; Buzoni-Gatel et al., 1999, 2001). Because overproduction of IFN-γ and synthesis of NO mediate this inflammation, inhibitors of production of NO like TBEs are expected to prevent early death in these mice.

Inhibitors of cell proliferation are known to be useful cancer chemopreventive and chemotherapeutic agents. The inventors will test TBE compounds for inhibition of proliferation of many malignant or premalignant cells (in vitro), e.g., human MCF-7 breast carcinoma, mouse L1210 leukemia, mouse B16 melanoma, and rat NRP-152 nonmalignant prostate epithelium. Furthermore, the inventors will test TBE compounds in L1210 leukemia and B16 melanoma in vivo.

The inventors also propose long term in vivo assays of suppression of mammary or colon carcinogenesis in rates. The inventors have been actively engaged for the past 20 years in the rat model for breast cancer that employs nitrosomethylurea (NMU) as the carcinogen and it would be straightforward to determine if any new TBEs were active in this model.

Example 4

TBE Suppression of NF-κB Activation

A Prophetic Example

Suppression of NF-κB activation by TBEs will be determined according to the methods (Suh et al., 1998), using standard gel shift assays (EMSAs). Briefly, nuclear proteins will be extracted from macrophages or other cells by detergent lysis and then incubated with a $^{32}$P-labeled NF-κB oligonucleotide probe containing an NF-κB response element, followed by gel shift analysis. For the new TBEs, the inventors will determine dose-response, kinetics of action, and interactions with other known effectors. Ability to block specific inducers of NF-κB activation, such as interferon-γ, TNF-α, LPS, phorbol ester, etc. will be measured. The inventors will adopt two approaches in the study of effects of TBEs on events leading to the degradation of IκB and activation of NF-κB. Efforts will be focused on two known, well characterized kinases that lead to the phosphorylation of IκB, namely IKK (IκB kinase), which phosphorylates IκB directly, and NIK (NF-κB inducing kinase), which can phosphorylate IKK to enhance its kinase activity.

The first approach is to use natural inducers such as IL-1β, TNF-α, or LPS to treat different cell lines. Lysates will be harvested and IKK will be immunoprecipitated. Using an in vivo kinase assay, recombinant GST-IκB (1-62) protein will be used to detect the activity of IKK, with or without treatment with TBEs.

Phosphorylated GST-IκB can be detected either using $^{32}$P-labeled ATP in kinase assay, or using a phospho-IκB specific antibody through Western analysis.

The second approach is to transfect IKK expression vectors in HeLa cells, with or without added NIK expression vectors. After immunoprecipitation with an antibody against HA, IKK activities in the absence (basal activity) or presence (induced activity) of NIK will be measured as detailed above. The inventors will subsequently study the effects of TBEs on these transfected kinase activities. Detailed methods for all of the above have been published by Rossi et al. (2000).

Example 5

Biological Evaluation of iNOS Activation

Reagents

Recombinant mice IFN-γ (LPS content, <10 pg/mL) were purchased from R & D systems (Minneapolis, Minn.). Polyclonal iNOS, IgG and peroxidase-conjugated secondary antibody were obtained from Santa Cruz (Santa Cruz, Calif.). All other chemicals were purchased from Sigma Chemical Co. (St. Louis, Mo.). Inhibitory test compounds were dissolved in DMSO before addition to cell cultures; final concentrations of inhibitory test compounds in DMSO were 0.1% or less. Controls with just DMSO were run in all cases.

Cell Culture

Female CD-1 mice, 5-10 weeks of age were obtained from the Charles River Breeding Laboratories (Wilmington, Mass.). To obtain primary macrophages, female CD-1 mice were injected intraperitoneally with 2 mL of 4% thioglycollate broth (Difco Laboratories, Detroit, Mich.). Four days after injection, peritoneal macrophages were harvested and processed according to Bogden et al. (1992). Cells were seeded in 96-well plates at 2×10$^5$ cells/well and incubated for 48 h with 10 ng/mL of IFN-γ in the presence or absence of inhibitory test compounds.

Measurement of Nitric Oxide (NO) Production in Mouse Macrophages

Nitrite accumulation was used as an indicator of NO production in the medium and was assayed by the Griess reaction. One hundred μL of Griess reagent was added to 100 μL of each supernatant from IFN-γ or inhibitory test compound-treated cells in triplicate. The plates were read at 550 nm against a standard curve of sodium nitrite. The protein determination was performed by Bradford protein assay (Ding et al., 1990).

SDS-PAGE and Western Blot Analyses of iNOS Protein in Primary Macrophages

For the evaluation of iNOS activation in vivo, female CD-1 mice were injected with 2 mL of 4% thioglycollate broth 3 days before IFN-γ stimulation. On day 3, test compounds were prepared in 0.1 mL volume of solvent mixture (DMSO: Ethanol:Water=2:2:1) and gavaged once to mice (6 per group). Then, 1 hr later, IFN-γ (0.5 μg/mouse) was given intraperitoneally. Ten hours after IFN-γ stimulation, mice were sacrificed, and peritoneal macrophages were collected and plated in 6-well plates. Cells were kept in incubators with 5% $CO_2$ at 37° C. for 12 hrs. The accumulation of nitric oxide in the supernatant was measured by the Griess reaction, as described above. To obtain total proteins, cells were washed and scraped into cold PBS, and then centrifuged at 500 g for 10 min at 4° C. The cell pellets were resuspended in 50 mM Tris-buffer (pH 7.4), and 100 mM NaCl, containing 0.5% of NP-40, 5 μg/mL of aprotinin, 10 μg/mL of leupeptin and 100 μM of PMSF, and then centrifuged to obtain whole cell lysates. The proteins (20-50 μg) were electrophoresed on 7.5% reducing SDS-PAGE and transferred in 20% methanol, 25 mM Tris, 192 mM glycine (pH 8.3) to 0.2 micron nitrocellulose membranes. The membranes were blocked with 5% non-fat milk in Tris-buffered saline (25 mM Tris, pH 7.5, 150 mM NaCl, 0.02% $NaN_3$) with 0.2% Tween-20 (Tween-TBS) for 1 h, then incubated with antibody to iNOS for 2-3 h, washed and finally incubated for 45 min with a 1:10,000 dilution of secondary antibody conjugated with horseradish peroxidase. The membranes were washed and then developed using a chemiluminescence system (enhanced chemiluminescence detection reagents; Amersham).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, and those listed in the Appendix, to the extent that they provide exemplary procedural or other details supplementary to those set forth herein, are specifically incorporated herein by reference.

U.S. Pat. No. 4,683,195
U.S. Pat. No. 6,025,395
Abraham and Kappas, *Free Radic Biol Med.*, 39(1):1-25, 2005
Ahmad et al., "Triterpenoid CDDO-Me blocks the NF-κB pathway by direct inhibition of IKKβ on Cys-179", *J. Biol. Chem.*, Sep. 24, 2006.
Amstutz et al., *Helv. Chim. Acta.*, 70:2232-2244, 1987.
Araujo et al., *J. Immunol.*, 171(3):1572-1580, 2003.

Ausubel et al., In: *Current Protocols in Molecular Biology*, John, Wiley & Sons, Inc, NY, 1994.
Bach, *Hum. Immunol.* 67(6):430-432, 2006
Baeuerle and Baltimore, *Cell*, 87:13-20, 1996.
Bagasra et al., *Proc. Natl. Acad. Sci. USA*, 92:12041-12045, 1995.
Baldwin, *Annu. Rev. Immunol.*, 14:649-681, 1996.
Bargou et al., *J. Clin. Invest.*, 100:2961-2969, 1997.
Barkett and Golmore, *Oncogene*, 18:6910-6924, 1999.
Barnes and Karin, *N. Engl. J. Med.*, 336:1066-1071, 1997.
Beal, *Curr. Opin. Neurobiol.*, 6:661-666, 1996.
Bogdan et al., *J. Biol. Chem.*, 267:23301-23308, 1992.
Boolbol et al. *Cancer Res.*, 56:2556-2560, 1996.
Buzoni-Gatel et al., *Gastroenterolog*, 120:914-924, 2001.
Buzoni-Gatel et al., *J. Immunol.*, 162:5846-5852, 1999.
Cai et al., *Helv. Chim. Acta.*, 78:732-757, 1995.
Cassady and Suffness, In *Anticancer Agents Based on Natural Product Models*; Academic Press, NY, 254-269, 1980.
Charney, In: *The Molecular Basis of Optical Activity*; Wiley Interscience, NY, 167-191, 1979.
Chung and Wasicak, *Tetrahedron Lett.*, 31:3957-3960, 1990.
Clinton et al., *J. Am. Chem. Soc.*, 83:1478-1491, 1961.
Corey and Ruden, *Tetrahedron Lett.*, 1495-1499, 1973.
Coyle and Puttfarcken, *Science*, 262:689-695, 1993.
Culver et al., *Science*, 256:1550-1552, 1992.
Dinkova-Kostova et al., *Proc. Natl. Acad. Sci. USA*, 102(12): 4584-4589, 2005
Ding et al., *J. Immunol.*, 145:940-944, 1990.
DuBois et al., *Gastroenterology*, 110:1259-1262, 1996.
Favaloro et al., *J. Med. Chem.*, 45:4801-4805, 2002.
Finkbeiner and Stiles, *J. Am. Chem. Soc.*, 85:616-622, 1963.
Gait, In: *Oligonucleotide Synthesis: A Practical Approach*, IRL Press Oxford, United Kingdom, 1984.
Genain and Nauser, *J. Mol. Med.*, 75:187-197, 1997.
Glover, In: *DNA Cloning*, Volumes I and II, 1985.
Ghosh et al., *Annu. Rev. Immunol.*, 16:225-260, 1998.
Grieco and Speake, *J. Org. Chem.*, 63:5929-5936, 1998.
Guttridge et al., *Mol. Cell. Biol.*, 19:5785-5799, 1999.
Hames and Higgins, In: *Nucleic acid hybridisation: a practical approach*, IRL, Oxford, UK, 1985.
Hinz et al., *Mol. Cell. Biol.*, 19:2690-2698, 1999.
Hirota et al., *Agric. Biol. Chem.*, 54:1073-1075, 1990.
Honda et al., *Med. Chem. Lett.*, 7:1623-1628, 1997.
Honda et al., *Bioorg. Med. Chem. Lett.*, 9:3429-3434, 1999.
Honda et al., *Bioorg. Med. Chem. Lett.*, 19:2711-2714, 1998.
Honda et al., *J. Med. Chem.*, 43:1866-1877, 2000a.
Honda et al., *J. Med. Chem.*, 43:4233-4246, 2000b.
Honda et al., *Bioorg. Med. Chem. Lett.*, 12:1027-1030, 2002.
Honda et al., *Org. Biomol. Chem.*, 1:438/11391, 2003.
Honda et al., *Org. Prep. Proced. Int.*, 37:546-550, 2005.
Huang et al., *Cancer Res.*, 54:701708, 1994.
Huang et al., *Clin Cancer Res.*, 6:2573-2581, 2000.
Hyer et al., *Cancer Res.*, 65(10:4799-4808, 2005.
Ikeda et al., *Cancer Res.*, 63:5551-5558, 2003.
Iguchi et al., *J. Org. Chem.*, 58:5690-5698, 1993.
Ishikawa et al., *Circulation*, 104(15):1831-1836, 2001.
Johnson and Shelberg, *J. Am. Chem. Soc.*, 67:1745-1754, 1945.
Joyce et al., *J. Biol. Chem.*, 274:25245-25249, 1999.
Kahne and Collum, *Tetrahedron Lett.*, 22:5011-5014, 1981.
Kaltschmidt et al. *Proc. Natl. Acad. Sci. USA*, 94:2642-2647, 1997.
Kerwin et al., *J. Org. Chem.*, 52:1686-1695, 1987.
Khan et al., *Proc. Natl. Acad. Sci. USA*, 94:13955-13960, 1997.
Kowalski and Reddy, *J. Org. Chem.*, 57:7194-7208, 1992.
Kruger et al., *J Pharmacol Exp Ther.*, 2006 Sep. 7.
Liby et al., *Cancer Res.*, 65:4789-4798, 2005.
Liotta et al., *J. Org. Chem.*, 46:2920-2923, 1981.
Lee et al., *Experimental Parasitology*, 91:212-221, 1999.
Liu et al., *FASEB J.*, 20(2):207-216, 2006.
Luo et al., *J. Clin. Invest.*, 115(10):2625-2631, 2005.
MacMicking et al., *Cell*, 81:641-650, 1995.
Mayer and Walker, In: *Immunochemical Methods in Cell and Molecular Biology*, Academic Press, 1988.
Marnett, *Cancer Res.*, 52:5575-5589, 1992.
McGeer and McGeer, *Brain Res. Brain Res. Rev.*, 21:195-218, 1995.
McGeer et al., *Neurology*, 19:331-338, 1996.
Mella et al., *Tetrahedron*, 44:1673-1678, 1988.
Merrill and Benvenist, *Trends Neurosci.*, 19:331-338, 1996.
Moncada et al., *Pharmacol. Rev.*, 43:109-141, 1991.
Morse and Choi, *Am. J. Respir. Crit. Care Med.*, 27(1):8-16, 2002.
Morse and Choi, *Am. J. Respir. Crit. Care Med.*, 172(6):660-670, 2005.
Murray and Zweifel, *Synthesis*, 150-151, 1980.
Muzart, *Tetrahedron Lett.*, 28:4665-4668, 1987.
Nathan and Xie, *Cell*, 78:915-918, 1994.
Nicholson et al., *Shock*, 11:253-258, 1999.
Nishino et al., *Cancer Res.*, 48:5210-5215, 1988.
Ohshima and Bartsch, *Mutat. Res.*, 305:253-264, 1994.
Omura and Swern, *Tetrahedron*, 34:1651-1660, 1978.
Oshima et al., *Cell*, 87:803-809, 1996.
Pahl, *Oncogene*, 18:6853-6866, 1999.
Paul et al., *Inorg. Chem.*, 41:3699-3704, 2002.
Place et al., *Clin. Cancer Res.*, 9:2798-2806, 2003.
Prescott and White, *Cell*, 87:783-786, 1996.
Rayet and Gélinas, *Oncogene*, 18:6938-6947, 1999.
Reddy et al., *Cancer Res.*, 56:4566-4569, 1996.
Rossi et al., *Nature*, 403:103-108, 2000.
Ruest et al., *Syn. Comm.*, 6:169-174, 1976.
Sacerdoti et al., *Curr Neurovasc Res.* 2(2):103-111, 2005.
Salvemini et al., *J. Clin. Invest.*, 93:1940-1947, 1994.
Sambrook et. al., In: *Molecular Cloning: A Laboratory Manual*, $2^{nd}$. Ed., Cold Spring Harbor Laboratory Press, Cold Spring Harbor, N.Y., 1989.
Satoh et al., *Proc Natl Acad Sci USA*, 103(3):768-773, 2006.
Sheng et al. *Gastroenterology*, 113:1883-1891, 1997.
Shishodia et al., *Clin. Cancer Res.*, 12(6):1828-1838, 2006.
Siebert and Masferrer, *Receptor*, 94:17-23, 1994.
Simonian and Coyle, *Annu. Rev. Pharmacol. Toxicol.*, 36:83-106, 1996
Singh et al., *J. Pharm. Pharmacol.*, 44:456-458, 1992.
Sonogashira et al., *Tetrahedron Lett.*, 4467-4470, 1975.
Sporn and Roberts, *J. Clin. Invest.*, 78:329-332, 1986.
Sterzycki, *Synthesis*, 724-725, 1979.
Stewart et al., *Neurology*, 48:626-632, 1997.
Strejan et al., *J. Neuroimmunol.*, 7:27, 1984.
Suh et al., *Cancer Research*, 58:717-723, 1998.
Suh et al., *Cancer Research*, 59:336-341, 1999.
Takahashi et al., *Cancer Res.*, 57:1233-1237, 1997.
Tamir and Tannenbaum, *Biochim. Biophys. Acta.*, 1288:F31-F36, 1996.
Tsujii and DuBois, *Cell*, 83:493-501, 1995.
Vodovotz et al., In; *Handbook of Experimental Immunology*, Volumes I-IV, 1996.
Wang et al., *Mol. Endocrinol.*, 14(10):1550-1556, 2006.
Weir and Blackwell, In: *Handbook Of Experimental Immunology*, Volumes I-IV, 1986.
Wermuth and Stahl, In: *Pharmaceutical Salts: Properties, Selection and Use—A Handbook*, Verlag Helvetica Chimica Acta, 2002.
Williams et al., *Clin. Neurosci.*, 2(3-4):229-245, 1994.
Yates et al., *Cancer Res.*, 66(4): 2488-2494, 2006.
Yue et al., *Cancer & Biology Therapy*, 5(5):492-497, 2006.
Zou et al., *Cancer Research*, 64:7570-7578, 2004.
Zhou et al., *Am J Pathol.*, 166(1):27-37, 2005.

What is claimed is:

1. A method of treating lung cancer, leukemia, or multiple myeloma in an individual in need thereof, comprising administering to the individual a therapeutically effective amount of a compound having the formula:

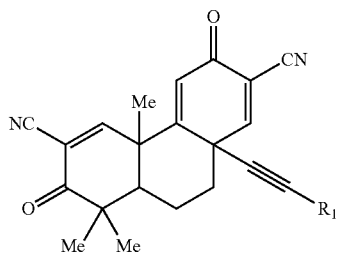

wherein $R_1$ is —H, hydroxy, amino, cyano, halo, nitro, or substituted or unsubstituted versions of $C_1$-$C_{15}$-alkyl, $C_2$-$C_{15}$-alkenyl, $C_2$-$C_{15}$-alkynyl, $C_6$-$C_{15}$-aryl, $C_7$-$C_{15}$-aralkyl, $C_1$-$C_{15}$-heteroaryl, $C_2$-$C_{15}$-heteroaralkyl, $C_1$-$C_{15}$-acyl, $C_1$-$C_{15}$-alkoxy, $C_2$-$C_{15}$-alkenyloxy, $C_2$-$C_{15}$-alkynyloxy, $C_6$-$C_{15}$-aryloxy, $C_7$-$C_{15}$-aralkoxy, $C_1$-$C_{15}$-heteroaryloxy, $C_2$-$C_{15}$-heteroaralkyloxy, $C_1$-$C_{15}$-acyloxy, $C_1$-$C_{15}$-alkylamino, $C_2$-$C_{15}$-alkenylamino, $C_2$-$C_{15}$alkynylamino, $C_6$-$C_{15}$-arylamino, $C_7$-$C_{15}$-aralkylamino, $C_1$-$C_{15}$-heteroarylamino, $C_2$-$C_{15}$-heteroaralkylamino, $C_2$-$C_{15}$-amido, or $C_0$-$C_{15}$-silyl;

or a pharmaceutically acceptable salt or tautomer thereof.

2. The method of claim 1, wherein the cancer is leukemia.

3. The method of claim 1, wherein the cancer is multiple myeloma.

4. The method of claim 1, wherein the individual is a human.

5. The method of claim 1, wherein —$R_1$ is selected from the group consisting of —H, —$CH_3$, —$CH_2CH_3$, —Si$(CH_3)_3$, —Si$(CH_3)_2C(CH_3)_3$, —$C_6H_5$, —F, —Cl, —Br, —$CH_2OH$, —$CH_2OCH_3$, —$CH_2OCH_2CH_3$, —$CH_2OCH_2CF_3$, —$CH_2COCH_3$, —$CH_2N(CH_3)_2$, —$CH_2CH_2NH_2$, —$CH_2CH_2NHCO_2C(CH_3)_3$, —CN, —C≡CH, —C≡CCH$_3$, —C≡CSi(CH$_3$)$_3$, —CH=CH$_2$, —CH=CHCH$_3$, —COH, —COCH$_3$, —COCH$_2$CH$_3$, —COC$_6$H$_5$, —CO$_2$H, —CO$_2$CH$_3$, —CONH$_2$, —CONHCH$_3$, —CON(CH$_3$)$_2$, —CONHCH$_2$CH$_3$, —CON(CH$_2$CH$_3$)$_2$, —CONHCH$_2$CF$_3$,

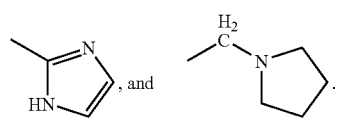

6. The method of claim 1, wherein the compound is further defined as:

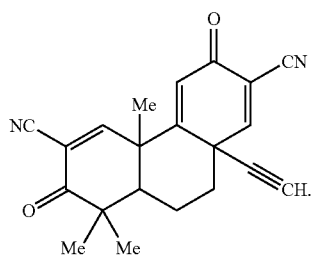

7. The method of claim 1, wherein the compound is further defined as:

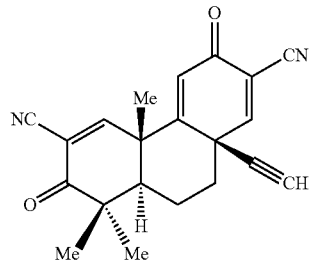

substantially free from other optical isomers.

8. The method of claim 1, wherein the compound is further defined as:

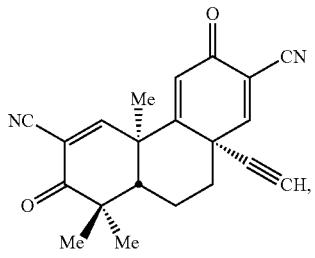

substantially free from other optical isomers.

9. The method of claim 1, wherein the compound is further defined as:

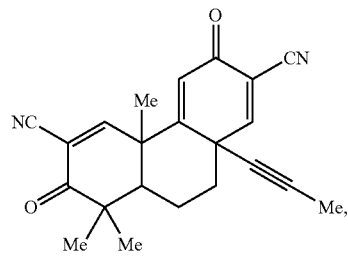

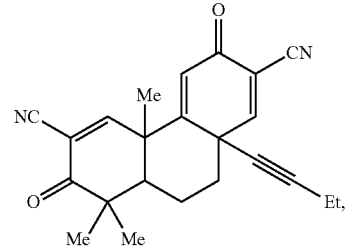

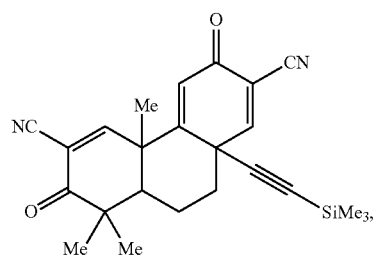

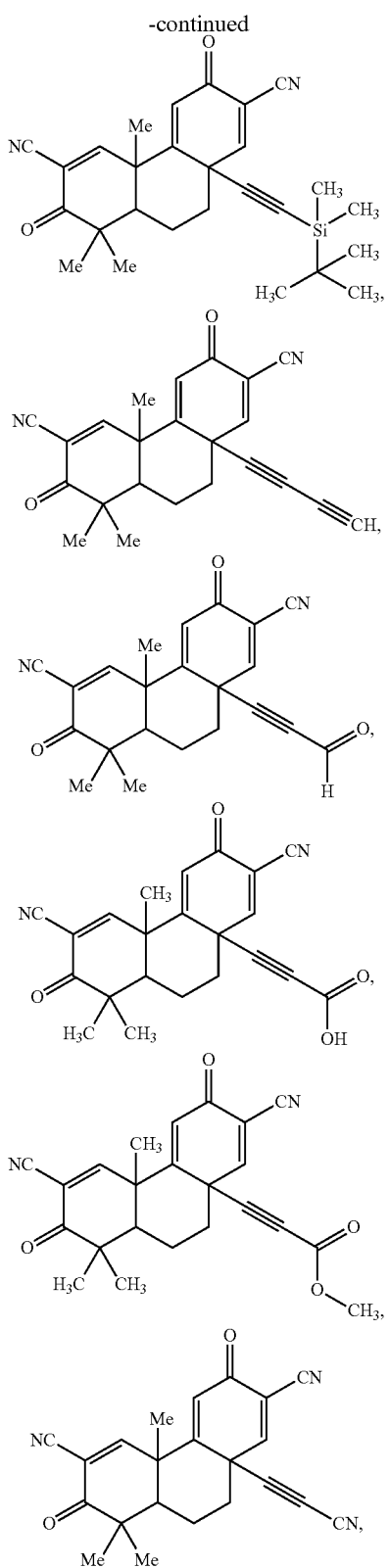
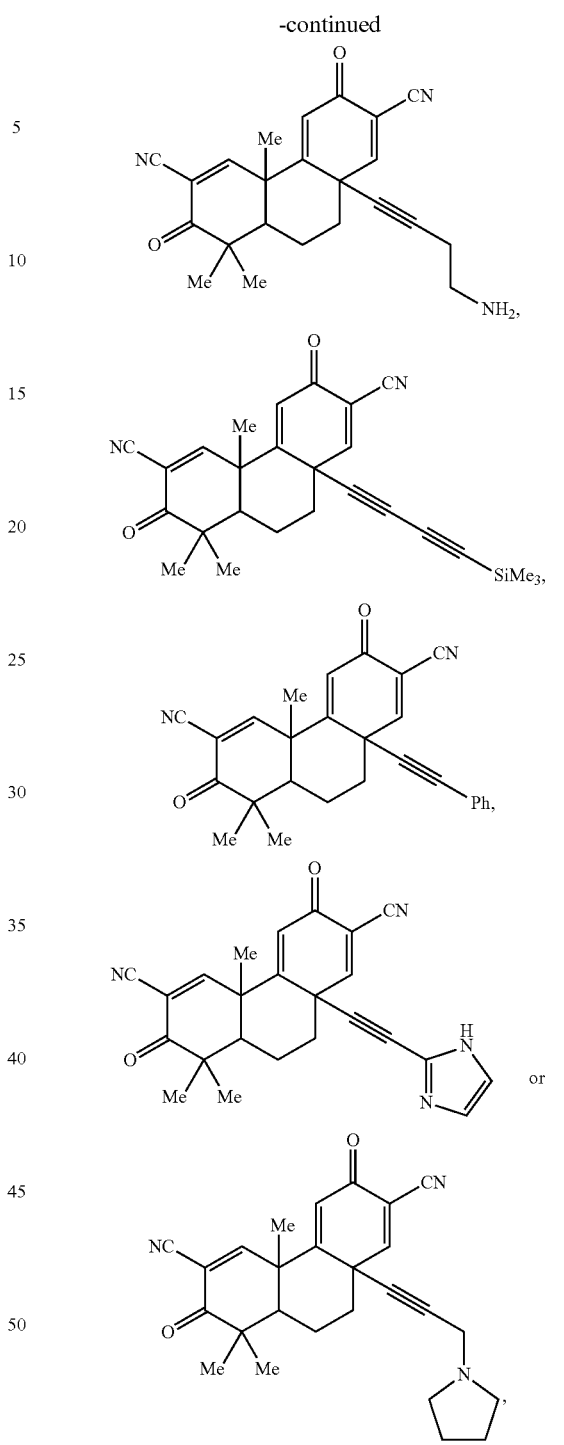
or a pharmaceutically acceptable salt of any of the above structures.
* * * * *

UNITED STATES PATENT AND TRADEMARK OFFICE
CERTIFICATE OF CORRECTION

| | | |
|---|---|---|
| PATENT NO. | : 8,067,394 B2 | Page 1 of 1 |
| APPLICATION NO. | : 12/777120 | |
| DATED | : November 22, 2011 | |
| INVENTOR(S) | : Tadashi Honda et al. | |

It is certified that error appears in the above-identified patent and that said Letters Patent is hereby corrected as shown below:

In column 1, lines 10-13, delete paragraph and insert
--This invention was made with government support under grant numbers CA-105294 and CA-078814 awarded by the National Institutes of Health. The government has certain rights in the invention.-- therefor.

Signed and Sealed this
Twenty-first Day of February, 2012

David J. Kappos
*Director of the United States Patent and Trademark Office*